US011739345B2

(12) United States Patent
Berguig et al.

(10) Patent No.: US 11,739,345 B2
(45) Date of Patent: Aug. 29, 2023

(54) METHODS OF TREATING PHENYLKETONURIA

(71) Applicant: BIOMARIN PHARMACEUTICAL INC., Novato, CA (US)

(72) Inventors: Geoffrey Berguig, Greenebrae, CA (US); Rajeev Mahimkar, Novato, CA (US); Hassibullah Akeefe, San Ramon, CA (US); Peter Colosi, Fairfax, CA (US)

(73) Assignee: BIOMARIN PHARMACEUTICAL INC., Novato, CA (US)

( * ) Notice: Subject to any disclaimer, the term of this patent is extended or adjusted under 35 U.S.C. 154(b) by 837 days.

(21) Appl. No.: 16/407,015

(22) Filed: May 8, 2019

(65) Prior Publication Data

US 2019/0376081 A1 Dec. 12, 2019

Related U.S. Application Data

(60) Provisional application No. 62/819,414, filed on Mar. 15, 2019, provisional application No. 62/802,608, filed on Feb. 7, 2019, provisional application No. 62/755,207, filed on Nov. 2, 2018, provisional application No. 62/669,292, filed on May 9, 2018.

(51) Int. Cl.

| | |
|---|---|
| ***C12N 15/864*** | (2006.01) |
| ***C12N 15/12*** | (2006.01) |
| ***C12N 15/63*** | (2006.01) |
| ***A61K 48/00*** | (2006.01) |
| ***C12N 7/01*** | (2006.01) |
| ***C12N 7/02*** | (2006.01) |
| ***C12N 15/86*** | (2006.01) |
| ***A61P 3/00*** | (2006.01) |
| ***C12N 7/00*** | (2006.01) |
| ***G01N 33/94*** | (2006.01) |

(52) U.S. Cl.

CPC .......... *C12N 15/86* (2013.01); *A61K 48/0066* (2013.01); *A61P 3/00* (2018.01); *C12N 7/00* (2013.01); *G01N 33/9406* (2013.01); *C12N 2830/50* (2013.01)

(58) Field of Classification Search

None

See application file for complete search history.

(56) References Cited

U.S. PATENT DOCUMENTS

| | | | | |
|---|---|---|---|---|
| 4,745,051 | A | 5/1988 | Smith et al. | |
| 4,994,371 | A | 2/1991 | Davie et al. | |
| 6,204,059 | B1 | 3/2001 | Samulski et al. | |
| 6,531,298 | B2 | 3/2003 | Stafford et al. | |
| 7,198,951 | B2 | 4/2007 | Gao et al. | |
| 7,323,324 | B2 | 1/2008 | Narimatsu et al. | |
| 7,531,341 | B1 | 5/2009 | Vellard et al. | |
| 7,534,595 | B2 | 5/2009 | Vellard et al. | |
| 7,537,923 | B2 | 5/2009 | Kakkis et al. | |
| 7,560,263 | B2 | 7/2009 | Kakkis et al. | |
| 7,566,462 | B2 | 7/2009 | Jungles et al. | |
| 7,732,599 | B2 | 6/2010 | Moser et al. | |
| 7,790,433 | B2 | 9/2010 | Kakkis et al. | |
| 7,906,111 | B2 | 3/2011 | Wilson et al. | |
| 8,003,126 | B2 | 8/2011 | Jungles et al. | |
| 8,178,670 | B2 | 5/2012 | Henderson et al. | |
| 9,249,405 | B2 | 2/2016 | Simioni | |
| 9,393,323 | B2 | 7/2016 | Nathwani et al. | |
| 9,447,168 | B2 | 9/2016 | Nathwani et al. | |
| 9,504,762 | B2 | 11/2016 | Colosi et al. | |
| 9,557,340 | B2 | 1/2017 | Foehr et al. | |
| 9,695,220 | B2 | 7/2017 | Vandenberghe et al. | |
| 10,610,606 | B2 | 4/2020 | Seymour et al. | |
| 2002/0031799 | A1 | 3/2002 | Stafford et al. | |
| 2003/0138772 | A1 | 7/2003 | Gao et al. | |
| 2003/0148506 | A1 | 8/2003 | Kotin et al. | |
| 2003/0166284 | A1 | 9/2003 | Srivastava et al. | |
| 2004/0142416 | A1 | 7/2004 | Laipis et al. | |
| 2008/0249052 | A1 | 10/2008 | Duan et al. | |
| 2010/0129405 | A1 | 5/2010 | Schmidt et al. | |
| 2010/0216709 | A1* | 8/2010 | Scheule | C12N 15/86 514/44 R |
| 2011/0201088 | A1 | 8/2011 | Beall et al. | |
| 2011/0244550 | A1 | 10/2011 | Simioni | |
| 2013/0045186 | A1 | 2/2013 | Gao et al. | |
| 2015/0071883 | A1 | 3/2015 | Colosi | |
| 2015/0110858 | A1* | 4/2015 | DeRosa | A61K 38/44 514/44 R |
| 2015/0158930 | A1 | 6/2015 | Nathwani et al. | |
| 2016/0215024 | A1 | 7/2016 | Vandenberghe et al. | |
| 2017/0119906 | A1 | 5/2017 | Riley | |

(Continued)

FOREIGN PATENT DOCUMENTS

| | | |
|---|---|---|
| EP | 127839 A2 | 12/1984 |
| EP | 127839 A3 | 12/1984 |

(Continued)

OTHER PUBLICATIONS

Akinc et al., 2005, "Exploring polyethylenimine-mediated DNA transfection and the proton sponge hypothesis," J. Gene Med., 7(5):657-663.
Andersen et al., 1993, "Herpesvims-mediated gene delivery into the rat brain: specificity and efficiency of the neuron-specific enolase promoter," Cell Mol. Neurobiol., 13(5):503-515.
Arbuthnot et al., 1996, "In vitro and in vivo hepatoma cell-specific expression of a gene transferred with an adenoviral vector," Hum. Gene. Ther., 7(13):1503-1514.
Batts et al., 1995, "Chronic hepatitis. An update on terminology and reporting," Am. J. Surg. Pathol., 19(12):1409-1417.

(Continued)

*Primary Examiner* — Maria Marvich
(74) *Attorney, Agent, or Firm* — Jones Day

(57) ABSTRACT

Provided herein are methods of treating phenylketonuria by normalizing levels of amino acids, neurotransmitters, and neurotransmitter metabolites in a subject having phenylketonuria.

61 Claims, 75 Drawing Sheets

Specification includes a Sequence Listing.

(56) References Cited

U.S. PATENT DOCUMENTS

| | | | | |
|---|---|---|---|---|
| 2017/0216408 | A1 | 8/2017 | Anguela et al. | |
| 2019/0231901 | A1* | 8/2019 | Seymour | A61K 48/0066 |
| 2020/0024579 | A1 | 1/2020 | Colosi et al. | |
| 2020/0069819 | A1 | 3/2020 | Colosi et al. | |
| 2020/0362368 | A1 | 11/2020 | Colosi et al. | |

FOREIGN PATENT DOCUMENTS

| | | | |
|---|---|---|---|
| EP | 155476 | A1 | 9/1985 |
| EP | 127839 | B1 | 7/1992 |
| JP | 2003235562 | A | 8/2003 |
| JP | 2007507223 | A | 3/2007 |
| JP | 2015518705 | A | 7/2015 |
| JP | 2016535729 | A | 11/2016 |
| RU | 2273645 | C9 | 5/1999 |
| RU | 2228202 | C2 | 5/2004 |
| RU | 2273645 | C2 | 11/2006 |
| RU | 2502800 | C2 | 12/2013 |
| RU | 2015144234 | A | 4/2017 |
| RU | 2653444 | C2 | 5/2018 |
| WO | WO 1996005309 | A2 | 2/1996 |
| WO | WO 1996005309 | A3 | 2/1996 |
| WO | WO 1998010088 | A1 | 3/1998 |
| WO | WO 1999054440 | A1 | 10/1999 |
| WO | WO 2001083692 | A2 | 11/2001 |
| WO | WO 2001083692 | A3 | 11/2001 |
| WO | WO 2003042397 | A2 | 5/2003 |
| WO | WO 2003042397 | A3 | 5/2003 |
| WO | WO 2003074714 | A1 | 9/2003 |
| WO | WO 2003087383 | A1 | 10/2003 |
| WO | WO 2005033321 | A2 | 4/2005 |
| WO | WO 2005033321 | A3 | 5/2005 |
| WO | WO 2006073496 | A2 | 7/2006 |
| WO | WO 2006073496 | A3 | 7/2006 |
| WO | WO 2006119432 | A2 | 11/2006 |
| WO | WO 2006119432 | A3 | 11/2006 |
| WO | WO 2009091912 | A2 | 7/2009 |
| WO | WO 2009091912 | A3 | 7/2009 |
| WO | WO 2010127097 | A1 | 11/2010 |
| WO | WO 2011005968 | A1 | 1/2011 |
| WO | WO 2011119773 | A1 | 9/2011 |
| WO | WO 2011126808 | A2 | 10/2011 |
| WO | WO 2011126808 | A3 | 10/2011 |
| WO | WO 2011126808 | A9 | 10/2011 |
| WO | WO 2013123503 | A1 | 8/2013 |
| WO | WO 2013151666 | A2 | 10/2013 |
| WO | WO 2013151666 | A3 | 10/2013 |
| WO | WO 2013186563 | A2 | 12/2013 |
| WO | WO 2013186563 | A3 | 12/2013 |
| WO | WO 2014151341 | A1 | 9/2014 |
| WO | WO 2015038625 | A1 | 3/2015 |
| WO | WO 2015054653 | A2 | 4/2015 |
| WO | WO 2015054653 | A3 | 4/2015 |
| WO | WO 2015138348 | A1 | 9/2015 |
| WO | WO 2015138357 | A2 | 9/2015 |
| WO | WO 2015197869 | A1 | 12/2015 |
| WO | WO 2016004318 | A1 | 1/2016 |
| WO | WO 2016016119 | A1 | 2/2016 |
| WO | WO 2016049230 | A1 | 3/2016 |
| WO | WO 2016177911 | A1 | 11/2016 |
| WO | WO 2017019994 | A2 | 2/2017 |
| WO | WO 2017053677 | A1 | 3/2017 |
| WO | WO 2017066764 | A2 | 4/2017 |
| WO | WO 2017066764 | A3 | 4/2017 |
| WO | WO 2018022608 | A2 | 3/2018 |
| WO | WO 2018022608 | A3 | 3/2018 |
| WO | WO 2018126112 | A1 | 7/2018 |
| WO | WO 2018128689 | A1 | 7/2018 |
| WO | WO 2019152841 | A1 | 8/2019 |
| WO | WO 2019222132 | A1 | 11/2019 |
| WO | WO 2019222136 | A2 | 11/2019 |
| WO | WO 2019222136 | A3 | 11/2019 |
| WO | WO 2019222136 | A9 | 11/2019 |
| WO | WO 2020023612 | A1 | 1/2020 |
| WO | WO 2020214929 | A1 | 10/2020 |
| WO | WO 2020232044 | A1 | 11/2020 |
| WO | WO 2021202943 | A1 | 10/2021 |

OTHER PUBLICATIONS

Bedossa et al., 1996, "An algorithm for the grading of activity in chronic hepatitis C. The METAVIR Cooperative Study Group," Hepatology, 24(2):289-293.

Bello et al., 2014, "Novel adeno-associated viruses derived from pig tissues transduce most major organs in mice," Sci. Rep., 4:6644 (11 pages).

Berry et al., 2016, "Chemical Modulation of Endocytic Sorting Augments Adeno-associated Viral Transduction," J. Biol. Chem., 291(2):939-947 (Epub 2015).

Berry et al., 2016, "Modulation of intracellular calcium enhances AAV transduction in the CNS," Mol. Ther., 24 (Suppl 1): S14 (Abstract 30).

Bortolussi et al., 2014, "Life-long correction of hyperbilimbinemia with a neonatal liver-specific AAV-mediated gene transfer in a lethal mouse model of Crigler-Najjar Syndrome" Hum. Gene. Ther., 25(9):844-855.

Boshart et al., 1985, "A very strong enhancer is located upstream of an immediate early gene of human cytomegalovirus," Cell, 41(2):521-530.

Boutin et al., 2010, "Prevalence of semm IgG and neutralizing factors against adeno-associated vims (AAV) types 1, 2, 5, 6, 8, and 9 in the healthy population: implications for gene therapy using AAV vectors," Hum. Gene Ther., 21(6):704-712.

Brimble et al., 2016, "New and improved AAVenues: current status of hemophilia B gene therapy," Expert Opin. Biol. Ther., 16(1):79-92 (Epub 2015).

Burton et al., 2015, "A randomized, placebo-controlled, double-blind study of sapropterin to treat ADHD symptoms and executive function impairment in children and adults with sapropterin-responsive phenylketonuria," Mol. Genet. Metab., 114(3):415-424.

Calcedo et al., 2009, "Worldwide epidemiology of neutralizing antibodies to adeno-associated vimses," J. Infect. Dis., 199(3):381-390.

Calcedo et al., 2011, "Adeno-associated vims antibody profiles in newborns, children, and adolescents," Clin. Vaccine Immunol., 18(9):1586-1588.

Carbonell et al., 1988, "Synthesis of a gene coding for an insect-specific scorpion neurotoxin and attempts to express it using baculovims vectors," Gene, 73(2):409-418.

Chahal et al., 2014, "Production of adeno-associated vims (AAV) serotypes by transient transfection of HEK293 cell suspension cultures for gene delivery," J. Virol. Methods, 196:163-173 (Epub 2013).

Chen et al., 1996, "Expression of rat bone sialoprotein promoter in transgenic mice," J. Bone Miner. Res., 11(5):654-664.

Chicoine et al., 2014, "Plasmapheresis eliminates the negative impact of AAV antibodies on microdystrophin gene expression following vascular delivery," Mol. Ther., 22(2):338-347 (Epub 2013).

Chiorini et al., 1997, "Cloning of adeno-associated vims type 4 (AAV4) and generation of recombinant AAV4 particles," J. Virol., 71(9):6823-6833.

Chiorini et al., 1999, "Cloning and characterization of adeno-associated vims type 5," J. Virol., 73(2):1309-1319.

Chow et al., 1991, "Characterization of a novel liver-specific enhancer in the human prothrombin gene," J. Biol. Chem., 266(28):18927-18933.

Chu et al., 1981, "SV40 DNA transfection of cells in suspension: analysis of efficiency of transcription and translation of T-antigen," Gene., 13(2):197-202 and Errata.

ClinicalTrials.gov Identifier NCT03952156, "Gene Therapy Clinical Study in Adult PKU (pheNIX)," last updated Mar. 26, 2021 (9 pages).

Colella et al., 2017, "Emerging Issues in AAV-Mediated In Vivo Gene Therapy," Mol. Ther. Methods Clin. Dev., 8:87-104.

(56) References Cited

OTHER PUBLICATIONS

Corti et al., 2014, "B-Cell Depletion is Protective Against Anti-AAV Capsid Immune Response: A Human Subject Case Study," Mol. Ther. Methods Clin. Dev., 1:14033 (7 pages).
Costa et al., 1988, "The cell-specific enhancer of the mouse transthyretin (prealbumin) gene binds a common factor at one site and a liver-specific factor(s) at two other sites," Mol. Cell Biol., 8(1):81-90.
Cunningham et al., 2008, "Gene Delivery to the Juvenile Mouse Liver Using AAV2/8 Vectors," Mol. Ther., 16(6):1081-1088 (Epub 2016).
Dabkowska et al., 2012, "The effect of neutral helper lipids on the structure of cationic lipid monolayers," J. R. Soc. Interface, 9(68):548-561.
Dang et al., 1995, "Structure of the hepatic control region of the human apolipoprotein E/C-I gene locus," J. Biol. Chem., 270(38):22577-22585.
De Simone et al., 1987, "Cis- and trans-acting elements responsible for the cell-specific expression of the human alpha 1-antitrypsin gene," EMBO J., 6(9):2759-2766.
Deverman et al., 2016, "Cre-dependent selection yields AAV variants for widespread gene transfer to the adult brain," Nat. Biotechnol., 34(2):204-209.
Donnelly et al., 1997, "The cleavage activities of aphthovims and cardiovirus 2A proteins," J. Gen. Virol., 78 (Pt 1):13-21.
EBI Accession No. UniProt A0A0K1P7V4, Capside Protein, Nov. 11, 2015 (1 page).
Eisensmith et al., 1996, "Somatic gene therapy for phenylketonuria and other hepatic deficiencies," J. Inherit Metab. Dis., 19(4):412-423.
Fagiuoli et al., 2013, "Monogenic diseases that can be cured by liver transplantation," J. Hepatol., 59(3):595-612.
Falese et al., 2017, "Strategy to detect pre-existing immunity to AAV gene therapy," Gene. Ther., 24(12):768-778.
Fang et al., 1994, "Gene therapy for phenylketonuria: phenotypic correction in a genetically deficient mouse model by adenovims-mediated hepatic gene transfer," Gene Ther., 1(4):247-254.
Frain et al., 1990, "Binding of a liver-specific factor to the human albumin gene promoter and enhancer," Mol. Cell Biol., 10(3):991-999.
Friesen et al., 1986, "The regulation of baculovims gene expression," Curr. Top. Microbiol. Immunol., 131:31-49.
Fu et al., 2017, "Differential Prevalence of Antibodies Against Adeno-Associated Vims in Healthy Children and Patients with Mucopolysaccharidosis III: Perspective for AAV-Mediated Gene Therapy," Hum. Gene. Ther. Clin. Dev., 28(4):187-196.
Furler et al., 2001, "Recombinant AAV vectors containing the foot and mouth disease vims 2A sequence confer efficient bicistronic gene expression in cultured cells and rat substantia nigra neurons," Gene. Ther., 8(11):864-873.
Gao et al., 2003, "Adeno-associated vimses undergo substantial evolution in primates during natural infections," Proc. Natl. Acad. Sci. USA, 100(10):6081-6086.
Gao et al., 2004, "Clades of Adeno-associated vimses are widely disseminated in human tissues," J. Virol., 78(12):6381-6388.
Gao et al., 2011, "Exploiting natural diversity of AAV for the design of vectors with novel properties," Methods Mol. Biol., 807:93-118.
GenBank Accession No. AAB95450.1, "capsid protein VP1 [Adeno-associated virus-6]," Jan. 12, 1998 (2 pages).
GenBank Accession No. AAB95452.1, "capsid protein VP1 [Adeno-associated virus 3B]," Jan. 12, 1998 (2 pages).
GenBank Accession No. AAT46337.1, "capsid protein [Adeno-associated virus 10]," Nov. 30, 2004 (2 pages).
GenBank Accession No. AAT46339.1, "capsid protein [Adeno-associated virus 11]," Nov. 30, 2004 (2 pages).
GenBank Accession No. ABI16639.1, "VP1 [Adeno-associated virus 12]," Feb. 20, 2008 (2 pages).
GenBank Accession No. ABZ10812.1, "capsid protein [Adeno-associated virus 13]," Sep. 23, 2008 (2 pages).
GenBank Accession No. AF028704.1, "Adeno-associated virus 6, complete genome," Jan. 12, 1998 (3 pages).
GenBank Accession No. AF028705.1, "Adeno-associated virus 3B, complete genome," Jan. 12, 1998 (3 pages).
GenBank Accession No. AF043303.1, "Adeno-associated virus 2, complete genome," May 20, 2010 (4 pages).
GenBank Accession No. AF085716.1, "Adeno-associated virus 5 DNA binding trs helicase (Rep22) and capsid protein (VP1) genes, complete cds," Feb. 9, 1999 (3 pages).
GenBank Accession No. AX753250.1, "Sequence 5 from Patent EP1310571," Jun. 23, 2003 (2 pages).
GenBank Accession No. AY631965.1, "Adeno-associated virus 10 nonstructural protein and capsid protein genes, complete cds," Nov. 30, 2004 (3 pages).
GenBank Accession No. AY631966.1, "Adeno-associated virus 11 nonstructural protein and capsid protein genes, complete cds," Nov. 30, 2004 (3 pages).
GenBank Accession No. DQ813647.1, "Adeno-associated virus 12 Rep78 and VP1 genes, complete cds," Feb. 20, 2008 (3 pages).
GenBank Accession No. EU285562.1, "Adeno-associated virus 13 nonstructural protein and capsid protein genes, complete cds," Sep. 23, 2008 (3 pages).
GenBank Accession No. J01901, "Adeno-associated virus 2, complete genome," Apr. 27, 1993 (3 pages).
GenBank Accession No. NC_001401.2, "Adeno-associated virus-2, complete genome," Aug. 13, 2018 (6 pages).
GenBank Accession No. NC_001729.1, "Adeno-associated virus-3, complete genome," Aug. 13, 2018 (3 pages).
GenBank Accession No. NC_001829.1, "Adeno-associated virus-4, complete genome," Aug. 13, 2018 (3 pages).
GenBank Accession No. NC_002077.1, "Adeno-associated virus-1, complete genome," Aug. 13, 2018 (3 pages).
GenBank Accession No. NC_006152.1, "Adeno-associated virus 5, complete genome," Aug. 13, 2018 (3 pages).
GenBank Accession No. NC_006260.1, "Adeno-associated virus-7, complete genome," Aug. 13, 2018 (3 pages).
GenBank Accession No. NC_006261.1, "Adeno-associated virus-8, complete genome," Aug. 13, 2018 (3 pages).
GenBank Accession No. NP_043941.1, "capsid protein [Adeno-associated virus-3]," Aug. 13, 2018 (2 pages).
GenBank Accession No. NP_044927.1, "capsid [Adeno-associated virus-4]," Aug. 13, 2018 (2 pages).
GenBank Accession No. U89790, "Adeno-associated virus 4, complete genome," Aug. 21, 1997 (3 pages).
GenBank Accession No. YP_068409.1, "capsid protein [Adeno-associated virus-5]," Aug. 13, 2018 (2 pages).
GenBank Accession No. YP_077178.1, "capsid protein [Adeno-associated virus-7]," Aug. 13, 2018 (2 pages).
GenBank Accession No. YP_077180.1, "capsid protein [Adeno-associated virus-8]," Aug. 13, 2018 (2 pages).
GenBank Accession No. YP_680426.1, "major coat protein VP1 [Adeno-associated virus-2]," Aug. 13, 2018 (2 pages).
George et al., 2017, "Hemophilia B Gene Therapy with a High-Specific-Activity Factor IX Variant," N. Engl. J. Med., 377(23):2215-2227.
Ghosh et al., 2007, "Expanding adeno-associated viral vector capacity: a tale of two vectors," Biotechnol. Genet. Eng. Rev., 24:165-177.
Gibson et al., 2009, "Enzymatic assembly of DNA molecules up to several hundred kilobases," Nat. Methods, 6(5):343-345 and Online Methods.
Gibson et al., 2011, "Enzymatic assembly of overlapping DNA fragments," Methods Enzymol., 498:349-361.
Gnirke et al., 2009, "Solution hybrid selection with ultra-long oligonucleotides for massively parallel targeted sequencing," Nat. Biotechnol., 27(2):182-189.
Gossen et al., 1992, "Tight control of gene expression in mammalian cells by tetracycline-responsive promoters," Proc. Natl. Acad. Sci. USA, 89(12):5547-5551.
Gossen et al., 1995, "Transcriptional activation by tetracyclines in mammalian cells," Science, 268(5218):1766-1769.
Graham et al., 1973, "A new technique for the assay of infectivity of human adenovirus 5 DNA," Virology, 52(2):456-467.

(56) References Cited

OTHER PUBLICATIONS

Greenberg et al., 2016, "Prevalence of AAV1 neutralizing antibodies and consequences for a clinical trial of gene transfer for advanced heart failure," Gene. Ther., 23(3):313-319 (Epub 2015).
Grimm et al., 2008, "In vitro and in vivo gene therapy vector evolution via multispecies interbreeding and retargeting of adeno-associated vimses," J. Virol., 82(12):5887-5911.
Grosse et al., 2017, "Relevance of Assembly-Activating Protein for Adeno-associated Virus Vector Production and Capsid Protein Stability in Mammalian and Insect Cells," J. Virol., 91(20):e01198-17 (30 pages).
Halbert et al., 2000, "Repeat transduction in the mouse lung by using adeno-associated virus vectors with different serotypes," J. Virol., 74(3):1524-1532.
Halbert et al., 2006, "Prevalence of neutralizing antibodies against adeno-associated virus (AAV) types 2, 5, and 6 in cystic fibrosis and normal populations: Implications for gene therapy using AAV vectors," Hum. Gene. Ther., 17(4):440-447.
Hansal et al., 1998, "Induction of antigen-specific hyporesponsiveness by transplantation of hemopoietic cells containing an MHC class I transgene regulated by a lymphocyte-specific promoter," J. Immunol., 161(3):1063-1068.
Harding et al., 2006, "Complete correction of hyperphenylalaninemia following liver-directed, recombinant AAV2/8 vector-mediated gene therapy in murine phenylketonuria," Gene Ther., 13(5):457-462.
Harding, 2008, "Progress toward cell-directed therapy for phenylketonuria," Clin. Genet., 74(2):97-104.
Harris et al., 2011, "Comparison of a fluorogenic anti-FXa assay with a central laboratory chromogenic anti-FXa assay for measuring LMWH activity in patient plasmas," Thromb. Res., 128(6):e125-e129.
Harvey et al., 1998, "Inducible control of gene expression: prospects for gene therapy," Curr. Opin. Chem. Biol., 2(4):512-518.
Hauck et al., 2003, "Characterization of tissue tropism determinants of adeno-associated virus type 1," J. Virol., 77(4):2768-2774.
Hill et al., 1965, "An automated procedure for blood phenylalanine," Clin. Chem., 11:541-546.
Hinderer et al., 2018, "Severe Toxicity in Nonhuman Primates and Piglets Following High-Dose Intravenous Administration of an Adeno-Associated Virus Vector Expressing Human SMN," Hum. Gene. Then, 29(3):285-298.
Hirosue et al., 2007, "Effect of inhibition of dynein function and microtubule-altering drugs on AAV2 transduction," Virology, 367(1):10-18.
Hirsch et al., 2010, "Little vector, big gene transduction: fragmented genome reassembly of adeno-associated virus," Mol. Ther., 18(1):6-8.
Hurlbut et al., 2010, "Preexisting immunity and low expression in primates highlight translational challenges for liver-directed AAV8-mediated gene therapy," Mol. Ther., 18(11):1983-1994.
Jacobs et al., 2011, "Adeno-associated viral vectors for correction of inborn errors of metabolism: progressing towards clinical application," Curr. Pharm. Des., 17(24):2500-2515.
Kajigaya et al., 1991, "Self-assembled B19 parvovirus capsids, produced in a baculovims system, are antigenically and immunogenically similar to native virions," Proc. Natl. Acad. Sci. USA, 88(11):4646-4650.
Kato et al., 2010, "Silkworm expression system as a platform technology in life science," Appl. Microbiol. Biotechnol., 85(3):459-470.
Khan et al., 2019, "The phenylketonuria-associated substitution R68S converts phenylalanine hydroxylase to a constitutively active enzyme but reduces its stability," J. Biol. Chem., 294(12):4359-4367.
Kim et al., 1997, "Codon optimization for high-level expression of human erythropoietin (EPO) in mammalian cells," Gene, 199(1-2):293-301.
Kirnbauer et al., 1996, "Virus-like particles of bovine papillomavirus type 4 in prophylactic and therapeutic immunization," Virology, 219(1):37-44.
Klump et al., 2001, "Retroviral vector-mediated expression of HoxB4 in hematopoietic cells using a novel coexpression strategy," Gene. Ther., 8(10):811-817.
Knappskog et al., 1997, "Effect of mutations at Cys237 on the activation state and activity of human phenylalanine hydroxylase," FEBS Lett., 409(1):7-11.
Kok et al., 2013, "Adeno-associated vims-mediated rescue of neonatal lethality in argininosuccinate synthetase-deficient mice," Mol. Ther., 21(10):1823-1831.
Kotin, 1994, "Prospects for the use of adeno-associated virus as a vector for human gene therapy," Hum. Gene. Ther., 5(7):793-801.
Kurachi et al., 1995, "Role of intron I in expression of the human factor IX gene," J. Biol. Chem., 270(10):5276-5281.
La Du et al., 1963, "A quantitative micromethod for the determination of phenylalanine and tyrosine in blood and its application in the diagnosis of phenylketonuria in infants," Pediatrics, 31:39-46.
Laipis et al., 2003, "Recombinant AAV-based gene therapy of phenylketonuria in the Pah (enu2) missense mutant mouse," Mol. Ther., 7:S391-S392.
Lambert et al., 1995, "Regional 5-hydroxyindoleacetic acid production in humans," Life Sci., 57(3):255-267.
Lebacq-Veheyden et al., 1988, "Posttranslational processing of endogenous and of baculovirus-expressed human gastrin-releasing peptide precursor," Mol. Cell Biol., 8(8):3129-3135.
Li et al., 1999, "Synthetic muscle promoters: activities exceeding naturally occurring regulatory sequences," Nat. Biotechnol., 17(3):241-245.
Li et al., 2012, "Neutralizing antibodies against adeno-associated virus examined prospectively in pediatric patients with hemophilia," Gene. Ther., 19(3):288-294.
Liu et al., 2013, "A practical guide to the monitoring and management of the complications of systemic corticosteroid therapy," Allergy Asthma Clin. Immunol., 9(1):30 (25 pages).
Liu et al., 2014, "Neutralizing antibodies against AAV2, AAV5 and AAV8 in healthy and HIV-1-infected subjects in China: implications for gene therapy using AAV vectors," Gene. Ther., 21(8):732-738.
Luckow et al., 1988, "Trends in the development of baculovims expression vectors," Nature Biotechnol., 6:47-55.
Maeda et al., 1985, "Production of human alpha-interferon in silkworm using a baculovims vector," Nature, 315(6020):592-594.
Magari et al., 1997, "Pharmacologic control of a humanized gene therapy system implanted into nude mice," J. Clin. Invest, 100(11):2865-2872.
Majowicz et al., 2017, "Successful Repeated Hepatic Gene Delivery in Mice and Non-human Primates Achieved by Sequential Administration of AAV5 chand AAV1," Mol. Ther., 25(8):1831-1842.
Manno et al., 2006, "Successful transduction of liver in hemophilia by AAV-Factor IX and limitations imposed by the host immune response," Nat. Med., 12(3):342-347 with Erratum and Corrigendum.
Marsic et al., 2014, "Vector design Tour de Force: integrating combinatorial and rational approaches to derive novel adeno-associated virus variants," Mol. Ther., 22(11):1900-1909.
Martin et al., 1988, "Glycosylation and processing of high levels of active human glucocerebrosidase in invertebrate cells using a baculovirus expression vector," DNA, 7(2):99-106.
Masat et al., 2013, "Humoral immunity to AAV vectors in gene therapy: challenges and potential solutions," Discov. Med., 15(85):379-389.
Mays et al., 2013, "Mapping the structural determinants responsible for enhanced T cell activation to the immunogenic adeno-associated virus capsid from isolate rhesus 32.33," J. Virol., 87(17):9473-9485.
McCaman et al., 1962, "Fluorimetric method for the determination of phenylalanine in serum," J. Lab. Clin. Med., 59(5):885-890.
McIntosh et al., 2012, "Successful attenuation of humoral immunity to viral capsid and transgenic protein following AAV-mediated gene transfer with a non-depleting CD4 antibody and cyclosporine," Gene. Then, 19(1):78-85 (Epub 2011).
McIntosh et al., 2013, "Therapeutic levels of FVIII following a single peripheral vein administration of rAAV vector encoding a novel human factor VIII variant," Blood, 121(17):3335-3344.

(56) References Cited

OTHER PUBLICATIONS

McKenna et al., 1998, "Establishment of NewTrichoplusia niCell Lines in Serum-Free Medium for Baculovirus and Recombinant Protein Production," J. Invertebrate Pathology, 71(1):82-90.
Meadows et al., 2019, "Threshold for Pre-existing Antibody Levels Limiting Transduction Efficiency of Systemic rAAV9 Gene Delivery: Relevance for Translation," Mol. Ther. Methods Clin. Dev., 13:453-462.
Meliani et al., 2015, "Determination of anti-adeno-associated virus vector neutralizing antibody titer with an in vitro reporter system," Hum. Gene. Ther. Methods, 26(2):45-53.
Mendell et al., 2017, "Single-Dose Gene-Replacement Therapy for Spinal Muscular Atrophy" N. Engl. J. Med., 377:1713-1722.
Merrifield, 1963, "Solid Phase Peptide Synthesis. I. The Synthesis of a Tetrapeptide," J. Am. Chem. Soc., 85(14):2149-2154.
Miao et al., 2000, "Inclusion of the hepatic locus control region, an intron, and untranslated region increases and stabilizes hepatic factor IX gene expression in vivo but not in vitro," Mol. Ther., 1(6):522-532.
Miesbach et al., 2018, "Gene therapy with adeno-associated virus vector 5-human factor IX in adults with hemophilia B," Blood, 131(9):1022-1031 (Epub 2017).
Mietzsch et al., 2014, "OneBac: platform for scalable and high-titer production of adeno-associated virus serotype 1-12 vectors for gene therapy," Hum. Gene. Ther., 25(3):212-222.
Miller, 1988, "Baculoviruses as gene expression vectors," Annu. Rev. Microbiol., 42:177-199.
Mingozzi et al., 2007, "CD8(+) T-cell responses to adeno-associated vims capsid in humans," Nat. Med., 13(4):419-422.
Mingozzi et al., 2012, "Pharmacological modulation of humoral immunity in a nonhuman primate model of AAV gene transfer for hemophilia B," Mol. Ther., 20(7):1410-1416.
Mingozzi et al., 2013, "Prevalence and pharmacological modulation of humoral immunity to AAV vectors in gene transfer to synovial tissue," Gene. Ther., 20(4):417-424 (Epub 2012).
Mingozzi et al., 2017, "Overcoming the Host Immune Response to Adeno-Associated Virus Gene Delivery Vectors: The Race Between Clearance, Tolerance, Neutralization, and Escape," Annu. Rev. Virol., 4(1):511-534.
Mitchell et al., 2013, "Arsenic trioxide stabilizes accumulations of adeno-associated virus virions at the perinuclear region, increasing transduction in vitro and in vivo," J. Virol., 87(8):4571-4583.
Mitchell et al., 2013, "Mechamstic insights into the enhancement of adeno-associated virus transduction by proteasome inhibitors," J. Virol., 87(23):13035-13041.
Miyajima et al., 1987, "Use of the silkworm, *Bombyx mori*, and an insect baculovims vector for high-level expression and secretion of biologically active mouse interleukin-3," Gene, 58(2-3):273-281.
Miyamoto et al., 1957, "Competitive inhibition of mammalian tyrosinase by phenylalanine and its relationship to hair pigmentation in phenylketonuria," Nature, 179(4552):199-200.
Miyatake et al., 1997, "Transcriptional targeting of herpes simplex virus for cell-specific replication," J. Virol., 71(7):5124-5132.
Mochizuki et al., 2004, "Long-term correction of hyperphenylalaninemia by AAV-mediated gene transfer leads to behavioral recovery in phenylketonuria mice," Gene. Ther., 11(13):1081-1086.
Moskalenko et al., 2000, "Epitope mapping of human anti-adeno-associated virus type 2 neutralizing antibodies: implications for gene therapy and virus structure," J. Virol., 74(4):1761-1766.
Muyldermans et al., 2001, "Single domain camel antibodies: current status," J. Biotechnol., 74(4):277-302.
Muzyczka, 1992, "Use of adeno-associated virus as a general transduction vector for mammalian cells," Curr. Top. Microbiol. Immunol., 158:97-129.
Nagasaki et al., 1999, "Reversal of hypopigmentation in phenylketonuria mice by adenovirus-mediated gene transfer," Pediatr. Res., 45:465-473.
Nathwani et al., 2006, "Self-complementary adeno-associated virus vectors containing a novel liver-specific human factor IX expression cassette enable highly efficient transduction of murine and nonhuman primate liver," Blood, 107(7):2653-2661.
Nathwani et al., 2007, "Safe and efficient transduction of the liver after peripheral vein infusion of self-complementary AAV vector results in stable therapeutic expression of human FIX in nonhuman primates," Blood, 109(4):1414-1421.
Nathwani et al., 2011, "Adenovirus-associated virus vector-mediated gene transfer in hemophilia B," N. Engl. J. Med., 365(25):2357-2365.
Nathwani et al., 2014, "Long-term safety and efficacy of factor IX gene therapy in hemophilia B," N. Engl. J. Med., 371(21):1994-2004.
No et al., 1996, "Ecdysone-inducible gene expression in mammalian cells and transgenic mice," Proc. Natl. Acad. Sci. USA, 93(8):3346-3351.
Nonnenmacher et al., 2012, "Intracellular transport of recombinant adeno-associated virus vectors," Gene. Ther., 19(6):649-658.
Oh et al., 2004, "Long-term enzymatic and phenotypic correction in the phenylketonuria mouse model by adeno-associated virus vector-mediated gene transfer," Pediatr. Res., 56(2):278-284.
Ojala et al., 2018, "In Vivo Selection of a Computationally Designed SCHEMA AAV Library Yields a Novel Variant for Infection of Adult Neural Stem Cells in the SVZ," Mol. Ther., 26(1):304-319 (Epub 2017).
Okuyama et al., 1996, "Liver-directed gene therapy: a retroviral vector with a complete LTR and the ApoE enhancer-alpha 1-antitrypsin promoter dramatically increases expression of human alpha 1-antitiypsin in vivo," Hum. Gene Ther., 7(5):637-645.
Olson et al., 1998, "College of American Pathologists Conference XXXI on laboratory monitoring of anticoagulant therapy: laboratory monitoring of unfractionated heparin therapy," Arch. Pathol. Lab. Med., 122(9):782-798.
Peden et al., 2009, "Striatal readministration of rAAV vectors reveals an immune response against AAV2 capsids that can be circumvented," Mol. Ther., 17(3):524-537.
Peterson et al., 1988, "Blood phenylalanine estimation for the patient with phenylketonuria using a portable device," Biochem. Med. Metab. Biol., 39(1):98-104.
Pey et al., 2008, "Identification of pharmacological chaperones as potential therapeutic agents to treat phenylketonuria," J. Clin. Invest., 118(8):2858-2867.
Piccioli et al., 1991, "Neuroantibodies: molecular cloning of a monoclonal antibody against substance P for expression in the central nervous system," Proc. Natl. Acad. Sci. USA, 88(13):5611-5615.
Piccioli et al., 1995, "Neuroantibodies: ectopic expression of a recombinant anti-substance P antibody in the central nervous system of transgenic mice," Neuron., 15(2):373-384.
Rangarajan et al., 2017, "AAV5-Factor VIII Gene Transfer in Severe Hemophilia A," N. Engl. J. Med., 377(26):2519-2530.
Rodrigues et al., 2018, "Pharmaceutical Development of AAV-Based Gene Therapy Products for the Eye," Pharm. Res., 36(2):29 (20 pages).
Ronzitti et al., 2016, "A translationally optimized AAV-UGT1A1 vector drives safe and long-lasting correction of Crigler-Najjar syndrome," Mol. Ther. Methods Clin. Dev., 3:16049 (10 pages).
Rouet et al., 1992, "A potent enhancer made of clustered liver-specific elements in the transcription control sequences of human alpha 1-microglobulin/bikunin gene," J. Biol. Chem., 267(29):20765-20773.
Rouet et al., 1995, "Hierarchy and positive/negative interplays of the hepatocyte nuclear factors HNF-1, -3 and -4 in the liver-specific enhancer for the human alpha-1-microglobulin/bikunin precursor," Nucleic Acids Res., 23(3):395-404.
Rouet et al., 1998, "An array of binding sites for hepatocyte nuclear factor 4 of high and low affinities modulates the liver-specific enhancer for the human alpha 1-microglobulin/bikunin precursor," Biochem. J., 334 (Pt 3):577-584.
Ruddell et al., 2008, "The function of serotonin within the liver," J. Hepatol., 48(4):666-675.
Rudy et al., 1987, "Phenylalanine and tyrosine in semm and eluates from dried blood spots as determined by reversed-phase liquid chromatography," Clin. Chem., 33(7):1152-1154.

(56) References Cited

OTHER PUBLICATIONS

Ruffing et al., 1992, "Assembly of viruslike particles by recombinant structural proteins of adeno-associated virus type 2 in insect cells," J. Virol., 66(12):6922-6930.
Ruffing et al., 1994, "Mutations in the carboxy terminus of adeno-associated virus 2 capsid proteins affect viral infectivity: lack of an RGD integrin-binding motif," J. Gen. Virol., 75 (Pt 12):3385-3392.
Russell et al., 2017, "Efficacy and safety of voretigene neparvovec (AAV2-hRPE65v2) in patients with RPE65-mediated inherited retinal dystrophy: a randomised, controlled, open-label, phase 3 trial," Lancet, 390(10097):849-860.
Rutledge et al., 1998, "Infectious clones and vectors derived from adeno-associated virus (AAV) serotypes other than AAV type 2," J. Virol., 72(1):309-319.
Samulski et al., 1989, "Helper-free stocks of recombinant adeno-associated viruses: normal integration does not require viral gene expression," J. Virol., 63(9):3822-3828.
Sandberg et al., 2001, "Structural and functional characteristics of the B-domain-deleted recombinant factor VIII protein, r-VIII SQ," Thromb. Haemost., 85(1):93-100.
Sandig et al., 1996, "HBV-derived promoters direct liver-specific expression of an adenovirally transduced LDL receptor gene," Gene Ther., 3(11):1002-1009.
Sands, 2011, "AAV-mediated liver-directed gene therapy," Methods Mol. Biol., 807:141-157.
Santos-Sierra et al., 2012, "Novel pharmacological chaperones that correct phenylketonuria in mice," Hum. Mol. Genet., 21(8):1877-1887.
Sawin et al., 2014, "Differential effects of low-phenylalanine protein sources on brain neurotransmitters and behavior in C57B1/6-Pah(enu2) mice," Mol. Genet. Metab., 111(4):452-461.
Scallan et al., 2006, "Human immunoglobulin inhibits liver transduction by AAV vectors at low AAV2 neutralizing titers in SCID mice," Blood, 107(5):1810-1817 (Epub 2005).
Schnepp et al., 2005, "Characterization of adeno-associated virus genomes isolated from human tissues," J. Virol., 79(23):14793-14803.
Schuck et al., 2015, "Phenylketonuria Pathophysiology: on the Role of Metabolic Alterations," Agind Dis., 6(5):390-399.
Shachter et al., 1993, "Localization of a liver-specific enhancer in the apolipoprotein E/C-I/C-II gene locus," J. Lipid Res., 34(10):1699-1707.
Sharp et al., 1987, "The codon Adaptation Index—a measure of directional synonymous codon usage bias, and its potential applications," Nucleic Acids Res., 15(3):1281-1295.
Shedlovsky et al., 1993, "Mouse models of human phenylketonuria," Genetics, 134(4):1205-1210.
Smith et al., 1985, "Modification and secretion of human interleukin 2 produced in insect cells by a baculovims expression vector," Proc. Natl. Acad. Sci. USA, 82(24):8404-8408.
Soriano et al., 2002, "Gene therapy and pediatric liver disease," J. Pediatr. Gastroenterol. Nutr., 35 Suppl 1:S51-S54.
Srivastava et al., 1983, "Nucleotide sequence and organization of the adeno-associated virus 2 genome," J. Virol., 45(2):555-564.
Stein et al., 1997, "The osteocalcin gene: a model for multiple parameters of skeletal-specific transcriptional control," Mol. Biol. Rep., 24(3):185-196.
Sun et al., 2013, "Assessment of a passive immunity mouse model to quantitatively analyze the impact of neutralizing antibodies on adeno-associated virus-mediated gene transfer," J. Immunol. Methods, 387(1-2):114-120 (Epub 2012).
Svyatchenko et al., 2012, "Oncolytic Adenovimses in Anti-Cancer Therapy: Current Status and Perspectives," Molekuliamaia Biologiia, 46(4):556-569 (in Russian with English abstract).
Thomas et al., 2018, "Pegvaliase for the treatment of phenylketonuria: Results of a long-term phase 3 clinical trial program (PRISM)," Mol. Genet. Metab., 124(1):27-38.
Tsukerman, 1985, "Simple method of mass screening for phenylketonuria," Lab. Delo. 6:326-327 (in Russian with English abstract).
Viecelli et al., 2014, "Treatment of phenylketonuria using minicircle-based naked-DNA gene transfer to murine liver," Hepatology, 60(3):1035-1043.
Viecelli et al., 2016, "Minicircles show improved hepatic expression of their transgene from a natural endogenous promoter and are lost upon partial hepatectomy due to the episomal nature of the vector," Mol. Ther., 24(1):S142.
Virella-Lowell et al., 2000, "Inhibition of recombinant adeno-associated vims (rAAV) transduction by bronchial secretions from cystic fibrosis patients," Gene. Ther., 7(20): 1783-1789.
Vlak et al., 1988, "Functional studies on the p10 gene of Autographa califomica nuclear polyhedrosis virus using a recombinant expressing a p10-beta-galactosidase fusion gene," J. Gen. Virol., 69:765-776.
Wang et al., 1997, "Ligand-inducible and liver-specific target gene expression in transgenic mice," Nat. Biotechnol., 15(3):239-243.
Wang et al., 1997, "Positive and negative regulation of gene expression in eukaryotic cells with an inducible transcriptional regulator," Gene. Ther., 4(5):432-441.
Wang et al., 1999, "Sustained correction of bleeding disorder in hemophilia B mice by gene therapy," Proc. Natl. Acad. Sci. USA, 96(7):3906-3 910.
Wang et al., 2001, "Mutagenesis of the regulatory domain of phenylalanine hydroxylase," Proc. Natl. Acad. Sci. USA, 98(4):1537-1542.
Wang et al., 2010, "The pleiotropic effects of natural AAV infections on liver-directed gene transfer in macaques," Mol. Ther., 18(1):126-134 (Epub 2009).
Wang et al., 2012, "Hepatic gene transfer in neonatal mice by adeno-associated virus serotype 8 vector," Hum. Gene. Ther., 23(5):533-539.
Ward et al., 2011, "Codon optimization of human factor VIII cDNAs leads to high-level expression," Blood, 117(3):798-807 (Epub 2010).
Weinberg et al., 2014, "Recombinant adeno-associated virus utilizes cell-specific infectious entry mechanisms," J. Virol., 88(21):12472-12484.
Winn et al., 2018, "Blood phenylalanine reduction corrects CNS dopamine and serotonin deficiencies and partially improves behavioral performance in adult phenylketonuric mice," Mol. Genet. Metab., 123(1):6-20.
Wong et al., 2016, "Benzoyl chloride derivatization with liquid chromatography-mass spectrometry for targeted metabolomics of neurochemicals in biological samples," J. Chromatogr. A., 1446:78-90.
Wu et al., 2000, "Mutational analysis of the adeno-associated virus type 2 (AAV2) capsid gene and construction of AAV2 vectors with altered tropism," J. Virol.,74(18):8635-8647.
Yan et al., 2005, "Inverted terminal repeat sequences are important for intermolecular recombination and circularization of adeno-associated virus genomes," J. Virol., 79(1):364-379.
Yan et al., 2012, "Human thyroxine binding globulin (TBG) promoter directs efficient and sustaining transgene expression in liver-specific pattern," Gene, 506(2):289-294.
Yano et al., 2016, "Evaluation of Tetrahydrobiopterin Therapy with Large Neutral Amino Acid Supplementation in Phenylketonuria: Effects on Potential Peripheral Biomarkers, Melatonin and Dopamine, for Brain Monoamine Neurotransmitters," PLoS One, 11(8):e0160892 (14 pages).
Zhao et al., 2000, "BPV1 E2 protein enhances packaging of full-length plasmid DNA in BPV1 pseudovirions," Virology, 272(2):382-393.
Zincarelli et al., 2008, "Analysis of AAV serotypes 1-9 mediated gene expression and tropism in mice after systemic injection," Mol. Ther., 16(6):1073-1080.
Zinn et al., 2015, "In Silico Reconstruction of the Viral Evolutionary Lineage Yields a Potent Gene Therapy Vector," Cell Rep., 12(6):1056-1068.
Zur Megede et al., 2000, "Increased expression and immunogenicity of sequence-modified human immunodeficiency virus type 1 gag gene," J. Virol., 74(6):2628-2635.
Appel et al., 2014, "Nucleic acids: From A to Z," edited by S. Muller, p. 27 (in Russian with English translation).

(56) References Cited

OTHER PUBLICATIONS

Bowles et al., 2003, "Marker rescue of adeno-associated vims (AAV) capsid mutants: a novel approach for chimeric AAV production," J. Virol., 77(1):423-432.
GenBank Accession No. HZ323618.1, "JP 2015518705-A/1411: Modified Polynucleotides for the Production of Biologics and Proteins Associated with Human Disease," Nov. 26, 2015 (2 pages).
GenBank Accession No. JC111928.1, "Sequence 573 fromPatent WO2013151666," Jan. 28, 2014 (2 pages).
Mochizuki et al., 2004, "Adeno-associated virus (AAV) vector-mediated liver- and muscle-directed transgene expression using various kinds of promoters and serotypes," Gene. Ther. Mol. Biol., 8:9-18.
Shen et al., 2007, "Characterization of the relationship of AAV capsid domain swapping to liver transduction efficiency," Mol. Ther., 15(11):1955-1962.
Hafid et al., 2015, "Phenylketonuria: a review of current and future treatments," Transl. Pediatr., 4(4):304-317.
Grisch-Chan et al., 2017, "Low-Dose Gene Therapy for Murine PKU Using Episomal Naked DNA Vectors Expressing PAH from Its Endogenous Liver Promoter," Mol. Ther. Nucleic Acids, 7:339-349.
Kume, 2013, "Attempt at Codon Optimization in PKU Gene Therapy," Development and Implementation of Gene and Cell Therapy for Pediatric Congenital and Intractable Diseases—Summary and Collaborative Research Report for Fiscal Year 2012, pp. 20-24, in Japanese with machine English translation (16 pages).
Viecelli et al., 2011, "A006_2012 Abstract—Development of Minicircle—DNA Vectors as Non-Viral Liver-Directed Gene Therapy for Hepatic Diseases," presented in RE(ACT) International Congress on Research on Rare and Orphan Diseases, Feb. 29 to Mar. 2, 2011, Basel, Sitzerland, Mol. Syndromol. 2:265-266 (3 pages).
Yagi et al., 2011, "Complete restoration of phenylalanine oxidation in phenylketonuria mouse by a self-complementary adeno-associated virus vector," J. Gene. Med., 13(2): 114-122.

* cited by examiner

FIG. 5A Phenylalanine
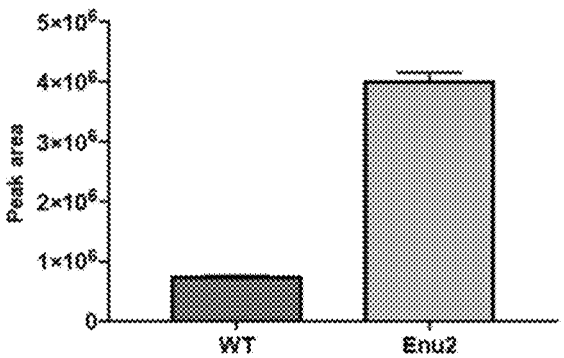
FIG. 5B Tyrosine
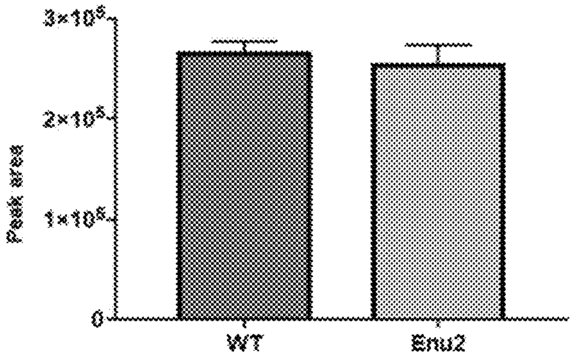
FIG. 5C DOPAC
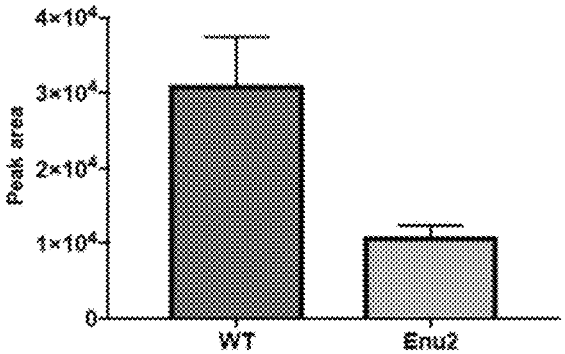
FIG. 5D Homovanilic Acid
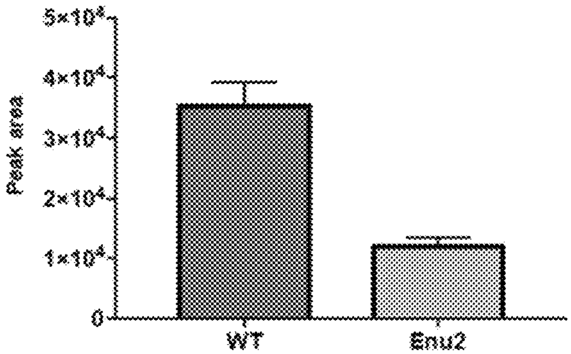

FIG. 7A Phenylalanine
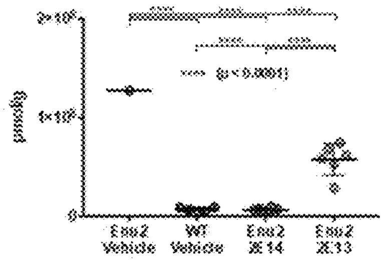
FIG. 7B Tyrosine
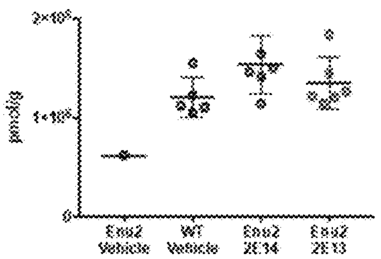
FIG. 7C Dopamine
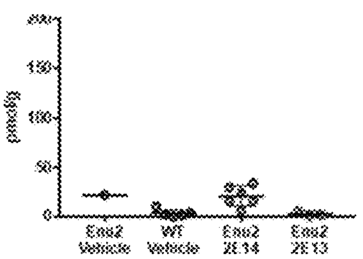
FIG. 7D DOPAC
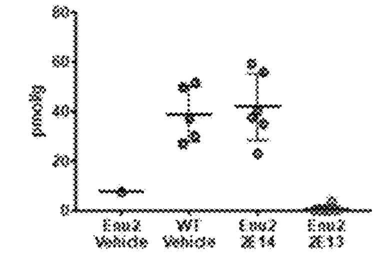
FIG. 7E 3MT
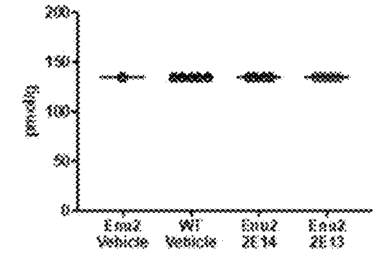
FIG. 7F Homovanillic Acid
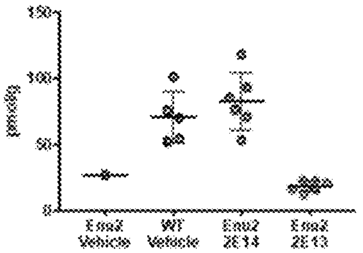
FIG. 7G Norepinephrine
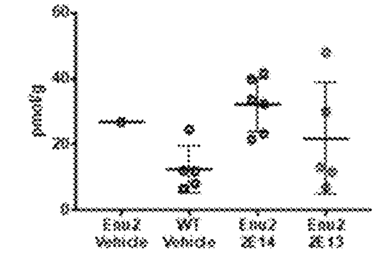
FIG. 7H Tryptophan
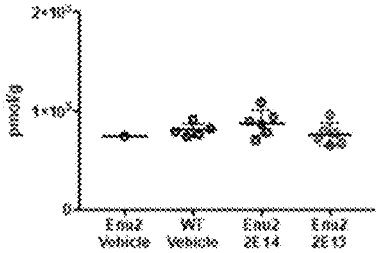
FIG. 7I Serotonin
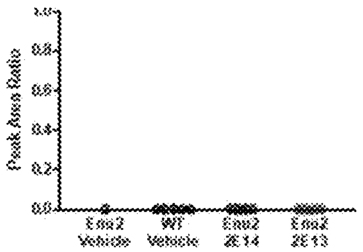

dopamine norepinephrine dopamine

DOPAC

Brain Dopamine

Brain DOPAC

Phenylalanine
Tyrosine
Tryptophan
Phenylalanine
Tyrosine
L-DOPA
Tryptophan
5-Hydroxytryptophan
Phenethylamine
Phenylethanolamine
Dopamine
Norepinephrine
Tryptamine
Serotonin
PAA
MA
DOPAC
DOPEG
IAA
5-HIAA
HVA
MOPEG
PAG
MA
HVA
MOPEG
IAA
5-HIAA

| copies/ml | 1000-HEX | PAHmid | Kan-R |
|---|---|---|---|
| ~4.2 kb band | 2.11E+09 | 4.06E+11 | 4.04E+09 |
| 2.8 kb band | 1.9E+09 | 5.84E+11 | 3.32E+09 |

Figure 35
kDa
64
51
39
WT + Vehicle
WT + huPAH
WT + muPAH

```
hPAH        ATGTCCACTGCGGTCCTGGAAAACCCAGGCTTGGGCAGGAAACTCTCTGACTTTGGACAG
NW2-Cop     ATGTCCACTGCTGTCCTGGAAAACCCAGGCTTGGGCAGGAAACTCTCTGACTTTGGACAG
NW-RCG      ATGTCCACTGCTGTCCTGGAAAACCCAGGCTTGGGCAGGAAACTCTCTGACTTTGGACAG
D20-Op      ATGTCCACTGCGGTGTTGGAAAACCCCGGACTGGGCAGAAAGTTGTCCGACTTCGGCCAG
D20-Cop1    ATGTCCACTGCGGTCCTGGAAAACCCTGGTCTGGGCCGCAAGCTTTCTGACTTTGGACAG
JCAT        ATGAGCACTGCTGTGCTGGAGAACCCTGGCCTGGGCAGAAAGCTGTCTGACTTTGGCCAG
Operon-1    ATGAGCACTGCTGTGCTGGAGAACCCTGGCCTGGGCAGAAAGCTGTCTGACTTTGGCCAG
Operon-2    ATGAGCACTGCTGTGCTGGAGAACCCTGGCCTGGGCAGAAAGCTGTCTGACTTTGGCCAG
            ***  ****** **  **** ***** **  ***** * **  * ** ***** ** ***

hPAH        GAAACAAGCTATATTGAAGACAACTGCAATCAAAATGGTGCCATATCACTGATCTTCTCA
NW2-Cop     GAAACAAGCTATATTGAAGACAACTGCAATCAAAATGGTGCCATATCACTGATCTTCTCA
NW-RCG      GAAACAAGCTATATTGAAGACAACTGCAATCAAAATGGTGCCATATCACTGATCTTCTCA
D20-Op      GAAACCTCTTACATTGAGGACAACTGCAACCAGAACGGGGCCATCTCACTGATCTTTTCG
D20-Cop1    GAAACCTCATACATTGAGGACAACTGTAACCAAAATGGTGCAATCAGCCTGATCTTCAGC
JCAT        GAGACCAGCTACATTGAGGACAACTGCAACCAGAATGGGGCCATCAGCCTGATCTTCAGC
Operon-1    GAGACCAGCTACATTGAGGACAACTGCAACCAGAATGGAGCCATCAGCCTGATCTTCAGC
Operon-2    GAGACCAGCTACATTGAGGACAACTGCAACCAGAATGGGGCCATCAGCCTGATCTTCAGC
            ** **    ** ***** ******** ** ** ** ** ** **    ********

hPAH        CTCAAAGAAGAAGTTGGTGCATTGGCCAAAGTATTGCGCTTATTTGAGGAGAATGATGTA
NW2-Cop     CTCAAAGAAGAAGTTGGTGCATTGGCCAAAGTACTGAGGTTATTTGAGGAGAATGATGTA
NW-RCG      CTCAAAGAAGAAGTTGGTGCATTGGCCAAAGTACTGAGGTTATTTGAGGAGAATGATGTA
D20-Op      CTGAAAGAAGAAGTCGGAGCTCTGGCCAAAGTGCTGCGCCTGTTCGAGGAAAACGACGTC
D20-Cop1    CTCAAGGAAGAAGTGGGAGCCCTGGCCAAGGTCCTGAGACTGTTTGAGGAGAATGATGTG
JCAT        CTGAAGGAGGAGGTGGGGGCCCTGGCCAAGGTGCTGAGACTGTTTGAGGAGAATGATGTG
Operon-1    CTGAAGGAGGAGGTGGGAGCCCTGGCCAAGGTGCTGAGACTGTTTGAGGAGAATGATGTG
Operon-2    CTGAAGGAGGAGGTGGGGGCCCTGGCCAAGGTGCTGAGACTGTTTGAGGAGAATGATGTG
            ** ** ** ** ** ** **  ******* **  ** *  * ** ***** ** ** **

hPAH        AACCTGACCCACATTGAATCTAGACCTTCTCGTTTAAAGAAAGATGAGTATGAATTTTTC
NW2-Cop     AACCTGACCCACATTGAATCTAGACCTTCTAGGTTAAAGAAAGATGAGTATGAATTTTTC
NW-RCG      AACCTGACCCACATTGAATCTAGACCTTCTAGGTTAAAGAAAGATGAGTATGAATTTTTC
D20-Op      AACCTGACCCACATCGAGTCAAGACCGAGCAGGCTGAAGAAGGATGAGTACGAGTTTTTC
D20-Cop1    AACCTGACCCACATTGAGTCCAGGCCCTCCAGACTGAAGAAGGATGAATACGAATTCTTC
JCAT        AACCTGACCCACATTGAGAGCAGACCCAGCAGACTGAAGAAGGATGAGTATGAGTTCTTC
Operon-1    AACCTGACCCACATTGAGAGCAGACCCAGCAGACTGAAGAAGGATGAGTATGAGTTCTTC
Operon-2    AACCTGACCCACATTGAGAGCAGACCCAGCAGACTGAAGAAGGATGAGTATGAGTTCTTC
            ************** **    ** **     *  * ***** ***** ** ** ** ***

hPAH        ACCCATTTGGATAAACGTAGCCTGCCTGCTCTGACAAACATCATCAAGATCTTGAGGCAT
NW2-Cop     ACCCATTTGGATAAAAGGAGCCTGCCTGCTCTGACAAACATCATCAAGATCTTGAGGCAC
NW-RCG      ACCCATTTGGATAAAAGGAGCCTGCCTGCTCTGACAAACATCATCAAGATCTTGAGGCAC
D20-Op      ACCCATCTCGACAAGAGATCCCTGCCTGCCCTGACCAATATTATCAAGATTTTGCGGCAC
D20-Cop1    ACCCACCTGGACAAGCGCTCCCTCCCTGCCCTCACCAACATCATTAAGATCCTGCGGCAC
JCAT        ACCCACCTGGACAAGAGAAGCCTGCCAGCCCTGACCAATATTATCAAGATCCTGAGGCAC
Operon-1    ACCCACCTGGACAAGAGAAGCCTGCCTGCCCTGACCAACATCATCAAGATCCTGAGACAC
Operon-2    ACCCACCTGGACAAGAGAAGCCTGCCTGCCCTGACCAACATCATCAAGATCCTGAGACAC
            *****  * ** **  *   *** ** ** ** ** ** ** ** *****  ** * **
```

Figure 41

```
hPAH          GACATTGGTGCCACTGTCCATGAGCTTTCACGAGATAAGAAGAAAGACACAGTGCCCTGG
NW2-Cop       GACATTGGTGCCACTGTCCACGAGCTTTCAAGGGATAAGAAGAAAGACACAGTGCCCTGG
NW-RCG        GACATTGGTGCCACTGTCCACGAGCTTTCAAGGGATAAGAAGAAAGACACAGTGCCCTGG
D20-Op        GACATTGGCGCAACCGTGCATGAACTCTCCCGGGACAAGAAGAAGGACACCGTGCCGTGG
D20-Cop1      GACATTGGAGCCACTGTGCATGAGTTGAGCCGGGACAAGAAGAAGGATACTGTGCCCTGG
JCAT          GATATTGGGGCCACAGTGCACGAGCTGAGCAGAGACAAGAAGAAGGACACAGTGCCCTGG
Operon-1      GATATTGGAGCCACTGTGCACGAGCTGAGCAGAGACAAGAAGAAGGACACTGTGCCCTGG
Operon-2      GATATTGGGGCCACTGTGCACGAGCTGAGCAGAGACAAGAAGAAGGACACTGTGCCCTGG
              ** ***** ** ** ** ** **  *     * ** ******** ** ** ***** ***

hPAH          TTCCCAAGAACCATTCAAGAGCTGGACAGATTTGCCAATCAGATTCTCAGCTATGGAGCG
NW2-Cop       TTCCCAAGAACTATTCAAGAGCTGGACAGATTTGCCAATCAGATTCTCAGCTATGGAGCT
NW-RCG        TTCCCAAGAACTATTCAAGAGCTGGACAGATTTGCCAATCAGATTCTCAGCTATGGAGCT
D20-Op        TTCCCCCGAACCATCCAGGAACTCGACCGCTTCGCTAACCAGATCCTGTCCTACGGCGCC
D20-Cop1      TTCCCGAGGACCATCCAGGAACTGGACCGGTTTGCCAACCAAATTCTGTCCTATGGAGCT
JCAT          TTCCCCAGGACTATCCAGGAGCTGGACAGGTTTGCCAACCAGATCCTGAGCTACGGAGCT
Operon-1      TTCCCCAGAACTATCCAGGAGCTGGACAGATTTGCCAACCAGATCCTGAGCTATGGAGCT
Operon-2      TTCCCCAGAACTATCCAGGAGCTGGACAGATTTGCCAACCAGATCCTGAGCTATGGGGCT
              *****  * ** ** ** ** ** *** * ** ** ** ** ** **   *** ** **

hPAH          GAACTGGATGCTGACCACCCTGGTTTTAAAGATCCTGTGTACCGTGCAAGACGGAAGCAG
NW2-Cop       GAACTGGATGCTGACCACCCTGGTTTTAAAGATCCTGTGTACAGGGCAAGAAGGAAGCAG
NW-RCG        GAACTGGATGCTGACCACCCTGGTTTTAAAGATCCTGTGTACAGGGCAAGAAGGAAGCAG
D20-Op        GAACTGGATGCCGATCACCCTGGATTCAAGGACCCAGTGTACAGAGCCCGGCGCAAGCAG
D20-Cop1      GAATTGGATGCAGACCACCCTGGCTTCAAGGACCCAGTGTACAGAGCAAGGAGAAAGCAG
JCAT          GAGCTGGATGCAGACCACCCTGGCTTCAAGGACCCTGTGTACAGAGCCAGGAGAAAGCAG
Operon-1      GAGCTGGATGCTGACCACCCTGGCTTCAAGGACCCTGTGTACAGAGCCAGAAGAAAGCAG
Operon-2      GAGCTGGATGCTGACCACCCTGGCTTCAAGGACCCTGTGTACAGAGCCAGAAGAAAGCAG
              **  ******* ** ******** ** ** ** ** ****** * **  *  * ******

hPAH          TTTGCTGACATTGCCTACAACTACCGCCATGGGCAGCCCATCCCTCGAGTGGAATACATG
NW2-Cop       TTTGCTGACATTGCCTACAACTACAGGCATGGGCAGCCCATCCCTAGGGTGGAATACATG
NW-RCG        TTTGCTGACATTGCCTACAACTACAGGCATGGGCAGCCCATCCCTAGGGTGGAATACATG
D20-Op        TTCGCCGATATCGCCTACAATTATCGGCACGGACAGCCAATCCCGAGGGTGGAGTACATG
D20-Cop1      TTTGCAGACATAGCCTACAACTACAGACATGGACAGCCCATCCCGAGGGTGGAGTACATG
JCAT          TTTGCAGATATAGCCTACAACTACAGGCACGGCCAGCCAATCCCTAGAGTGGAGTACATG
Operon-1      TTTGCTGACATTGCCTACAACTACAGACACGGCCAGCCCATCCCCAGAGTGGAGTACATG
Operon-2      TTTGCTGACATTGCCTACAACTACAGACACGGCCAGCCCATCCCCAGAGTGGAGTACATG
              ** ** ** ** ******** **  * ** ** ***** *****  * ***** ******

hPAH          GAGGAAGAAAAGAAAACATGGGGCACAGTGTTCAAGACTCTGAAGTCCTTGTATAAAACC
NW2-Cop       GAGGAAGAAAAGAAAACATGGGGCACAGTGTTCAAGACTCTGAAGTCCTTGTATAAAACC
NW-RCG        GAGGAAGAAAAGAAAACATGGGGCACAGTGTTCAAGACTCTGAAGTCCTTGTATAAAACC
D20-Op        GAGGAGGAAAAGAAAACCTGGGGAACTGTGTTCAAGACCTTGAAGTCCCTGTACAAGACT
D20-Cop1      GAAGAGGAGAAGAAAACCTGGGGCACTGTGTTTAAGACCCTCAAGAGCCTGTACAAGACC
JCAT          GAGGAGGAGAAGAAGACCTGGGGCACTGTGTTCAAGACCCTGAAGAGCCTGTACAAGACC
Operon-1      GAGGAGGAGAAGAAGACCTGGGGCACTGTGTTCAAGACCCTGAAGAGCCTGTACAAGACC
Operon-2      GAGGAGGAGAAGAAGACCTGGGGCACTGTGTTCAAGACCCTGAAGAGCCTGTACAAGACC
              ** ** ** ***** ** ***** ** ***** *****  * ***  * **** ** **
```

Figure 41 (continued)

```
hPAH            CATGCTTGCTATGAGTACAATCACATTTTTCCACTTCTTGAAAAGTACTGTGGCTTCCAT
NW2-Cop         CACGCTTGCTATGAGTACAATCACATTTTTCCACTTCTTGAAAAGTACTGTGGCTTCCAC
NW-RCG          CACGCTTGCTATGAGTACAATCACATTTTTCCACTTCTTGAAAAGTACTGTGGCTTCCAC
D20-Op          CACGCCTGCTACGAGTACAACCACATCTTCCCCCTGCTCGAAAAGTACTGCGGGTTCCAT
D20-Cop1        CACGCCTGCTATGAGTACAACCACATCTTCCCACTCCTGGAGAAATACTGTGGCTTCCAT
JCAT            CACGCCTGCTACGAGTACAACCACATCTTCCCCCTGCTGGAGAAGTACTGTGGCTTCCAC
Operon-1        CACGCCTGCTATGAGTACAACCACATCTTCCCCCTGCTGGAGAAGTACTGTGGCTTCCAC
Operon-2        CACGCCTGCTATGAGTACAACCACATCTTCCCCCTGCTGGAGAAGTACTGTGGCTTCCAC
                ** ** ***** ******** ***** ** ** ** ** ** ** ***** ** *****

hPAH            GAAGATAACATTCCCCAGCTGGAAGACGTTTCTCAGTTCCTGCAGACTTGCACTGGTTTC
NW2-Cop         GAAGATAACATTCCCCAGCTGGAAGATGTTTCTCAGTTCCTGCAGACTTGCACTGGTTTC
NW-RCG          GAAGATAACATTCCCCAGCTGGAAGATGTTTCTCAGTTCCTGCAGACTTGCACTGGTTTC
D20-Op          GAGGACAACATCCCCCAACTGGAAGATGTGTCGCAGTTCCTGCAAACCTGTACCGGATTC
D20-Cop1        GAGGACAACATCCCACAGCTGGAGGATGTGTCCCAGTTCCTGCAGACTTGCACTGGCTTC
JCAT            GAGGACAACATCCCCCAGCTGGAGGATGTGAGCCAGTTCCTGCAGACCTGCACAGGCTTC
Operon-1        GAGGACAACATCCCCCAGCTGGAGGATGTGAGCCAGTTCCTGCAGACCTGCACTGGCTTC
Operon-2        GAGGACAACATCCCCCAGCTGGAGGATGTGAGCCAGTTCCTGCAGACCTGCACTGGCTTC
                ** ** ***** ** ** ***** ** **    *********** ** ** ** ** ***

hPAH            CGCCTCCGACCTGTAGCTGGCCTGCTTTCCTCTCGGGATTTCTTGGGTGGCCTGGCCTTC
NW2-Cop         AGGCTCAGGCCTGTAGCTGGCCTGCTTTCCTCTAGGGATTTCTTGGGTGGCCTGGCCTTC
NW-RCG          AGGCTCAGGCCTGTAGCTGGCCTGCTTTCCTCTAGGGATTTCTTGGGTGGCCTGGCCTTC
D20-Op          CGGCTGAGGCCTGTCGCGGGACTTCTGTCCTCCCGGGATTTTCTTGGCGGTCTGGCCTTC
D20-Cop1        CGGTTGAGGCCTGTGGCTGGCCTGCTCTCCTCAAGGGACTTCTTGGGGGGACTGGCATTC
JCAT            AGGCTGAGACCAGTGGCAGGCCTGCTGAGCAGCAGGGACTTCCTGGGGGGCCTGGCCTTC
Operon-1        AGACTGAGACCTGTGGCTGGCCTGCTGAGCAGCAGAGACTTCCTGGGGGGCCTGGCCTTC
Operon-2        AGACTGAGACCTGTGGCTGGCCTGCTGAGCAGCAGAGACTTCCTGGGGGGCCTGGCCTTC
                 *  *  * ** ** ** ** ** **   *    * ** **  * ** ** ***** ***

hPAH            CGAGTCTTCCACTGCACACAGTACATCAGACATGGATCCAAGCCCATGTATACCCCCGAA
NW2-Cop         AGGGTCTTCCACTGCACACAGTACATCAGACACGGCTCCAAGCCCATGTATACCCCTGAA
NW-RCG          AGGGTCTTCCACTGCACACAGTACATCAGACACGGCTCCAAGCCCATGTATACCCCTGAA
D20-Op          CGGGTGTTCCACTGTACTCAGTACATTAGACACGGGAGCAAGCCTATGTACACTCCTGAA
D20-Cop1        AGGGTGTTCCACTGCACCCAATACATCAGACACGGCAGCAAGCCAATGTACACCCCTGAA
JCAT            AGAGTGTTCCACTGCACCCAGTATATCAGGCACGGCAGCAAGCCAATGTACACCCCTGAG
Operon-1        AGAGTGTTCCACTGCACCCAGTACATCAGACACGGCAGCAAGCCCATGTACACCCCTGAG
Operon-2        AGAGTGTTCCACTGCACCCAGTACATCAGACACGGCAGCAAGCCCATGTACACCCCTGAG
                 * ** ******** ** ** ** ** ** ** **   ****** ***** ** ** **

hPAH            CCTGACATCTGCCATGAGCTGTTGGGACATGTGCCCTTGTTTTCAGATCGCAGCTTTGCC
NW2-Cop         CCTGACATCTGCCACGAGCTGTTGGGACACGTGCCCTTGTTTTCAGATAGGAGCTTTGCC
NW-RCG          CCTGACATCTGCCACGAGCTGTTGGGACACGTGCCCTTGTTTTCAGATAGGAGCTTTGCC
D20-Op          CCCGACATTTGCCACGAACTCCTGGGTCATGTGCCCCTCTTCTCGGATCGGAGCTTCGCC
D20-Cop1        CCGGACATCTGCCACGAACTCCTGGGCCACGTCCCTCTGTTCTCGGACAGAAGCTTTGCC
JCAT            CCAGATATCTGCCACGAGCTGCTGGGCCACGTTCCCCTGTTCTCAGACAGAAGCTTTGCC
Operon-1        CCTGATATCTGCCACGAGCTGCTGGGCCACGTGCCCCTGTTCTCTGACAGAAGCTTTGCC
Operon-2        CCTGATATCTGCCACGAGCTGCTGGGCCACGTGCCCCTGTTCTCTGACAGAAGCTTTGCC
                ** ** ** ***** ** **  **** ** ** **  * ** ** **  * ***** ***
```

Figure 41 (continued)

```
hPAH            CAGTTTTCCCAGGAAATTGGCCTTGCCTCTCTGGGTGCACCTGATGAATACATTGAAAAG
NW2-Cop         CAGTTTTCCCAGGAAATTGGCCTTGCCTCTCTGGGTGCACCTGATGAATATATTGAAAAG
NW-RCG          CAGTTTTCCCAGGAAATTGGCCTTGCCTCTCTGGGTGCACCTGATGAATATATTGAAAAG
D20-Op          CAGTTCAGCCAAGAGATCGGTCTGGCTAGCTTGGGAGCACCCGACGAGTACATCGAGAAG
D20-Cop1        CAGTTCTCCCAAGAGATTGGCCTTGCCTCCCTGGGGGCCCCTGATGAATACATTGAAAAG
JCAT            CAGTTCAGCCAGGAGATTGGCCTGGCCAGCCTGGGGGCCCCTGACGAGTATATTGAGAAG
Operon-1        CAGTTCAGCCAGGAGATTGGCCTGGCCAGCCTGGGAGCCCCTGATGAGTATATTGAGAAG
Operon-2        CAGTTCAGCCAGGAGATTGGCCTGGCCAGCCTGGGGGCCCCTGATGAGTATATTGAGAAG
                *****   *** ** ** ** ** **     **** ** ** ** ** ** ** ** ***

hPAH            CTCGCCACAATTTACTGGTTTACTGTGGAGTTTGGGCTCTGCAAACAAGGAGACTCCATA
NW2-Cop         CTGGCCACAATCTACTGGTTTACTGTGGAGTTTGGGCTCTGCAAACAAGGAGACTCCATA
NW-RCG          CTGGCCACAATTTACTGGTTTACTGTGGAGTTTGGGCTCTGCAAACAAGGAGACTCCATA
D20-Op          CTGGCCACTATCTACTGGTTTACCGTGGAATTCGGACTGTGCAAGCAGGGGGACTCAATC
D20-Cop1        CTGGCCACAATCTACTGGTTCACTGTGGAATTTGGACTTTGCAAGCAGGGAGATAGCATC
JCAT            CTGGCCACTATCTACTGGTTCACAGTGGAGTTTGGCCTGTGCAAGCAGGGGGACAGCATC
Operon-1        CTGGCCACTATCTACTGGTTCACTGTGGAGTTTGGCCTGTGCAAGCAGGGGGACAGCATC
Operon-2        CTGGCCACTATCTACTGGTTCACTGTGGAGTTTGGCCTGTGCAAGCAGGGGGACAGCATC
                ** ***** ** ******** ** ***** ** ** ** ***** ** ** **    **

hPAH            AAGGCATATGGTGCTGGGCTCCTGTCATCCTTTGGTGAATTACAGTACTGCTTATCAGAG
NW2-Cop         AAGGCATATGGTGCTGGGCTCCTGTCATCCTTTGGTGAATTACAGTACTGCTTATCAGAG
NW-RCG          AAGGCATATGGTGCTGGGCTCCTGTCATCCTTTGGTGAATTACAGTACTGCTTATCAGAG
D20-Op          AAGGCCTATGGCGCGGGACTCCTGAGCTCCTTCGGGGAGCTGCAGTACTGCCTGTCCGAA
D20-Cop1        AAGGCCTACGGGGCTGGACTTCTGTCCTCCTTCGGTGAACTGCAGTACTGTCTGTCAGAG
JCAT            AAGGCCTATGGGGCTGGCCTGCTGAGCAGCTTTGGGGAGCTGCAGTACTGCCTGTCAGAG
Operon-1        AAGGCCTATGGAGCTGGCCTGCTGAGCAGCTTTGGGGAGCTGCAGTACTGCCTGTCTGAG
Operon-2        AAGGCCTATGGGGCTGGCCTGCTGAGCAGCTTTGGGGAGCTGCAGTACTGCCTGTCTGAG
                ***** ** ** ** ** ** ***     *** ** **  * ********  * ** **

hPAH            AAGCCAAAGCTTCTCCCCCTGGAGCTGGAGAAGACAGCCATCCAAAATTACACTGTCACG
NW2-Cop         AAGCCAAAGCTTCTCCCCCTGGAGCTGGAGAAGACAGCCATCCAAAATTACACTGTCACT
NW-RCG          AAGCCAAAGCTTCTCCCCCTGGAGCTGGAGAAGACAGCCATCCAAAATTACACTGTCACT
D20-Op          AAGCCAAAGCTGCTCCCTCTTGAACTGGAGAAAACGGCCATCCAGAACTACACCGTGACC
D20-Cop1        AAGCCCAAGCTGCTGCCCCTGGAACTGGAGAAAACTGCCATCCAAAACTACACTGTGACT
JCAT            AAGCCAAAGCTGCTGCCCCTGGAGCTGGAGAAGACAGCTATCCAGAACTACACTGTGACT
Operon-1        AAGCCCAAGCTGCTGCCCCTGGAGCTGGAGAAGACTGCCATCCAGAACTACACTGTGACT
Operon-2        AAGCCCAAGCTGCTGCCCCTGGAGCTGGAGAAGACTGCCATCCAGAACTACACTGTGACT
                ***** ***** ** ** ** ** ******** ** ** ***** ** ***** ** **

hPAH            GAGTTCCAGCCCCTGTATTACGTGGCAGAGAGTTTTAATGATGCCAAGGAGAAAGTAAGG
NW2-Cop         GAGTTCCAGCCCCTGTATTATGTGGCAGAGAGTTTTAATGATGCCAAGGAGAAAGTAAGG
NW-RCG          GAGTTCCAGCCCCTGTATTATGTGGCAGAGAGTTTTAATGATGCCAAGGAGAAAGTAAGG
D20-Op          GAATTCCAGCCGCTCTACTACGTCGCGGAGTCCTTCAACGATGCCAAGGAGAAGGTCCGC
D20-Cop1        GAGTTCCAGCCCCTCTACTATGTGGCTGAGTCCTTCAATGATGCCAAAGAAAAGGTCAGA
JCAT            GAGTTCCAGCCCCTGTACTATGTGGCAGAGAGCTTCAATGATGCCAAGGAGAAGGTGAGA
Operon-1        GAGTTCCAGCCCCTGTACTATGTGGCTGAGAGCTTCAATGATGCCAAGGAGAAGGTGAGA
Operon-2        GAGTTCCAGCCCCTGTACTATGTGGCTGAGAGCTTCAATGATGCCAAGGAGAAGGTGAGA
                ** ******** ** ** ** ** ** ***   ** ** ******** ** ** **  *
```

Figure 41 (continued)

```
hPAH        AACTTTGCTGCCACAATACCTCGGCCCTTCTCAGTTCGCTACGACCCATACACCCAAAGG
NW2-Cop     AACTTTGCTGCCACAATACCTAGGCCCTTCTCAGTTAGGTATGACCCATACACCCAAAGG
NW-RCG      AACTTTGCTGCCACAATACCTAGGCCCTTCTCAGTTAGGTATGACCCATACACCCAAAGG
D20-Op      AACTTCGCCGCAACTATCCCGCGGCCGTTTTCCGTGCGCTATGACCCGTACACACAACGC
D20-Cop1    AATTTTGCGGCCACCATTCCTAGGCCTTTCTCAGTCCGCTATGACCCTTACACCCAGAGA
JCAT        AACTTTGCTGCCACCATCCCCAGGCCCTTCTCTGTGAGATATGACCCCTACACCCAGAGG
Operon-1    AACTTTGCTGCCACCATCCCCAGACCCTTCTCTGTGAGATATGACCCCTACACCCAGAGA
Operon-2    AACTTTGCTGCCACCATCCCCAGACCCTTCTCTGTGAGATACGACCCCTACACCCAGAGA
            ** ** ** ** ** ** **  * ** ** ** **  * ** ***** ***** **  *

hPAH        ATTGAGGTCTTGGACAATACCCAGCAGCTTAAGATTTTGGCTGATTCCATTAACAGTGAA
NW2-Cop     ATTGAGGTCTTGGACAATACCCAGCAGCTTAAGATTTTGGCTGATTCCATTAACAGTGAA
NW-RCG      ATTGAGGTCTTGGACAATACCCAGCAGCTTAAGATTTTGGCTGATTCCATTAACAGTGAA
D20-Op      ATCGAAGTGCTGGACAACACCCAGCAACTTAAGATTCTGGCCGACTCGATCAACTCCGAG
D20-Cop1    ATTGAGGTGCTGGACAACACCCAGCAGCTCAAGATCCTGGCAGACTCCATCAACTCAGAA
JCAT        ATTGAGGTGCTGGACAACACCCAGCAGCTGAAGATCCTGGCAGACAGCATCAACAGTGAG
Operon-1    ATTGAGGTGCTGGACAACACCCAGCAGCTGAAGATCCTGGCTGACAGCATCAACTCTGAG
Operon-2    ATTGAGGTGCTGGACAACACCCAGCAGCTGAAGATCCTGGCTGACAGCATCAACTCTGAG
            ** ** **  ******* ******** ** *****  **** **    ** ***    **

hPAH        ATTGGAATCCTTTGCAGTGCCCTCCAGAAAATAAAGTAA
NW2-Cop     ATTGGAATCCTTTGCAGTGCCCTCCAGAAAATCAAGTAA
NW-RCG      ATTGGAATCCTTTGCAGTGCCCTCCAGAAAATAAAGTAA
D20-Op      ATTGGCATTCTGTGCTCGGCGCTGCAGAAGATCAAGTAA
D20-Cop1    ATTGGGATCTTGTGCTCGGCCCTCCAAAAGATCAAGTAA
JCAT        ATTGGTATCCTGTGCTCTGCCCTGCAGAAGATCAAGTAA
Operon-1    ATTGGCATCCTGTGCTCTGCCCTGCAGAAGATCAAGTAA
Operon-2    ATTGGCATCCTGTGCTCTGCCCTGCAGAAGATCAAGTGA
            ***** **  * ***    ** ** ** ** ** **** *
```

Figure 41 (continued)

| | hPAH | NW2-Cop | NW-RCG | D20-Op | D20-Cop1 | JCAT | Op-1 | Op-2 |
|---|---|---|---|---|---|---|---|---|
| hPAH | 100.0 | 96.5 | 96.6 | 79.7 | 80.5 | 79.7 | 80.7 | 80.6 |
| NW2-Cop | 96.5 | 100.0 | 99.9 | 77.3 | 82.1 | 82.2 | 83.0 | 82.8 |
| NW-RCG | 96.6 | 99.9 | 100.0 | 77.2 | 82.0 | 82.1 | 82.9 | 82.6 |
| D20-Op | 77.0 | 77.3 | 77.2 | 100.0 | 81.9 | 82.5 | 82.3 | 82.1 |
| D20-Cop1 | 80.5 | 82.1 | 82.0 | 81.9 | 100.0 | 87.1 | 87.9 | 87.7 |
| JCAT | 76.7 | 82.2 | 82.1 | 82.5 | 87.1 | 100.0 | 96.5 | 96.7 |
| Op-1 | 80.7 | 83.0 | 82.9 | 82.3 | 87.9 | 96.5 | 100.0 | 99.4 |
| Op-2 | 80.6 | 82.8 | 82.6 | 82.1 | 87.7 | 96.7 | 99.4 | 100.0 |

| | % Identity | G+C Content | CG Content |
|---|---|---|---|
| hPAH-WT | 100.0 | 47.0 | 46 |
| Nathwani | 96.5 | 47.0 | 10 |
| Nathwani-RCG | 96.6 | 47.0 | 7 |
| ATUM | 77.0 | 56.0 | 90 |
| ATUM-RCG | 80.5 | 53.0 | 22 |
| JCAT | 76.7 | 56.0 | 11 |
| GENEius-1 | 80.7 | 57.0 | 8 |
| GENEius-2 | 80.6 | 56.0 | 9 |

P = portal vein, C = central vein

FIG. 61A
FIG. 61B
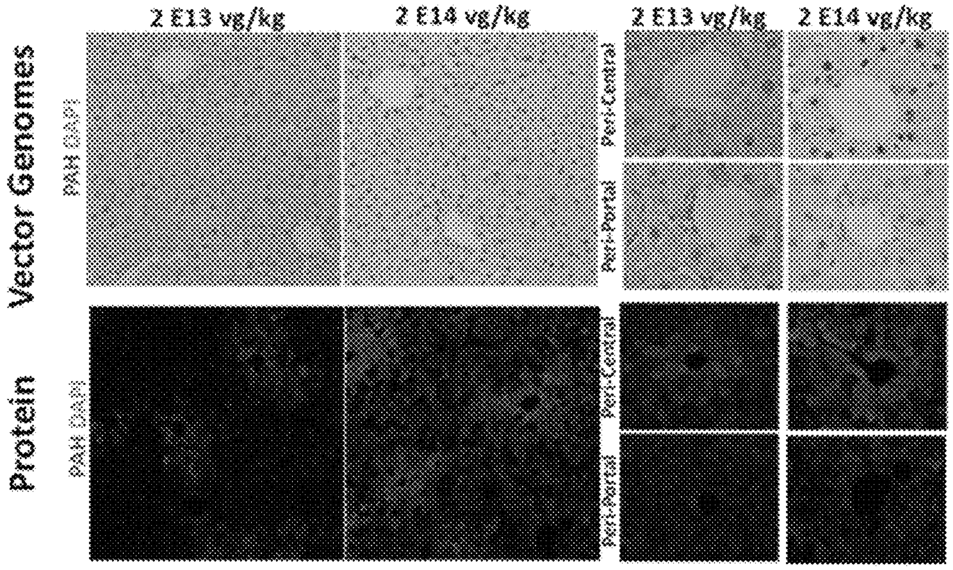
FIG. 61C
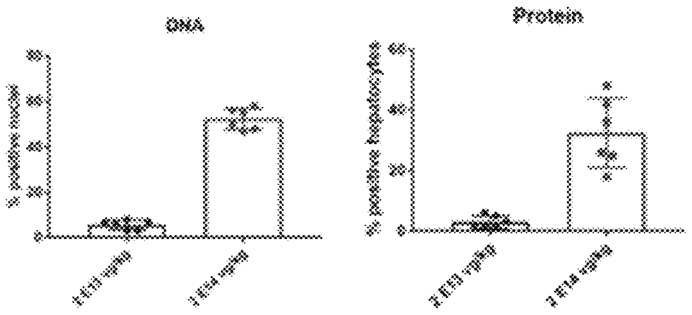

FIG. 62A
FIG. 62B
FIG. 62C
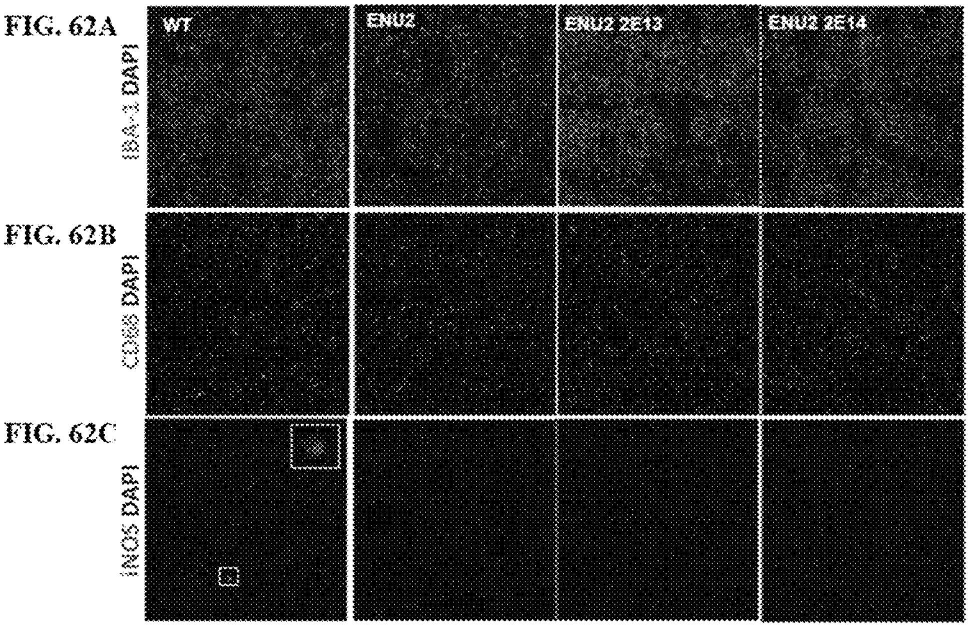
FIG. 62D
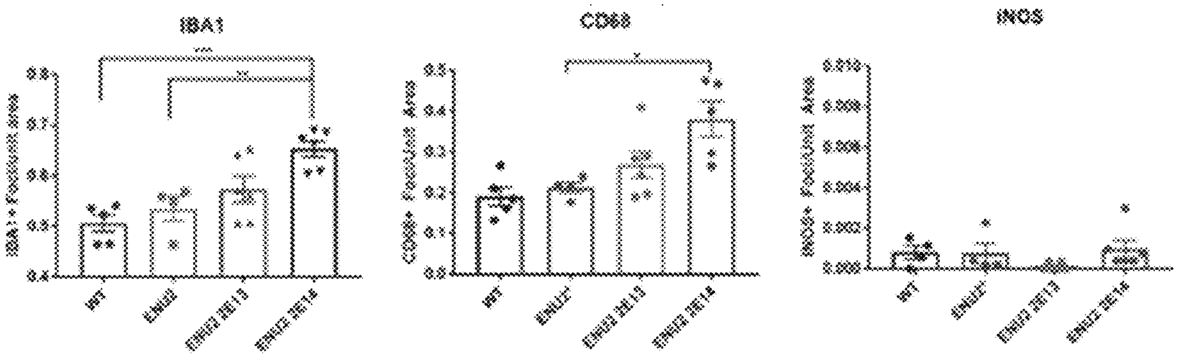

SEQUENCE LISTING

<160> NUMBER OF SEQ ID NOS: 23

<210> SEQ ID NO 1
<211> LENGTH: 1359
<212> TYPE: DNA
<213> ORGANISM: Homo sapiens
<220> FEATURE:
<223> OTHER INFORMATION: wild-type human PAH

<400> SEQUENCE: 1
atgtccactg cggtcctgga aaacccaggc ttgggcagga aactctctga ctttggacag 60
gaaacaagct atattgaaga caactgcaat caaaatggtg ccatatcact gatcttctca 120
ctcaaagaag aagttggtgc attggccaaa gtattgcgct tatttgagga gaatgatgta 180
aacctgaccc acattgaatc tagaccttct cgtttaaaga aagatgagta tgaatttttc 240
acccatttgg ataaacgtag cctgcctgct ctgacaaaca tcatcaagat cttgaggcat 300
gacattggtg ccactgtcca tgagctttca cgagataaga agaaagacac agtgccctgg 360
ttcccaagaa ccattcaaga gctggacaga tttgccaatc agattctcag ctatggagcg 420
gaactggatg ctgaccaccc tggttttaaa gatcctgtgt accgtgcaag acggaagcag 480
tttgctgaca ttgcctacaa ctaccgccat gggcagccca tccctcgagt ggaatacatg 540
gaggaagaaa agaaaacatg gggcacagtg ttcaagactc tgaagtcctt gtataaaacc 600
catgcttgct atgagtacaa tcacattttt ccacttcttg aaaagtactg tggcttccat 660
gaagataaca ttccccagct ggaagacgtt tctcagttcc tgcagacttg cactggtttc 720
cgcctccgac ctgtagctgg cctgctttcc tctcgggatt tcttgggtgg cctggccttc 780
cgagtcttcc actgcacaca gtacatcaga catggatcca agcccatgta tacccccgaa 840
cctgacatct gccatgagct gttgggacat gtgcccttgt tttcagatcg cagctttgcc 900
cagttttccc aggaaattgg ccttgcctct ctgggtgcac ctgatgaata cattgaaaag 960
ctcgccacaa tttactggtt tactgtggag tttgggctct gcaaacaagg agactccata 1020
aaggcatatg gtgctgggct cctgtcatcc tttggtgaat tacagtactg cttatcagag 1080
aagccaaagc ttctcccct ggagctggag aagacagcca tccaaaatta cactgtcacg 1140
gagttccagc ccctgtatta cgtggcagag agttttaatg atgccaagga gaaagtaagg 1200
aactttgctg ccacaatacc tcggcccttc tcagttcgct acgacccata cacccaaagg 1260
attgaggtct tggacaatac ccagcagctt aagattttgg ctgattccat taacagtgaa 1320
attggaatcc tttgcagtgc cctccagaaa ataaagtaa 1359

<210> SEQ ID NO 2
<211> LENGTH: 452
<212> TYPE: PRT
<213> ORGANISM: Homo sapiens
<220> FEATURE:
<223> OTHER INFORMATION: wild-type human PAH

<400> SEQUENCE: 2

Met Ser Thr Ala Val Leu Glu Asn Pro Gly Leu Gly Arg Lys Leu Ser
1 5 10 15

Asp Phe Gly Gln Glu Thr Ser Tyr Ile Glu Asp Asn Cys Asn Gln Asn
20 25 30

Gly Ala Ile Ser Leu Ile Phe Ser Leu Lys Glu Glu Val Gly Ala Leu
35 40 45

Ala Lys Val Leu Arg Leu Phe Glu Glu Asn Asp Val Asn Leu Thr His
50 55 60

```
Ile Glu Ser Arg Pro Ser Arg Leu Lys Lys Asp Glu Tyr Glu Phe Phe
65                  70                  75                  80

Thr His Leu Asp Lys Arg Ser Leu Pro Ala Leu Thr Asn Ile Ile Lys
                85                  90                  95

Ile Leu Arg His Asp Ile Gly Ala Thr Val His Glu Leu Ser Arg Asp
            100                 105                 110

Lys Lys Lys Asp Thr Val Pro Trp Phe Pro Arg Thr Ile Gln Glu Leu
        115                 120                 125

Asp Arg Phe Ala Asn Gln Ile Leu Ser Tyr Gly Ala Glu Leu Asp Ala
    130                 135                 140

Asp His Pro Gly Phe Lys Asp Pro Val Tyr Arg Ala Arg Arg Lys Gln
145                 150                 155                 160

Phe Ala Asp Ile Ala Tyr Asn Tyr Arg His Gly Gln Pro Ile Pro Arg
                165                 170                 175

Val Glu Tyr Met Glu Glu Glu Lys Lys Thr Trp Gly Thr Val Phe Lys
            180                 185                 190

Thr Leu Lys Ser Leu Tyr Lys Thr His Ala Cys Tyr Glu Tyr Asn His
        195                 200                 205

Ile Phe Pro Leu Leu Glu Lys Tyr Cys Gly Phe His Glu Asp Asn Ile
    210                 215                 220

Pro Gln Leu Glu Asp Val Ser Gln Phe Leu Gln Thr Cys Thr Gly Phe
225                 230                 235                 240

Arg Leu Arg Pro Val Ala Gly Leu Leu Ser Ser Arg Asp Phe Leu Gly
                245                 250                 255

Gly Leu Ala Phe Arg Val Phe His Cys Thr Gln Tyr Ile Arg His Gly
            260                 265                 270

Ser Lys Pro Met Tyr Thr Pro Glu Pro Asp Ile Cys His Glu Leu Leu
        275                 280                 285

Gly His Val Pro Leu Phe Ser Asp Arg Ser Phe Ala Gln Phe Ser Gln
    290                 295                 300

Glu Ile Gly Leu Ala Ser Leu Gly Ala Pro Asp Glu Tyr Ile Glu Lys
305                 310                 315                 320

Leu Ala Thr Ile Tyr Trp Phe Thr Val Glu Phe Gly Leu Cys Lys Gln
                325                 330                 335

Gly Asp Ser Ile Lys Ala Tyr Gly Ala Gly Leu Leu Ser Ser Phe Gly
            340                 345                 350

Glu Leu Gln Tyr Cys Leu Ser Glu Lys Pro Lys Leu Leu Pro Leu Glu
        355                 360                 365

Leu Glu Lys Thr Ala Ile Gln Asn Tyr Thr Val Thr Glu Phe Gln Pro
    370                 375                 380

Leu Tyr Tyr Val Ala Glu Ser Phe Asn Asp Ala Lys Glu Lys Val Arg
385                 390                 395                 400

Asn Phe Ala Ala Thr Ile Pro Arg Pro Phe Ser Val Arg Tyr Asp Pro
                405                 410                 415

Tyr Thr Gln Arg Ile Glu Val Leu Asp Asn Thr Gln Gln Leu Lys Ile
            420                 425                 430

Leu Ala Asp Ser Ile Asn Ser Glu Ile Gly Ile Leu Cys Ser Ala Leu
        435                 440                 445

Gln Lys Ile Lys
    450
```

<210> SEQ ID NO 3
<211> LENGTH: 405

<212> TYPE: DNA
<213> ORGANISM: Homo sapiens
<220> FEATURE:
<223> OTHER INFORMATION: hAAT promoter sequence

<400> SEQUENCE: 3
gatcttgcta ccagtggaac agccactaag gattctgcag tgagagcaga gggccagcta 60
agtggtactc tcccagagac tgtctgactc acgccacccc ctccaccttg gacacaggac 120
gctgtggttt ctgagccagg tacaatgact cctttcggta agtgcagtgg aagctgtaca 180
ctgcccaggc aaagcgtccg ggcagcgtag gcgggcgact cagatcccag ccagtggact 240
tagcccctgt ttgctcctcc gataactggg gtgaccttgg ttaatattca ccagcagcct 300
cccccgttgc ccctctggat ccactgctta aatacggacg aggacagggc cctgtctcct 360
cagcttcagg caccaccact gacctgggac agtgaatcgt aagta 405

<210> SEQ ID NO 4
<211> LENGTH: 321
<212> TYPE: DNA
<213> ORGANISM: Homo sapiens
<220> FEATURE:
<223> OTHER INFORMATION: HCR enhancer or ApoE enhancer sequence

<400> SEQUENCE: 4
aggctcagag gcacacagga gtttctgggc tcaccctgcc cccttccaac ccctcagttc 60
ccatcctcca gcagctgttt gtgtgctgcc tctgaagtcc acactgaaca aacttcagcc 120
tactcatgtc cctaaaatgg gcaaacattg caagcagcaa acagcaaaca cacagccctc 180
cctgcctgct gaccttggag ctggggcaga ggtcagagac ctctctgggc ccatgccacc 240
tccaacatcc actcgacccc ttggaatttc ggtggagagg agcagaggtt gtcctggcgt 300
ggtttaggta gtgtgagagg g 321

<210> SEQ ID NO 5

<400> SEQUENCE: 5

000

<210> SEQ ID NO 6
<211> LENGTH: 2734
<212> TYPE: DNA
<213> ORGANISM: Artificial Sequence
<220> FEATURE:
<223> OTHER INFORMATION: synthetic promoter sequence (hAAT promoter, HCR
      enhancer/ApoE enhancer)

<400> SEQUENCE: 6
aggctcagag gcacacagga gtttctgggc tcaccctgcc cccttccaac ccctcagttc 60
ccatcctcca gcagctgttt gtgtgctgcc tctgaagtcc acactgaaca aacttcagcc 120
tactcatgtc cctaaaatgg gcaaacattg caagcagcaa acagcaaaca cacagccctc 180
cctgcctgct gaccttggag ctggggcaga ggtcagagac ctctctgggc ccatgccacc 240
tccaacatcc actcgacccc ttggaatttc ggtggagagg agcagaggtt gtcctggcgt 300
ggtttaggta gtgtgagagg ggtcgacgat cttgctacca gtggaacagc cactaaggat 360
tctgcagtga gagcagaggg ccagctaagt ggtactctcc cagagactgt ctgactcacg 420
ccaccccctc caccttggac acaggacgct gtggtttctg agccaggtac aatgactcct 480
ttcggtaagt gcagtggaag ctgtacactg cccaggcaaa gcgtccgggc agcgtaggcg 540

```
ggcgactcag atcccagcca gtggacttag cccctgtttg ctcctccgat aactggggtg    600
accttggtta atattcacca gcagcctccc ccgttgcccc tctggatcca ctgcttaaat    660
acggacgagg acagggccct gtctcctcag cttcaggcac caccactgac ctgggacagt    720
gaatcgtaag tatgcctttc actgcgaggg gttctggaga ggcttctgag ctccccatgg    780
cccaggcagg cagcaggtct ggggcaggag gggggttgtg gagtgggtat ccgcctgctg    840
aggtgcaggg cagatggaga ggctgcagct gagctcctat tttcataata acagcagcca    900
tgagggttgt gtcctgtttc ccagtcctgc ccggtccccc ctcggtacct cctggtggat    960
acactggttc ctgtaagcag aagtggatga gggtgtctag gtctgcagtc ctggcacccc   1020
aggatggggg acaccagcca agatacagca acagcaacaa agcgcagcca tttctttctg   1080
tttgcacagc tcctctgtct gtcgggggct cctgtctgtt gtctcctata agcctcacca   1140
cctctcctac tgcttgggca tgcatctttc tccccttcta tagatgagga ggttaaggtc   1200
cagagagggg tggggaggaa cgccggctca cattctccat cccctccaga tatgaccagg   1260
aacagacctg tgccaggcct cagccttaca tcaaaatggg cctccccatg caccgtggac   1320
ctctgggccc tcctgtccca gtggaggaca ggaagctatg aggggcactg tcacccaggg   1380
ctcaagctgg cattcctgaa taatcgctct gcaccaggcc acggctaagc tcagtgcgtg   1440
attaagcctc ataaccctcc aaggcagtta ctagtgtgat tcccatttta cagatgagga   1500
agatggggac agagaggtga ataactggcc ccaaatcaca caccatccat aattcgggct   1560
caggcacctg gctccagtcc ccaaactctt gaacctggcc ctagtgtcac tgtttctctt   1620
gggtctcagg cgctggatgg ggaacaggaa acctgggctg gacttgaggc ctctctgatg   1680
ctcggtgact tcagacagtt gctcaacctc tctgttctct tgggcaaaac atgataacct   1740
ttgacttctg tcccctcccc tcaccccacc cgaccttgat ctctgaagtg ttggaaggat   1800
ttaatttttc ctgcactgag ttttggagac aggtcaaaaa gatgaccaag gccaaggtgg   1860
ccagtttcct atagaacgcc tctaaaagac ctgcagcaat agcagcaaga actggtattc   1920
tcgagaactt gctgcgcagc aggcacttct tggcatttta tgtgtattta atttcacaat   1980
agctctatga caaagtccac ctttctcatc tccaggaaac tgaggttcag agaggttaag   2040
taacttgtcc aaggtcacac agctaatagc aagttgacgt ggagcaatct ggcctcagag   2100
cctttaattt tagccacaga ctgatgctcc cctcttcatt tagccaggct gcctctgaag   2160
ttttctgatt caagacttct ggcttcagct ttgtacacag agatgattca atgtcaggtt   2220
ttggagtgaa atctgtttaa tcccagacaa aacatttagg attacatctc agttttgtaa   2280
gcaagtagct ctgtgatttt tagtgagtta tttaatgctc tttggggctc aatttttcta   2340
tctataaaat agggctaata atttgcacct tatagggtaa gctttgagga cagattagat   2400
gatacggtgc ctgtaaaaca ccaggtgtta gtaagtgtgg caatgatggt gacgctgagg   2460
ctgatgtttg cttagcatag ggttaggcag ctggcaggca gtaaacagtt ggataattta   2520
atggaaaatt tgccaaactc agatgctagc agctacaatc cagctaccat tctgctttta   2580
ttttatggtt gggataaggc tggattattc tgagtccaag ctaggccctt ttgctaatca   2640
tgttcatacc tcttatcttc ctcccacagc tcctgggcaa cgtgctggtc tgtgtgctgg   2700
cccatcactt tggcaaagaa ttgcgatcgc cacc                               2734
```

<210> SEQ ID NO 7
<211> LENGTH: 1359
<212> TYPE: DNA
<213> ORGANISM: Artificial Sequence
<220> FEATURE:
<223> OTHER INFORMATION: codon optimised human PAH sequence (GENEius 1/Operon1)

<400> SEQUENCE: 7

```
atgagcactg ctgtgctgga gaaccctggc ctgggcagaa agctgtctga ctttggccag     60

gagaccagct acattgagga caactgcaac cagaatggag ccatcagcct gatcttcagc    120

ctgaaggagg aggtgggagc cctggccaag gtgctgagac tgtttgagga gaatgatgtg    180

aacctgaccc acattgagag cagacccagc agactgaaga aggatgagta tgagttcttc    240

acccacctgg acaagagaag cctgcctgcc ctgaccaaca tcatcaagat cctgagacac    300

gatattggag ccactgtgca cgagctgagc agagacaaga agaaggacac tgtgccctgg    360

ttccccagaa ctatccagga gctggacaga tttgccaacc agatcctgag ctatggagct    420

gagctggatg ctgaccaccc tggcttcaag gaccctgtgt acagagccag aagaaagcag    480

tttgctgaca ttgcctacaa ctacagacac ggccagccca tccccagagt ggagtacatg    540

gaggaggaga agaagacctg ggcactgtg ttcaagaccc tgaagagcct gtacaagacc     600

cacgcctgct atgagtacaa ccacatcttc cccctgctgg agaagtactg tggcttccac    660

gaggacaaca tcccccagct ggaggatgtg agccagttcc tgcagacctg cactggcttc    720

agactgagac ctgtggctgg cctgctgagc agcagagact tcctgggggg cctggccttc    780

agagtgttcc actgcaccca gtacatcaga cacggcagca agcccatgta cacccctgag    840

cctgatatct gccacgagct gctgggccac gtgcccctgt tctctgacag aagctttgcc    900

cagttcagcc aggagattgg cctggccagc ctgggagccc ctgatgagta tattgagaag    960

ctggccacta tctactggtt cactgtggag tttggcctgt gcaagcaggg ggacagcatc   1020

aaggcctatg gagctggcct gctgagcagc tttggggagc tgcagtactg cctgtctgag   1080

aagcccaagc tgctgcccct ggagctggag aagactgcca tccagaacta cactgtgact   1140

gagttccagc ccctgtacta tgtggctgag agcttcaatg atgccaagga gaaggtgaga   1200

aactttgctg ccaccatccc cagacccttc tctgtgagat atgaccccta cacccagaga   1260

attgaggtgc tggacaacac ccagcagctg aagatcctgg ctgacagcat caactctgag   1320

attggcatcc tgtgctctgc cctgcagaag atcaagtaa                          1359
```

<210> SEQ ID NO 8
<211> LENGTH: 1359
<212> TYPE: DNA
<213> ORGANISM: Artificial Sequence
<220> FEATURE:
<223> OTHER INFORMATION: codon optimised human PAH sequence (GENEius 2/Operon2)

<400> SEQUENCE: 8

```
atgagcactg ctgtgctgga gaaccctggc ctgggcagaa agctgtctga ctttggccag     60

gagaccagct acattgagga caactgcaac cagaatgggg ccatcagcct gatcttcagc    120

ctgaaggagg aggtgggggc cctggccaag gtgctgagac tgtttgagga gaatgatgtg    180

aacctgaccc acattgagag cagacccagc agactgaaga aggatgagta tgagttcttc    240

acccacctgg acaagagaag cctgcctgcc ctgaccaaca tcatcaagat cctgagacac    300

gatattgggg ccactgtgca cgagctgagc agagacaaga agaaggacac tgtgccctgg    360

ttccccagaa ctatccagga gctggacaga tttgccaacc agatcctgag ctatggggct    420

gagctggatg ctgaccaccc tggcttcaag gaccctgtgt acagagccag aagaaagcag    480
```

-continued

```
tttgctgaca ttgcctacaa ctacagacac ggccagccca tccccagagt ggagtacatg    540

gaggaggaga agaagacctg ggcactgtg ttcaagaccc tgaagagcct gtacaagacc    600

cacgcctgct atgagtacaa ccacatcttc cccctgctgg agaagtactg tggcttccac    660

gaggacaaca tcccccagct ggaggatgtg agccagttcc tgcagacctg cactggcttc    720

agactgagac ctgtggctgg cctgctgagc agcagagact tcctgggggg cctggccttc    780

agagtgttcc actgcaccca gtacatcaga cacggcagca agcccatgta cacccctgag    840

cctgatatct gccacgagct gctgggccac gtgcccctgt tctctgacag aagctttgcc    900

cagttcagcc aggagattgg cctggccagc ctgggggccc ctgatgagta tattgagaag    960

ctggccacta tctactggtt cactgtggag tttggcctgt gcaagcaggg ggacagcatc   1020

aaggcctatg ggctggcct gctgagcagc tttggggagc tgcagtactg cctgtctgag   1080

aagcccaagc tgctgcccct ggagctggag aagactgcca tccagaacta cactgtgact   1140

gagttccagc ccctgtacta tgtggctgag agcttcaatg atgccaagga gaaggtgaga   1200

aactttgctg ccaccatccc cagacccttc tctgtgagat acgaccccta cacccagaga   1260

attgaggtgc tggacaacac ccagcagctg aagatcctgg ctgacagcat caactctgag   1320

attggcatcc tgtgctctgc cctgcagaag atcaagtga                          1359
```

<210> SEQ ID NO 9
<211> LENGTH: 1359
<212> TYPE: DNA
<213> ORGANISM: Artificial Sequence
<220> FEATURE:
<223> OTHER INFORMATION: codon optimised human PAH sequence (Nathwani / NW2-Cop)

<400> SEQUENCE: 9

```
atgtccactg ctgtcctgga aaacccaggc ttgggcagga aactctctga ctttggacag     60

gaaacaagct atattgaaga caactgcaat caaaatggtg ccatatcact gatcttctca    120

ctcaaagaag aagttggtgc attggccaaa gtactgaggt tatttgagga gaatgatgta    180

aacctgaccc acattgaatc tagaccttct aggttaaaga aagatgagta tgaatttttc    240

acccatttgg ataaaaggag cctgcctgct ctgacaaaca tcatcaagat cttgaggcac    300

gacattggtg ccactgtcca cgagctttca agggataaga agaaagacac agtgccctgg    360

ttcccaagaa ctattcaaga gctggacaga tttgccaatc agattctcag ctatggagct    420

gaactggatg ctgaccaccc tggttttaaa gatcctgtgt acagggcaag aaggaagcag    480

tttgctgaca ttgcctacaa ctacaggcat gggcagccca tccctagggt ggaatacatg    540

gaggaagaaa agaaaacatg gggcacagtg ttcaagactc tgaagtcctt gtataaaacc    600

cacgcttgct atgagtacaa tcacattttt ccacttcttg aaaagtactg tggcttccac    660

gaagataaca ttccccagct ggaagatgtt tctcagttcc tgcagacttg cactggtttc    720

aggctcaggc ctgtagctgg cctgctttcc tctagggatt tcttgggtgg cctggccttc    780

agggtcttcc actgcacaca gtacatcaga cacggctcca agcccatgta tacccctgaa    840

cctgacatct gccacgagct gttgggacac gtgcccttgt tttcagatag gagctttgcc    900

cagttttccc aggaaattgg ccttgcctct ctgggtgcac ctgatgaata tattgaaaag    960

ctggccacaa tctactggtt tactgtggag tttgggctct gcaaacaagg agactccata   1020

aaggcatatg gtgctgggct cctgtcatcc tttggtgaat tacagtactg cttatcagag   1080

aagccaaagc ttctcccccct ggagctggag aagacagcca tccaaaatta cactgtcact   1140
```

gagttccagc ccctgtatta tgtggcagag agttttaatg atgccaagga gaaagtaagg 1200
aactttgctg ccacaatacc taggcccttc tcagttaggt atgacccata cacccaaagg 1260
attgaggtct tggacaatac ccagcagctt aagattttgg ctgattccat taacagtgaa 1320
attggaatcc tttgcagtgc cctccagaaa atcaagtaa 1359

<210> SEQ ID NO 10
<211> LENGTH: 1359
<212> TYPE: DNA
<213> ORGANISM: Artificial Sequence
<220> FEATURE:
<223> OTHER INFORMATION: codon optimised human PAH sequence (Nathwani-
RCG / NW-RCG)

<400> SEQUENCE: 10
atgtccactg ctgtcctgga aaacccaggc ttgggcagga aactctctga ctttggacag 60
gaaacaagct atattgaaga caactgcaat caaaatggtg ccatatcact gatcttctca 120
ctcaaagaag aagttggtgc attggccaaa gtactgaggt tatttgagga gaatgatgta 180
aacctgaccc acattgaatc tagaccttct aggttaaaga aagatgagta tgaatttttc 240
acccatttgg ataaaaggag cctgcctgct ctgacaaaca tcatcaagat cttgaggcac 300
gacattggtg ccactgtcca cgagctttca agggataaga agaaagacac agtgccctgg 360
ttcccaagaa ctattcaaga gctggacaga tttgccaatc agattctcag ctatggagct 420
gaactggatg ctgaccaccc tggttttaaa gatcctgtgt acagggcaag aaggaagcag 480
tttgctgaca ttgcctacaa ctacaggcat gggcagccca tccctagggt ggaatacatg 540
gaggaagaaa agaaaacatg ggcacagtg ttcaagactc tgaagtcctt gtataaaacc 600
cacgcttgct atgagtacaa tcacattttt ccacttcttg aaaagtactg tggcttccac 660
gaagataaca ttccccagct ggaagatgtt tctcagttcc tgcagacttg cactggtttc 720
aggctcaggc ctgtagctgg cctgctttcc tctagggatt tcttgggtgg cctggccttc 780
agggtcttcc actgcacaca gtacatcaga cacggctcca agcccatgta tacccctgaa 840
cctgacatct gccacgagct gttgggacac gtgcccttgt tttcagatag gagctttgcc 900
cagttttccc aggaaattgg ccttgcctct ctgggtgcac ctgatgaata tattgaaaag 960
ctggccacaa tttactggtt tactgtggag tttgggctct gcaaacaagg agactccata 1020
aaggcatatg gtgctgggct cctgtcatcc tttggtgaat tacagtactg cttatcagag 1080
aagccaaagc ttctccccct ggagctggag aagacagcca tccaaaatta cactgtcact 1140
gagttccagc ccctgtatta tgtggcagag agttttaatg atgccaagga gaaagtaagg 1200
aactttgctg ccacaatacc taggcccttc tcagttaggt atgacccata cacccaaagg 1260
attgaggtct tggacaatac ccagcagctt aagattttgg ctgattccat taacagtgaa 1320
attggaatcc tttgcagtgc cctccagaaa ataaagtaa 1359

<210> SEQ ID NO 11
<211> LENGTH: 1359
<212> TYPE: DNA
<213> ORGANISM: Artificial Sequence
<220> FEATURE:
<223> OTHER INFORMATION: codon optimised human PAH sequence (ATUM
(DNA2.0-op/D20-P))

<400> SEQUENCE: 11
atgtccactg cggtgttgga aaaccccgga ctgggcagaa agttgtccga cttcggccag 60
gaaacctctt acattgagga caactgcaac cagaacgggg ccatctcact gatcttttcg 120

```
ctgaaagaag aagtcggagc tctggccaaa gtgctgcgcc tgttcgagga aaacgacgtc    180

aacctgaccc acatcgagtc aagaccgagc aggctgaaga aggatgagta cgagtttttc    240

acccatctcg acaagagatc cctgcctgcc ctgaccaata ttatcaagat tttgcggcac    300

gacattggcg caaccgtgca tgaactctcc cgggacaaga agaaggacac cgtgccgtgg    360

ttcccccgaa ccatccagga actcgaccgc ttcgctaacc agatcctgtc ctacggcgcc    420

gaactggatg ccgatcaccc tggattcaag gacccagtgt acagagcccg gcgcaagcag    480

ttcgccgata tcgcctacaa ttatcggcac ggacagccaa tcccgagggt ggagtacatg    540

gaggaggaaa agaaaacctg ggaactgtg ttcaagacct tgaagtccct gtacaagact     600

cacgcctgct acgagtacaa ccacatcttc cccctgctcg aaaagtactg cgggttccat    660

gaggacaaca tcccccaact ggaagatgtg tcgcagttcc tgcaaacctg taccggattc    720

cggctgaggc ctgtcgcggg acttctgtcc tcccgggatt ttcttggcgg tctggccttc    780

cgggtgttcc actgtactca gtacattaga cacgggagca agcctatgta cactcctgaa    840

cccgacattt gccacgaact cctgggtcat gtgcccctct tctcggatcg gagcttcgcc    900

cagttcagcc aagagatcgg tctggctagc ttgggagcac ccgacgagta catcgagaag    960

ctggccacta tctactggtt taccgtggaa ttcggactgt gcaagcaggg ggactcaatc   1020

aaggcctatg gcgcgggact cctgagctcc ttcggggagc tgcagtactg cctgtccgaa   1080

aagccaaagc tgctccctct tgaactggag aaaacggcca tccagaacta caccgtgacc   1140

gaattccagc cgctctacta cgtcgcggag tccttcaacg atgccaagga gaaggtccgc   1200

aacttcgccg caactatccc gcggccgttt tccgtgcgct atgacccgta cacacaacgc   1260

atcgaagtgc tggacaacac ccagcaactt aagattctgg ccgactcgat caactccgag   1320

attggcattc tgtgctcggc gctgcagaag atcaagtaa                          1359
```

<210> SEQ ID NO 12
<211> LENGTH: 1359
<212> TYPE: DNA
<213> ORGANISM: Artificial Sequence
<220> FEATURE:
<223> OTHER INFORMATION: codon optimised human PAH sequence (ATUM-RCG (DNA2.0-Cop1))

<400> SEQUENCE: 12

```
atgtccactg cggtcctgga aaaccctggt ctgggccgca agctttctga ctttggacag     60

gaaacctcat acattgagga caactgtaac caaaatggtg caatcagcct gatcttcagc    120

ctcaaggaag aagtgggagc cctggccaag gtcctgagac tgtttgagga gaatgatgtg    180

aacctgaccc acattgagtc caggccctcc agactgaaga aggatgaata cgaattcttc    240

acccacctgg acaagcgctc cctccctgcc ctcaccaaca tcattaagat cctgcggcac    300

gacattggag ccactgtgca tgagttgagc cgggacaaga agaaggatac tgtgccctgg    360

ttcccgagga ccatccagga actggaccgg tttgccaacc aaattctgtc ctatggagct    420

gaattggatg cagaccaccc tggcttcaag gacccagtgt acagagcaag gagaaagcag    480

tttgcagaca tagcctacaa ctacagacat ggacagccca tcccgagggt ggagtacatg    540

gaagaggaga agaaaacctg ggcactgtg tttaagaccc tcaagagcct gtacaagacc     600

cacgcctgct atgagtacaa ccacatcttc ccactcctgg agaaatactg tggcttccat    660

gaggacaaca tcccacagct ggaggatgtg tcccagttcc tgcagacttg cactggcttc    720

cggttgaggc ctgtggctgg cctgctctcc tcaagggact tcttgggggg actggcattc    780
```

agggtgttcc actgcaccca atacatcaga cacggcagca agccaatgta cacccctgaa 840
ccggacatct gccacgaact cctgggccac gtccctctgt tctcggacag aagctttgcc 900
cagttctccc aagagattgg ccttgcctcc ctgggggccc ctgatgaata cattgaaaag 960
ctggccacaa tctactggtt cactgtggaa tttggacttt gcaagcaggg agatagcatc 1020
aaggcctacg gggctggact tctgtcctcc ttcggtgaac tgcagtactg tctgtcagag 1080
aagcccaagc tgctgcccct ggaactggag aaaactgcca tccaaaacta cactgtgact 1140
gagttccagc ccctctacta tgtggctgag tccttcaatg atgccaaaga aaaggtcaga 1200
aattttgcgg ccaccattcc taggcctttc tcagtccgct atgaccctta cacccagaga 1260
attgaggtgc tggacaacac ccagcagctc aagatcctgg cagactccat caactcagaa 1320
attgggatct tgtgctcggc cctccaaaag atcaagtaa 1359

<210> SEQ ID NO 13
<211> LENGTH: 1359
<212> TYPE: DNA
<213> ORGANISM: Artificial Sequence
<220> FEATURE:
<223> OTHER INFORMATION: codon optimised human PAH sequence (JCAT (JCAT))

<400> SEQUENCE: 13
atgagcactg ctgtgctgga gaaccctggc ctgggcagaa agctgtctga ctttggccag 60
gagaccagct acattgagga caactgcaac cagaatgggg ccatcagcct gatcttcagc 120
ctgaaggagg aggtgggggc cctggccaag gtgctgagac tgtttgagga gaatgatgtg 180
aacctgaccc acattgagag cagacccagc agactgaaga aggatgagta tgagttcttc 240
acccacctgg acaagagaag cctgccagcc ctgaccaata ttatcaagat cctgaggcac 300
gatattgggg ccacagtgca cgagctgagc agagacaaga agaaggacac agtgccctgg 360
ttccccagga ctatccagga gctggacagg tttgccaacc agatcctgag ctacggagct 420
gagctggatg cagaccaccc tggcttcaag gaccctgtgt acagagccag gagaaagcag 480
tttgcagata tagcctacaa ctacaggcac ggccagccaa tccctagagt ggagtacatg 540
gaggaggaga agaagacctg ggcactgtg ttcaagaccc tgaagagcct gtacaagacc 600
cacgcctgct acgagtacaa ccacatcttc cccctgctgg agaagtactg tggcttccac 660
gaggacaaca tcccccagct ggaggatgtg agccagttcc tgcagacctg cacaggcttc 720
aggctgagac cagtggcagg cctgctgagc agcagggact tcctgggggg cctggccttc 780
agagtgttcc actgcaccca gtatatcagg cacggcagca agccaatgta cacccctgag 840
ccagatatct gccacgagct gctgggccac gttcccctgt tctcagacag aagctttgcc 900
cagttcagcc aggagattgg cctggccagc ctgggggccc ctgacgagta tattgagaag 960
ctggccacta tctactggtt cacagtggag tttggcctgt gcaagcaggg ggacagcatc 1020
aaggcctatg gggctggcct gctgagcagc tttggggagc tgcagtactg cctgtcagag 1080
aagccaaagc tgctgcccct ggagctggag aagacagcta tccagaacta cactgtgact 1140
gagttccagc ccctgtacta tgtggcagag agcttcaatg atgccaagga gaaggtgaga 1200
aactttgctg ccaccatccc caggcccttc tctgtgagat atgaccccta cacccagagg 1260
attgaggtgc tggacaacac ccagcagctg aagatcctgg cagacagcat caacagtgag 1320
attggtatcc tgtgctctgc cctgcagaag atcaagtaa 1359

<210> SEQ ID NO 14
<211> LENGTH: 2002
<212> TYPE: DNA
<213> ORGANISM: Artificial Sequence
<220> FEATURE:
<223> OTHER INFORMATION: composite globin/AIAT intron nucleic acid sequence

<400> SEQUENCE: 14

```
tgcctttcac tgcgaggggt tctggagagg cttctgagct ccccatggcc caggcaggca     60

gcaggtctgg ggcaggaggg gggttgtgga gtgggtatcc gcctgctgag gtgcagggca    120

gatggagagg ctgcagctga gctcctattt tcataataac agcagccatg agggttgtgt    180

cctgtttccc agtcctgccc ggtcccccct cggtacctcc tggtggatac actggttcct    240

gtaagcagaa gtggatgagg gtgtctaggt ctgcagtcct ggcaccccag gatgggggac    300

accagccaag atacagcaac agcaacaaag cgcagccatt tctttctgtt tgcacagctc    360

ctctgtctgt cgggggctcc tgtctgttgt ctcctataag cctcaccacc tctcctactg    420

cttgggcatg catctttctc cccttctata gatgaggagg ttaaggtcca gagaggggtg    480

gggaggaacg ccggctcaca ttctccatcc cctccagata tgaccaggaa cagacctgtg    540

ccaggcctca gccttacatc aaaatgggcc tccccatgca ccgtggacct ctgggccctc    600

ctgtcccagt ggaggacagg aagctatgag gggcactgtc acccagggct caagctggca    660

ttcctgaata atcgctctgc accaggccac ggctaagctc agtgcgtgat taagcctcat    720

aaccctccaa ggcagttact agtgtgattc ccattttaca gatgaggaag atggggacag    780

agaggtgaat aactggcccc aaatcacaca ccatccataa ttcgggctca ggcacctggc    840

tccagtcccc aaactcttga acctggccct agtgtcactg tttctcttgg gtctcaggcg    900

ctggatgggg aacaggaaac ctgggctgga cttgaggcct ctctgatgct cggtgacttc    960

agacagttgc tcaacctctc tgttctcttg ggcaaaacat gataaccttt gacttctgtc   1020

ccctcccctc accccacccg accttgatct ctgaagtgtt ggaaggattt aatttttcct   1080

gcactgagtt ttggagacag gtcaaaaaga tgaccaaggc caaggtggcc agtttcctat   1140

agaacgcctc taaaagacct gcagcaatag cagcaagaac tggtattctc gagaacttgc   1200

tgcgcagcag gcacttcttg gcattttatg tgtatttaat ttcacaatag ctctatgaca   1260

aagtccacct ttctcatctc caggaaactg aggttcagag aggttaagta acttgtccaa   1320

ggtcacacag ctaatagcaa gttgacgtgg agcaatctgg cctcagagcc tttaatttta   1380

gccacagact gatgctcccc tcttcattta gccaggctgc ctctgaagtt ttctgattca   1440

agacttctgg cttcagcttt gtacacagag atgattcaat gtcaggtttt ggagtgaaat   1500

ctgtttaatc ccagacaaaa catttaggat tacatctcag ttttgtaagc aagtagctct   1560

gtgattttta gtgagttatt taatgctctt tggggctcaa tttttctatc tataaaatag   1620

ggctaataat ttgcacctta tagggtaagc tttgaggaca gattagatga tacggtgcct   1680

gtaaaacacc aggtgttagt aagtgtggca atgatggtga cgctgaggct gatgtttgct   1740

tagcataggg ttaggcagct ggcaggcagt aaacagttgg ataatttaat ggaaaatttg   1800

ccaaactcag atgctagcag ctacaatcca gctaccattc tgcttttatt ttatggttgg   1860

gataaggctg gattattctg agtccaagct aggccctttt gctaatcatg ttcatacctc   1920

ttatcttcct cccacagctc ctgggcaacg tgctggtctg tgtgctggcc catcactttg   1980

gcaaagaatt gcgatcgcca cc                                            2002
```

<210> SEQ ID NO 15
<211> LENGTH: 2822
<212> TYPE: DNA
<213> ORGANISM: Artificial Sequence
<220> FEATURE:
<223> OTHER INFORMATION: Vector 1 (ApoE-HCR-hAAT.GI.hPAH.bGH) nucleic
acid sequence

<400> SEQUENCE: 15
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccgca cgcgtaggct cagaggcaca caggagtttc 180
tgggctcacc ctgcccccttt ccaacccctc agttcccatc ctccagcagc tgtttgtgtg 240
ctgcctctga agtccacact gaacaaactt cagcctactc atgtccctaa aatgggcaaa 300
cattgcaagc agcaaacagc aaacacacag ccctccctgc ctgctgacct tggagctggg 360
gcagaggtca gagacctctc tgggcccatg ccacctccaa catccactcg accccttgga 420
atttcggtgg agaggagcag aggttgtcct ggcgtggttt aggtagtgtg agaggggtcg 480
acgatcttgc taccagtgga acagccacta aggattctgc agtgagagca gagggccagc 540
taagtggtac tctcccagag actgtctgac tcacgccacc ccctccacct tggacacagg 600
acgctgtggt ttctgagcca ggtacaatga ctcctttcgg taagtgcagt ggaagctgta 660
cactgcccag gcaaagcgtc cgggcagcgt aggcgggcga ctcagatccc agccagtgga 720
cttagcccct gtttgctcct ccgataactg gggtgacctt ggttaatatt caccagcagc 780
ctcccccgtt gcccctctgg atccactgct taaatacgga cgaggacagg gccctgtctc 840
ctcagcttca ggcaccacca ctgacctggg acagtgaatc gtaagtacta gcagctacaa 900
tccagctacc attctgcttt tattttatgg ttgggataag gctggattat tctgagtcca 960
agctaggccc ttttgctaat catgttcata cctcttatct tcctcccaca gctcctgggc 1020
aacgtgctgg tctgtgtgct ggcccatcac tttggcaaag aattgcgatc gccaccatgt 1080
ccactgcggt cctggaaaac ccaggcttgg gcaggaaact ctctgacttt ggacaggaaa 1140
caagctatat tgaagacaac tgcaatcaaa atggtgccat atcactgatc ttctcactca 1200
aagaagaagt tggtgcattg gccaaagtat tgcgcttatt tgaggagaat gatgtaaacc 1260
tgacccacat tgaatctaga ccttctcgtt taaagaaaga tgagtatgaa tttttcaccc 1320
atttggataa acgtagcctg cctgctctga caaacatcat caagatcttg aggcatgaca 1380
ttggtgccac tgtccatgag ctttcacgag ataagaagaa agacacagtg ccctggttcc 1440
caagaaccat tcaagagctg gacagatttg ccaatcagat tctcagctat ggagcggaac 1500
tggatgctga ccaccctggt tttaaagatc ctgtgtaccg tgcaagacgg aagcagtttg 1560
ctgacattgc ctacaactac cgccatgggc agcccatccc tcgagtggaa tacatggagg 1620
aagaaaagaa aacatggggc acagtgttca agactctgaa gtccttgtat aaaacccatg 1680
cttgctatga gtacaatcac atttttccac ttcttgaaaa gtactgtggc ttccatgaag 1740
ataacattcc ccagctggaa gacgtttctc agttcctgca gacttgcact ggtttccgcc 1800
tccgacctgt agctggcctg ctttcctctc gggatttctt gggtggcctg gccttccgag 1860
tcttccactg cacacagtac atcagacatg gatccaagcc catgtatacc cccgaacctg 1920
acatctgcca tgagctgttg ggacatgtgc ccttgttttc agatcgcagc tttgcccagt 1980
tttcccagga aattggcctt gcctctctgg gtgcacctga tgaatacatt gaaaagctcg 2040
ccacaattta ctggtttact gtggagtttg ggctctgcaa acaaggagac tccataaagg 2100
catatggtgc tgggctcctg tcatcctttg gtgaattaca gtactgctta tcagagaagc 2160
caaagcttct ccccctggag ctggagaaga cagccatcca aaattacact gtcacggagt 2220
tccagcccct gtattacgtg gcagagagtt ttaatgatgc caaggagaaa gtaaggaact 2280
ttgctgccac aatacctcgg cccttctcag ttcgctacga cccatacacc caaaggattg 2340
aggtcttgga caatacccag cagcttaaga ttttggctga ttccattaac agtgaaattg 2400
gaatcctttg cagtgccctc cagaaaataa agtaacctcg agctgtgcct tctagttgcc 2460
agccatctgt tgtttgcccc tcccccgtgc cttccttgac cctggaaggt gccactccca 2520
ctgtcctttc ctaataaaat gaggaaattg catcgcattg tctgagtagg tgtcattcta 2580
ttctgggggg tggggtgggg caggacagca agggggagga ttgggaagac aatagcaggc 2640
atgctgggga tgcggtgggc tctatggacc ggtgcggccg caggaacccc tagtgatgga 2700
gttggccact ccctctctgc gcgctcgctc gctcactgag gccgggcgac caaaggtcgc 2760
ccgacgcccg ggctttgccc gggcggcctc agtgagcgag cgagcgcgca gctgcctgca 2820
gg 2822

<210> SEQ ID NO 16
<211> LENGTH: 2822
<212> TYPE: DNA
<213> ORGANISM: Artificial Sequence
<220> FEATURE:
<223> OTHER INFORMATION: GENEius1 (ApoE-HCR-hAAT.GI.hPAHco1.bGH) nucleic acid sequence

<400> SEQUENCE: 16
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccgca cgcgtaggct cagaggcaca caggagtttc 180
tgggctcacc ctgccccctt ccaacccctc agttcccatc ctccagcagc tgtttgtgtg 240
ctgcctctga agtccacact gaacaaactt cagcctactc atgtccctaa aatgggcaaa 300
cattgcaagc agcaaacagc aaacacacag ccctccctgc ctgctgacct tggagctggg 360
gcagaggtca gagacctctc tgggcccatg ccacctccaa catccactcg accccttgga 420
atttcggtgg agaggagcag aggttgtcct ggcgtggttt aggtagtgtg agaggggtcg 480
acgatcttgc taccagtgga acagccacta aggattctgc agtgagagca gagggccagc 540
taagtggtac tctcccagag actgtctgac tcacgccacc ccctccacct tggacacagg 600
acgctgtggt ttctgagcca ggtacaatga ctcctttcgg taagtgcagt ggaagctgta 660
cactgcccag gcaaagcgtc cgggcagcgt aggcgggcga ctcagatccc agccagtgga 720
cttagcccct gtttgctcct ccgataactg gggtgacctt ggttaatatt caccagcagc 780
ctcccccgtt gcccctctgg atccactgct taaatacgga cgaggacagg gccctgtctc 840
ctcagcttca ggcaccacca ctgacctggg acagtgaatc gtaagtacta gcagctacaa 900
tccagctacc attctgcttt tattttatgg ttgggataag gctggattat tctgagtcca 960
agctaggccc ttttgctaat catgttcata cctcttatct tcctcccaca gctcctgggc 1020
aacgtgctgg tctgtgtgct ggcccatcac tttggcaaag aattgcgatc gccaccatga 1080
gcactgctgt gctggagaac cctggcctgg gcagaaagct gtctgacttt ggccaggaga 1140
ccagctacat tgaggacaac tgcaaccaga atggagccat cagcctgatc ttcagcctga 1200
aggaggaggt gggagccctg gccaaggtgc tgagactgtt tgaggagaat gatgtgaacc 1260
tgacccacat tgagagcaga cccagcagac tgaagaagga tgagtatgag ttcttcaccc 1320
acctggacaa gagaagcctg cctgccctga ccaacatcat caagatcctg agacacgata 1380
ttggagccac tgtgcacgag ctgagcagag acaagaagaa ggacactgtg ccctggttcc 1440
ccagaactat ccaggagctg gacagatttg ccaaccagat cctgagctat ggagctgagc 1500
tggatgctga ccaccctggc ttcaaggacc ctgtgtacag agccagaaga aagcagtttg 1560
ctgacattgc ctacaactac agacacggcc agcccatccc cagagtggag tacatggagg 1620
aggagaagaa gacctggggc actgtgttca agaccctgaa gagcctgtac aagacccacg 1680
cctgctatga gtacaaccac atcttccccc tgctggagaa gtactgtggc ttccacgagg 1740
acaacatccc ccagctggag gatgtgagcc agttcctgca gacctgcact ggcttcagac 1800
tgagacctgt ggctggcctg ctgagcagca gagacttcct gggggggcctg gccttcagag 1860 tgttccactg cacccagtac atcagacacg gcagcaagcc catgtacacc cctgagcctg 1920
atatctgcca cgagctgctg ggccacgtgc ccctgttctc tgacagaagc tttgcccagt 1980
tcagccagga gattggcctg gccagcctgg gagcccctga tgagtatatt gagaagctgg 2040
ccactatcta ctggttcact gtggagtttg gcctgtgcaa gcagggggac agcatcaagg 2100
cctatggagc tggcctgctg agcagctttg ggagctgcca gtactgcctg tctgagaagc 2160
ccaagctgct gcccctggag ctggagaaga ctgccatcca gaactacact gtgactgagt 2220
tccagcccct gtactatgtg gctgagagct tcaatgatgc caaggagaag gtgagaaact 2280
ttgctgccac catccccaga cccttctctg tgagatatga cccctacacc cagagaattg 2340
aggtgctgga caacacccag cagctgaaga tcctggctga cagcatcaac tctgagattg 2400
gcatcctgtg ctctgccctg cagaagatca agtaacctcg agctgtgcct tctagttgcc 2460
agccatctgt tgtttgcccc tcccccgtgc cttccttgac cctggaaggt gccactccca 2520
ctgtcctttc ctaataaaat gaggaaattg catcgcattg tctgagtagg tgtcattcta 2580
ttctgggggg tggggtgggg caggacagca agggggagga ttgggaagac aatagcaggc 2640
atgctgggga tgcggtgggc tctatggacc ggtgcggccg caggaacccc tagtgatgga 2700
gttggccact ccctctctgc gcgctcgctc gctcactgag gccgggcgac caaaggtcgc 2760
ccgacgcccg ggctttgccc gggcggcctc agtgagcgag cgagcgcgca gctgcctgca 2820
gg 2822

<210> SEQ ID NO 17
<211> LENGTH: 4635
<212> TYPE: DNA
<213> ORGANISM: Artificial Sequence
<220> FEATURE:
<223> OTHER INFORMATION: Large Intron-Vector 1 (ApoE-HCR-hAAT.cG-AIATI.hPAH.bGH) sequence

<400> SEQUENCE: 17
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccgca cgcgtaggct cagaggcaca caggagtttc 180
tgggctcacc ctgccccctt ccaacccctc agttcccatc ctccagcagc tgtttgtgtg 240
ctgcctctga agtccacact gaacaaactt cagcctactc atgtccctaa aatgggcaaa 300
cattgcaagc agcaaacagc aaacacacag ccctccctgc ctgctgacct tggagctggg 360
gcagaggtca gagacctctc tgggcccatg ccacctccaa catccactcg acccccttgga 420

```
atttcggtgg agaggagcag aggttgtcct ggcgtggttt aggtagtgtg agaggggtcg    480
acgatcttgc taccagtgga acagccacta aggattctgc agtgagagca gagggccagc    540
taagtggtac tctcccagag actgtctgac tcacgccacc ccctccacct tggacacagg    600
acgctgtggt ttctgagcca ggtacaatga ctcctttcgg taagtgcagt ggaagctgta    660
cactgcccag gcaaagcgtc cgggcagcgt aggcgggcga ctcagatccc agccagtgga    720
cttagcccct gtttgctcct ccgataactg gggtgacctt ggttaatatt caccagcagc    780
ctcccccgtt gcccctctgg atccactgct taaatacgga cgaggacagg gccctgtctc    840
ctcagcttca ggcaccacca ctgacctggg acagtgaatc gtaagtatgc ctttcactgc    900
gaggggttct ggagaggctt ctgagctccc catggcccag gcaggcagca ggtctggggc    960
aggagggggg ttgtggagtg ggtatccgcc tgctgaggtg cagggcagat ggagaggctg   1020
cagctgagct cctattttca taataacagc agccatgagg gttgtgtcct gtttcccagt   1080
cctgcccggt ccccctcgg tacctcctgg tggatacact ggttcctgta agcagaagtg    1140
gatgagggtg tctaggtctg cagtcctggc accccaggat gggggacacc agccaagata   1200
cagcaacagc aacaaagcgc agccatttct ttctgtttgc acagctcctc tgtctgtcgg   1260
gggctcctgt ctgttgtctc ctataagcct caccacctct cctactgctt gggcatgcat   1320
ctttctcccc ttctatagat gaggaggtta aggtccagag aggggtgggg aggaacgccg   1380
gctcacattc tccatcccct ccagatatga ccaggaacag acctgtgcca ggcctcagcc   1440
ttacatcaaa atgggcctcc ccatgcaccg tggacctctg ggccctcctg tcccagtgga   1500
ggacaggaag ctatgagggg cactgtcacc cagggctcaa gctggcattc ctgaataatc   1560
gctctgcacc aggccacggc taagctcagt gcgtgattaa gcctcataac cctccaaggc   1620
agttactagt gtgattccca ttttacagat gaggaagatg gggacagaga ggtgaataac   1680
tggccccaaa tcacacacca tccataattc gggctcaggc acctggctcc agtccccaaa   1740
ctcttgaacc tggccctagt gtcactgttt ctcttgggtc tcaggcgctg gatggggaac   1800
aggaaacctg ggctggactt gaggcctctc tgatgctcgg tgacttcaga cagttgctca   1860
acctctctgt tctcttgggc aaaacatgat aacctttgac ttctgtcccc tcccctcacc   1920
ccacccgacc ttgatctctg aagtgttgga aggatttaat ttttcctgca ctgagttttg   1980
gagacaggtc aaaaagatga ccaaggccaa ggtggccagt ttcctataga acgcctctaa   2040
aagacctgca gcaatagcag caagaactgg tattctcgag aacttgctgc gcagcaggca   2100
cttcttggca ttttatgtgt atttaatttc acaatagctc tatgacaaag tccacctttc   2160
tcatctccag gaaactgagg ttcagagagg ttaagtaact tgtccaaggt cacacagcta   2220
atagcaagtt gacgtggagc aatctggcct cagagccttt aattttagcc acagactgat   2280
gctcccctct tcatttagcc aggctgcctc tgaagttttc tgattcaaga cttctggctt   2340
cagctttgta cacagagatg attcaatgtc aggttttgga gtgaaatctg tttaatccca   2400
gacaaaacat ttaggattac atctcagttt tgtaagcaag tagctctgtg atttttagtg   2460
agttatttaa tgctctttgg ggctcaattt ttctatctat aaaatagggc taataatttg   2520
caccttatag ggtaagcttt gaggacagat tagatgatac ggtgcctgta aaacaccagg   2580
tgttagtaag tgtggcaatg atggtgacgc tgaggctgat gtttgcttag catagggtta   2640
ggcagctggc aggcagtaaa cagttggata atttaatgga aaatttgcca aactcagatg   2700
ctagcagcta caatccagct accattctgc ttttatttta tggttgggat aaggctggat   2760
```

-continued

```
tattctgagt ccaagctagg ccctttttgct aatcatgttc atacctctta tcttcctccc   2820

acagctcctg ggcaacgtgc tggtctgtgt gctggcccat cactttggca aagaattgcg   2880

atcgccacca tgtccactgc ggtcctggaa aacccaggct tgggcaggaa actctctgac   2940

tttggacagg aaacaagcta tattgaagac aactgcaatc aaaatggtgc catatcactg   3000

atcttctcac tcaaagaaga agttggtgca ttggccaaag tattgcgctt atttgaggag   3060

aatgatgtaa acctgaccca cattgaatct agaccttctc gtttaaagaa agatgagtat   3120

gaatttttca cccatttgga taaacgtagc ctgcctgctc tgacaaacat catcaagatc   3180

ttgaggcatg acattggtgc cactgtccat gagctttcac gagataagaa gaaagacaca   3240

gtgccctggt tcccaagaac cattcaagag ctggacagat ttgccaatca gattctcagc   3300

tatggagcgg aactggatgc tgaccaccct ggttttaaag atcctgtgta ccgtgcaaga   3360

cggaagcagt ttgctgacat tgcctacaac taccgccatg ggcagcccat ccctcgagtg   3420

gaatacatgg aggaagaaaa gaaaacatgg ggcacagtgt tcaagactct gaagtccttg   3480

tataaaaccc atgcttgcta tgagtacaat cacatttttc cacttcttga aaagtactgt   3540

ggcttccatg aagataacat tccccagctg gaagacgttt ctcagttcct gcagacttgc   3600

actggtttcc gcctccgacc tgtagctggc ctgctttcct ctcgggattt cttgggtggc   3660

ctggccttcc gagtcttcca ctgcacacag tacatcagac atggatccaa gcccatgtat   3720

acccccgaac ctgacatctg ccatgagctg ttgggacatg tgcccttgtt ttcagatcgc   3780

agctttgccc agttttccca ggaaattggc cttgcctctc tgggtgcacc tgatgaatac   3840

attgaaaagc tcgccacaat ttactggttt actgtggagt ttgggctctg caaacaagga   3900

gactccataa aggcatatgg tgctgggctc ctgtcatcct ttggtgaatt acagtactgc   3960

ttatcagaga agccaaagct tctcccccctg gagctggaga agacagccat ccaaaattac   4020

actgtcacgg agttccagcc cctgtattac gtggcagaga gttttaatga tgccaaggag   4080

aaagtaagga actttgctgc cacaatacct cggcccttct cagttcgcta cgacccatac   4140

acccaaagga ttgaggtctt ggacaatacc cagcagctta agattttggc tgattccatt   4200

aacagtgaaa ttggaatcct ttgcagtgcc ctccagaaaa taaagtaacc tcgagctgtg   4260

ccttctagtt gccagccatc tgttgtttgc ccctcccccg tgccttcctt gaccctggaa   4320

ggtgccactc ccactgtcct ttcctaataa aatgaggaaa ttgcatcgca ttgtctgagt   4380

aggtgtcatt ctattctggg gggtggggtg gggcaggaca gcaaggggga ggattgggaa   4440

gacaatagca ggcatgctgg ggatgcggtg ggctctatgg accggtgcgg ccgcaggaac   4500

ccctagtgat ggagttggcc actccctctc tgcgcgctcg ctcgctcact gaggccgggc   4560

gaccaaaggt cgcccgacgc ccgggctttg cccgggcggc ctcagtgagc gagcgagcgc   4620

gcagctgcct gcagg                                                     4635
```

<210> SEQ ID NO 18
<211> LENGTH: 4635
<212> TYPE: DNA
<213> ORGANISM: Artificial Sequence
<220> FEATURE:
<223> OTHER INFORMATION: Large Intron-GENEius 1(ApoE-HCR-hAAT.cG-AIATI.hPAHco1.bGH) sequence

<400> SEQUENCE: 18

```
cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120
```

-continued

```
actccatcac taggggttcc tgcggccgca cgcgtaggct cagaggcaca caggagtttc    180
tgggctcacc ctgcccccttt ccaacccctc agttcccatc ctccagcagc tgtttgtgtg    240
ctgcctctga agtccacact gaacaaactt cagcctactc atgtccctaa aatgggcaaa    300
cattgcaagc agcaaacagc aaacacacag ccctccctgc ctgctgacct tggagctggg    360
gcagaggtca gagacctctc tgggcccatg ccacctccaa catccactcg acccccttgga    420
atttcggtgg agaggagcag aggttgtcct ggcgtggttt aggtagtgtg agaggggtcg    480
acgatcttgc taccagtgga acagccacta aggattctgc agtgagagca gagggccagc    540
taagtggtac tctcccagag actgtctgac tcacgccacc ccctccacct tggacacagg    600
acgctgtggt ttctgagcca ggtacaatga ctcctttcgg taagtgcagt ggaagctgta    660
cactgcccag gcaaagcgtc cgggcagcgt aggcgggcga ctcagatccc agccagtgga    720
cttagcccct gtttgctcct ccgataactg gggtgacctt ggttaatatt caccagcagc    780
ctcccccgtt gcccctctgg atccactgct taaatacgga cgaggacagg gccctgtctc    840
ctcagcttca ggcaccacca ctgacctggg acagtgaatc gtaagtatgc ctttcactgc    900
gaggggttct ggagaggctt ctgagctccc catggcccag gcaggcagca ggtctggggc    960
aggagggggg ttgtggagtg ggtatccgcc tgctgaggtg cagggcagat ggagaggctg   1020
cagctgagct cctattttca taataacagc agccatgagg gttgtgtcct gtttcccagt   1080
cctgcccggt ccccccctcgg tacctcctgg tggatacact ggttcctgta agcagaagtg   1140
gatgagggtg tctaggtctg cagtcctggc accccaggat gggggacacc agccaagata   1200
cagcaacagc aacaaagcgc agccatttct ttctgtttgc acagctcctc tgtctgtcgg   1260
gggctcctgt ctgttgtctc ctataagcct caccacctct cctactgctt gggcatgcat   1320
ctttctcccc ttctatagat gaggaggtta aggtccagag aggggtgggg aggaacgccg   1380
gctcacattc tccatcccct ccagatatga ccaggaacag acctgtgcca ggcctcagcc   1440
ttacatcaaa atgggcctcc ccatgcaccg tggacctctg ggccctcctg tcccagtgga   1500
ggacaggaag ctatgagggg cactgtcacc cagggctcaa gctggcattc ctgaataatc   1560
gctctgcacc aggccacggc taagctcagt gcgtgattaa gcctcataac cctccaaggc   1620
agttactagt gtgattccca ttttacagat gaggaagatg gggacagaga ggtgaataac   1680
tggccccaaa tcacacacca tccataattc gggctcaggc acctggctcc agtccccaaa   1740
ctcttgaacc tggccctagt gtcactgttt ctcttgggtc tcaggcgctg gatggggaac   1800
aggaaacctg ggctggactt gaggcctctc tgatgctcgg tgacttcaga cagttgctca   1860
acctctctgt tctcttgggc aaaacatgat aacctttgac ttctgtcccc tcccctcacc   1920
ccacccgacc ttgatctctg aagtgttgga aggatttaat ttttcctgca ctgagttttg   1980
gagacaggtc aaaaagatga ccaaggccaa ggtggccagt ttcctataga acgcctctaa   2040
aagacctgca gcaatagcag caagaactgg tattctcgag aacttgctgc gcagcaggca   2100
cttcttggca ttttatgtgt atttaatttc acaatagctc tatgacaaag tccacctttc   2160
tcatctccag gaaactgagg ttcagagagg ttaagtaact tgtccaaggt cacacagcta   2220
atagcaagtt gacgtggagc aatctggcct cagagccttt aattttagcc acagactgat   2280
gctcccctct tcatttagcc aggctgcctc tgaagttttc tgattcaaga cttctggctt   2340
cagctttgta cacagagatg attcaatgtc aggttttgga gtgaaatctg tttaatccca   2400
gacaaaacat ttaggattac atctcagttt tgtaagcaag tagctctgtg atttttagtg   2460
agttatttaa tgctctttgg ggctcaattt ttctatctat aaaatagggc taataatttg   2520
```

caccttatag ggtaagcttt gaggacagat tagatgatac ggtgcctgta aaacaccagg 2580
tgttagtaag tgtggcaatg atggtgacgc tgaggctgat gtttgcttag catagggtta 2640
ggcagctggc aggcagtaaa cagttggata atttaatgga aaatttgcca aactcagatg 2700
ctagcagcta caatccagct accattctgc ttttatttta tggttgggat aaggctggat 2760
tattctgagt ccaagctagg cccttttgct aatcatgttc atacctctta tcttcctccc 2820
acagctcctg ggcaacgtgc tggtctgtgt gctggcccat cactttggca aagaattgcg 2880
atcgccacca tgagcactgc tgtgctggag aaccctggcc tgggcagaaa gctgtctgac 2940
tttggccagg agaccagcta cattgaggac aactgcaacc agaatggagc catcagcctg 3000
atcttcagcc tgaaggagga ggtgggagcc ctggccaagg tgctgagact gtttgaggag 3060
aatgatgtga acctgaccca cattgagagc agacccagca gactgaagaa ggatgagtat 3120
gagttcttca cccacctgga caagagaagc ctgcctgccc tgaccaacat catcaagatc 3180
ctgagacacg atattggagc cactgtgcac gagctgagca gagacaagaa gaaggacact 3240
gtgccctggt tccccagaac tatccaggag ctggacagat ttgccaacca gatcctgagc 3300
tatggagctg agctggatgc tgaccaccct ggcttcaagg accctgtgta cagagccaga 3360
agaaagcagt ttgctgacat tgcctacaac tacagacacg gccagcccat ccccagagtg 3420
gagtacatgg aggaggagaa gaagacctgg ggcactgtgt tcaagaccct gaagagcctg 3480
tacaagaccc acgcctgcta tgagtacaac cacatcttcc ccctgctgga gaagtactgt 3540
ggcttccacg aggacaacat cccccagctg gaggatgtga gccagttcct gcagacctgc 3600
actggcttca gactgagacc tgtggctggc ctgctgagca gcagagactt cctgggggc 3660 ctggccttca gagtgttcca ctgcacccag tacatcagac acggcagcaa gcccatgtac 3720
acccctgagc ctgatatctg ccacgagctg ctgggccacg tgcccctgtt ctctgacaga 3780
agctttgccc agttcagcca ggagattggc ctggccagcc tgggagcccc tgatgagtat 3840
attgagaagc tggccactat ctactggttc actgtggagt ttggcctgtg caagcagggg 3900
gacagcatca aggcctatgg agctggcctg ctgagcagct ttggggagct gcagtactgc 3960
ctgtctgaga agcccaagct gctgcccctg gagctggaga agactgccat ccagaactac 4020
actgtgactg agttccagcc cctgtactat gtggctgaga gcttcaatga tgccaaggag 4080
aaggtgagaa actttgctgc caccatcccc agacccttct ctgtgagata tgacccctac 4140
acccagagaa ttgaggtgct ggacaacacc cagcagctga agatcctggc tgacagcatc 4200
aactctgaga ttggcatcct gtgctctgcc ctgcagaaga tcaagtaacc tcgagctgtg 4260
ccttctagtt gccagccatc tgttgtttgc ccctcccccg tgccttcctt gaccctggaa 4320
ggtgccactc ccactgtcct ttcctaataa aatgaggaaa ttgcatcgca ttgtctgagt 4380
aggtgtcatt ctattctggg gggtggggtg gggcaggaca gcaaggggga ggattgggaa 4440
gacaatagca ggcatgctgg ggatgcggtg ggctctatgg accggtgcgg ccgcaggaac 4500
ccctagtgat ggagttggcc actccctctc tgcgcgctcg ctcgctcact gaggccgggc 4560
gaccaaaggt cgcccgacgc ccgggctttg cccgggcggc ctcagtgagc gagcgagcgc 4620
gcagctgcct gcagg 4635

<210> SEQ ID NO 19
<211> LENGTH: 4640
<212> TYPE: DNA
<213> ORGANISM: Artificial Sequence
<220> FEATURE:

-continued

<223> OTHER INFORMATION: hPAH+truncated 2nd intron (ApoE-HCR-hAAT.hPAH-
      tI2.bGH) sequence

<400> SEQUENCE: 19

```
cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tgcggccgca cgcgtaggct cagaggcaca caggagtttc    180

tgggctcacc ctgccccctt ccaacccctc agttcccatc ctccagcagc tgtttgtgtg    240

ctgcctctga agtccacact gaacaaactt cagcctactc atgtccctaa aatgggcaaa    300

cattgcaagc agcaaacagc aaacacacag ccctccctgc ctgctgacct tggagctggg    360

gcagaggtca gagacctctc tgggcccatg ccacctccaa catccactcg accccttgga    420

atttcggtgg agaggagcag aggttgtcct ggcgtggttt aggtagtgtg agaggggtcg    480

acgatcttgc taccagtgga acagccacta aggattctgc agtgagagca gagggccagc    540

taagtggtac tctcccagag actgtctgac tcacgccacc ccctccacct tggacacagg    600

acgctgtggt ttctgagcca ggtacaatga ctcctttcgg taagtgcagt ggaagctgta    660

cactgcccag gcaaagcgtc cgggcagcgt aggcgggcga ctcagatccc agccagtgga    720

cttagcccct gtttgctcct ccgataactg gggtgacctt ggttaatatt caccagcagc    780

ctcccccgtt gcccctctgg atccactgct taaatacgga cgaggacagg gccctgtctc    840

ctcagcttca ggcaccacca ctgacctggg acagtgaatc agccagagac ctcactcccg    900

gggagccagc atgtccactg cggtcctgga aaacccaggc ttgggcagga aactctctga    960

ctttggacag gaaacaagct atattgaaga caactgcaat caaaatggtg ccatatcact   1020

gatcttctca ctcaaagaag aagttggtgc attggccaaa gtattgcgct tatttgaggt   1080

cagtgctaca atcatgtttg tcttggataa tgtcgtagca aacttccatg ttcttttcta   1140

gttagatgca atgaaaagaa cacaggatct ggaacaggca gatttgaatt tgagctcaag   1200

tttttacatt aaccaactgt gtgaccttag ttaagtcatt caatctctct gagcttcagt   1260

ttttccattc ataatatagt gctgataata tgtgccttgt cagtttcaac aggaactttg   1320

tgatgaaata atgtgttttg taaaatgcct aatcatatgt gtgattaggc atgattaact   1380

ataagtcata tgtgacacgt gattacattt cacataacat gtaatcacat gtgtcacatg   1440

tgattacagt taaagagtaa acaagaaata aatattaatt cttttattca ctaaattaat   1500

attgattgtc ttctatgtat aagtgtaaaa taatatgcaa gacaccgtcc ctttcttcaa   1560

gtagcttaac ccaaaactat gctttagaaa atagctaatg ttcttcaaga cattggtaaa   1620

tgtcttatga ttaaagtggt tccataatta ataaacttgg gaaattcggg catattattt   1680

tacctgattt ctttattata ggacttttag agtctataaa actaattata ctaagttgtt   1740

tacagagaga aatgtatgta ttattttcca aacttacttg actgtggatc ctttttattt   1800

taagaacatg tattcacatc tgggaacaga gtttaggaaa cgttgatttg ggtgtttgct   1860

gggcagccaa acttcacaga actccaaata ggtttcctca gccagattcc ttccgagtac   1920

tatgctaata tttttggtgg gattttgtcc cacctgaaaa tacattgctt tatgctaaga   1980

ttcctgtgac ctctctagct gattgggagg caggggtagc acattggtca gggctgtgca   2040

catacttagt gctcagtgtg tttgggcatg caatcaacaa atccttttgg ggcatgactg   2100

gatacgatta gatatcttgt gaaaacctat gatgttctca gcactgtggg tggggaggaa   2160

gatgggggac acatagaaat tgtaaggaag agaaactgcc tcctttagga tctaacaggg   2220
```

gaagcaaata ttctgagcag ctggggaggg aaggcagagc atgagaagtt atctcagtaa 2280
aaggtagctt tatagacatg atcttattca gtctaatgaa aataacatga ggtaggagct 2340
atttctgccc ccatttttca gagatagaaa ctgatgctta gaggggttag gtaaatgtgc 2400
ccaaggtcaa acagctagta aatacggaag aaatcattta aacccaggca ttctgagtct 2460
agaacctaca tacactctta actgctattc agtactgccc cagacagaac gggcttcata 2520
gtttgcaggg cgcagtgcaa aatgaaaacg tggggtctct tcctcaataa caggaaataa 2580
tgctgttaaa agtactaaaa tatataactt tatcctttct tctgtggtct ctctcatgtc 2640
ctgttatggt gtttttgatt tgccatttag ttgtgctctc ctcccctggg caccttggcc 2700
ctctaactgc tgggttccct gtccagccag ggctgggctg acagccaagc ccctaccaag 2760
gatggggaaa tccatcttcc atttccgtgg acctgctgca ccaacccaca gtgatgagct 2820
atcccccaag agattgtaac ctctggaatg agaatggaaa ggaagcttgc ctgaacttgg 2880
ttttaaagaa gaaaaagtaa acaacttttg caaatttaag gacttttta tactcttata 2940
aaaataattg tattcttgaa ctctccattt tgttgcgtta ggttttcctg ttctggttct 3000
gcatctttgg cctgcgttag ttccagtgac tgtctcctca ccctccccat tctctcttct 3060
aggagaatga tgtaaacctg acccacattg aatctagacc ttctcgttta aagaaagatg 3120
agtatgaatt tttcacccat ttggataaac gtagcctgcc tgctctgaca aacatcatca 3180
agatcttgag gcatgacatt ggtgccactg tccatgagct ttcacgagat aagaagaaag 3240
acacagtgcc ctggttccca agaaccattc aagagctgga cagatttgcc aatcagattc 3300
tcagctatgg agcggaactg gatgctgacc accctggttt taaagatcct gtgtaccgtg 3360
caagacggaa gcagtttgct gacattgcct acaactaccg ccatgggcag cccatccctc 3420
gagtggaata catggaggaa gaaaagaaaa catggggcac agtgttcaag actctgaagt 3480
ccttgtataa aacccatgct tgctatgagt acaatcacat tttccactt cttgaaaagt 3540
actgtggctt ccatgaagat aacattcccc agctggaaga cgtttctcag ttcctgcaga 3600
cttgcactgg tttccgcctc cgacctgtag ctggcctgct ttcctctcgg gatttcttgg 3660
gtggcctggc cttccgagtc ttccactgca cacagtacat cagacatgga tccaagccca 3720
tgtatacccc cgaacctgac atctgccatg agctgttggg acatgtgccc ttgttttcag 3780
atcgcagctt tgcccagttt tcccaggaaa ttggccttgc ctctctgggt gcacctgatg 3840
aatacattga aaagctcgcc acaatttact ggtttactgt ggagtttggg ctctgcaaac 3900
aaggagactc cataaaggca tatggtgctg ggctcctgtc atcctttggt gaattacagt 3960
actgcttatc agagaagcca aagcttctcc ccctggagct ggagaagaca gccatccaaa 4020
attacactgt cacggagttc cagcccctgt attacgtggc agagagtttt aatgatgcca 4080
aggagaaagt aaggaacttt gctgccacaa tacctcggcc cttctcagtt cgctacgacc 4140
catacaccca aaggattgag gtcttggaca atacccagca gcttaagatt ttggctgatt 4200
ccattaacag tgaaattgga atcctttgca gtgccctcca gaaaataaag taacctcgag 4260
ctgtgccttc tagttgccag ccatctgttg tttgcccctc ccccgtgcct tccttgaccc 4320
tggaaggtgc cactcccact gtcctttcct aataaaatga ggaaattgca tcgcattgtc 4380
tgagtaggtg tcattctatt ctggggggtg gggtggggca ggacagcaag ggggaggatt 4440
gggaagacaa tagcaggcat gctggggatg cggtgggctc tatggaccgg tgcggccgca 4500
ggaaccccta gtgatggagt tggccactcc ctctctgcgc gctcgctcgc tcactgaggc 4560
cgggcgacca aaggtcgccc gacgcccggg ctttgcccgg gcggcctcag tgagcgagcg 4620
agcgcgcagc tgcctgcagg 4640

<210> SEQ ID NO 20
<211> LENGTH: 2822
<212> TYPE: DNA
<213> ORGANISM: Artificial Sequence
<220> FEATURE:
<223> OTHER INFORMATION: pFB-ApoE-hAAT-hPAH-Genius2 (vector sequence)

<400> SEQUENCE: 20
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccgca cgcgtaggct cagaggcaca caggagtttc 180
tgggctcacc ctgcccccctt ccaacccctc agttcccatc ctccagcagc tgtttgtgtg 240
ctgcctctga agtccacact gaacaaactt cagcctactc atgtccctaa aatgggcaaa 300
cattgcaagc agcaaacagc aaacacacag ccctccctgc ctgctgacct tggagctggg 360
gcagaggtca gagacctctc tgggcccatg ccacctccaa catccactcg acccccttgga 420 atttcggtgg agaggagcag aggttgtcct ggcgtggttt aggtagtgtg agaggggtcg 480
acgatcttgc taccagtgga acagccacta aggattctgc agtgagagca gagggccagc 540
taagtggtac tctcccagag actgtctgac tcacgccacc ccctccacct tggacacagg 600
acgctgtggt ttctgagcca ggtacaatga ctcctttcgg taagtgcagt ggaagctgta 660
cactgcccag gcaaagcgtc cgggcagcgt aggcgggcga ctcagatccc agccagtgga 720
cttagcccct gtttgctcct ccgataactg gggtgacctt ggttaatatt caccagcagc 780
ctcccccgtt gcccctctgg atccactgct taaatacgga cgaggacagg gccctgtctc 840
ctcagcttca ggcaccacca ctgacctggg acagtgaatc gtaagtacta gcagctacaa 900
tccagctacc attctgcttt tattttatgg ttgggataag gctggattat tctgagtcca 960
agctaggccc ttttgctaat catgttcata cctcttatct tcctcccaca gctcctgggc 1020
aacgtgctgg tctgtgtgct ggcccatcac tttggcaaag aattgcgatc gccaccatga 1080
gcactgctgt gctggagaac cctggcctgg gcagaaagct gtctgacttt ggccaggaga 1140
ccagctacat tgaggacaac tgcaaccaga atggggccat cagcctgatc ttcagcctga 1200
aggaggaggt gggggccctg gccaaggtgc tgagactgtt tgaggagaat gatgtgaacc 1260
tgacccacat tgagagcaga cccagcagac tgaagaagga tgagtatgag ttcttcaccc 1320
acctggacaa gagaagcctg cctgccctga ccaacatcat caagatcctg agacacgata 1380
ttggggccac tgtgcacgag ctgagcagag acaagaagaa ggacactgtg ccctggttcc 1440
ccagaactat ccaggagctg gacagatttg ccaaccagat cctgagctat ggggctgagc 1500
tggatgctga ccaccctggc ttcaaggacc ctgtgtacag agccagaaga aagcagtttg 1560
ctgacattgc ctacaactac agacacggcc agcccatccc cagagtggag tacatggagg 1620
aggagaagaa gacctggggc actgtgttca agaccctgaa gagcctgtac aagacccacg 1680
cctgctatga gtacaaccac atcttccccc tgctggagaa gtactgtggc ttccacgagg 1740
acaacatccc ccagctggag gatgtgagcc agttcctgca gacctgcact ggcttcagac 1800
tgagacctgt ggctggcctg ctgagcagca gagacttcct ggggggcctg gccttcagag 1860
tgttccactg cacccagtac atcagacacg gcagcaagcc catgtacacc cctgagcctg 1920
atatctgcca cgagctgctg ggccacgtgc ccctgttctc tgacagaagc tttgcccagt 1980

-continued

```
tcagccagga gattggcctg gccagcctgg gggcccctga tgagtatatt gagaagctgg   2040

ccactatcta ctggttcact gtggagtttg gcctgtgcaa gcagggggac agcatcaagg   2100

cctatggggc tggcctgctg agcagctttg ggagctgca gtactgcctg tctgagaagc    2160

ccaagctgct gcccctggag ctggagaaga ctgccatcca gaactacact gtgactgagt   2220

tccagcccct gtactatgtg gctgagagct tcaatgatgc caaggagaag gtgagaaact   2280

ttgctgccac catccccaga cccttctctg tgagatacga cccctacacc cagagaattg   2340

aggtgctgga caacacccag cagctgaaga tcctggctga cagcatcaac tctgagattg   2400

gcatcctgtg ctctgccctg cagaagatca agtgacctcg agctgtgcct tctagttgcc   2460

agccatctgt tgtttgcccc tcccccgtgc cttccttgac cctggaaggt gccactccca   2520

ctgtcctttc ctaataaaat gaggaaattg catcgcattg tctgagtagg tgtcattcta   2580

ttctgggggg tggggtgggg caggacagca agggggagga ttgggaagac aatagcaggc   2640

atgctgggga tgcggtgggc tctatggacc ggtgcggccg caggaacccc tagtgatgga   2700

gttggccact ccctctctgc gcgctcgctc gctcactgag gccgggcgac caaaggtcgc   2760

ccgacgcccg ggctttgccc gggcggcctc agtgagcgag cgagcgcgca gctgcctgca   2820

gg                                                                  2822
```

<210> SEQ ID NO 21
<211> LENGTH: 2822
<212> TYPE: DNA
<213> ORGANISM: Artificial Sequence
<220> FEATURE:
<223> OTHER INFORMATION: pFB-ApoE-hAAT-hPAH-JCAT (vector sequence)

<400> SEQUENCE: 21

```
cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tgcggccgca cgcgtaggct cagaggcaca caggagtttc    180

tgggctcacc ctgccccctt ccaacccctc agttcccatc ctccagcagc tgtttgtgtg    240

ctgcctctga agtccacact gaacaaactt cagcctactc atgtccctaa aatgggcaaa    300

cattgcaagc agcaaacagc aaacacacag ccctccctgc ctgctgacct tggagctggg    360

gcagaggtca gagacctctc tgggcccatg ccacctccaa catccactcg acccccttgga   420

atttcggtgg agaggagcag aggttgtcct ggcgtggttt aggtagtgtg agaggggtcg    480

acgatcttgc taccagtgga acagccacta aggattctgc agtgagagca gagggccagc    540

taagtggtac tctcccagag actgtctgac tcacgccacc ccctccacct tggacacagg    600

acgctgtggt ttctgagcca ggtacaatga ctcctttcgg taagtgcagt ggaagctgta    660

cactgcccag gcaaagcgtc cgggcagcgt aggcgggcga ctcagatccc agccagtgga    720

cttagcccct gtttgctcct ccgataactg ggtgaccttt ggttaatatt caccagcagc    780

ctcccccgtt gcccctctgg atccactgct taaatacgga cgaggacagg gccctgtctc    840

ctcagcttca ggcaccacca ctgacctggg acagtgaatc gtaagtacta gcagctacaa    900

tccagctacc attctgcttt tattttatgg ttgggataag gctggattat tctgagtcca    960

agctaggccc ttttgctaat catgttcata cctcttatct tcctcccaca gctcctgggc   1020

aacgtgctgg tctgtgtgct ggcccatcac tttggcaaag aattgcgatc gccaccatga   1080

gcactgctgt gctggagaac cctggcctgg gcagaaagct gtctgacttt ggccaggaga   1140

ccagctacat tgaggacaac tgcaaccaga atggggccat cagcctgatc ttcagcctga   1200
```

aggaggaggt gggggccctg gccaaggtgc tgagactgtt tgaggagaat gatgtgaacc 1260
tgacccacat tgagagcaga cccagcagac tgaagaagga tgagtatgag ttcttcaccc 1320
acctggacaa gagaagcctg ccagccctga ccaatattat caagatcctg aggcacgata 1380
ttggggccac agtgcacgag ctgagcagag acaagaagaa ggacacagtg ccctggttcc 1440
ccaggactat ccaggagctg gacaggtttg ccaaccagat cctgagctac ggagctgagc 1500
tggatgcaga ccaccctggc ttcaaggacc ctgtgtacag agccaggaga aagcagtttg 1560
cagatatagc ctacaactac aggcacggcc agccaatccc tagagtggag tacatggagg 1620
aggagaagaa gacctggggc actgtgttca agaccctgaa gagcctgtac aagacccacg 1680
cctgctacga gtacaaccac atcttccccc tgctggagaa gtactgtggc ttccacgagg 1740
acaacatccc ccagctggag gatgtgagcc agttcctgca gacctgcaca ggcttcaggc 1800
tgagaccagt ggcaggcctg ctgagcagca gggacttcct gggggggcctg gccttcagag 1860 tgttccactg cacccagtat atcaggcacg gcagcaagcc aatgtacacc cctgagccag 1920
atatctgcca cgagctgctg ggccacgttc ccctgttctc agacagaagc tttgcccagt 1980
tcagccagga gattggcctg gccagcctgg gggcccctga cgagtatatt gagaagctgg 2040
ccactatcta ctggttcaca gtggagtttg gcctgtgcaa gcagggggac agcatcaagg 2100
cctatggggc tggcctgctg agcagctttg gggagctgca gtactgcctg tcagagaagc 2160
caaagctgct gcccctggag ctggagaaga cagctatcca gaactacact gtgactgagt 2220
tccagcccct gtactatgtg gcagagagct tcaatgatgc caaggagaag gtgagaaact 2280
ttgctgccac catccccagg cccttctctg tgagatatga cccctacacc cagaggattg 2340
aggtgctgga caacacccag cagctgaaga tcctggcaga cagcatcaac agtgagattg 2400
gtatcctgtg ctctgccctg cagaagatca agtaacctcg agctgtgcct tctagttgcc 2460
agccatctgt tgtttgcccc tcccccgtgc cttccttgac cctggaaggt gccactccca 2520
ctgtcctttc ctaataaaat gaggaaattg catcgcattg tctgagtagg tgtcattcta 2580
ttctgggggg tggggtgggg caggacagca agggggagga ttgggaagac aatagcaggc 2640
atgctgggga tgcggtgggc tctatggacc ggtgcggccg caggaacccc tagtgatgga 2700
gttggccact ccctctctgc gcgctcgctc gctcactgag gccgggcgac caaaggtcgc 2760
ccgacgcccg ggctttgccc gggcggcctc agtgagcgag cgagcgcgca gctgcctgca 2820
gg 2822

<210> SEQ ID NO 22
<211> LENGTH: 2674
<212> TYPE: DNA
<213> ORGANISM: Artificial Sequence
<220> FEATURE:
<223> OTHER INFORMATION: pFB-hPAHV1-TBG2uGlob (vector sequence)

<400> SEQUENCE: 22
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccgca cgcgtcaggt taatttttaa aaagcagtca 180
aaagtccaag tggcccttgg cagcatttac tctctctgtt tgctctggtt aataatctca 240
ggagcacaaa cattccagat ccaggttaat ttttaaaaag cagtcaaaag tccaagtggc 300
ccttggcagc atttactctc tctgtttgct ctggttaata atctcaggag cacaaacatt 360

-continued

```
ccagatccgg cgcgccaggg ctggaagcta cctttgacat catttcctct gcgaatgcat    420
gtataatttc tacagaacct attagaaagg atcacccagc ctctgctttt gtacaacttt    480
cccttaaaaa actgccaatt ccactgctgt ttggcccaat agtgagaact ttttcctgct    540
gcctcttggt gcttttgcct atggccccta ttctgcctgc tgaagacact cttgccagca    600
tggacttaaa cccctccagc tctgacaatc ctctttctct tttgttttac atgaagggtc    660
tggcagccaa agcaatcact caaagttcaa accttatcat tttttgcttt gttcctcttg    720
gccttggttt tgtacatcag ctttgaaaat accatcccag ggttaatgct ggggttaatt    780
tataactaag agtgctctag ttttgcaata caggacatgc tataaaaatg gaaagatgtt    840
gctttctgag agatgcaggt ggattcttgg gcatttgctg taagtactag cagctacaat    900
ccagctacca ttctgctttt attttatggt tgggataagg ctggattatt ctgagtccaa    960
gctaggccct tttgctaatc atgttcatac ctcttatctt cctcccacag ctcctgggca   1020
acgtgctggt ctgtgtgctg gcccatcact ttggcaaaga attgcgatcg ccaccatgtc   1080
cactgcggtc ctggaaaacc caggcttggg caggaaactc tctgactttg gacaggaaac   1140
aagctatatt gaagacaact gcaatcaaaa tggtgccata tcactgatct tctcactcaa   1200
agaagaagtt ggtgcattgg ccaaagtatt gcgcttattt gaggagaatg atgtaaacct   1260
gacccacatt gaatctagac cttctcgttt aaagaaagat gagtatgaat ttttcaccca   1320
tttggataaa cgtagcctgc ctgctctgac aaacatcatc aagatcttga ggcatgacat   1380
tggtgccact gtccatgagc tttcacgaga taagaagaaa gacacagtgc cctggttccc   1440
aagaaccatt caagagctgg acagatttgc caatcagatt ctcagctatg gagcggaact   1500
ggatgctgac caccctggtt ttaaagatcc tgtgtaccgt gcaagacgga agcagtttgc   1560
tgacattgcc tacaactacc gccatgggca gcccatccct cgagtggaat acatggagga   1620
agaaaagaaa acatggggca cagtgttcaa gactctgaag tccttgtata aaacccatgc   1680
ttgctatgag tacaatcaca tttttccact tcttgaaaag tactgtggct tccatgaaga   1740
taacattccc cagctggaag acgtttctca gttcctgcag acttgcactg gtttccgcct   1800
ccgacctgta gctggcctgc tttcctctcg ggatttcttg ggtggcctgg ccttccgagt   1860
cttccactgc acacagtaca tcagacatgg atccaagccc atgtataccc ccgaacctga   1920
catctgccat gagctgttgg gacatgtgcc cttgttttca gatcgcagct ttgcccagtt   1980
ttcccaggaa attggccttg cctctctggg tgcacctgat gaatacattg aaaagctcgc   2040
cacaatttac tggtttactg tggagtttgg gctctgcaaa caaggagact ccataaaggc   2100
atatggtgct gggctcctgt catcctttgg tgaattacag tactgcttat cagagaagcc   2160
aaagcttctc cccctggagc tggagaagac agccatccaa aattacactg tcacggagtt   2220
ccagcccctg tattacgtgg cagagagttt taatgatgcc aaggagaaag taaggaactt   2280
tgctgccaca atacctcggc ccttctcagt tcgctacgac ccatacaccc aaaggattga   2340
ggtcttggac aatacccagc agcttaagat tttggctgat tccattaaca gtgaaattgg   2400
aatcctttgc agtgccctcc agaaaataaa gtaacctcga gctgtgcctt ctagttgcca   2460
gccatctgtt gtttgcccct cccccgtgcc ttccttgacc ctggaaggtg ccactcccac   2520
tgtcctttcc taataaaatg aggaaattgc atcgcattgt ctgagtaggt gtcattctat   2580
tctggggggt ggggtggggc aggacagcaa gggggaggat tgggaagaca atagcaggca   2640
tgctggggat gcggtgggct ctatggaccg gtgc                               2674
```

<210> SEQ ID NO 23
<211> LENGTH: 2387
<212> TYPE: DNA
<213> ORGANISM: Artificial Sequence
<220> FEATURE:
<223> OTHER INFORMATION: pFB-hPAHV1-TTR (vector sequence)

<400> SEQUENCE: 23

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccgcg tctgtctgca catttcgtag agcgagtgtt    180
ccgatactct aatctcccta ggcaaggttc atattgactt aggttactta ttctcctttt    240
gttgactaag tcaataatca gaatcagcag gtttggagtc agcttggcag ggatcagcag    300
cctgggttgg aaggaggggg tataaaagcc ccttcaccag gagaagccgt cacacagatc    360
cacaagctcc tgacaggagg cttcccttcg actcttcctc ctttgcctcg ctggactggt    420
atttgtgtct gaagctggcc ccgcggtaag tactagcagc tacaatccag ctaccattct    480
gcttttattt tatggttggg ataaggctgg attattctga gtccaagcta ggcccttttg    540
ctaatcatgt tcatacctct tatcttcctc ccacagctcc tgggcaacgt gctggtctgt    600
gtgctggccc atcactttgg caaagaattg cgatcgccac catgtccact gcggtcctgg    660
aaaacccagg cttgggcagg aaactctctg actttggaca ggaaacaagc tatattgaag    720
acaactgcaa tcaaaatggt gccatatcac tgatcttctc actcaaagaa gaagttggtg    780
cattggccaa agtattgcgc ttatttgagg agaatgatgt aaacctgacc cacattgaat    840
ctagaccttc tcgtttaaag aaagatgagt atgaattttt cacccatttg gataaacgta    900
gcctgcctgc tctgacaaac atcatcaaga tcttgaggca tgacattggt gccactgtcc    960
atgagctttc acgagataag aagaaagaca cagtgccctg gttcccaaga accattcaag   1020
agctggacag atttgccaat cagattctca gctatggagc ggaactggat gctgaccacc   1080
ctggttttaa agatcctgtg taccgtgcaa gacggaagca gtttgctgac attgcctaca   1140
actaccgcca tgggcagccc atccctcgag tggaatacat ggaggaagaa aagaaaacat   1200
ggggcacagt gttcaagact ctgaagtcct tgtataaaac ccatgcttgc tatgagtaca   1260
atcacatttt tccacttctt gaaaagtact gtggcttcca tgaagataac attccccagc   1320
tggaagacgt ttctcagttc ctgcagactt gcactggttt ccgcctccga cctgtagctg   1380
gcctgctttc ctctcgggat ttcttgggtg gcctggcctt ccgagtcttc cactgcacac   1440
agtacatcag acatggatcc aagcccatgt ataccccga acctgacatc tgccatgagc   1500
tgttgggaca tgtgcccttg ttttcagatc gcagctttgc ccagttttcc caggaaattg   1560
gccttgcctc tctgggtgca cctgatgaat acattgaaaa gctcgccaca atttactggt   1620
ttactgtgga gtttgggctc tgcaaacaag gagactccat aaaggcatat ggtgctgggc   1680
tcctgtcatc ctttggtgaa ttacagtact gcttatcaga gaagccaaag cttctccccc   1740
tggagctgga gaagacagcc atccaaaatt acactgtcac ggagttccag cccctgtatt   1800
acgtggcaga gagttttaat gatgccaagg agaaagtaag gaactttgct gccacaatac   1860
ctcggccctt ctcagttcgc tacgacccat acacccaaag gattgaggtc ttggacaata   1920
cccagcagct taagattttg gctgattcca ttaacagtga aattggaatc ctttgcagtg   1980
ccctccagaa aataaagtaa cctcgagctg tgccttctag ttgccagcca tctgttgttt   2040
gcccctcccc cgtgccttcc ttgaccctgg aaggtgccac tcccactgtc ctttcctaat   2100
```

-continued

```
aaaatgagga aattgcatcg cattgtctga gtaggtgtca ttctattctg gggggtgggg 2160

tggggcagga cagcaagggg gaggattggg aagacaatag caggcatgct ggggatgcgg 2220

tgggctctat ggaccggtgc ggccgcagga acccctagtg atggagttgg ccactccctc 2280

tctgcgcgct cgctcgctca ctgaggccgg gcgaccaaag gtcgcccgac gcccgggctt 2340

tgcccgggcg gcctcagtga gcgagcgagc gcgcagctgc ctgcagg 2387
```

METHODS OF TREATING PHENYLKETONURIA

CROSS-REFERENCE TO RELATED APPLICATIONS

This application claims the benefit of U.S. Provisional Patent Application No. 62/819,414, filed Mar. 15, 2019, U.S. Provisional Patent Application No. 62/802,608, filed Feb. 7, 2019, U.S. Provisional Patent Application No. 62/755,207, filed Nov. 2, 2018, and U.S. Provisional Patent Application No. 62/669,292, filed May 9, 2018, each of which is incorporated by reference herein in its entirety.

SEQUENCE LISTING

This application incorporates by reference in its entirety the Computer Readable Form (CRF) of a Sequence Listing in ASCII text format submitted via EFS-Web. The Sequence Listing text file submitted via EFS-Web is entitled "11808-407-999.txt," was created on Jul. 18, 2019, and having a size of 68,907 bytes.

1. FIELD

Provided herein is a use of amino acid, neurotransmitter, and neurotransmitter metabolite levels in subjects having phenylketonuria (PKU) to optimize an effective dose of a PKU therapeutic. Also provided are methods of treating subjects having PKU comprising administering an effective amount of a PKU therapeutic where the effective amount is one that normalizes levels of amino acids, neurotransmitters, and neurotransmitter metabolites in the subject. Also provided herein is an optimized coding sequence of phenylalanine hydroxylase (PAH), which may be used in such vectors as recombinant adeno-associated virus (rAAV) vectors to achieve long term expression of PAH, the enzyme responsible for the metabolism of phenylalanine, in the liver of a subject. Also provided are methods of treatment utilizing the vectors in a gene replacement approach.

2. BACKGROUND

Phenylketonuria (PKU) is an inborn error of amino acid metabolism that results from impaired activity of hepatic phenylalanine hydroxylase (PAH), the enzyme responsible for the metabolism of phenylalanine. Patients with PAH mutations that lead to PKU and hyperphenylalaninemia (HPA) display elevated levels of phenylalanine, impaired neurophysiologic functioning, and reduced cognitive development. For patients with severe PKU, there is the potential for irreversible mental retardation unless phenylalanine levels are maintained at low levels using dietary restrictions. The neurological symptoms of PKU are caused by the abnormal production of a number of neurotransmitters in subjects having PKU resulting from a loss of PAH which is required to convert phenylalanine into the precursor metabolite required for the synthesis of a number of neurotransmitters.

Current treatment for PKU includes the lifetime adherence to a diet that is low in the amino acid phenylalanine. This dietary therapy is difficult to maintain and does not always eliminate the damaging neurological effects that can be caused by elevated phenylalanine levels. Less than ideal dietary control during pregnancy can lead to birth defects. In addition, it is very difficult for PKU/HPA patients to live a normal life while following the restricted diet, and dietary therapy can be associated with deficiencies of several nutrients, some of which are detrimental for brain development. Most low phenylalanine diet products have organoleptic properties sufficiently unsatisfactory that compliance with this treatment is compromised. Therefore, development of a therapeutic treatment would replace or supplement the current dietary treatment and prevent the neurological damages inflicted on those individuals with PKU, particularly for those patients with the most severe forms of the disease. However, an optimal PKU therapeutic would be one that normalizes levels of amino acids, neurotransmitters, and neurotransmitter metabolites whose levels are altered as a result of insufficient PAH activity. Accordingly, there is a clinical need for PKU therapeutics that when delivered in an effective amount are able to normalize levels of particular amino acids, neurotransmitters, and neurotransmitter metabolites in subjects having PKU.

Gene therapy offers the potential of a cure through continuous endogenous production of PAH following a single administration of vector. This would represent a major clinical advance with significant implications for other congenital disorders that lack effective treatment. Adeno-associated virus (AAV) is a small, replication-defective, non-enveloped animal virus that infects humans and some other primate species. Several features of AAV make this virus an attractive vehicle for delivery of therapeutic proteins by gene therapy, including, for example, that AAV is not known to cause human disease and induces a mild immune response, and that AAV vectors can infect both dividing and quiescent cells without integrating into the host cell genome. Gene therapy vectors using AAV have been successfully used in some clinical trials, for example, for the delivery of human Factor IX (FIX) to the liver of adults for the treatment of Hemophilia B.

Despite their positive features, AAV gene therapy vectors do have some drawbacks. In particular, the cloning capacity of AAV vectors is limited as a consequence of the DNA packaging capacity of the virus. The single-stranded DNA genome of wild-type AAV is about 4.7 kilobases (kb). In practice, AAV genomes of up to about 5.0 kb appear to be completely packaged, i.e., be full-length, into AAV virus particles. With the requirement that the nucleic acid genome in AAV vectors must have two AAV inverted terminal repeats (ITRs) of about 145 bases, the DNA packaging capacity of an AAV vector is such that a maximum of about 4.4 kb of protein-coding sequence can be encapsidated.

PKU poses several new challenges due to the distinct molecular and biochemical properties of PAH relating to the size of the PAH cDNA and efficiency of PAH protein expression, as well as the unique functional properties of the enzyme, such as cellular localization, regulation of activity, and potential for heterodimerization with mutant PAH. Several attempts of vector-mediated PAH expression have been performed on mice. See, e.g., Harding et al, Complete correction of hyperphenylalaninemia following liver-directed, recombinant AAV2/8 vector mediated gene therapy in murine phenylketonuria Gene Ther. 2006 March; 13(5): 457-6 and Viecelli et al, Treatment of Phenylketonuria Using Minicircle-Based Naked-DNA Gene Transfer to Murine Liver Hepatology. 2014 September; 60(3): 1035-1043 (see also WO2018126112). However, the evaluations of delivery efficiency, immune stimulation, long-term expression stability and safety are either lacking or not optimal. Thus, more efficient AAV.hPAH vectors are needed for PKU treatment.

3. SUMMARY

The embodiments described herein relate to an AAV gene therapy vector for delivering functional human phenylalanine hydroxylase (PAH) to a subject in need thereof.

In one aspect, provided is the use of a replication deficient adeno-associated virus (AAV) to deliver a human phenylalanine hydroxylase (PAH) gene to liver cells of patients (human subjects) diagnosed with PKU. The recombinant AAV vector (rAAV) used for delivering the hPAH gene ("rAAV.hPAH" or "AAV-PAH") should have a tropism for the liver (e.g., an rAAV bearing an AAV5 capsid), and the hPAH transgene should be controlled by liver-specific expression control elements. In one embodiment, the expression control elements include one or more of the following: an enhancer; a promoter; an intron; and a polyA signal. Such elements are further described herein.

In one embodiment, the hPAH transgene is contained within a recombinant adeno-associated virus (rAAV) vector genome which comprises (a) an AAV 5' inverted terminal repeat (ITR) sequence; (b) a promoter; (c) a codon optimized sequence encoding a human phenylalanine hydroxylase (hPAH); and (d) an AAV 3' ITR. In a specific embodiment, the codon optimized PAH sequence is SEQ ID NO: 7. The promoter may be a synthetic promoter sequence comprising portions of an hAAT promoter, a hepatic control region (HCR) enhancer, and an ApoE enhancer. In a specific embodiment, the sequence of the promoter is SEQ ID NO: 6. The AAV 5' ITR and/or AAV 3' ITR may be from a heterologous AAV pseudotype. In a specific embodiment, the ITR sequences are derived from AAV2. In another embodiment, the vector genome further comprises a polyadenylation signal sequence, which may be a bovine growth hormone (bGH) polyadenylation signal. In yet another embodiment, the vector genome further comprises an intron. In certain embodiments, the intron is a composite globin/A1AT intron sequence. In a specific embodiment, the intron sequence is SEQ ID NO: 14. The vector genome may be about 4 kb to about 5 kb in size. In a specific embodiment, the vector genome sequence is SEQ ID NO: 18.

In another aspect, provided herein is a recombinant adeno-associated virus (rAAV) particle comprising an AAV capsid and the vector genome as described in one or more of the embodiments herein. In one embodiment, the AAV capsid is an AAV5 capsid. In another embodiment, the rAAV particle is ApoE-HCR-hAAT.cGA1ATI.hPAHco1.bGH. In another embodiment, the rAAV particle is provided with a pharmaceutical composition.

In another aspect, provided herein is an isolated nucleic acid molecule comprising a nucleotide sequence having at least 80% homology to the nucleotide sequence of SEQ ID NO: 7 and which encodes functional PAH. In one embodiment, the functional PAH is a human PAH. The coding sequence for hPAH is, in one embodiment, codon optimized for expression in humans. Such sequence may share less than 80% identity to the native hPAH coding sequence (SEQ ID NO: 1). In one embodiment, the hPAH coding sequence is that shown in SEQ ID NO: 7. In another embodiment, the codon optimized PAH nucleic acid comprises a reduced CpG di-nucleotide content. In a specific embodiment, the CpG di-nucleotide content is less than 25.

In another aspect, provided herein is a pharmaceutical composition comprising the vector genome described herein or the rAAV particle described herein, and a pharmaceutically acceptable carrier. In another aspect, provided herein is an immunogenic composition comprising the vector genome described herein or the rAAV particle described herein, and a pharmaceutically acceptable carrier. In another aspect, provided here is a vaccine comprising the vector genome described herein, or the rAAV particle described herein, and a pharmaceutically acceptable carrier.

A further aspect provided herein is a method of expressing a protein in a subject comprising administering to the subject a composition comprising the rAAV particle described herein, thereby expressing the encoded PAH protein in the liver of the subject.

In yet another aspect, a method of treating a patient having phenylketonuria is provided which comprises administering the rAAV vector genome described herein, the rAAV particle described herein, the pharmaceutical composition described herein, the immunogenic composition described herein, or the vaccine described herein. In one embodiment, the rAAV particle is delivered at about $1\times10^{12}$ to about $1\times10^{15}$ μg/kg in an aqueous suspension. Another embodiment provided herein is a use of the rAAV vector genome described herein, the rAAV particle described herein, the pharmaceutical composition described herein, the immunogenic composition described herein, or the vaccine described herein for treatment of PKU in a subject.

Provided herein is a method of treating a subject having phenylketonuria (PKU) involving the steps of administering an effective amount of a PKU therapeutic to the subject where the effective amount of the PKU therapeutic is one which alters the levels of one or more amino acids, neurotransmitters, or neurotransmitter metabolites in the subject.

In one embodiment, the method includes the step of measuring the levels of one or more amino acids, neurotransmitters, or neurotransmitter metabolites in a biological sample obtained from the subject after administration of the effective amount of the PKU therapeutic, where an effective amount of PKU therapeutic is one which alters the levels of one or more neurotransmitter or neurotransmitter metabolites in the subject. In another embodiment, the method results in ameliorating a neurocognitive symptom of phenylketonuria (PKU) in a subject having PKU. In certain embodiments, the neurocognitive symptoms include decreased IQ, attention deficits, and deficits in executive functions including strategic planning, inhibitory control, working memory, and cognitive flexibility. In another embodiment, the one or more amino acids, neurotransmitters, or neurotransmitter metabolites include phenylethalyamine, phenylethanolamine, tyramine, dopamine, norepinephrine, tryptamine, hydroxytryptamine, phenylacetic acid, phenylacetylglutamine, mandelic acid, hydroxyphenylacetic acid, 3,4-dihydroxyphenylacetic acid (DOPAC), 3,4-dihydromandelic acid (DOMA), homovanillic acid, vanillylmandelic acid, dihydroxyphenylethyleneglycol (DOPEG), methylphenylethyleneglycol (MOPEG), indoleacetic acid, and hydroxyindoleacetic acid.

In another embodiment, the sample obtained from the subject includes blood, serum, plasma, cerebrospinal fluid (CSF), and urine. In a certain embodiment the sample is CSF. In one embodiment, the sample is plasma.

In another embodiment, the PKU therapeutic includes KUVAN® (sapropterin dihydrochloride), PALYNZIQ® (pegvaliase-pqpz), and/or a PKU gene therapy. In a further embodiment the PKU therapeutic includes a PKU cell therapy (see, e.g., Harding, C., *Clin Genet*., August; 74(2) pages 97-104 (2008)) and/or a pharmacological chaperone that maintains PAH protein stability, helps with the misfolded PAH, and/or increases enzymatic activity. (see e.g., Santos-Sierra et al., *Human Molecular Genetics*, Volume 21, Issue 8, 15 Apr. 2012, pages 1877-1887; Angel et al., *J Clin Invest.* 2008 Aug. 1; 118(8): pages 2858-2867.)

In another embodiment, the PKU gene therapy comprises an adeno-associated viral (AAV) vector that expresses a transgene comprising phenylalanine hydroxylase (PAH) or pegvaliase. In another embodiment, the effective amount of PKU gene therapy is greater than 1E12 vg/kg body weight of the subject. In another embodiment, the effective amount of PKU gene therapy is greater than 1E11 vg/kg body weight of the subject. In another embodiment, the effective amount of PKU gene therapy is greater than 1E10 g/kg body weight of the subject.

In another embodiment, the PKU therapeutic is selected with the proviso that it is not KUVAN®. In another embodiment, the PKU therapeutic is selected with the proviso that it is not PALYNZIQ® (pegvaliase-pqpz). In further embodiments, the PKU therapeutic is selected with the proviso that the AAV vector is not AAV8 or AAVHSC15.

In another embodiment, the levels of one or more amino acids, neurotransmitters, or neurotransmitter metabolites are measured at least one month after administering the PKU therapeutic. In another embodiment the levels of one or more amino acids, neurotransmitters, or neurotransmitter metabolites are measured at least three months after administering the PKU therapeutic. In yet another embodiment the levels of one or more amino acids, neurotransmitters, or neurotransmitter metabolites are measured at least six months after administering the PKU therapeutic.

In other embodiments, the altered levels of the one or more amino acids, neurotransmitters, or neurotransmitter metabolites is within 5% of a reference level of the one or more amino acids, neurotransmitters, or neurotransmitter metabolites, where the reference level is obtained as the average of the levels of one or more amino acids, neurotransmitters, or neurotransmitter metabolites obtained from neurotypical subjects (e.g., at least 5, 10, 15 or more neurotypical subjects). In yet other embodiments, the altered levels of the one or more amino acids, neurotransmitters, or neurotransmitter metabolites is within 10% of a reference level of the one or more amino acids, neurotransmitters, or neurotransmitter metabolites, where the reference level is obtained as the average of the levels of one or more amino acids, neurotransmitters, or neurotransmitter metabolites obtained from neurotypical subjects (e.g., at least 5, 10, 15 or more neurotypical subjects). In further embodiments, the altered levels of the one or more amino acids, neurotransmitters, or neurotransmitter metabolites is within 20% of a reference level of the one or more amino acids, neurotransmitters, or neurotransmitter metabolites, where the reference level is obtained as the average of the levels of one or more amino acids, neurotransmitters, or neurotransmitter metabolites obtained from neurotypical subjects (e.g., at least 5, 10, 15 or more neurotypical subjects).

In another embodiment, provided is a method of measuring an amino acid, neurotransmitter, or neurotransmitter metabolite level in a biological sample from a subject involving the steps of obtaining the biological sample from the subject; precipitating the sample with cold acetonitrile containing a heavy-labeled internal standard; pelleting the sample by centrifugation; transferring the supernatant to a fresh container; adding sodium carbonate and benzoyl chloride or ethyl chloroformate and pyridine to the supernatant; adding formic acid to the supernatant after it has reacted with the sodium carbonate and benzoyl chloride or ethyl chloroformate and pyridine; and analyzing the resultant reactant supernatant by LC/MS, thereby detecting and measuring the level of the neurotransmitter or neurotransmitter metabolite. In certain embodiments, the levels of amino acids, neurotransmitters, and neurotransmitter metabolites are determined using the method of measuring that results from reacting the sample with benzoyl chloride or ethyl chloroformate and pyridine.

As used herein, an "AAV vector" refers to nucleic acids, either single-stranded or double-stranded, having an AAV 5' inverted terminal repeat (ITR) sequence and an AAV 3' ITR flanking a protein-coding sequence (in one embodiment, a functional therapeutic protein-encoding sequence, e.g. PAH) operably linked to transcription regulatory elements that are heterologous to the AAV viral genome, i.e., one or more promoters and/or enhancers and, optionally, a polyadenylation sequence and/or one or more introns inserted between exons of the protein-coding sequence. A single-stranded AAV vector refers to nucleic acids that are present in the genome of an AAV virus particle, and can be either the sense strand or the anti-sense strand of the nucleic acid sequences disclosed herein. The size of such single-stranded nucleic acids is provided in bases. A double-stranded AAV vector refers to nucleic acids that are present in the DNA of plasmids, e.g., pUC19, or genome of a double-stranded virus, e.g., baculovirus, used to express or transfer the AAV vector nucleic acids. The size of such double-stranded nucleic acids in provided in base pairs (bp).

The term "inverted terminal repeat (ITR)" as used herein refers to the art-recognized regions found at the 5' and 3' termini of the AAV genome which function in cis as origins of DNA replication and as packaging signals for the viral genome. AAV ITRs, together with the AAV rep coding region, provide for efficient excision and rescue from, and integration of a nucleotide sequence interposed between two flanking ITRs into a host cell genome. Sequences of certain AAV-associated ITRs are disclosed by Yan et al., *J. Virol.* (2005) vol. 79, pp. 364-379 which is herein incorporated by reference in its entirety. ITR sequences that find use herein may be full length, wild-type AAV ITRs or fragments thereof that retain functional capability, or may be sequence variants of full-length, wild-type AAV ITRs that are capable of functioning in cis as origins of replication. AAV ITRs useful in the recombinant AAV PAH vectors of the embodiments provided herein may be derived from any known AAV serotype and, in certain embodiments, derived from the AAV2 or AAV5 serotype.

A "transcription regulatory element" refers to nucleotide sequences of a gene involved in regulation of genetic transcription including a promoter, plus response elements, activator and enhancer sequences for binding of transcription factors to aid RNA polymerase binding and promote expression, and operator or silencer sequences to which repressor proteins bind to block RNA polymerase attachment and prevent expression. The term "liver specific transcription regulatory element" refers to a regulatory element that modulates gene expression specifically in the liver tissue. Examples of liver specific regulatory elements include, but are not limited to, the mouse transthyretin promoter (mTTR), the endogenous human factor VIII promoter (F8), human alpha-1-antitrypsin promoter (hAAT) and active fragments thereof, human albumin minimal promoter, and mouse albumin promoter. Promoters can also include generic promoters such as CBA or viral promoters such as CMV. Enhancers derived from liver-specific transcription factor binding sites are also contemplated, such as EBP, DBP, HNF1, HNF3, HNF4, HNF6, and Enh1.

In one embodiment, the AAV vector comprises a nucleic acid encoding a functionally active phenylalanine hydroxylase (PAH) protein. The PAH encoding sequence may be wild-type, codon optimized, or a variant (see, e.g., Fang et al., *Gene Ther.*, vol. 1, pages 247-254 (1994); Eisensmith et al., *J. Inherit. Metab. Dis.*, vol. 19, pages 412-423 (1996); Nagasaki et al., *Pediatr. Res.*, vol. 45, pages 465-473 (1999); Laipis et al., *Mol. Ther.*, vol. 7, pages S391-S392 (2003);

Knappskog P M and Martinez A., *FEBS Lett., vol.* 409, pages 7-11 (1997); Khan et al., *J Biol Chem*., vol. 12, pages 4359-4367 (2019); Wang G A et al., *Proc Natl Acad Sci USA*., vol. 98, pages 1537-42 (2001)).

As used herein, wild-type PAH has the following amino acid sequence:

```
                                            (SEQ ID NO: 2)
MSTAVLENPG LGRKLSDFGQ ETSYIEDNCN QNGAISLIFS

LKEEVGALAK VLRLFEENDV NLTHIESRPS RLKKDEYEFF

THLDKRSLPA LTNIIKILRH DIGATVHELS RDKKKDTVPW

FPRTIQELDR FANQILSYGA ELDADHPGFK DPVYRARRKQ

FADIAYNYRH GQPIPRVEYM EEEKKTWGTV FKTLKSLYKT

HACYEYNHIF PLLEKYCGFH EDNIPQLEDV SQFLQTCTGF

RLRPVAGLLS SRDFLGGLAF RVFHCTQYIR HGSKPMYTPE

PDICHELLGH VPLFSDRSFA QFSQEIGLAS LGAPDEYIEK

LATIYWFTVE FGLCKQGDSI KAYGAGLLSS FGELQYCLSE

KPKLLPLELE KTAIQNYTVT EFQPLYYVAE SFNDAKEKVR

NFAATIPRPF SVRYDPYTQR IEVLDNTQQL KILADSINSE

IGILCSALQK IK.
```

In other embodiments, the recombinant AAV vector comprises a nucleic acid comprising an AAV2 5' inverted terminal repeat (ITR) (which may or may not be modified as known in the art), a liver-specific transcription regulatory region, a codon-optimized therapeutic protein coding region, optionally one or more introns, a polyadenylation sequence, and an AAV2 3' ITR (which may or may not be modified as known in the art). In certain embodiments, the therapeutic protein is human PAH or variants thereof. In other embodiments, the liver-specific transcription regulatory region comprises a shortened ApoE enhancer sequence; a 186 base human alpha anti-trypsin (hAAT) proximal promoter, including 42 bases of the 5' untranslated region (UTR); one or more enhancers selected from the group consisting of (i) a 34 base human ApoE/C1 enhancer, (ii) a 32 base human AAT promoter distal X region, and (iii) 80 additional bases of distal element of the human AAT proximal promoter; and a nucleic acid encoding human PAH. In another embodiment, the liver-specific transcription regulatory region comprises an α-microglobulin enhancer sequence and the 186 base human alpha anti-trypsin (AAT) proximal promoter.

Other embodiments provided herein are directed to vector constructs encoding a functional PAH polypeptide, wherein the constructs comprise one or more of the individual elements of the above described constructs and combinations thereof, in one or more different orientation(s). Another embodiment provided herein is directed to the above described constructs in an opposite orientation. In another embodiment, provided are recombinant AAV virus particles comprising the herein described AAV PAH vectors and their use for the treatment of PKU in subjects. In one embodiment the subjects are juvenile subjects.

The AAV vectors provided herein in single strand form are less than about 7.0 kb in length, or are less than 6.5 kb in length, or are less than 6.4 kb in length, or are less than 6.3 kb in length, or are less than 6.2 kb in length, or are less than 6.0 kb in length, or are less than 5.8 kb in length, or are less than 5.6 kb in length, or are less than 5.5 kb in length, or are less than 5.4 kb in length, or are less than 5.3 kb in length, or are less than 5.2 kb in length or are less than 5.0 kb in length, or are less than 4.8 kb in length, or are less than 4.6 kb in length, or are less than 4.5 kb in length, or are less than 4.4 kb in length, or are less than 4.3 kb in length, or are less than 4.2 kb in length, or are less than 4.1 kb in length, or are less than 4.0 kb in length, or are less than 3.9 kb in length, or are less than 3.8 kb in length, or are less than 3.7 kb in length, or are less than 3.6 kb in length, or are less than 3.5 kb in length, or are less than 3.4 kb in length, or are less than 3.3 kb in length, or are less than 3.2 kb in length, or are less than 3.1 kb in length, or are less than 3.0 kb in length, or are less than 2.9 kb in length, or are less than 2.8 kb in length, or are less than 2.7 kb in length, or are less than 2.6 kb in length. The AAV vectors provided herein in single strand form range from about 5.0 kb to about 6.5 kb in length, or range from about 4.8 kb to about 5.2 k in length, or 4.8 kb to 5.3 kb in length, or range from about 4.9 kb to about 5.5 kb in length, or about 4.8 kb to about 6.0 kb in length, or about 5.0 kb to 6.2 kb in length or about 5.1 kb to about 6.3 kb in length, or about 5.2 kb to about 6.4 kb in length, or about 5.5 kb to about 6.5 kb in length or range from about 4.0 kb to about 5.0 kb in length, or range from about 3.8 kb to about 4.8 k in length, or 3.6 kb to 4.6 kb in length, or range from about 3.4 kb to about 4.4 kb in length, or range from about 3.2 kb to about 4.2 kb in length, or range from about 3.0 kb to 4.0 kb in length, or range from about 3.0 kb to about 4.0 kb in length, or range from about 2.8 kb to about 3.8 kb in length, or range from about 2.6 kb to about 3.6 kb in length, or range from about 5.0 kb to about 4.5 kb in length, or range from about 4.5 kb to about 4.0 kb in length, or range from about 3.5 kb to about 4.0 kb in length, or range from about 3.0 kb to about 3.5 kb in length, or range from 2.5 kb to 3.0 kb in length.

In another embodiment, provided are methods of producing recombinant adeno-associated virus (AAV) particles comprising any of the AAV vectors provided herein. The methods comprise the steps of culturing a cell that has been transfected with any of the AAV vectors provided herein (in association with various AAV cap and rep genes) and recovering recombinant therapeutic AAV virus particles from the supernatant of the transfected cell.

The cells useful for recombinant AAV production provided herein are any cell type susceptible to baculovirus infection, including insect cells such as High Five, Sf9, Se301, SeIZD2109, SeUCR1, Sf9, Sf900+, Sf21, BTI-TN-5B1-4, MG-1, Tn368, HzAm1, BM-N, Ha2302, Hz2E5, and Ao38. In another embodiment, mammalian cells such as HEK293, HeLa, CHO, NSO, SP2/0, PER.C6, Vero, RD, BHK, HT 1080, A549, Cos-7, ARPE-19, and MRC-5 can be used.

Also provided herein is a recombinant viral particle comprising any of the AAV vectors provided herein or any viral particle produced by the forgoing methods.

An "AAV virion" or "AAV viral particle" or "AAV vector particle" or "AAV virus" refers to a viral particle composed of at least one AAV capsid protein and an encapsidated polynucleotide AAV vector as described herein. If the particle comprises a heterologous polynucleotide (i.e., a polynucleotide other than a wild-type AAV genome such as a transgene to be delivered to a mammalian cell), it is typically referred to as an "AAV vector particle" or simply an "AAV vector". Thus, production of AAV vector particles necessarily includes production of AAV vector, as such a vector is contained within an AAV vector particle.

As used herein "therapeutic AAV virus" refers to an AAV virion, AAV viral particle, AAV vector particle, or AAV virus that comprises a heterologous polynucleotide that encodes a therapeutic protein.

As used herein "therapeutic protein" refers to a polypeptide that has a biological activity that replaces or compensates for the loss or reduction of activity of an endogenous protein. For example, a functional phenylalanine hydroxylase (PAH) is a therapeutic protein for phenylketonuria (PKU).

In another embodiment, provided herein is the use of an effective amount of recombinant AAV PAH virus for the preparation of a medicament for the treatment of a subject suffering from PKU. In one embodiment, the subject suffering from PKU is a human. In one embodiment, the medicament is administered by intravenous (IV) administration. In another embodiment, administration of the medicament results in expression of PAH protein in the bloodstream of the subject sufficient to alter the neurotransmitter metabolite or neurotransmitter levels in the subject. In certain embodiments, the medicament also comprises a prophylactic and/or therapeutic corticosteroid for the prevention and/or treatment of any hepatotoxicity associated with administration of the AAV PAH virus. The medicament comprising a prophylactic or therapeutic corticosteroid treatment may comprise at least 5, 10, 15, 20, 25, 30, 35, 40, 45, 50, 55, 60, or more mg/day of the corticosteroid. In certain embodiments, the medicament comprising a prophylactic or therapeutic corticosteroid may be administered over a continuous period of at least about 3, 4, 5, 6, 7, 8, 9, 10 weeks, or more. In another embodiment, the PKU therapy provided herein optionally includes tyrosine supplements.

Other embodiments will be evident to one skilled in the art upon reading the present specification.

4. DESCRIPTION OF DRAWINGS

FIG. 1 is a liquid chromatography-mass spectrometry (LC/MS) chromatogram of phenylalanine derived amino acids, neurotransmitters, and neurotransmitter metabolites after reaction with ethyl chloroformate and pyridine.

FIG. 2A-I is a set of graphs comparing the levels of various amino acids, neurotransmitters, and neurotransmitter metabolites measured in the brains of wild-type and Enu2 mice. As seen in the graphs phenylalanine is elevated in Enu2 mice compared to wild-type mice whereas all other measured amino acids, neurotransmitters, and neurotransmitter metabolites were decreased in Enu2 mice compared to wild-type mice.

FIG. 3A-I is a set of graphs comparing the levels of various amino acids, neurotransmitters, and neurotransmitter metabolites measured in the brains of wild-type and Enu2 mice treated with vehicle, 2E13 vg/kg or 2E14 vg/kg AAV-PAH. The 2E14 vg/kg dose of AAV-PAH increased the levels of the measured amino acids (except phenylalanine which was reduced to wild-type levels), neurotransmitters, and neurotransmitter metabolites to the levels measured in wild-type mice. In contrast, the 2E13 vg/kg dose of AAV-PAH did not completely restore the levels of the measured amino acids, neurotransmitters, and neurotransmitter metabolites.

FIG. 4 is a plot showing the correlation between brain and plasma phenylalanine levels. Phenylalanine levels were measured in both the brain and plasma of vehicle treated wild-type mice and Enu2 mice treated with vehicle or 2E13 vg/kg AAV-PAH or 2E14 vg/kg AAV-PAH. The plot shows that there is a correlation between brain and plasma phenylalanine in each animal tested regardless of treatment status.

FIG. 5A-D is a set of graphs showing amino acid (phenylalanine (A) and tyrosine (B)) and neurotransmitter metabolite (DOPAC (C) and homovanillic acid (D)) levels in the plasma of wild-type and Enu2 mice. Enu2 mice have lower levels of neurotransmitter metabolites in their plasma compared to wild-type mice. The mass spec measurements for each of the analytes is provided as peak area derived from the counts per minute (cpm) of signal detected.

FIG. 6A-D is a set of graphs showing the correlation of each of phenylalanine (A), tyrosine (B), DOPAC (C), and homovanillic acid (D) in the brain and plasma of wild-type and Enu2 mice.

FIG. 7A-I is a set of graphs comparing the levels of various amino acids, neurotransmitters, and neurotransmitter metabolites measured in the plasma of vehicle treated wild-type mice and Enu2 mice treated with vehicle, 2E13 vg/kg or 2E14 vg/kg AAV-PAH. The 2E14 vg/kg dose of AAV-PAH increased the levels of the measured amino acids (except phenylalanine which was reduced to wild-type levels), neurotransmitters, and neurotransmitter metabolites to those seen in wild-type mice. In contrast, the 2E13 vg/kg dose of AAV-PAH did not completely restore the levels of the measured amino acids, neurotransmitter metabolites, and neurotransmitters.

FIG. 8A-C is a set of graphs showing the correlation between brain and plasma levels of phenylalanine (A), DOPAC (B), and homovanillic acid (C) in vehicle treated wild-type mice and Enu2 mice treated with vehicle, 2E13 vg/kg or 2E14 vg/kg AAV-PAH.

FIG. 9A-D is a set of graphs showing a negative correlation between plasma and brain phenylalanine levels and the levels of DOPAC (A, B) and homovanillic acid (C, D) in vehicle treated wild-type mice and Enu2 mice treated with vehicle, 2E13 vg/kg or 2E14 vg/kg AAV-PAH.

FIG. 10A-C shows a chemical structure (A) and a set of graphs showing the levels of dopamine (B) and norepinephrine (C) in the brains of vehicle treated wild-type mice and Enu2 mice treated with vehicle, 2E13 vg/kg or 2E14 vg/kg AAV-PAH.

FIG. 11A-C shows a chemical structure (A) and a set of graphs showing the levels of dopamine (B) and DOPAC (C) in the brains of vehicle treated wild-type mice and Enu2 mice treated with vehicle, 2E13 vg/kg or 2E14 vg/kg AAV-PAH.

FIG. 12A-B is a set of graphs showing the levels of DOPAC (A) and homovanillic acid (B) in the plasma of vehicle treated wild-type mice and Enu2 mice treated with vehicle, 2E13 vg/kg or 2E14 vg/kg AAV-PAH.

FIG. 13A-D shows the correlations between the levels of DOPAC (A, B) and homovanillic acid (C, D) in both the brain and plasma of vehicle treated wild-type mice and Enu2 mice treated with vehicle, 2E13 vg/kg or 2E14 vg/kg AAV-PAH. This data shows that plasma levels of DOPAC and homovanillic acid can act as surrogate markers for the levels of these neurotransmitter metabolites in the brain.

FIG. 14A-F is a set of graphs showing the levels of brain and plasma phenylalanine (A, D), tyrosine (B, E), and tryptophan (C, F) in vehicle treated Enu2 mice and in Enu2 mice treated with Peg-PAL (PegPal-10k) for three days.

FIG. 15A-C is a set of graphs that show the levels of the neurotransmitters dopamine (A), norepinephrine (B), and serotonin (C) in the brains of vehicle treated Enu2 mice and in Enu2 mice treated with Peg-PAL (PegPal-10k) for three days.

FIG. 16A-F is a set of graphs that show the levels of DOPAC (A, D), homovanillic acid (B, E), and 5-hydroxyindolacetic acid (C,F) in the brains and plasma of vehicle treated Enu2 mice and in Enu2 mice treated with Peg-PAL (PegPal-10k) for three days.

FIG. 17A-C is a set of graphs that show the levels of phenylalanine (A), tyrosine (B), and tryptophan (C) in the plasma of Enu2 mice 72 hours after treatment with either vehicle or a single dose of PALYNZIQ® (pegvaliase-pqpz).

FIG. 18A-F is a set of graphs that show the levels of phenylalanine (A), tyrosine (B), and tryptophan (C) in the brains of Enu2 mice 72 hours after treatment with either vehicle or a single dose of PALYNZIQ® (pegvaliase-pqpz), and the correlation between indicated markers following PALYNZIQ® (pegvaliase-pqpz) treatment in Enu2 mice (D-F).

FIG. 19A-H is a set of graphs that show the levels of phenethylamine (A), dopamine (B), norepinephrine (C), and serotonin (D) in the plasma and brains of Enu2 mice 72 hours after treatment with either vehicle or a single dose of PALYNZIQ® (pegvaliase-pqpz), and the correlation between indicated markers following PALYNZIQ® (pegvaliase-pqpz) treatment in Enu2 mice (E-H).

FIG. 20A-H is a set of graphs that show the levels of phenylacetylglycine (A), homovanillic acid (B), 3-methoxy-4-hydroxyphenylglycol (C), and 5-hydroxyindolacetic acid (D) in the plasma of Enu2 mice 72 hours after treatment with either vehicle or a single dose of PALYNZIQ® (pegvaliase-pqpz), and the correlation between indicated markers following PALYNZIQ® (pegvaliase-pqpz) treatment in Enu2 mice (E-H).

FIG. 21A-21C shows the levels of homovanillic acid (HVA) (A), 3-methoxy-4-hydroxyphenylglycol (MOPEG) (B), and 5-hydroxyindolacetic acid (5HIAA) (C) in the brains of Enu2 mice 72 hours after treatment with either vehicle or a single dose of PALYNZIQ® (pegvaliase-pqpz).

FIG. 22A-F shows Tyr supplementation in combination with PALYNZIQ® (pegvaliase-pqpz) treatment increases brain norepinephrine levels in $PAH^{Enu2}$ mice. $PAH^{WT}$ mice following treatment with either vehicle or PALYNZIQ® (pegvaliase-pqpz). Plasma levels of Tyr (C) and brain levels of Tyr (D), dopamine (E), and norepinephrine (F) were measured in $PAH^{Enu2}$ and $PAH^{WT}$ mice. Tukey's multiple comparison test with adjusted p-values was used to determine significance (**=p<0.0001; *=p<0.001; **=p<0.01; *=p<0.05) in A-F. Tyr, tyrosine.

FIG. 23A-T shows the plasma levels of key neurotransmitter metabolites were influenced by a reduction of Phe after 12 months of PALYNZIQ® (pegvaliase-pqpz). All data refer to samples from a subset of subjects that achieved either Phe levels <360 μM (Group 1) or >900 μM (Group 2). (A-D) All neurotransmitter metabolites trended toward control values by 12 months. (E-H) Correlation of plasma neurotransmitter metabolites and plasma Phe. Tukey's multiple comparison test with adjusted p-values was used to determine significance (**=p<0.0001; *=p<0.001; **=p<0.01; *=p<0.05) in A-D. For E-H, r, p-values, and 95% confidence intervals calculated by linear fit to log-transformed data. For E-L, data available at baseline, month 6 and month 12 are included. Shaded regions represent upper and lower limit of control subjects. Plasma Phe reduction in most subjects with PKU results in a change in other neurotransmitter metabolites in >900 μM group (M-P) with a greater trend in the <360 μM group (Q-T) subjects with PKU after 12 months of PALYNZIQ® (pegvaliase-pqpz) treatment. 5-hydroxyindole acetic acid (5HIAA); control (Ctrl); homovanillic acid (HVA); 3-methoxy-4-hydroxyphenylglycol (MOPEG); phenylacetylglycine (PAG); phenylalanine (Phe);

FIG. 24A-D shows that ADHDi subscale for a subset of subjects with ADHDi scores ≥9 at baseline were inversely correlated with an increase in MOPEG. Correlation of change in ADHDi subscale and change in plasma HVA with ADHDi scores >9 (n=17) (A) or <9 (n=7) (B) at baseline or MOPEG with ADHDi scores >9 (C) or <9 (D) at baseline; score >9 indicating symptoms of inattention. Blue and red dots indicate subjects from <360 and >900 μM groups, respectively. The r and p values for each data set were determined after fitting a linear regression to each data set. 5HIAA, 5-hydroxyindole acetic acid; ADHD-RS IV, inattention subscale domain of attention deficit hyperactivity disorder rating scale; 3-methoxy-4-hydroxyphenylglycol (MOPEG); phenylacetylglycine (PAG); phenylalanine (Phe); phenylketonuria (PKU).

FIG. 25 depicts the neurotransmitter biosynthesis pathway. Metabolites of Phe and other neurotransmitters derived from Tyr and Trp can be detected in the plasma as surrogates for brain metabolism. Blue represents molecules originating within the plasma whereas red represents metabolites that have their primary origin within the brain or gastrointestinal tract (see, e.g., Lambert et al., *Life Sci*., volume 57 pages255-67 (1995); Ruddell et al., *J Hepatol*., vol. 48 pages 666-675 (2008) (see Ruddell FIG. 1 and legend)). 5-HIAA, 5-hydroxyindole acetic acid; AADC, amino acid decarboxylase; ALDH2, aldehyde dehydrogenase; AR, aldehyde reductase; COMT, catecho-O-methyltransferase; DBH, dopamine beta-hydroxylase; DOPAC, 3,4-dihydroxypheyl-acetic acid; DOPEG, 3,4-dihydroxy-phenylethyleneglycol; HVA, homovanillic acid; IAA, indoleacetic acid; LAT1, large L-type neutral amino acid transporter 1; MA, mandelic acid; MAO, monoamine oxidase; MOPEG, 3-methoxy-4-hydroxyphenylglycol; PAA, phenylacetic acid; PAG, phenylacetylglycine; PAH, phenylalanine hydroxylase; PEA, phenylethylamine; TH, tyrosine hydroxylase; TPH, tryptophan hydroxylase.

FIG. 26 is a schematic representation of ApoE-HCR-hAAT.GI.hPAH.bGH gene therapy vector. (Also refered to as Vector #1 or WT-hPAH vector)

FIG. 27A-B shows a restriction Enzyme Digest of ApoE-HCR-hAAT.GI.hPAH.bGH gene therapy vector, including a schematic of restriction map (A), and the gel electrophoresis analysis of the restriction digested vector (B).

FIG. 28A-B shows ddPCR analysis of ApoE-HCR-hAAT.GI.hPAH.bGH gene therapy vector by showing gel electrophoresis analysis of ddPCR reaction (A), and a schematic of gene therapy vector with quantitation of amplified DNA regions (B).

FIG. 29A-B compares the plasma Phe levels measured in wild-type and Enu2 mice treated with vehicle, 2E13 vg/kg or 2E14 vg/kg AAV-PAH (A) or 6E13 vg/kg AAV-PAH (B).

FIG. 32A-E shows that high dose AAV-PAH normalizes brain amino acids Phe (A) and Tyr (B), and neurotransmitter levels (C-D) of ENU2 mice to wildtype levels. Chemical pathway is also described (E).

Figure 33:
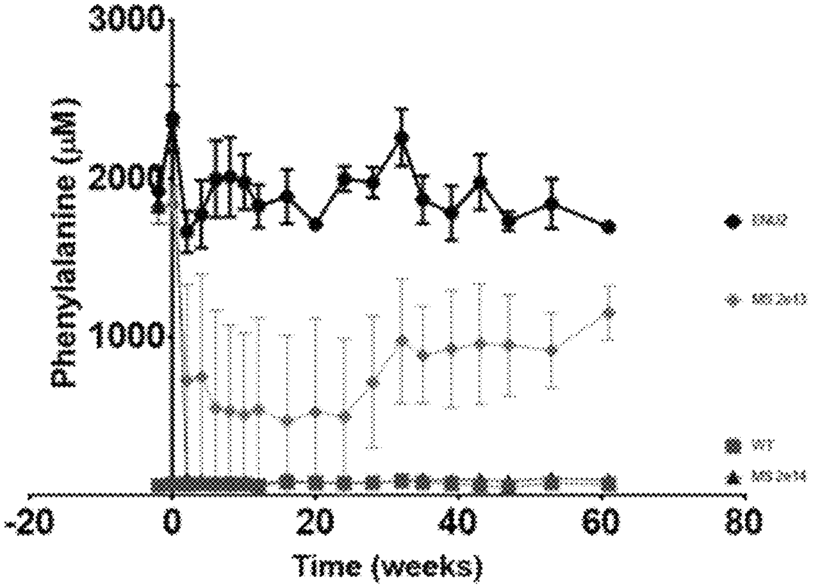

FIG. 33 shows that ENU2 mice treated with ApoE-HCR-hAAT.GI.muPAH.bGH vector reduced phenylalanine levels for a duration of 60 weeks.

Figure 34:
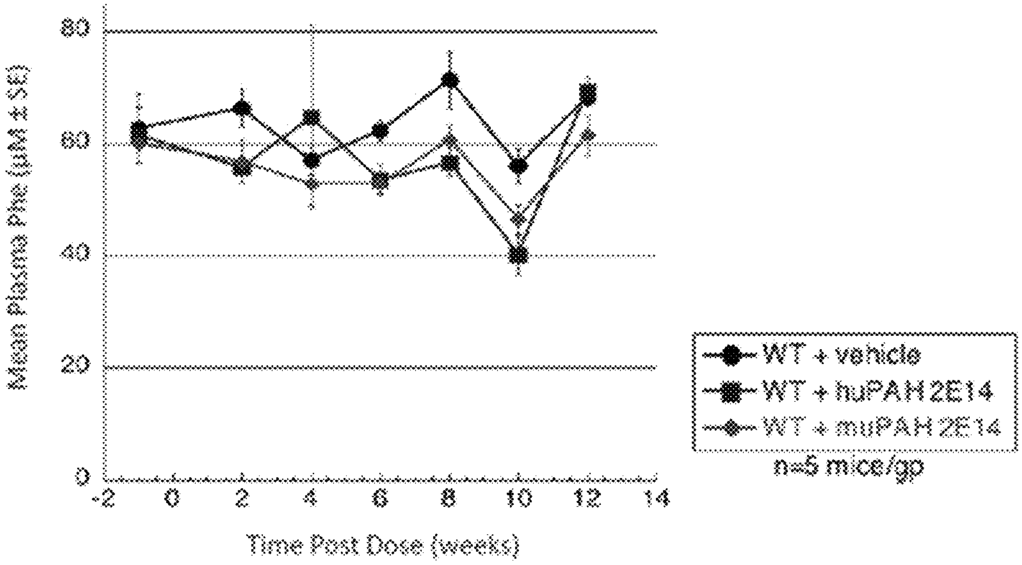

FIG. 34 shows minimal change in Phe levels caused by increased PAH protein in wild-type mice treated with ApoE- HCR-hAAT.GI.hPAH.bGH vector or ApoE-HCR-hAAT.GI.muPAH.bGH vector.

Figure 35:

FIG. 35 is a western blot which shows increased levels of the PAH protein in the treated mice of FIG. 34 despite minimal Phe level change.

Figure 36A:
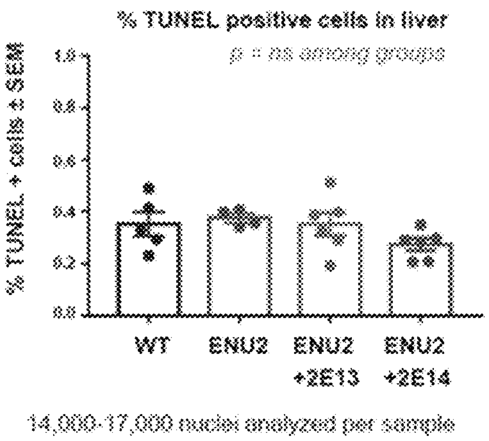
Figure 36B:
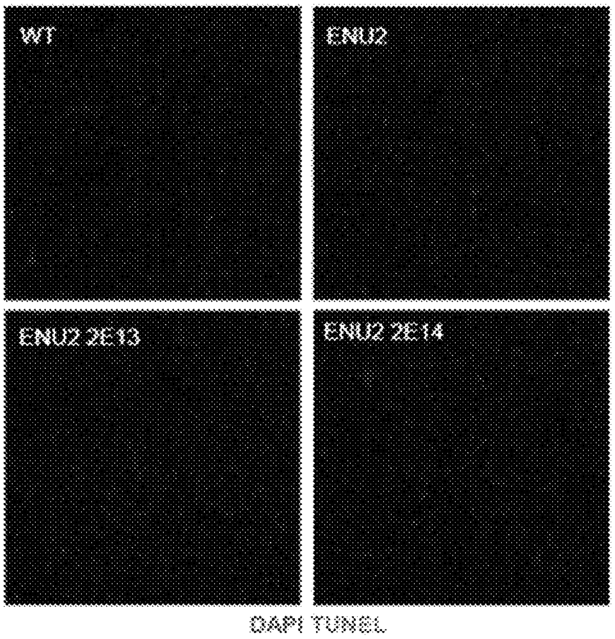

FIG. 36A-B depicts quantification of staining (A) and staining (B) that shows no significant TUNEL staining in the livers of animals treated with AAV5-hPAH at 2E13 or 2E14 vg/kg 12 weeks post-dose.

Figure 37:
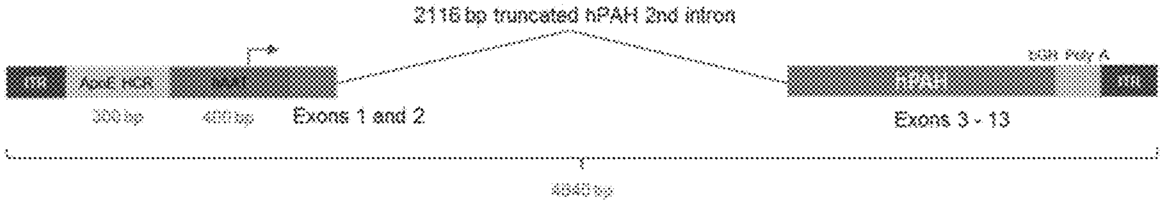

FIG. 37 is a schematic representation of the ApoE-HCR-hAAT.hPAH-t12.bGH vector.

Figure 38:
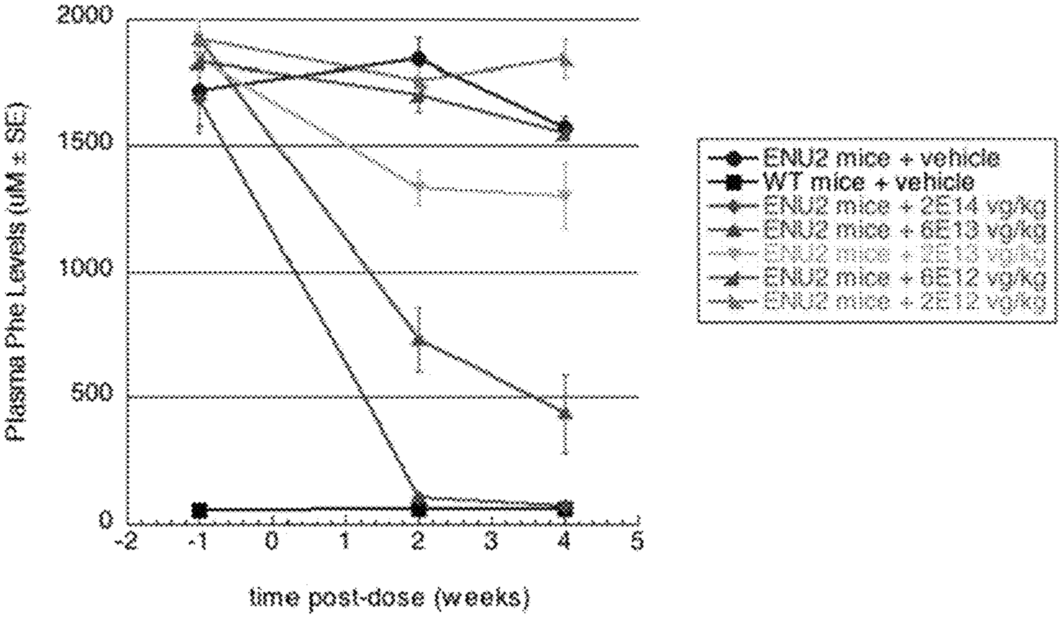
Figure 39A:
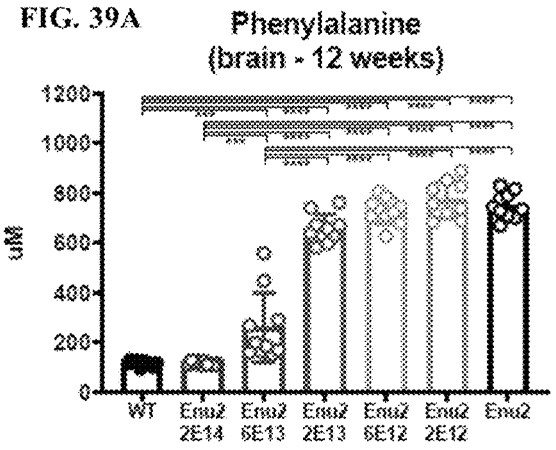
Figure 39B:
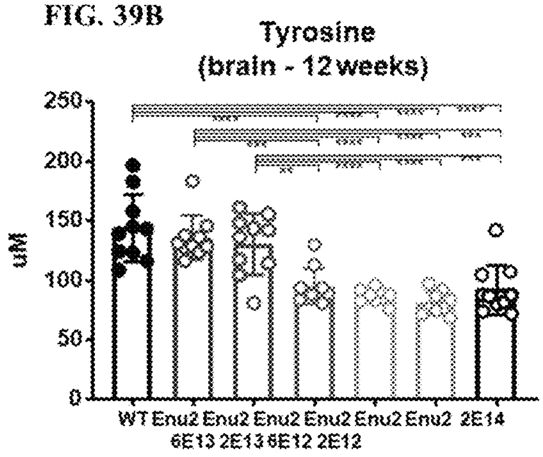
Figure 39C:
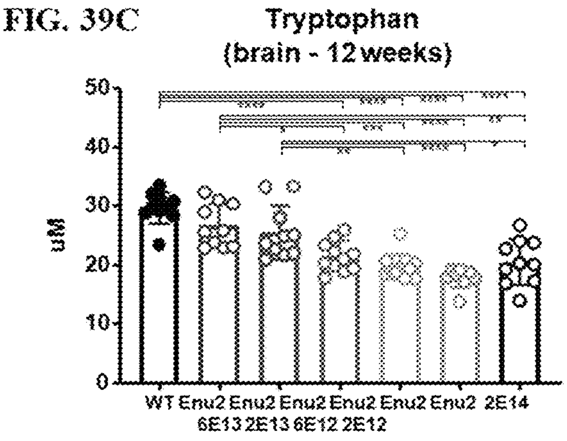
Figure 39D:
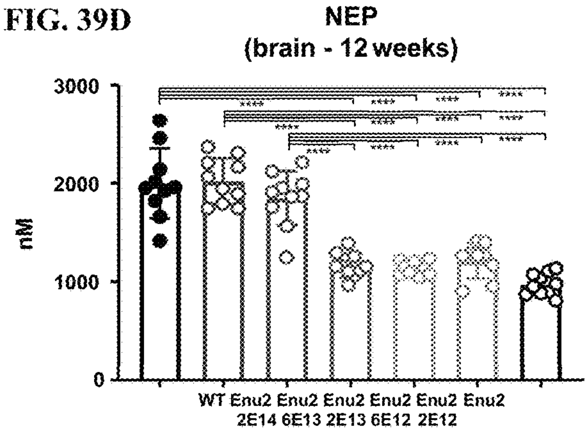

FIG. 38 is a graph that shows plasma Phe levels were reduced in mice receiving the ApoE-HCR-hAAT.hPAH-t12.bGH vector in a dose-dependent fashion.

FIG. 39A-D are graphs that show high dose ApoE-HCR-hAAT.hPAH-t12.bGH vector corrects (A-C) amino acid levels and (D) neurotransmitter levels in the brain.

Figure 40:
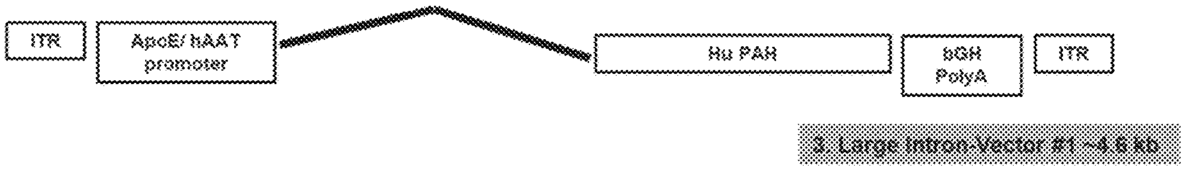

FIG. 40 is a schematic representation of ApoE-HCR-hAAT.cG-A1ATI.hPAH.bGH vector.

FIG. 41 shows the sequence alignment of codop-hPAH DNA sequences hPAH (SEQ ID NO: 1), NW2-Cop (SEQ ID NO: 9), NW-RCG (SEQ ID NO: 10), D20-Op (SEQ ID NO: 11), D20-Cop1 (SEQ ID NO: 12), JCAT (SEQ ID NO: 13), Operon-1 (SEQ ID NO: 7), and Operon-2 (SEQ ID NO: 8).

Figures 42A, 42B, 42C:
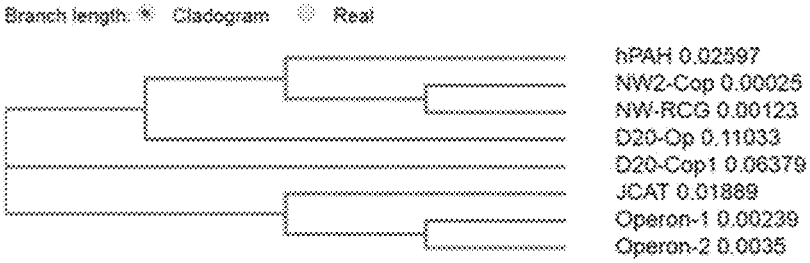

FIG. 42A-C analyzes the codop-hPAH sequences with charts that compare percent sequence identities (A), cladogram relationships (B), and GC content (C).

Figure 43A:
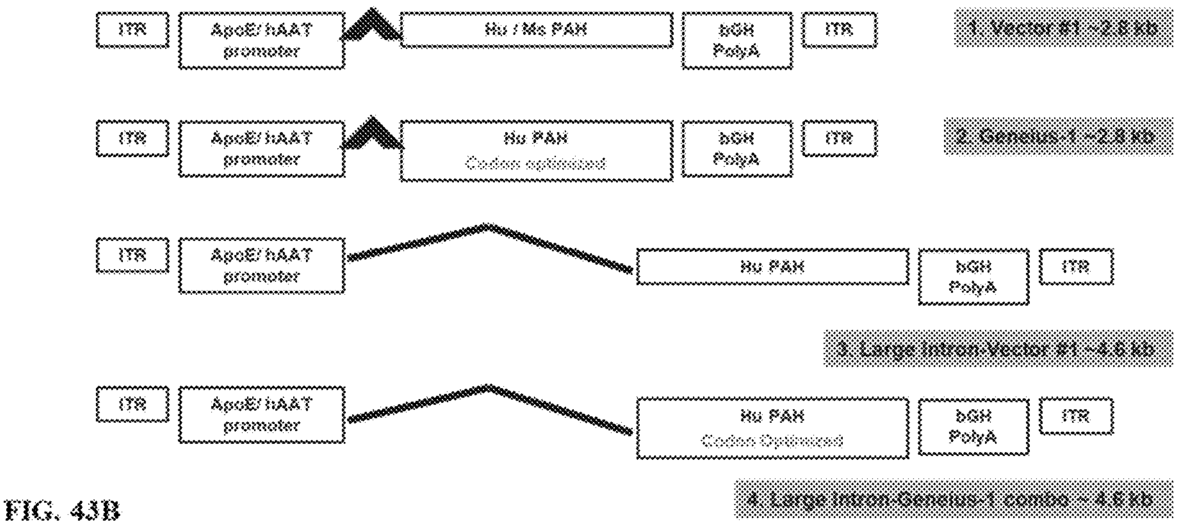
Figure 43B:
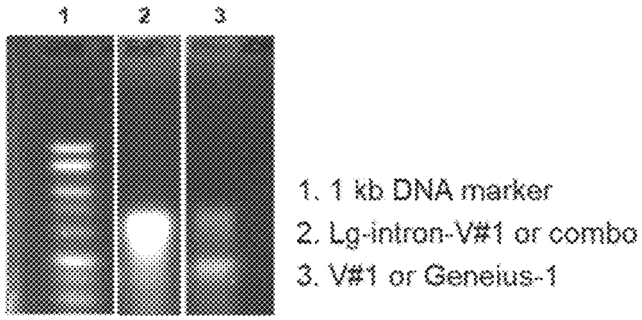

FIG. 43A-B shows AAV5-PAH vector designs and DNA structure.

Figure 44A:
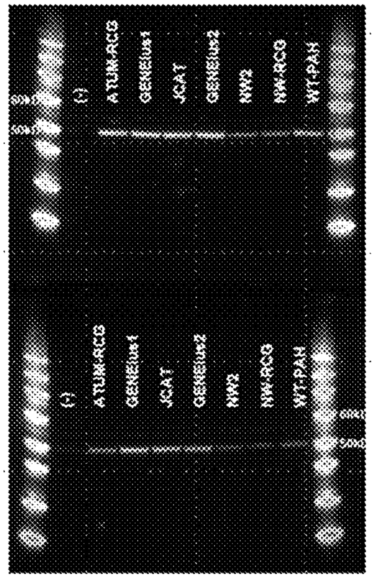
Figure 44B:
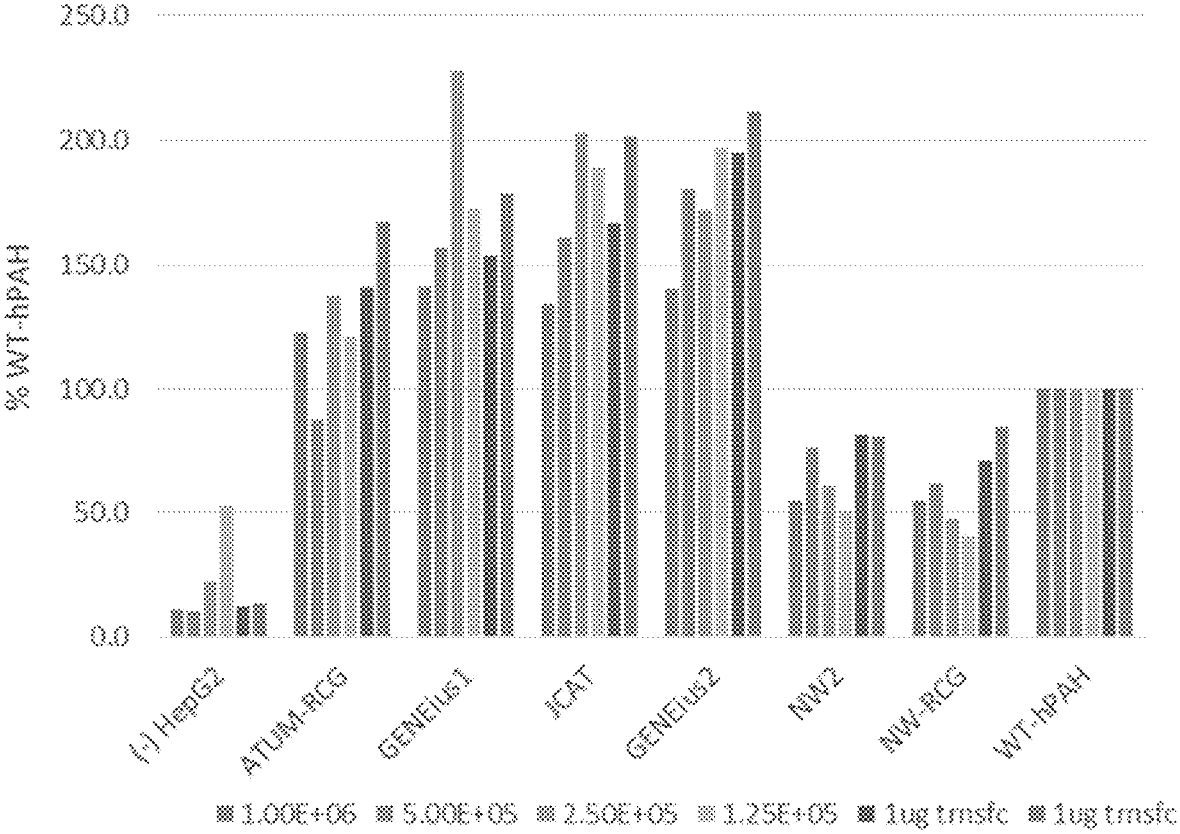

FIG. 44A-B is a comparison of codon optimized hPAH versions by HEPG2 liver cell transduction or transfection.

Figure 45A:
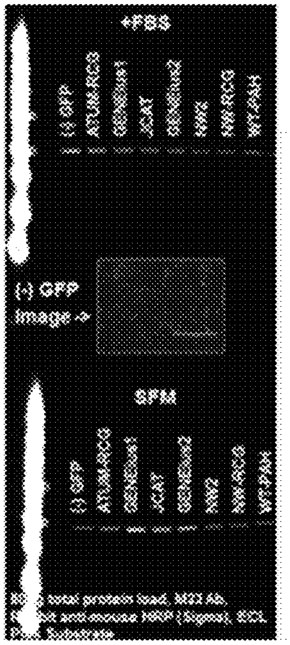
Figure 45B:
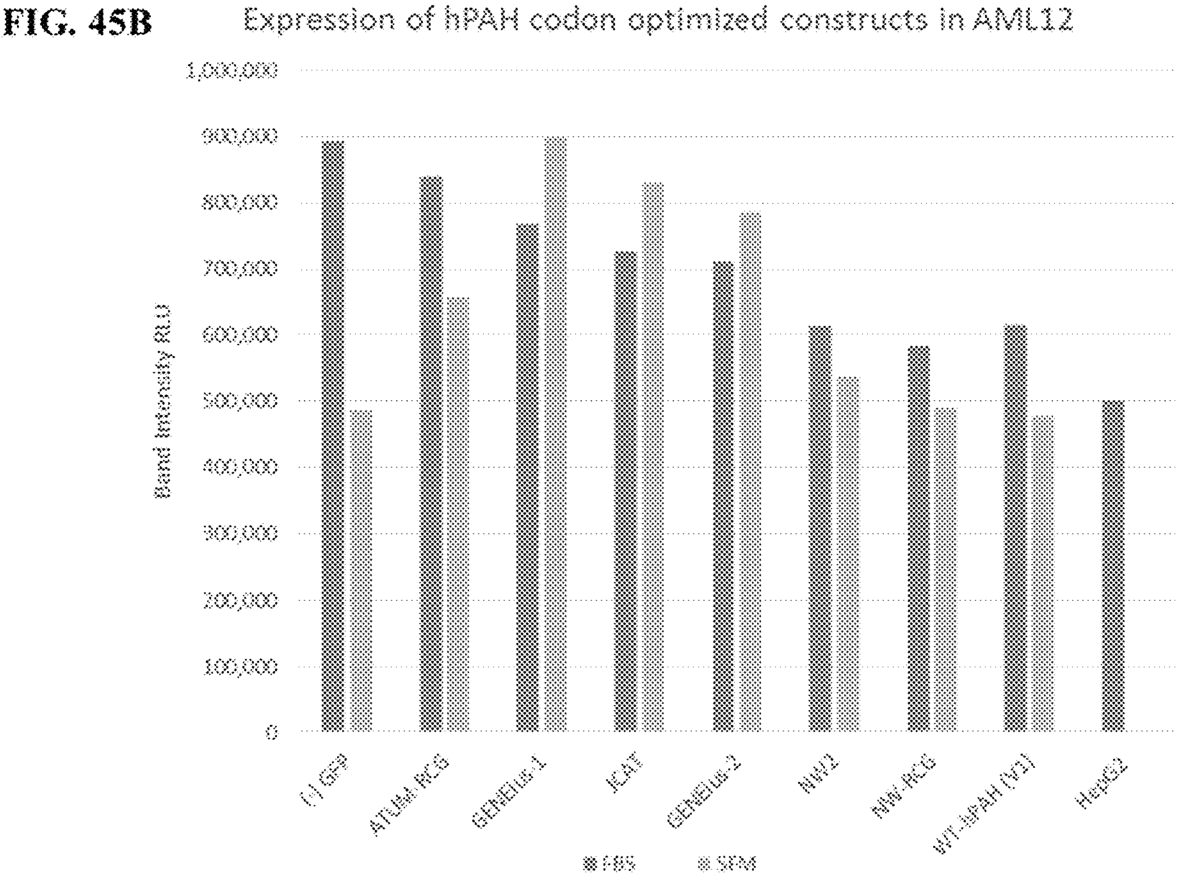

FIG. 45A-B is a comparison of codon optimized hPAH versions by AML12 transduction.

Figure 46A:
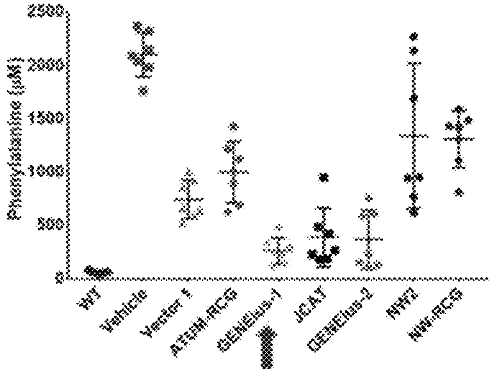
Figure 46B:
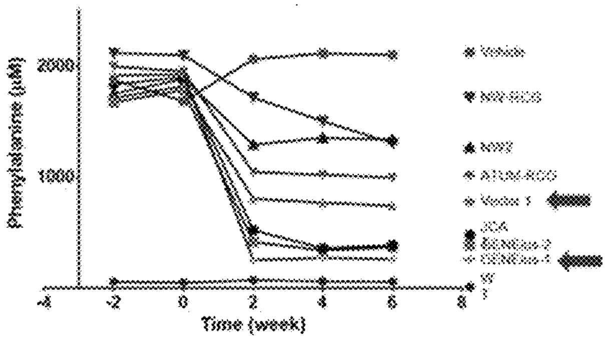

FIG. 46A-B show plasma Phe levels in Enu2 mice treated with AAV-codop PAH constructs have varying plasma phenylalanine concentrations at two weeks (A) and over a 6 week time period (B).

Figure 47:
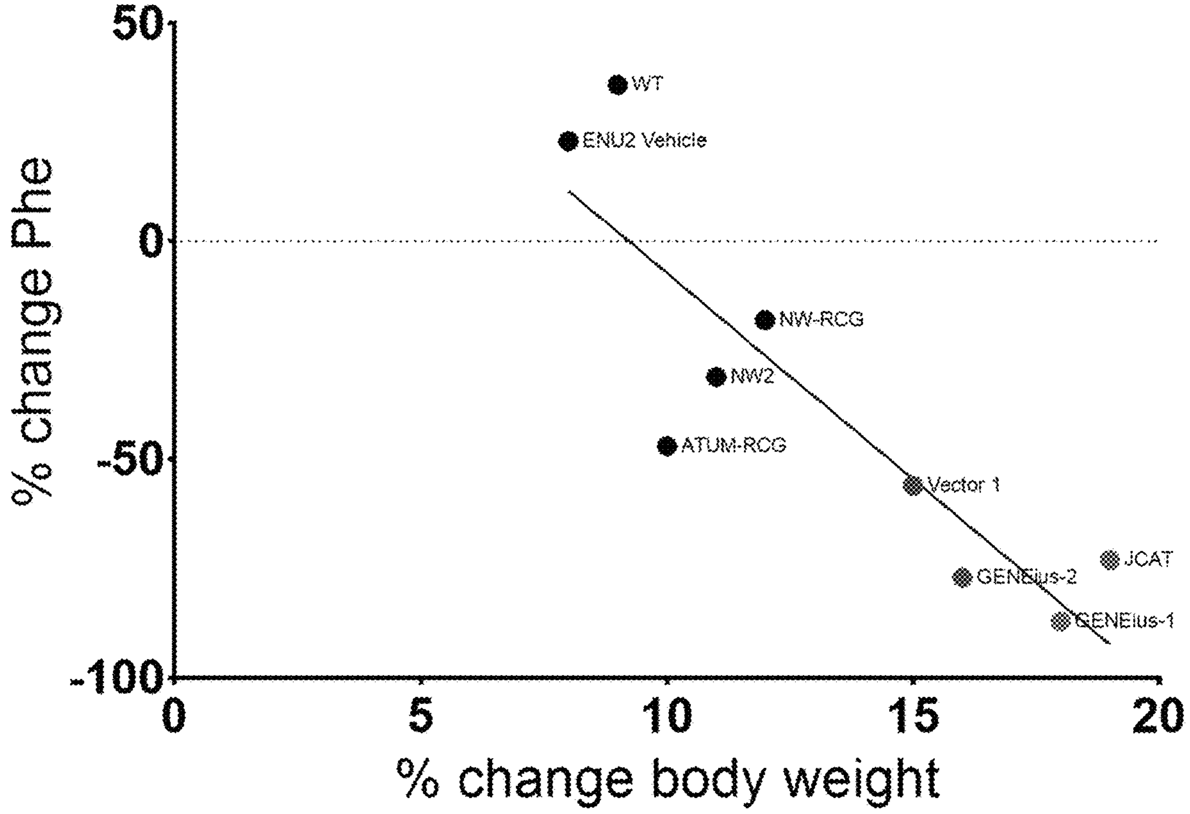

FIG. 47 shows a correlation between increased change in body weight and reduction in percentage change of Phe measured in ENU2 mice treated with AAV-codop PAH constructs.

Figure 48A:
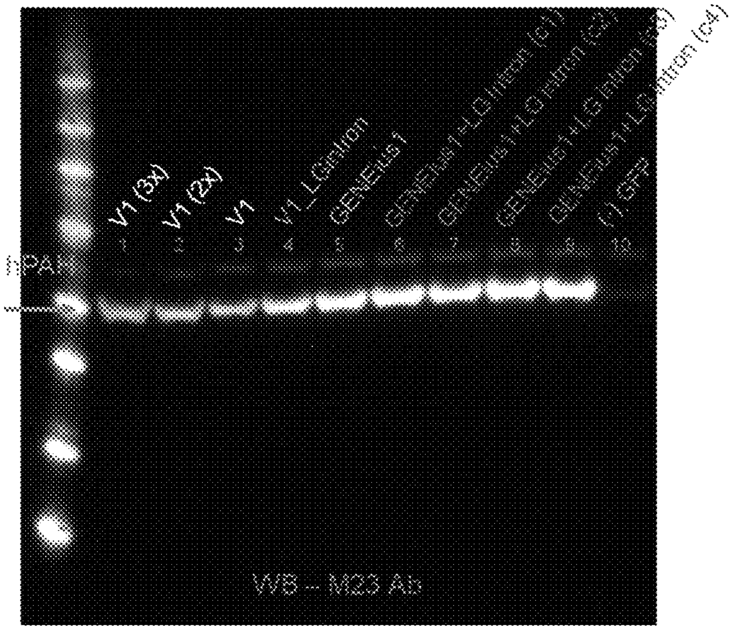
Figure 48B:
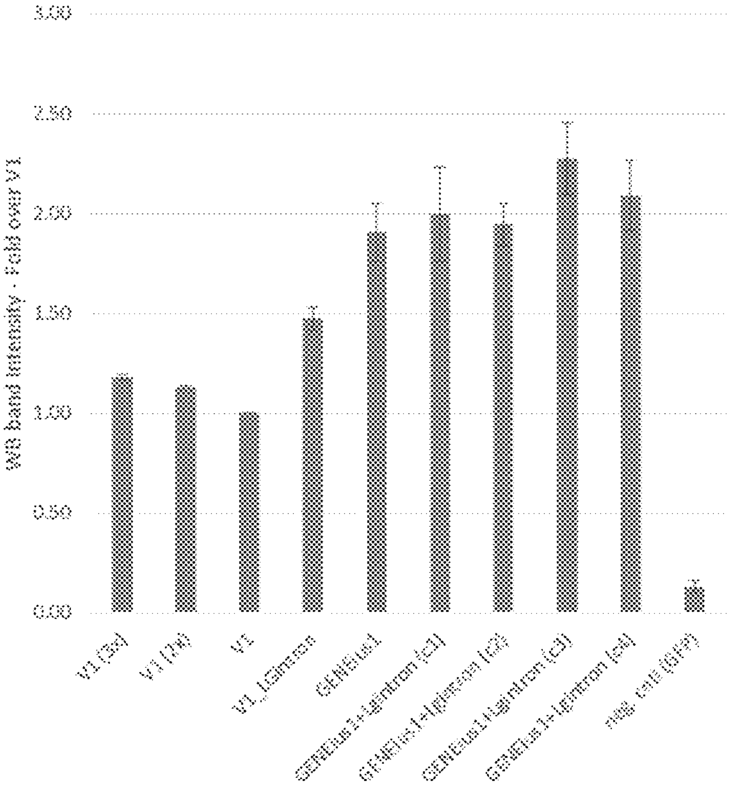

FIG. 48A-B compares V1 (ApoE-HCR-hAAT.GI.hPAHco1.bGH), V1+LG intron (ApoE-HCR-hAAT.cGA1ATI.hPAH.bGH), Geneius1 (ApoE-HCR-hAAT.GI.hPAHco1.bGH) and the vector (ApoE-HCR-hAAT.cGA1ATI.hPAHco1.bGH) herein refered to as "Vector 2" via HepG2 transfection.

Figure 49A:
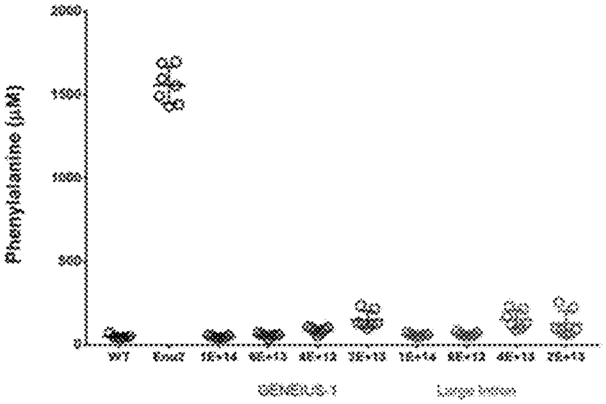
Figure 49B:
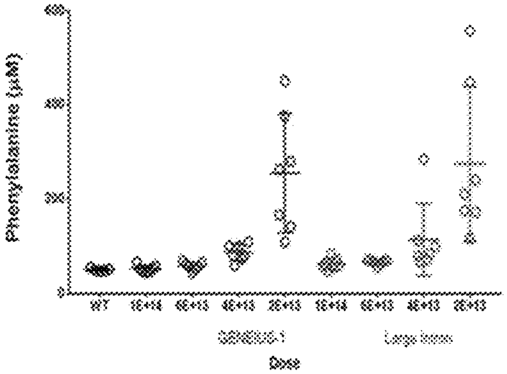
Figure 49C:
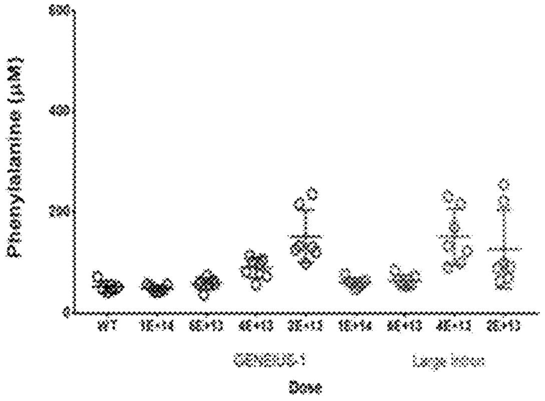

FIG. 49A-C shows a dose response curve of AAV5-PAH modified with Geneius-1, or Large Intron (A). AAV5-PAH variants were administered in ENU2 mice at various doses and plasma Phe was determined at 2 weeks (B) and 4 weeks (C).

Figure 50A:
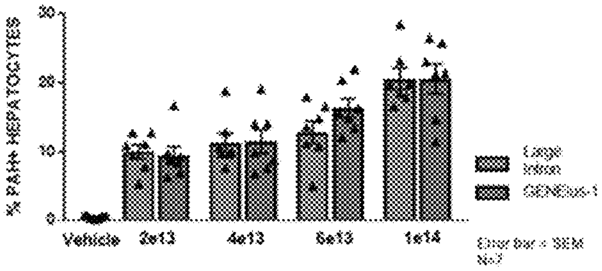
Figure 50B:
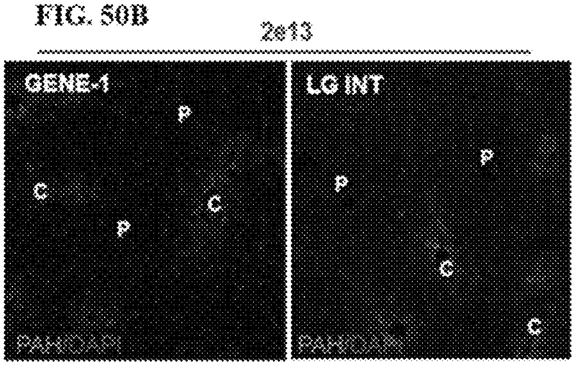
Figure 50C:
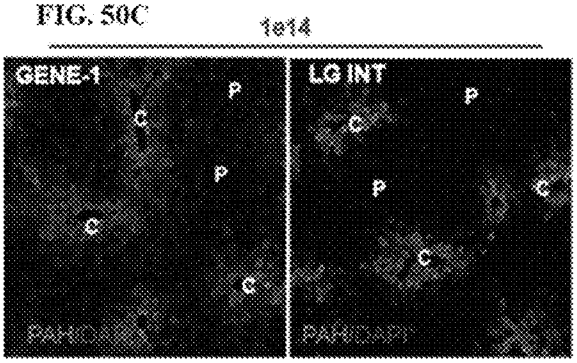

FIG. 50A-C shows dose response (A) and PAH biodistribution (B, C) of GENEius-1 and Large Intron AAV-PAH Constructs.

Figure 51A:
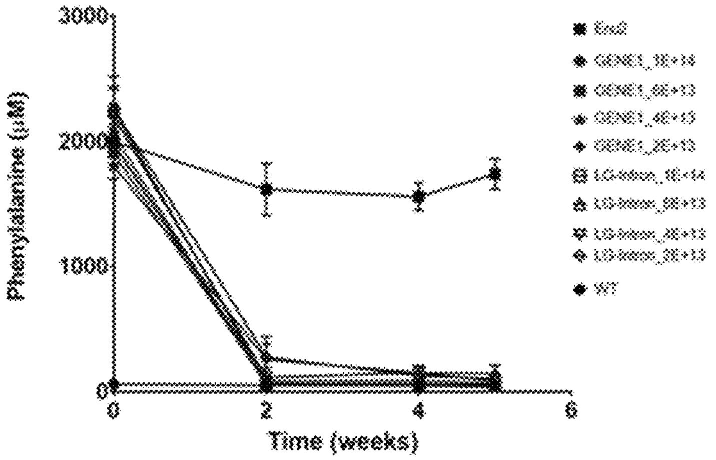
Figure 51B:
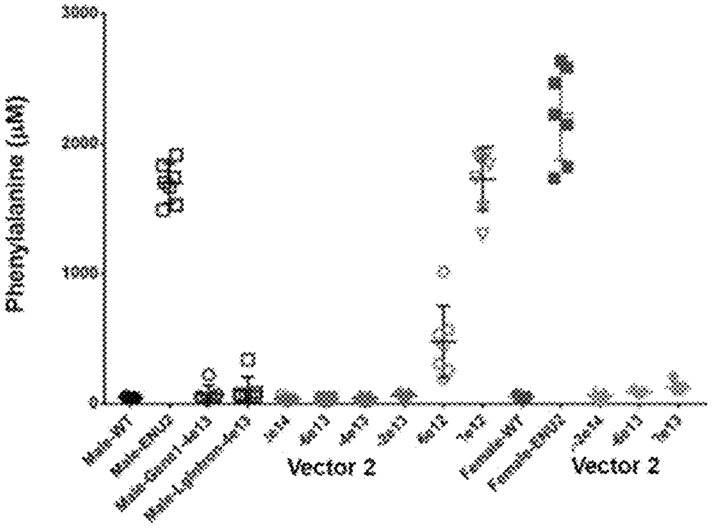

FIG. 51A-B shows dose responses AAV5-PAH variants in male and female ENU2 mice over 5 weeks (A). A dose response of the AAV5-PAH variants administered in ENU2 mice at the 2 week timepoint was examined to to more clearly identify efficacy differences of the different doses of Vector 2 administration (B).

Figure 52:
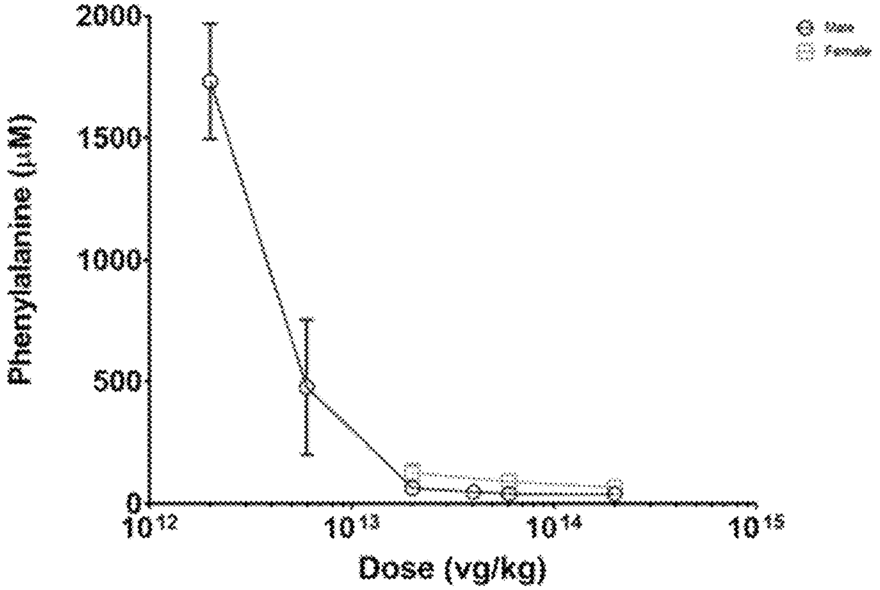

FIG. 52 shows a graph of phenylalanine levels in ENU2 mice when treated with increasing concentrations of Vector 2.

Figure 53:
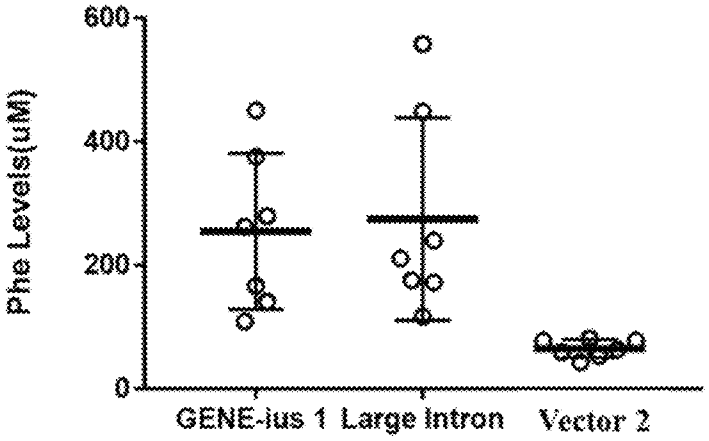

FIG. 53 compares Phe levels in male ENU2 mice at 2 weeks treated with 2e13 vg/kg of the vector candidates.

Figure 54A:
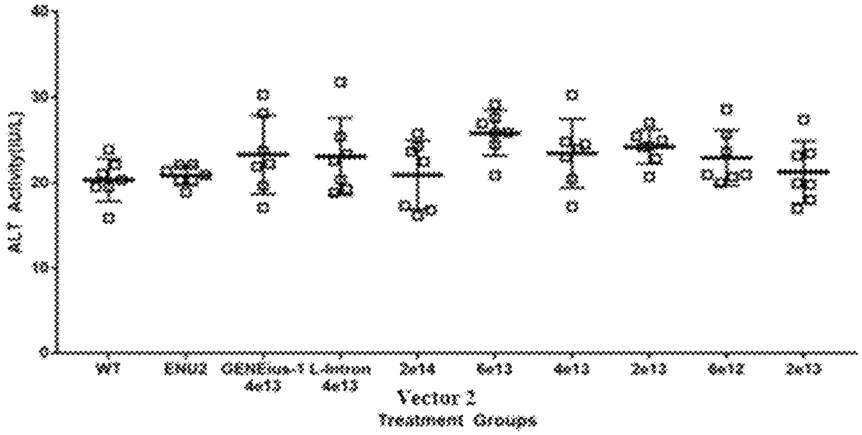
Figure 54B:
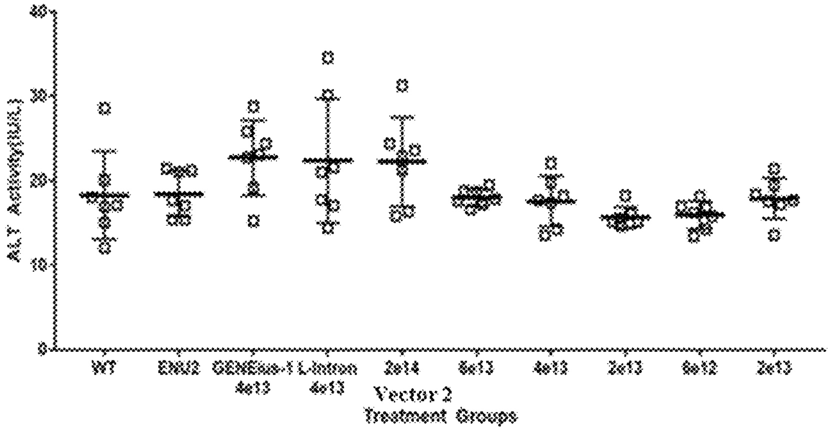

FIG. 54A-B shows plasma ALT Levels in ENU2 mice in a prebleed (A) or 2 weeks after treatment with either Vector 2, Codop, and LgIntron Constructs (B).

Figure 55:
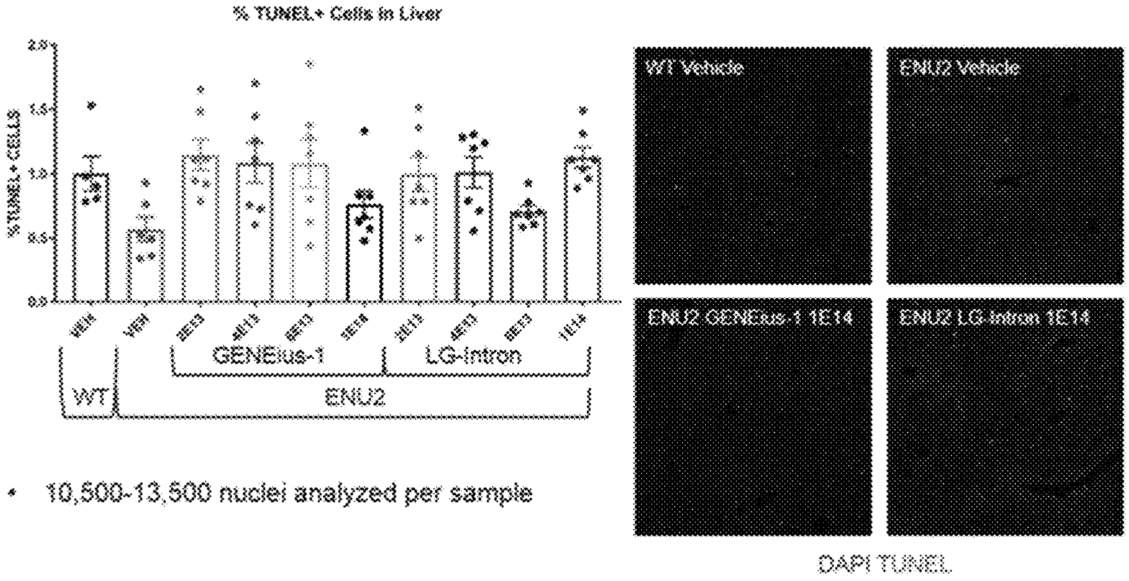

FIG. 55 show a graphical quantification of TUNEL Staining and the staining of liver tissue in ENU2 mice treated with Codop or LgIntron AAV-PAH Constructs.

Figure 56A:
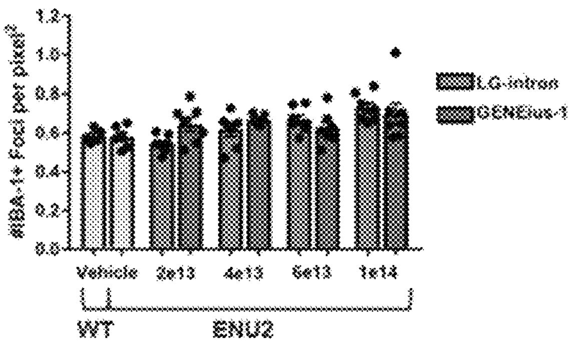
Figure 56B:
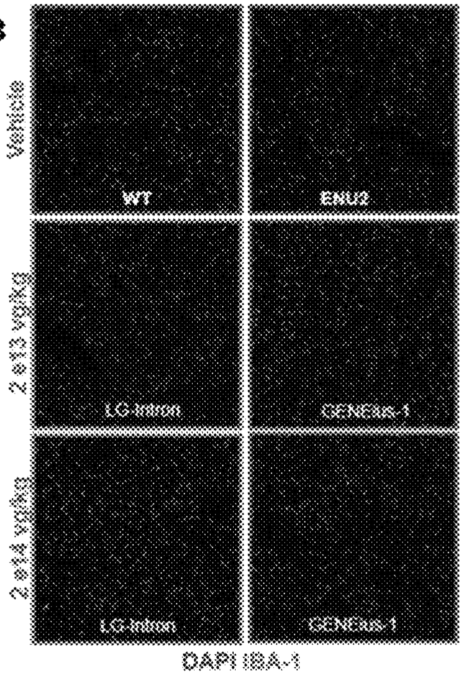

FIG. 56A-B show a graphical quantifications of IBA staining (A) and IBA staining (B) of liver tissue in ENU2 mice treated Codop or LgIntron AAV-PAH Constructs that shows no statistically relevant difference in the number of IBA-1(+) foci.

Figure 57A:
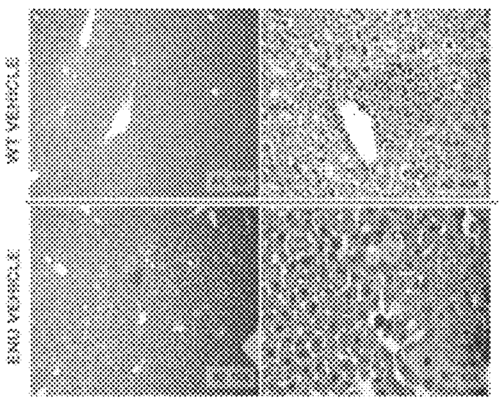
Figure 57B:
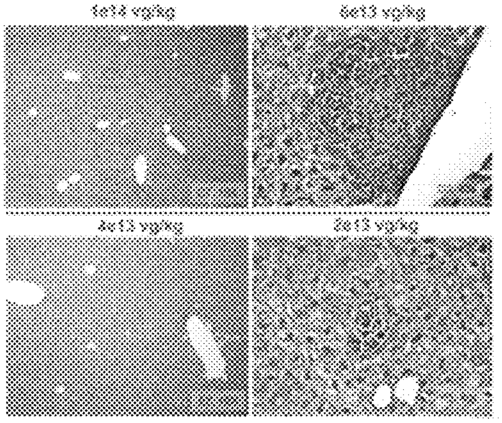
Figure 57C:
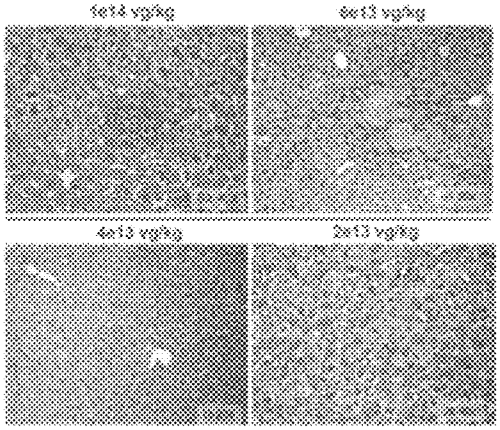

FIG. 57A-C show H&E (hematoxylin and eosin) staining of liver tissue in ENU2 mice treated with vehicle (A), Codop AAV-PAH Construct (B), or LgIntron AAV-PAH Construct (C) compared to normal wildtype mouse tissue.

Figure 58A:
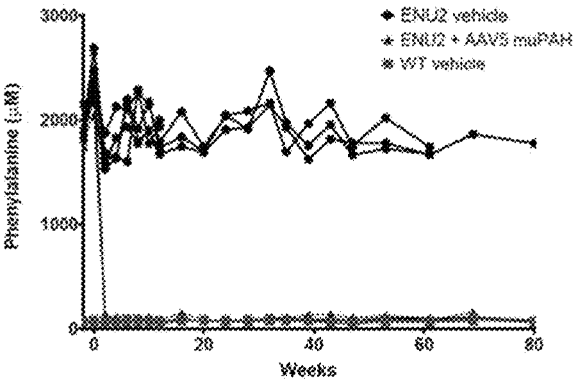
Figure 58B:
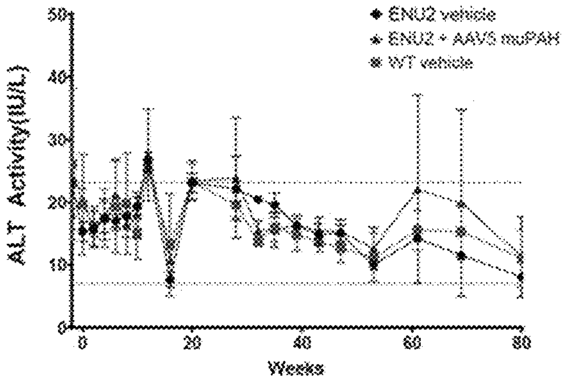
Figure 58C:
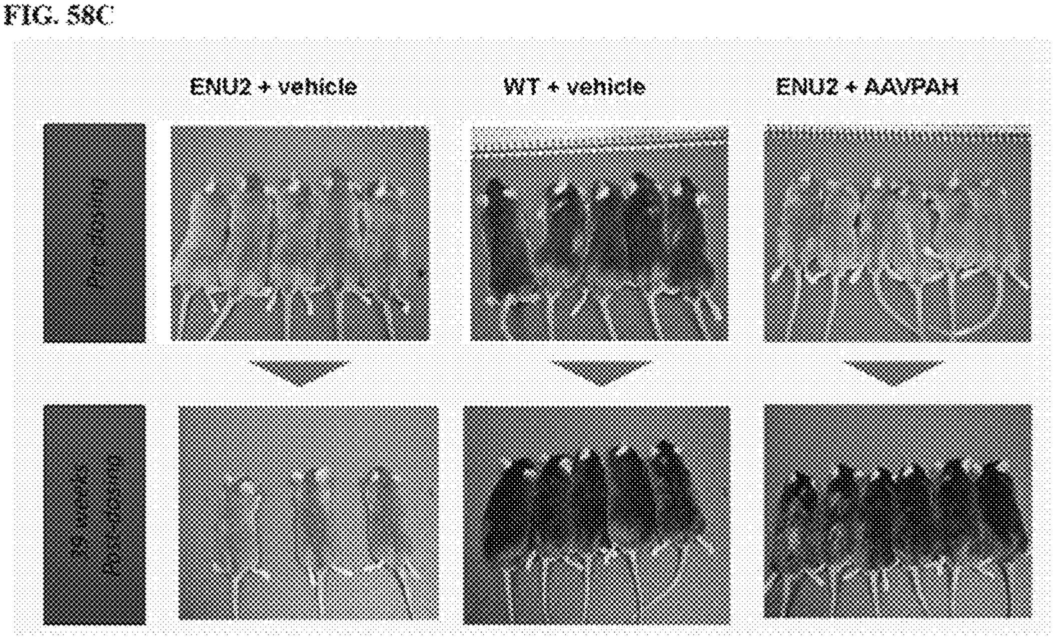

FIG. 58A-C shows that plasma phe in ENU2 mice treated with AAV5-muPAH is restore to WT levels (A), while ALT levels remain the same between the groups (B). ENU2 mice treated with AAV5-muPAH changed coat color to dark brown, similar to WT (C).

Figure 59A:
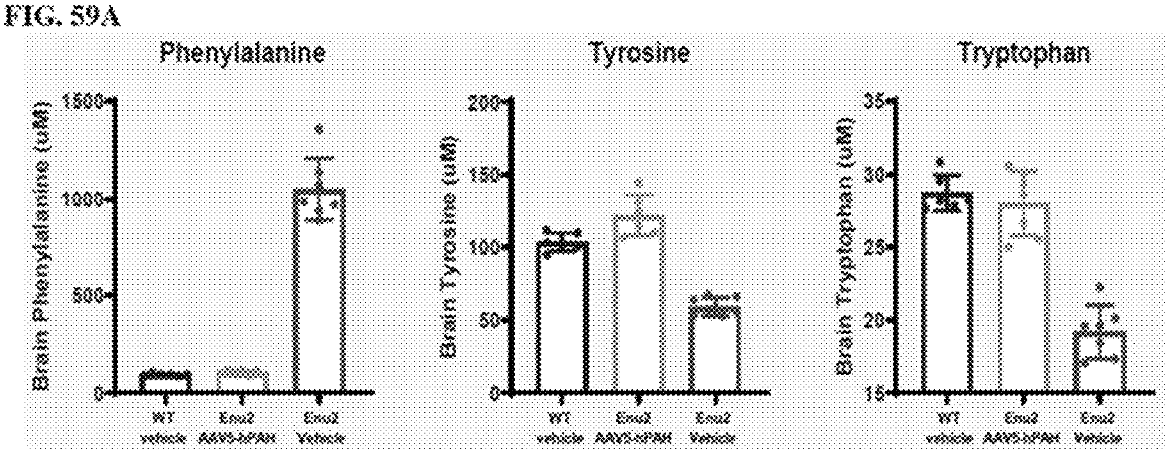
Figure 59B:
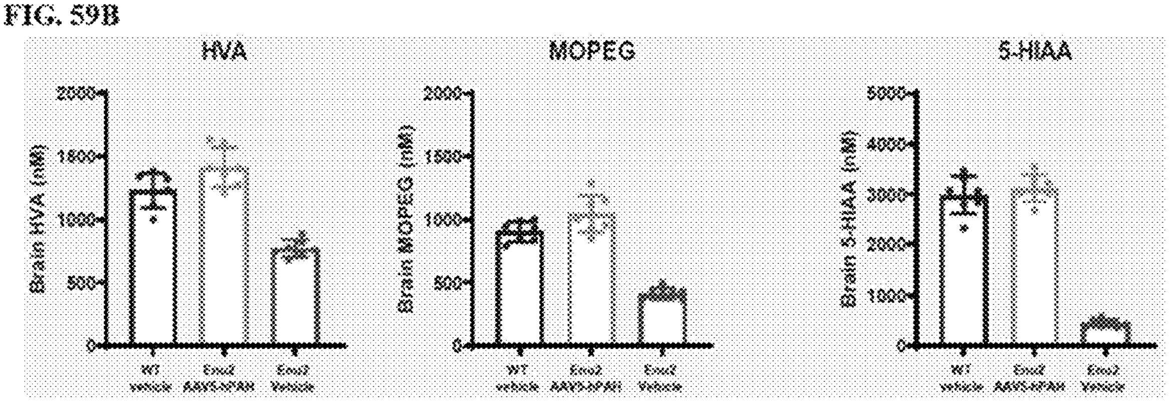

FIG. 59A-B shows levels of brain amino acids (A) and neurotransmitters (B) are restored to WT levels in ENU2 mice treated with AAV5-muPAH.

Figure 60A:
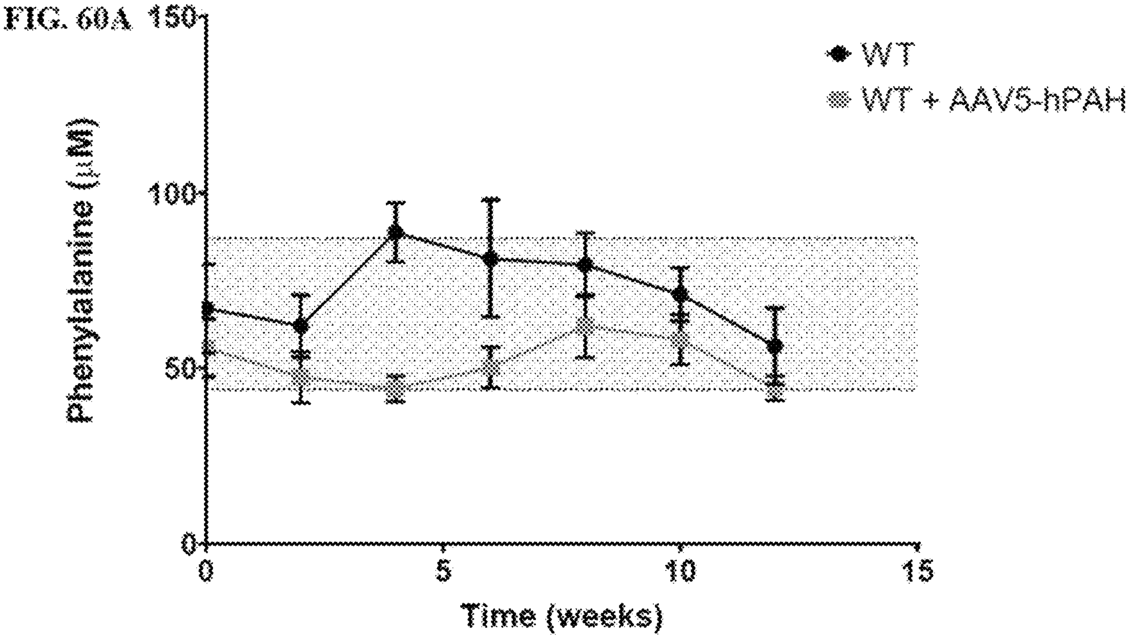
Figure 60B:
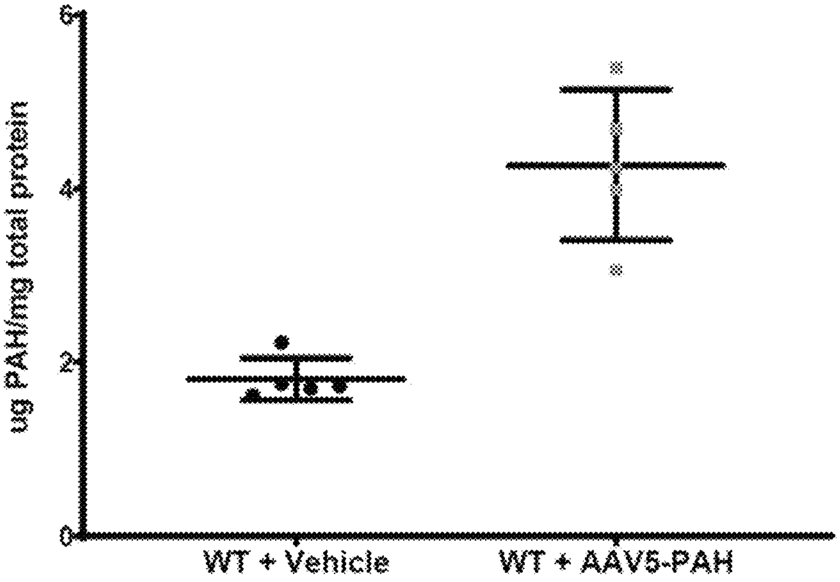

FIG. 60A-B shows wild type mice treated with AAV5-hPAH retain normal Phe levels (A) throughout the study while expressing two-fold increased PAH protein expression compared to vehicle-treated WT mice (B).

FIG. 61A-C shows hPAH DNA (A) and protein (B) in stained hepatocytes in AAV-hPAH-treated ENU2 mice, and quantification (C).

FIG. 62A-D shows an evaluation of inflammatory markers following administration of AAV5-hPAH in WT of ENU2 mice. (A) IBA1 and (B) CD68 (M1/M2 activated) macrophages were measured in mouse liver tissues. iNOS (M1 activated), a pro-inflammatory macrophage marker showed no increase between the groups (C). Graphical quantification of the staining (D).

Figure 63:
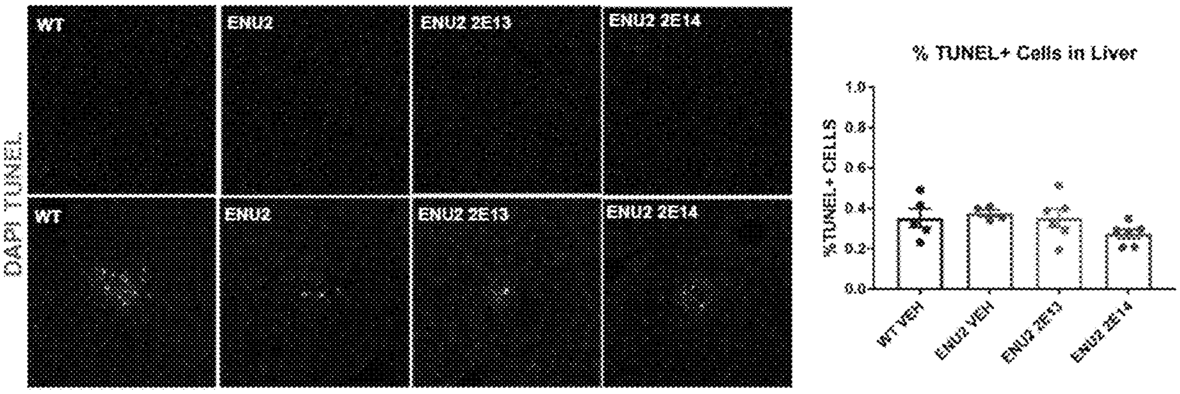

FIG. 63 shows TUNEL staining of liver tissue of ENU2 or WT mice treated with AAV-hPAH. Staining shows no significant increase in apopototic cell death in gene therapy-treated groups as compared to control mice.

Figure 64:
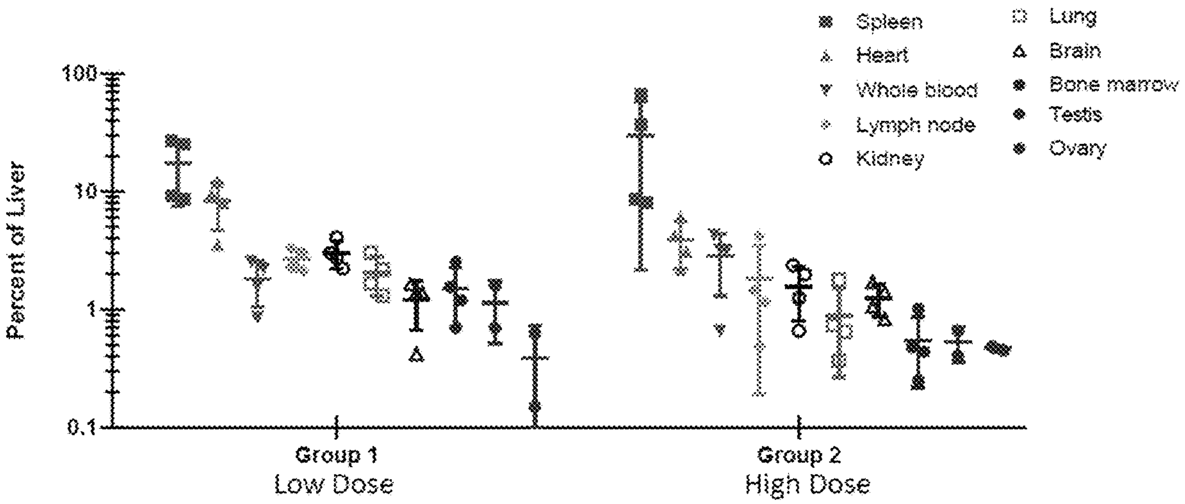

FIG. 64 shows the biodistribution of Vector 2 delivered at two different dose levels to cynomolus monkeys by IV injection. Results are presented as a percent of the genomic vector DNA extracted from the liver.

Figure 65A:
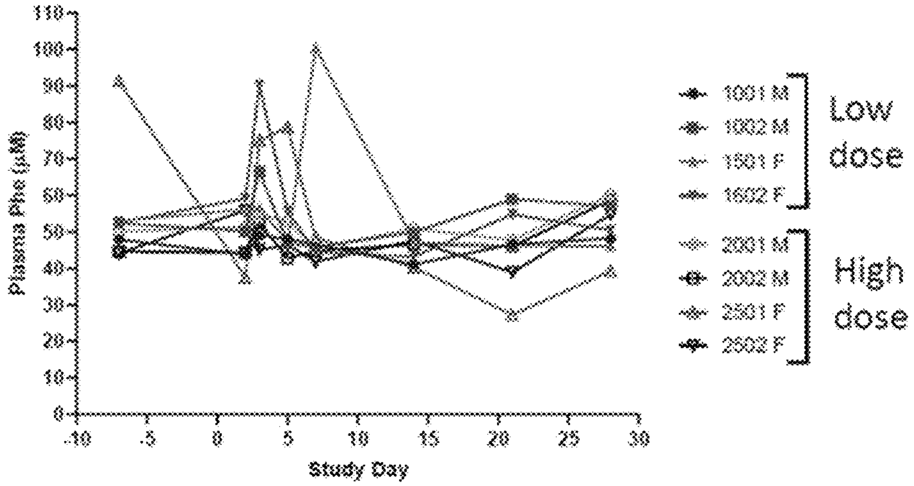
Figure 65B:
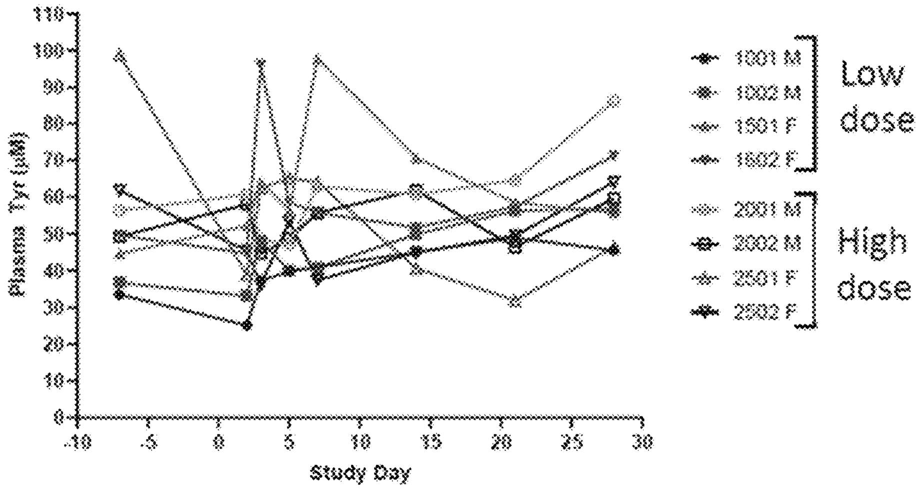

FIG. 65A-B shows the plasma phenylalanine (A) and tyrosine (B) levels of cynomolgus monkeys treated with either a high dose or low dose of Vector 2 over a time course of 30 days.

Figure 66A:
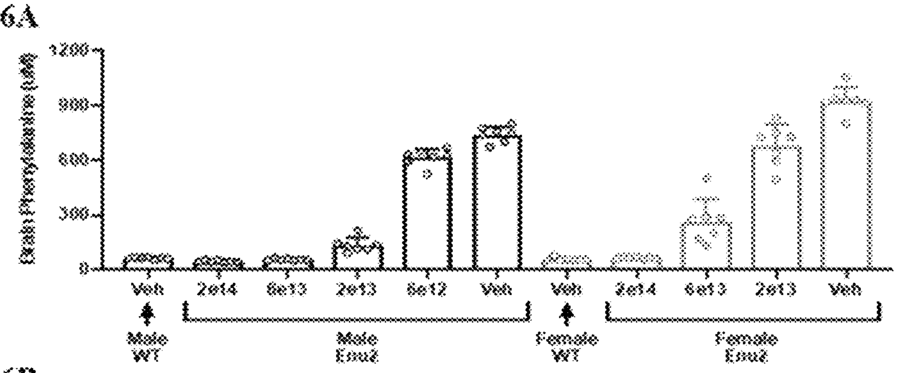
Figure 66B:
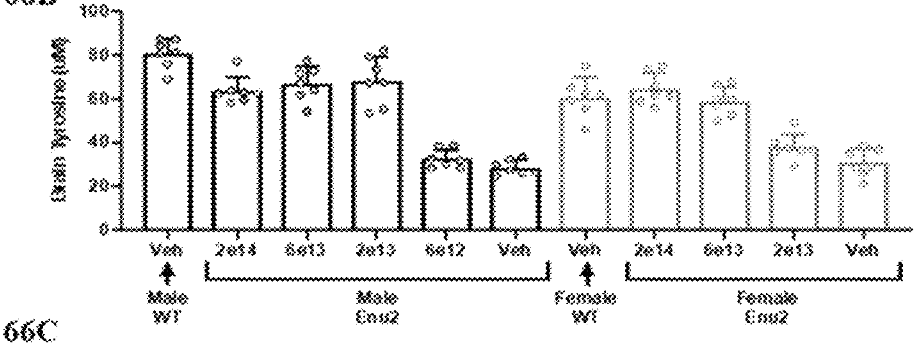
Figure 66C:
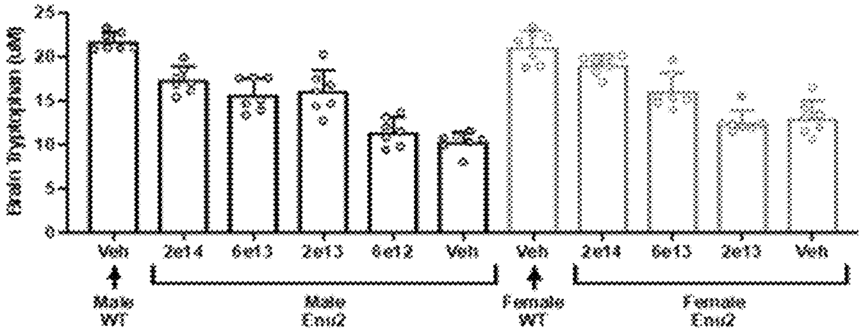

FIG. 66A-C shows administration of ENU2 mice with Vector 2 resulted in correction of amino acid levels in brain homogenates.

FIG. 67A-D shows administration of ENU2 mice with Vector 2 resulted in correction of neurotransmitter levels in brain homogenates.

Figure 68A:
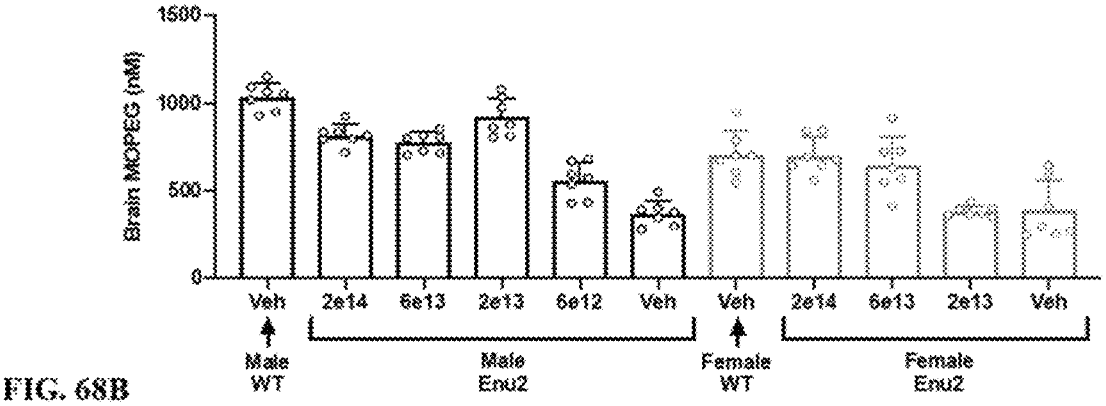
Figure 68B:
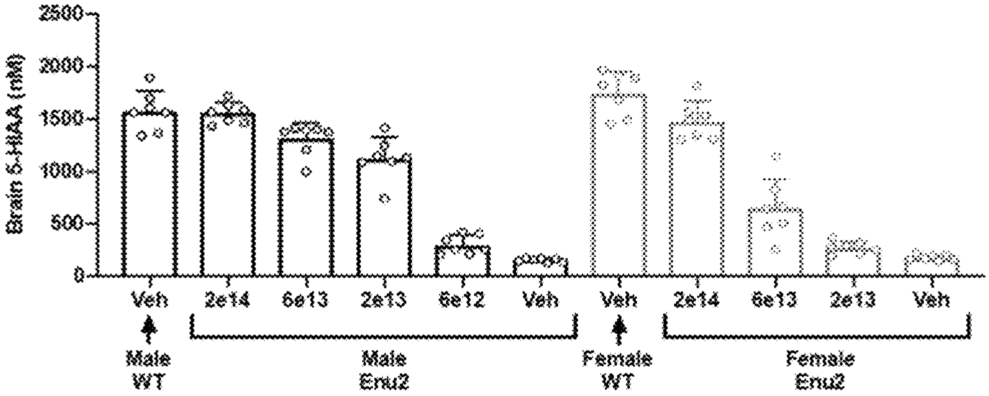
Figure 68C:
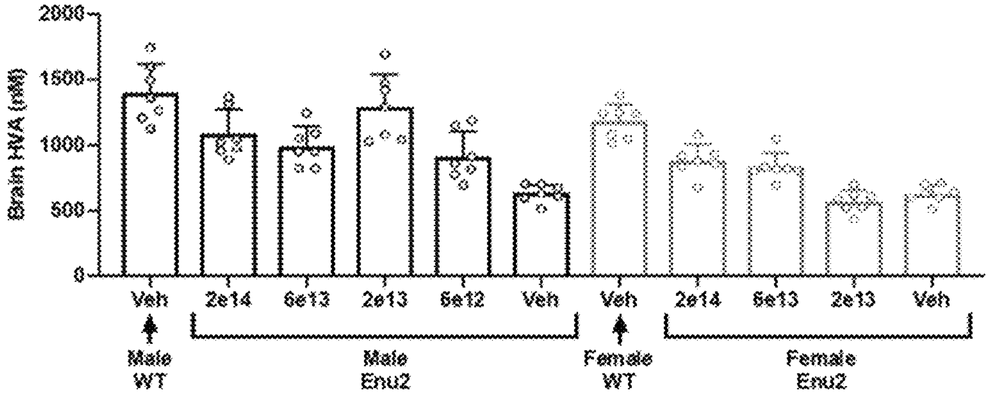

FIG. 68A-C shows neurotransmitter metabolite correction observed with high-dose Vector 2.

5. DETAILED DESCRIPTION

In one embodiment, provided herein is the use of amino acid, neurotransmitter, and neurotransmitter metabolite levels in subjects having phenylketonuria (PKU) to optimize an effective dose of a PKU therapeutic. In another embodiment, provided are methods of treating subjects having PKU comprising administering an effective amount of a PKU therapeutic where the effective amount is one that normalizes levels of amino acids, neurotransmitter metabolites, and neurotransmitters in the subject.

In one embodiment, provided herein are AAV vectors encoding functionally active therapeutic proteins (e.g., completely packaged AAV PAH vectors, AAV PAH vectors, and isolated nucleic acid molecules comprising a nucleotide sequence having substantial homology to the nucleotide sequence of SEQ ID NO: 1). In another embodiment, the recombinant AAV therapeutic protein vectors have improved transgene expression, as well as improved AAV virus production yield and simplified purification. In certain embodiments, introducing one or more introns into the therapeutic protein-coding region, codon optimization, and/or reconfiguring the number and positioning of enhancers enhances expression.

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N.Y. 1989). For purposes of the present disclosure, the following terms are defined below.

As used herein, in the context of gene delivery, the term "vector" or "gene delivery vector" may refer to a particle that functions as a gene delivery vehicle, and which comprises nucleic acid (i.e., the vector genome) packaged within, for example, an envelope or capsid. A gene delivery vector may be a viral gene delivery vector or a non-viral gene delivery vector. Alternatively, in some contexts, the term "vector" may be used to refer only to the vector genome. Viral vectors suitable for use herein may be a parvovirus, an adenovirus, a retrovirus, a lentivirus or a herpes simplex virus. The parvovirus may be an adenovirus-associated virus (AAV).

As used herein, an "AAV vector" refers to nucleic acids, either single-stranded or double-stranded, having an AAV 5' inverted terminal repeat (ITR) sequence and an AAV 3' ITR flanking a protein-coding sequence (in one embodiment, a functional therapeutic protein-encoding sequence, e.g. PAH) operably linked to transcription regulatory elements that are heterologous to the AAV viral genome, i.e., one or more promoters and/or enhancers and, optionally, a polyadenylation sequence and/or one or more introns inserted between exons of the protein-coding sequence. A single-stranded AAV vector refers to nucleic acids that are present in the genome of an AAV virus particle, and can be either the sense strand or the anti-sense strand of the nucleic acid sequences disclosed herein. The size of such single-stranded nucleic acids is provided in bases. A double-stranded AAV vector refers to nucleic acids that are present in the DNA of plasmids, e.g., pUC19, or genome of a double-stranded virus, e.g., baculovirus, used to express or transfer the AAV vector nucleic acids. The size of such double-stranded nucleic acids in provided in base pairs (bp).

The term "inverted terminal repeat (ITR)" as used herein refers to the art-recognized regions found at the 5' and 3' termini of the AAV genome which function in cis as origins of DNA replication and as packaging signals for the viral genome. AAV ITRs, together with the AAV rep coding region, provide for efficient excision and rescue from, and integration of a nucleotide sequence interposed between two flanking ITRs into a host cell genome. Sequences of certain AAV-associated ITRs are disclosed by Yan et al., *J. Virol.* (2005) vol. 79, pp. 364-379 which is herein incorporated by reference in its entirety. ITR sequences that find use herein may be full length, wild-type AAV ITRs or fragments thereof that retain functional capability, or may be sequence variants of full-length, wild-type AAV ITRs that are capable of functioning in cis as origins of replication. AAV ITRs useful in the recombinant AAV PAH vectors of the embodiments provided herein may be derived from any known AAV serotype and, in certain embodiments, derived from the AAV1, AAV2, AAV3, AAV4, AAV5, AAV6, AAV7, AAV8, or AAV9 serotype.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A "transcription regulatory element" refers to nucleotide sequences of a gene involved in regulation of genetic transcription including a promoter, plus response elements, activator and enhancer sequences for binding of transcription factors to aid RNA polymerase binding and promote expression, and operator or silencer sequences to which repressor proteins bind to block RNA polymerase attachment and prevent expression. The term "liver specific transcription regulatory element" refers to a regulatory element that modulates gene expression specifically in the liver tissue. Examples of liver specific regulatory elements include, but are not limited to, the mouse thyretin promoter (mTTR), the endogenous human factor VIII promoter (F8), human alpha-1-antitrypsin promoter (hAAT) and active fragments thereof, human albumin minimal promoter, and mouse albumin promoter. Enhancers derived from liver-specific transcription factor binding sites are also contemplated, such as EBP, DBP, HNF1, HNF3, HNF4, HNF6, and Enh1.

As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element. For instance, a promoter is operably linked to a coding sequence if the promoter effects transcription or expression of the coding sequence.

In one embodiment, the AAV vector comprises a nucleic acid encoding a functionally active phenylalanine hydroxylase (PAH) protein. The PAH encoding sequence may be wild-type, codon optimized, or a variant (see, e.g., Fang et al., *Gene Ther.*, vol. 1, pages 247-254 (1994); Eisensmith et al., *J. Inherit. Metab. Dis.*, vol. 19, pages 412-423 (1996); Nagasaki et al., *Pediatr. Res.*, vol. 45, pages 465-473 (1999); and Laipis et al., *Mol. Ther.*, vol. 7, pages S391-S392 (2003)).

As used herein, wild-type PAH has the following nucleic acid sequence:

(SEQ ID NO: 1)

```
ATGTCCACTGCGGTCCTGGAAAACCCAGGCTTGGGCAGGAAACTCTCTGA

CTTTGGACAGGAAACAAGCTATATTGAAGACAACTGCAATCAAAATGGTG

CCATATCACTGATCTTCTCACTCAAAGAAGAAGTTGGTGCATTGGCCAAA
```

-continued

```
GTATTGCGCTTATTTGAGGAGAATGATGTAAACCTGACCCACATTGAATC

TAGACCTTCTCGTTTAAAGAAAGATGAGTATGAATTTTTCACCCATTTGG

ATAAACGTAGCCTGCCTGCTCTGACAAACATCATCAAGATCTTGAGGCAT

GACATTGGTGCCACTGTCCATGAGCTTTCACGAGATAAGAAGAAAGACAC

AGTGCCCTGGTTCCCAAGAACCATTCAAGAGCTGGACAGATTTGCCAATC

AGATTCTCAGCTATGGAGCGGAACTGGATGCTGACCACCCTGGTTTTAAA

GATCCTGTGTACCGTGCAAGACGGAAGCAGTTTGCTGACATTGCCTACAA

CTACCGCCATGGGCAGCCCATCCCTCGAGTGGAATACATGGAGGAAGAAA

AGAAAACATGGGGCACAGTGTTCAAGACTCTGAAGTCCTTGTATAAAACC

CATGCTTGCTATGAGTACAATCACATTTTTCCACTTCTTGAAAAGTACTG

TGGCTTCCATGAAGATAACATTCCCCAGCTGGAAGACGTTTCTCAGTTCC

TGCAGACTTGCACTGGTTTCCGCCTCCGACCTGTAGCTGGCCTGCTTTCC

TCTCGGGATTTCTTGGGTGGCCTGGCCTTCCGAGTCTTCCACTGCACACA

GTACATCAGACATGGATCCAAGCCCATGTATACCCCCGAACCTGACATCT

GCCATGAGCTGTTGGGACATGTGCCCTTGTTTTCAGATCGCAGCTTTGCC

CAGTTTTCCCAGGAAATTGGCCTTGCCTCTCTGGGTGCACCTGATGAATA

CATTGAAAAGCTCGCCACAATTTACTGGTTTACTGTGGAGTTTGGGCTCT

GCAAACAAGGAGACTCCATAAAGGCATATGGTGCTGGGCTCCTGTCATCC

TTTGGTGAATTACAGTACTGCTTATCAGAGAAGCCAAAGCTTCTCCCCCT

GGAGCTGGAGAAGACAGCCATCCAAAATTACACTGTCACGGAGTTCCAGC

CCCTGTATTACGTGGCAGAGAGTTTTAATGATGCCAAGGAGAAAGTAAGG

AACTTTGCTGCCACAATACCTCGGCCCTTCTCAGTTCGCTACGACCCATA

CACCCAAAGGATTGAGGTCTTGGACAATACCCAGCAGCTTAAGATTTTGG

CTGATTCCATTAACAGTGAAATTGGAATCCTTTGCAGTGCCCTCCAGAAA

ATAAAGTAA
```

As used herein, wild-type PAH has the following amino acid sequence:

```
                                         (SEQ ID NO: 2)
MSTAVLENPG LGRKLSDFGQ ETSYIEDNCN QNGAISLIFS

LKEEVGALAK VLRLFEENDV NLTHIESRPS RLKKDEYEFF

THLDKRSLPA LTNIIKILRH DIGATVHELS RDKKKDTVPW

FPRTIQELDR FANQILSYGA ELDADHPGFK DPVYRARRKQ

FADIAYNYRH GQPIPRVEYM EEEKKTWGTV FKTLKSLYKT

HACYEYNHIF PLLEKYCGFH EDNIPQLEDV SQFLQTCTGF

RLRPVAGLLS SRDFLGGLAF RVFHCTQYIR HGSKPMYTPE

PDICHELLGH VPLFSDRSFA QFSQEIGLAS LGAPDEYIEK

LATIYWFTVE FGLCKQGDSI KAYGAGLLSS FGELQYCLSE

KPKLLPLELE KTAIQNYTVT EFQPLYYVAE SFNDAKEKVR

NFAATIPRPF SVRYDPYTQR IEVLDNTQQL KILADSINSE

IGILCSALQK IK.
```

According to a first aspect of the disclosure, there is provided an AAV vector comprising a nucleotide sequence having substantial homology to the nucleotide sequence of SEQ ID NO: 1 and which encodes functional PAH. The term substantial homology can be further defined with reference to a percent (%) homology. This is discussed in further detail elsewhere herein.

The term "isolated" when used in relation to a nucleic acid molecule of the present disclosure typically refers to a nucleic acid sequence that is identified and separated from at least one contaminant nucleic acid with which it is ordinarily associated in its natural source. Isolated nucleic acid may be present in a form or setting that is different from that in which it is found in nature. Isolated nucleic acid molecules therefore are distinguished from the nucleic acid molecule as it exists in natural cells.

As used herein, the term "variant" refers to a polynucleotide (or polypeptide) having a sequence substantially similar to a reference polynucleotide (or polypeptide). Procedures for the introduction of nucleotide and amino acid changes in a polynucleotide, protein or polypeptide are known to the skilled artisan (see, e.g., Sambrook et al. (1989)). In the case of a polynucleotide, a variant can have deletions, substitutions, additions of one or more nucleotides at the 5' end, 3' end, and/or one or more internal sites in comparison to the reference polynucleotide. Similarities and/or differences in sequences between a variant and the reference polynucleotide can be detected using conventional techniques known in the art, for example polymerase chain reaction (PCR) and hybridization techniques. Variant polynucleotides also include synthetically derived polynucleotides, such as those generated, for example, by using site-directed mutagenesis. Generally, a variant of a polynucleotide, including, but not limited to, a DNA, can have at least about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polynucleotide as determined by sequence alignment programs known by skilled artisans. In the case of a polypeptide, a variant can have deletions, substitutions, additions of one or more amino acids in comparison to the reference polypeptide. Similarities and/or differences in sequences between a variant and the reference polypeptide can be detected using conventional techniques known in the art, for example Western blot. Generally, a variant of a polypeptide, can have at least about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polypeptide as determined by sequence alignment programs known by skilled artisans.

The term "identity," "homology" and grammatical variations thereof, mean that two or more referenced entities are the same, when they are "aligned" sequences. Thus, by way of example, when two polypeptide sequences are identical, they have the same amino acid sequence, at least within the referenced region or portion. Where two polynucleotide sequences are identical, they have the same polynucleotide sequence, at least within the referenced region or portion. The identity can be over a defined area (region or domain) of the sequence. An "area" or "region" of identity refers to a portion of two or more referenced entities that are the same. Thus, where two protein or nucleic acid sequences are identical over one or more sequence areas or regions they share identity within that region. An "aligned" sequence refers to multiple polynucleotide or protein (amino acid)

sequences, often containing corrections for missing or additional bases or amino acids (gaps) as compared to a reference sequence. "Substantial homology" means that a molecule is structurally or functionally conserved such that it has or is predicted to have at least partial structure or function of one or more of the structures or functions (e.g., a biological function or activity) of the reference molecule, or relevant/corresponding region or portion of the reference molecule to which it shares homology.

"Percent (%) nucleic acid sequence identity" is defined as the percentage of nucleotides in a candidate sequence that are identical with a reference sequence after aligning the respective sequences and introducing gaps, if necessary, to achieve the maximum percent sequence identity. Alignment for purposes of determining percent nucleic acid sequence identity can be achieved in various ways that are within the skill in the art, for instance, using publicly available computer software such as ALIGN or Megalign (DNASTAR) software. Those skilled in the art can determine appropriate parameters for measuring alignment, including any algorithms needed to achieve maximal alignment over the full length of the sequences being compared.

"Percent (%) amino acid sequence identity" with respect to the PAH amino acid sequences identified herein is defined as the percentage of amino acid residues in a candidate sequence that are identical to the amino acid residues in a PAH polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as ALIGN or Megalign (DNASTAR) software. Those skilled in the art can determine appropriate parameters for measuring alignment, including any algorithms needed to achieve maximal alignment over the full length of the sequences being compared.

"Codon optimization" or "codon optimized" refers to changes made in the nucleotide sequence so that it is more likely to be expressed at a relatively high level compared to the non-codon optimized sequence. It does not change the amino acid for which each codon encodes.

As used herein, an "intron" is broadly defined as a sequence of nucleotides that is removable by RNA splicing. "RNA splicing" means the excision of introns from a pre-mRNA to form a mature mRNA. Insertion of an intron into an expressed sequence can be accomplished by any method known in the art. The only limitation of where the intron is inserted is in consideration of the packaging limitations of the AAV virus particles (about 5 kbp).

An "AAV virion" or "AAV viral particle" or "AAV vector particle" or "AAV virus" refers to a viral particle composed of at least one AAV capsid protein and an encapsidated polynucleotide AAV vector as described herein. If the particle comprises a heterologous polynucleotide (i.e., a polynucleotide other than a wild-type AAV genome such as a transgene to be delivered to a mammalian cell), it is typically referred to as an "AAV vector particle" or simply an "AAV vector". Thus, production of AAV vector particles necessarily includes production of an AAV vector, as such a vector is contained within an AAV vector particle.

As used herein "therapeutic AAV virus" refers to an AAV virion, AAV viral particle, AAV vector particle, or AAV virus that comprises a heterologous polynucleotide that encodes a therapeutic protein. An "AAV vector" as used herein refers to a vector comprising one or more polynucleotides of interest (or transgenes) that are flanked by AAV terminal repeat sequences (ITRs) and operably linked to one or more expression control elements. Such AAV vectors can be replicated and packaged into infectious viral particles when present in a host cell that has been transfected with a vector encoding and expressing rep and cap gene products.

As used herein "therapeutic protein" refers to a polypeptide that has a biological activity that replaces or compensates for the loss or reduction of activity of an endogenous protein. For example, a functional phenylalanine hydroxylase (PAH) is a therapeutic protein for phenylketonuria (PKU).

"Neurotransmitter" as used herein refers to a chemical that is released from a nerve cell which thereby transmits an impulse from the nerve cell to another nerve, muscle, organ, or other tissue. A neurotransmitter is a messenger of neurologic information from one cell to another. In certain embodiments, neurotransmitters include phenethylamine, tyramine, dopamine, norepinephrine, epinephrine, tryptamine, and serotonin. "Neurotransmitter metabolite" as used herein refers to the products following degradation of the neurotransmitters, one or two enzymatic steps downstream. Non-limiting examples of neurotransmitter metabolites include phenylacetic acid, phenylacetylglycine, phenylacetylglutamine, DOPAC, homovanillic acid, dihydroxyphenylethylene glycol (DOPEG), 3-methoxy-4-hydroxyphenylglycol (MHPG, MOPEG), indoleacetic acid and 5-hydroxyindoleacetic acid. Non-limiting examples of neurotransmitters and metabolites are also shown in FIG. 24.

"Phenylketonuria (PKU)" as used herein refers to an inherited metabolic disease caused by a deficiency of the enzyme phenylalanine hydroxylase (PAH). This results in elevated, levels of phenylalanine (Phe) and reduced levels of neurotransmitters and neurotransmitter metabolites which can affect brain function, causing severe intellectual disability, behavioral abnormalities, delayed speech and seizures.

"Treat" or "treatment" as used herein refers to therapeutic treatment which refers to a treatment administered to a subject who exhibits signs or symptoms of pathology, i.e., PKU, for the purpose of diminishing or eliminating those signs or symptoms. The signs or symptoms can be biochemical, cellular, histological, functional, subjective or objective. "Treat" or "treatment" refers to the reduction or amelioration of the progression, severity, and/or duration of a disease (or symptom related thereto) associated with elevated phenylalanine levels (e.g., PKU).

"Ameliorate" as used herein refers to the action of lessening the severity of symptoms, progression, or duration of a disease.

As used herein "stably treating" or "stable treatment" refers to using a therapeutic AAV virus administered to a subject where the subject stably expresses a therapeutic protein expressed by the therapeutic AAV virus. Stably expressed therapeutic protein means that the protein is expressed for a clinically significant length of time. "Clinically significant length of time" as used herein means expression at therapeutically effective levels for a length of time that has a meaningful impact on the quality of life of the subject. In certain embodiments a meaningful impact on the quality of life is demonstrated by the lack of a need to administer alternative therapies intravenously or subcutaneously. In certain embodiments clinically significant length of time is expression for at least six months, for at least eight months, for at least one year, for at least two years, for at least three years, for at least four years, for at least five years, for at least six years, for at least seven years, for at least eight years, for at least nine years, for at least ten years, or for the life of the subject.

As used herein, the term "effective amount" refers to an amount sufficient to effect beneficial or desirable biological and/or clinical results.

As used herein, a "subject" refers to an animal that is the object of treatment, observation or experiment. "Animal" includes cold- and warm-blooded vertebrates and invertebrates such as fish, shellfish, reptiles, and in particular, mammals. "Mammal," as used herein, refers to an individual belonging to the class Mammalia and includes, but not limited to, humans, domestic and farm animals, zoo animals, sports and pet animals. Non-limiting examples of mammals include mice; rats; rabbits; guinea pigs; dogs; cats; sheep; goats; cows; horses; primates, such as monkeys, chimpanzees and apes, and, in particular, humans. In some embodiments, the mammal is a human. However, in some embodiments, the mammal is not a human.

In general, a "pharmaceutically acceptable carrier" is one that is not toxic or unduly detrimental to cells. Exemplary pharmaceutically acceptable carriers include sterile, pyrogen-free water and sterile, pyrogen-free, phosphate buffered saline. Pharmaceutically acceptable carriers include physiologically acceptable carriers. The term "pharmaceutically acceptable carrier" includes any and all solvents, dispersion media, coatings, antibacterial and antifungal agents, isotonic and absorption delaying agents, and the like that are physiologically compatible".

By "pharmaceutically acceptable" it is meant a material that is not biologically or otherwise undesirable, i.e., the material may be administered to a subject without causing any undesirable biological effects. Thus, such a pharmaceutical composition may be used, for example, in transfection of a cell ex vivo or in administering a viral particle or cell directly to a subject.

A carrier may be suitable for parenteral administration, which includes intravenous, intraperitoneal or intramuscular administration. Alternatively, the carrier may be suitable for sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions provided herein is contemplated.

"Neurotypical" or "neurotypical subject" as used herein refers to a subject or group of subjects that do not suffer from and do not have symptoms of any neurological or neurocognitive diseases or conditions. In certain embodiments, neurotypical subjects have levels of neurotransmitter and neurotransmitter metabolite levels that are within the normal range of a healthy human being or the normal range determined from the average levels of a group of normal human beings. When applied to animal subjects, such as mice, neurotypical neurotransmitter and neurotransmitter metabolite levels are those measured in wild-type control animals.

KUVAN® (sapropterin dihydrochloride) is the first and only FDA-approved medication for PKU to reduce blood Phe levels in patients with hyperphenylalaninemia (HPA) due to tetrahydrobiopterin (BH4-) responsive PKU. KUVAN® is a pharmaceutical formulation of BH4, the natural cofactor for the PAH enzyme, which stimulates activity of the residual PAH enzyme to metabolize Phe into tyrosine. KUVAN® is described in U.S. Pat. Nos. 7,732,599, 8,003,126, 7,566,462, and 8,178,670, each of which is incorporated by reference in its entirety.

PALYNZIQ® (pegvaliase-pqpz) (pegylated recombinant phenylalanine ammonia lyase or 'PEG-PAL') is an investigational enzyme substitution therapy for the treatment of phenylketonuria (PKU). PALYNZIQ® (pegvaliase-pqpz) is described in U.S. Pat. Nos. 7,531,341, 7,534,595, 7,537,923, 7,790,433, 7,560,263, 9,557,34. each of which is incorporated by reference in its entirety.

"PKU therapy" as used herein refers to any therapeutic intervention of a subject having PKU that ameliorates PKU symptoms or reduces the levels of serum phenylalanine. "PKU gene therapy" as used herein refers to any therapeutic intervention of a subject having PKU that involves the replacement or restoration of phenylalanine hydroxylase activity through the delivery of one or more nucleic acid molecules to the cells of the subject that replace or restore the expression of biologically active phenylalanine hydroxylase enzymatic activity. In certain embodiments, PKU gene therapy refers to gene therapy involving an adeno associated viral (AAV) vector that expresses human phenylalanine hydroxylase.

"Neurocognitive symptoms" as used herein refers to specific neurological, behavioral, and cognitive symptoms associated with subjects having phenylketonuria. In particular, the loss of phenylalanine hydroxylase activity results in the inability of subjects having phenylketonuria from producing sufficient neurotransmitter levels. The inability to produce sufficient neurotransmitters directly results in a number of neurological, cognitive, and behavioral symptoms. In one embodiment, neurocognitive symptoms decreased IQ, attention deficits, and deficits in executive functions including strategic planning, inhibitory control, working memory, and cognitive flexibility.

Enu2 mice are described by Shedlovsky A, et al. (Mouse models of human phenylketonuria, (1993), *Genetics*, vol. 134, pages 1205-1210). These mice carry a T835C missense mutation in exon 7 of their phenylalanine hydroxylase gene that results in a phenylalanine to serine substitution at amino acid 263 (F263S) of the enzyme. Homozygous mutant Enu2 mice show severe hyperphenylalanemia. They are hypopigmented unless maintained on a low phenylalanine diet. Females are fertile but do not rear their young when maintained on a standard mouse diet. The coat color of the background strain, BTBR+$^T$ tf/tf, is black and tan ($a^t/a^t$). This strain is also homozygous for the gene tufted (tf/tf) resulting in various molting patterns in the mouse coat. These effects, limited to the mouse coat, may make the mice appear malformed.

5.1 AAV Vectors

As used herein, the term "AAV" is a standard abbreviation for adeno-associated virus. Adeno-associated virus is a single-stranded DNA parvovirus that grows only in cells in which certain functions are provided by a co-infecting helper virus. There are currently thirteen serotypes of AAV that have been characterized. General information and reviews of AAV can be found in, for example, Carter, 1989, Handbook of Parvoviruses, Vol. 1, pp. 169-228; and Berns, 1990, Virology, pp. 1743-1764, Raven Press, (New York). However, it is fully expected that these same principles will be applicable to additional AAV serotypes since it is well known that the various serotypes are quite closely related, both structurally and functionally, even at the genetic level. (See, e.g., Blacklowe, 1988, pp. 165-174 of Parvoviruses and Human Disease, J. R. Pattison, ed.; and Rose, Comprehensive Virology 3:1-61 (1974)). For example, all AAV serotypes apparently exhibit very similar replication properties mediated by homologous rep genes; and all bear three related capsid proteins. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control.

In one embodiment, AAV vectors can be replicated and packaged into infectious viral particles when present in a host cell that has been transfected with a vector encoding and expressing rep and cap gene products.

In some embodiments, the viral vector comprises a 5' inverted terminal repeat (ITR) of AAV and a 3' AAV ITR, a promoter, a polynucleotide encoding PAH, and a posttranscriptional regulatory element, where the promoter, the polynucleotide encoding PAH and the posttranscription regulatory element are located downstream of the 5' AAV ITR and upstream of the 3' AAV ITR. The viral vector can, for example, be used to produce high levels of PAH in a subject for therapeutic purposes.

In certain embodiments, the recombinant AAV vector comprises a nucleic acid comprising an AAV2 5' inverted terminal repeat (ITR) (which may or may not be modified as known in the art), a liver-specific transcription regulatory region, a codon-optimized therapeutic protein coding region, optionally one or more introns, a polyadenylation sequence, and an AAV2 3' ITR (which may or may not be modified as known in the art). In certain embodiments, the therapeutic protein is human PAH or variants thereof. In other embodiments, the liver-specific transcription regulatory region comprises a shortened ApoE enhancer sequence; a 186 base human alpha anti-trypsin (hAAT) proximal promoter, including 42 bases of the 5' untranslated region (UTR); one or more enhancers selected from the group consisting of (i) a 34 base human ApoE/C1 enhancer, (ii) a 32 base human AAT promoter distal X region, and (iii) 80 additional bases of distal element of the human AAT proximal promoter; and a nucleic acid encoding human PAH. In another embodiment, the liver-specific transcription regulatory region comprises an α-microglobulin enhancer sequence and the 186 base human alpha anti-trypsin (AAT) proximal promoter.

Other embodiments provided herein are directed to vector constructs encoding a functional PAH polypeptide, wherein the constructs comprise one or more of the individual elements of the above described constructs and combinations thereof, in one or more different orientation(s). Another embodiment provided herein is directed to the above described constructs in an opposite orientation. In another embodiment, provided are recombinant AAV virus particles comprising the herein described AAV PAH vectors and their use for the treatment of PKU in subjects. In one embodiment the subjects are juvenile subjects.

The AAV vectors provided herein in single strand form are less than about 7.0 kb in length, or are less than 6.5 kb in length, or are less than 6.4 kb in length, or are less than 6.3 kb in length, or are less than 6.2 kb in length, or are less than 6.0 kb in length, or are less than 5.8 kb in length, or are less than 5.6 kb in length, or are less than 5.5 kb in length, or are less than 5.4 kb in length, or are less than 5.3 kb in length, or are less than 5.2 kb in length or are less than 5.0 kb in length. The AAV vectors provided herein in single strand form range from about 5.0 kb to about 6.5 kb in length, or range from about 4.8 kb to about 5.2 k in length, or 4.8 kb to 5.3 kb in length, or range from about 4.9 kb to about 5.5 kb in length, or about 4.8 kb to about 6.0 kb in length, or about 5.0 kb to 6.2 kb in length or about 5.1 kb to about 6.3 kb in length, or about 5.2 kb to about 6.4 kb in length, or about 5.5 kb to about 6.5 kb in length.

Generation of the viral vector can be accomplished using any suitable genetic engineering techniques well known in the art, including, without limitation, the standard techniques of restriction endonuclease digestion, ligation, transformation, plasmid purification, and DNA sequencing, for example as described in Sambrook et al. (Molecular Cloning: A Laboratory Manual. Cold Spring Harbor Laboratory Press, N.Y. (1989)).

The viral vector can incorporate sequences from the genome of any known organism. The sequences can be incorporated in their native form or can be modified in any way to obtain a desired activity. For example, the sequences can comprise insertions, deletions or substitutions.

5.1.1 Promoter

Various promoters can be operably linked with a nucleic acid comprising the coding region of the protein of interest in the viral vector disclosed herein. In some embodiments, the promoter can drive the expression of the protein of interest in a cell infected with a virus derived from the viral vector, such as a target cell. The promoter can be naturally-occurring or non-naturally occurring. In some embodiments the promoter is a synthetic promoter. In one embodiment the synthetic promoter comprises sequences that do not exist in nature and which are designed to regulate the activity of an operably linked gene. In another embodiment the synthetic promoter comprises fragments of natural promoters to form new stretches of DNA sequence that do not exist in nature. Synthetic promoters are typically comprised of regulatory elements, promoters, enhancers, introns, splice donors and acceptors that are designed to produce enhanced tissue specific expression. Examples of promoters, include, but are not limited to, viral promoters, plant promoters and mammalian promoters. In another embodiment the promoter is a liver specific promoter. Specific examples of liver specific promoters include LP1, HLP, HCR-hAAT, ApoE-hAAT, LSP, TBG and TTR. These promoters are described in more detail in the following references: LP1: Nathwani A. et al. Blood. 2006 Apr. 1; 107(7): 2653-2661; hybrid liver specific promoter (HLP): McIntosh J. et al. Blood. 2013 Apr. 25; 121(17): 3335-3344; HCR-hAAT: Miao C H et al. Mol Ther. 2000; 1: 522-532; ApoE-hAAT: Okuyama T et al. Human Gene Therapy, 7, 637-645 (1996); LSP: Wang L et al. Proc Natl Acad Sci USA. 1999 Mar. 30; 96(7): 3906-3910, thyroxine binding globulin (TBG) promoter: Yan et al., Gene 506:289-294 (2012), and transthyretin (TTR) promoter: Costa et al., Mol. Cell. Biol. 8:81-90 (1988).

In some embodiments, the promoter comprises the human alphal anti-trypsin (hAAT) promoter complex. In some embodiments, the promoter comprises at least a portion of the hAAT promoter. The portion of the hAAT promoter can comprise a nucleic acid sequence having at least about 90%, at least about 95%, at least about 96%, at least about 97%, at least about 98%, at least about 99%, or more, sequence identity to SEQ ID NO: 3.

In some embodiments, the promoter comprises a liver specific enhancer. In some embodiments, the promoter comprises a hepatic control region (HCR) enhancer. In some embodiments, the promoter comprises at least a portion of the HCR enhancer. For example, the HCR enhancer can comprise a nucleic acid sequence having at least about 90%, at least about 95%, at least about 96%, at least about 97%, at least about 98%, at least about 99%, or more, sequence identity to SEQ ID NO: 4.

In some embodiments, the promoter comprises a liver-specific apolipoprotein E (ApoE) enhancer. In some embodiments, the promoter comprises at least a portion of the ApoE enhancer. For example, the ApoE enhancer can comprise a nucleic acid sequence having at least about 90%, at least about 95%, at least about 96%, at least about 97%, at least about 98%, at least about 99%, or more, sequence identity to SEQ ID NO: 4.

In some embodiments, the promoter is a synthetic promoter comprising at least a portion of the hAAT promoter, at least a portion of the HCR enhancer, and at least a portion of the ApoE enhancer. In some embodiments, the promoter can include a nucleic acid sequence having at least about 90%, at least about 95%, at least about 96%, at least about 97%, at least about 98%, at least about 99%, or more, sequence identity to SEQ ID NO: 6.

In some embodiments, the promoter comprises multiple copies of one or more of the enhancers identified above. In some embodiments, the promoter constructs comprise one or more of the individual enhancer elements described above and combinations thereof, in one or more different orientation(s).

In some embodiments, the promoter is operably linked with a polynucleotide encoding one or more proteins of interest. In some embodiments, the promoter is operably linked with a polynucleotide encoding the PAH protein.

The size of the promoter can vary. Because of the limited packaging capacity of AAV, it is preferred to use a promoter that is small in size, but at the same time allows high level production of the protein(s) of interest in host cells. For example, in some embodiments the promoter is at most about 1.5 kb, at most about 1.4 kb, at most about 1.35 kb, at most about 1.3 kb, at most about 1.25 kb, at most about 1.2 kb, at most about 1.15 kb, at most about 1.1 kb, at most about 1.05 kb, at most about 1 kb, at most about 800 base pairs, at most about 600 base pairs, at most about 400 base pairs, at most about 200 base pairs, or at most about 100 base pairs.

5.1.2 Regulatory Elements

Various additional regulatory elements can be used in the viral vectors, for example enhancers to further increase expression level of the protein of interest in a host cell, a polyadenylation signal, a ribosome binding sequence, and/or a consensus splice acceptor or splice donor site. In some embodiments, the regulatory element can facilitate maintenance of the recombinant DNA molecule extrachromosomally in a host cell and/or improve vector potency (e.g. scaffold/matrix attachment regions (S/MARs)). Such regulatory elements are well known in the art.

The viral vectors disclosed herein may include regulatory elements such as a transcription initiation region and/or a transcriptional termination region. Examples of a transcription termination region include, but are not limited to, polyadenylation signal sequences. Examples of polyadenylation signal sequences include, but are not limited to, Bovine growth hormone (bGH) poly(A), SV40 late poly(A), rabbit beta-globin (rBG) poly(A), thymidine kinase (TK) poly(A) sequences, and any variants thereof. In some embodiments, the transcriptional termination region is located downstream of the posttranscriptional regulatory element. In some embodiments, the transcriptional termination region is a polyadenylation signal sequence. In some embodiments, the transcriptional termination region is bGH poly(A) sequence.

In some embodiments, the viral vectors can include additional transcription and translation initiation sequences, and/or additional transcription and translation terminators, which are known in the art.

5.1.3 Protein of Interest

As used herein, a "protein of interest" can be any PAH protein, including naturally-occurring and non-naturally occurring variants thereof. In some embodiments, a polynucleotide encoding one or more PAH proteins of interest can be inserted into the viral vectors disclosed herein, wherein the polynucleotide is operably linked with the promoter. In some instances, the promoter can drive the expression of the protein(s) of interest in a host cell (e.g., a human liver cell).

In a first aspect, the present disclosure provides an isolated nucleic acid molecule comprising a nucleotide sequence homologous to the nucleotide sequence of SEQ ID NO: 1 and which encodes functional wild-type phenylalanine hydroxylase (PAH) (SEQ ID NO:2).

As described herein, the nucleotide sequence encoding the PAH protein can be modified to improve expression efficiency of the protein. The methods that can be used to improve the transcription and/or translation of a gene herein are not particularly limited. For example, the nucleotide sequence can be modified to better reflect host codon usage to increase gene expression (e.g., protein production) in the host (e.g., a mammal). As another non-limiting example for the modification, one or more of the splice donors and/or splice acceptors in the nucleotide sequence of the protein of interest is modified to reduce the potential for extraneous splicing. As another non-limiting example for the modification, one or more introns can be inserted within or adjacent to the nucleotide sequence of the protein of interest to optimize AAV vector packaging and enhance expression.

In certain embodiments, the nucleic acid molecule has at least 75%, at least 80%, at least 85%, at least 90%, at least 95% homology, or at least 98% homology to the nucleotide sequence of SEQ ID NO: 1. In one embodiment, the nucleic acid molecule encodes for a functional PAH protein, that is to say it encodes for PAH which, when expressed, has the functionality of wild type PAH. In certain embodiments, the nucleic acid molecule, when expressed in a suitable system (e.g. a host cell), produces a functional PAH protein and at a relatively high level. Since the PAH that is produced is functional, it will have a conformation which is the same as at least a portion of the wild type PAH. In certain embodiments, a functional PAH protein produced as described herein allows at least some reduction in Phe levels to take place in a subject suffering from PKU.

In another embodiment, the nucleotide sequence coding for a functional PAH has an improved codon usage bias for the human cell as compared to naturally occurring nucleotide sequence coding for the corresponding non-codon optimized sequence. The adaptiveness of a nucleotide sequence encoding a functional PAH to the codon usage of human cells may be expressed as codon adaptation index (CAI). A codon adaptation index is herein defined as a measurement of the relative adaptiveness of the codon usage of a gene towards the codon usage of highly expressed human genes. The relative adaptiveness (w) of each codon is the ratio of the usage of each codon, to that of the most abundant codon for the same amino acid. The CAI is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, Nucleic Acids Research 15: 1281-1295; also see: Kim et al., Gene. 1997, 199:293-301; zur Megede et al., Journal of Virology, 2000, 74: 2628-2635). In certain embodiments, a nucleic acid molecule encoding a PAH has a CAI of at least 0.75, 0.80, 0.85, 0.90, 0.95, or 0.99

The nucleotide sequence of SEQ ID NO:7, also referenced as GENEius 1 (hPAHco1), is a codon optimized human PAH nucleic acid sequence which is based on the sequence of the wild-type human PAH nucleotide sequence (SEQ ID NO:1). The nucleotide sequence of SEQ ID NO:7 is a PAH sequence that has been codon optimized using Operon/Eurofins Genomics codon optimization software in conjunction with manually reducing CpG di-nucleotide content and removing any extra ORF in the sense and anti-sense direction. CpG di-nucleotide content has been shown to activate TLR9 in dendritic cells leading to potential immune activation and CTL responses. Our product in the AAV-vector genome delivered is ssDNA, thus reducing the CpG content, which may reduce liver inflammation and ALT.

In one embodiment, the nucleic acid molecule has at least 75%, at least 80%, at least 85%, at least 90%, at least 95% homology, or 98% homology to the nucleotide sequence of SEQ ID NO: 7. In another embodiment, a nucleotide sequence may have at least about 335, at least about 360, at least about 380, at least about 405, at least about 425, at least about 440 of all codons coding for the functional PAH being identical to the codons (in corresponding positions) in SEQ ID NO: 7. In another embodiment, the nucleic acid molecule has about 218 codon changes as compared to the wild-type PAH coding sequence and which has a CAI of about 0.96.

In one embodiment, SEQ ID NO:7 and sequences which are similar to it, i.e. those sequences which have a relatively high level of homology, all show surprisingly high levels of expression of functional protein. In this regard, SEQ ID NOs: 7, 8, 9, 10, 11, 12 and 13 are codon optimized PAH nucleic acid sequences, the % homology of which are 80.7%, 80.6%, 96.5%, 96.6%, 77.0%, 80.5% and 76.7% respectively, compared to SEQ ID NO: 1.

In one embodiment, the nucleic acid molecule has at least 75%, at least 80%, at least 85%, at least 90%, at least 95% homology, or 98% homology to the nucleotide sequence of SEQ ID NO: 8. In one embodiment, a nucleotide sequence may also have at least about 335, at least about 360, at least about 380, at least about 405, at least about 425, at least about 440 of all codons coding for the functional PAH being identical to the codons (in corresponding positions) in SEQ ID NO: 8. In another embodiment, the nucleic acid molecule has about 219 codon changes as compared to the wild-type PAH coding sequence and which has a CAI of about 0.96.

The nucleotide sequence of SEQ ID NO: 8, also referenced as GENEius 2 (hPAHco2), is a codon optimized PAH nucleic acid sequence which is based on the sequence of the wild-type human PAH nucleotide sequence (SEQ ID NO:1). The nucleotide sequence of SEQ ID NO:8 is a PAH sequence that has been codon optimized using Operon/Eurofins Genomics codon optimization software in conjunction with manually reducing CpG di-nucleotide content and removing any extra ORF in the sense and anti-sense direction.

In one embodiment, the nucleic acid molecule has at least 75%, at least 80%, at least 85%, at least 90%, at least 95% homology, or 98% homology to the nucleotide sequence of SEQ ID NO: 9. In another embodiment, the nucleotide sequence may also have at least about 335, at least about 360, at least about 380, at least about 405, at least about 425, at least about 440 of all codons coding for the functional PAH being identical to the codons (in corresponding positions) in SEQ ID NO: 9. In another embodiment, the nucleic acid molecule has about 37 codon changes as compared to the wild-type PAH coding sequence and which has a CAI of about 0.79.

The nucleotide sequence of SEQ ID NO: 9, also referenced as Nathwani (NW2-Cop, hPAHco3), is a codon optimized PAH nucleic acid sequence which is based on the sequence of the wild-type human PAH nucleotide sequence (SEQ ID NO:1). The nucleotide sequence of SEQ ID NO:9 is a human PAH sequence that has been codon optimized using codon usage table that Amit Nathwani used for Factor VIII codon optimization.

In one embodiment, the nucleic acid molecule has at least 75%, at least 80%, at least 85%, at least 90%, at least 95% homology, or 98% homology to the nucleotide sequence of SEQ ID NO: 10. In another embodiment, the nucleotide sequence may also have at least about 335, at least about 360, at least about 380, at least about 405, at least about 425, at least about 440 of all codons coding for the functional PAH being identical to the codons (in corresponding positions) in SEQ ID NO: 10. In another embodiment, the nucleic acid molecule has about 34 codon changes as compared to the wild-type PAH coding sequence and which has a CAI of about 0.79.

The nucleotide sequence of SEQ ID NO: 10, also referenced as Nathwani-RCG (NW-RCG, hPAHco4), is a codon optimized PAH nucleic acid sequence which is based on the sequence of the wild-type human PAH nucleotide sequence (SEQ ID NO:1). The nucleotide sequence of SEQ ID NO:10 is a human PAH sequence that has been codon optimized using codon usage table that Amit Nathwani used for Factor VIII codon optimization in conjunction with manually reducing CpG di-nucleotide content and removing any extra ORF in the sense and anti-sense direction.

In a certain embodiment, the nucleic acid molecule provided herein has at least 75%, at least 80%, at least 85%, at least 90%, at least 95% homology, or 98% homology to the nucleotide sequence of SEQ ID NO: 11. In a certain embodiment, the nucleotide sequence provided herein may also have at least about 335, at least about 360, at least about 380, at least about 405, at least about 425, at least about 440 of all codons coding for the functional PAH being identical to the codons (in corresponding positions) in SEQ ID NO: 11. In another embodiment, provided herein is a nucleic acid molecule which has about 228 codon changes as compared to the wild-type PAH coding sequence and which has a CAI of about 0.84.

The nucleotide sequence of SEQ ID NO: 11, also referenced as ATUM (DNA2.0-op/D20-P, hPAHco5), is a codon optimized PAH nucleic acid sequence which is based on the sequence of the wild-type human PAH nucleotide sequence (SEQ ID NO:1). The nucleotide sequence of SEQ ID NO:11 is a human PAH sequence that has been codon optimized using the DNA2.0 codon optimization algorithm.

In a certain embodiment, provided herein is a nucleic acid molecule which has at least 75%, at least 80%, at least 85%, at least 90%, at least 95% homology, or 98% homology to the nucleotide sequence of SEQ ID NO: 12. In a certain embodiment, the nucleotide sequence may also have at least about 335, at least about 360, at least about 380, at least about 405, at least about 425, at least about 440 of all codons coding for the functional PAH being identical to the codons (in corresponding positions) in SEQ ID NO: 12. In another embodiment, provided herein is a nucleic acid molecule which has about 228 codon changes as compared to the wild-type PAH coding sequence and which has a CAI of about 0.85.

The nucleotide sequence of SEQ ID NO: 12, also referenced as ATUM-RCG (DNA2.0-Cop1, hPAHco6), is a codon optimised PAH nucleic acid sequence which is based on the sequence of the wild-type human PAH nucleotide sequence (SEQ ID NO:1). The nucleotide sequence of SEQ ID NO:12 is a human PAH sequence that has been codon optimized using the DNA2.0 codon optimization algorithm in conjunction with manually reducing CpG di-nucleotide content and removing any extra ORF in the sense and anti-sense direction.

In certain embodiments, provided herein is a nucleic acid molecule which has at least 75%, at least 80%, at least 85%, at least 90%, at least 95% homology, or 98% homology to the nucleotide sequence of SEQ ID NO: 13. In a certain embodiment, a nucleotide sequence may also have at least about 335, at least about 360, at least about 380, at least about 405, at least about 425, at least about 440 of all codons coding for the functional PAH being identical to the codons (in corresponding positions) in SEQ ID NO: 13. In another embodiment, provided herein is a nucleic acid molecule which has about 238 codon changes as compared to the wild-type PAH coding sequence and which has a CAI of about 0.95.

The nucleotide sequence of SEQ ID NO: 13, also referenced as JCAT (hPAHco7), is a codon optimized PAH nucleic acid sequence which is based on the sequence of the wild-type human PAH nucleotide sequence (SEQ ID NO:1). The nucleotide sequence of SEQ ID NO:13 is a human PAH sequence that has been codon optimized using the Java Codon Adaptation Tool (www.jcat.de, Grote et al., *Nucleic Acids Res.* 2005 Jul. 1; 33) in conjunction with manually reducing CpG di-nucleotide content and removing any extra ORF in the sense and anti-sense direction.

Generally, codon optimization does not change the amino acid for which each codon encodes. It simply changes the nucleotide sequence so that it is more likely to be expressed at a relatively high level compared to the non-codon optimized sequence. This means that the nucleotide sequences of the nucleic acid provided herein and, for example, SEQ ID NO: 7 (or SEQ ID NO: 8-13) may be different but when they are translated the amino acid sequence of the protein that is produced is the same.

However, in one embodiment, the nucleic acid molecule may encode for a protein having between 0 and 350, between 0 and 300, between 0 and 250, between 0 and 200, between 0 and 150, between 0 and 100, between 0 and 50, between 0 and 30, between 0 and 20, between 0 and 15, between 0 and 10, or between 0 and 5 amino acid changes to the protein encoded by the nucleotide sequence of SEQ ID NO: 7, SEQ ID NO: 8, SEQ ID NO: 9, SEQ ID NO: 10, SEQ ID NO: 11, SEQ ID NO: 12 or SEQ ID NO: 13. If the nucleic acid molecule encodes for a protein comprising a sequence of having changes to any of the amino acids, the protein should still be a functional protein. A skilled person will appreciate that minor changes can be made to some of the amino acids of the protein without adversely affecting the function of the protein.

In some embodiments, the codon optimized hPAH nucleic acid molecule has a CpG di-nucleotide content of less than 25, less than 20, less than 15, or less than 10. In another embodiment, the codon optimized hPAH nucleic acid molecule has a GC content of less than 65%, less than 60%, or less than 58%.

It would be well within the capabilities of a skilled person to produce a nucleic acid molecule provided herein. This could be done, for example, using chemical synthesis of a given sequence. Further, suitable methods would be apparent to those skilled in the art for determining whether a nucleic acid described herein expresses a functional protein. For example, one suitable in vitro method involves inserting the nucleic acid into a vector, such as an AAV vector, transducing host cells, such as 293T or HeLa cells, with the vector, and assaying for PAH activity. Alternatively, a suitable in vivo method involves transducing a vector containing the nucleic acid into PKU mice and assaying for functional PAH in the plasma of the mice. Suitable methods are described in more detail below.

In some embodiments, the vector comprises one or more introns. The introns may facilitate processing of the RNA transcript in mammalian host cells, increase expression of the protein of interest and/or optimize packaging of the vector into AAV particles. Non-limiting examples of such an intron are a β-globin intron, A1AT intron and/or hPAH intron. In some embodiments, the intron is a synthetic intron. For example, the synthetic intron can include a nucleotide sequence having at least about 90%, at least about 95%, at least about 96%, at least about 97%, at least about 98%, at least about 99%, or more, sequence identity to SEQ ID NO: 14. The location and size of the intron in the vector can vary. In some embodiments, the intron is located between the promoter and the sequence encoding the protein of interest. In some embodiments, the intron is located within the promoter. In some embodiments, the intron includes an enhancer element. In some embodiments, the intron is located within the sequence encoding the protein of interest, preferably between exons of the sequence encoding the protein of interest. In some embodiments, the intron may comprise all or a portion of a naturally occurring intron within the sequence encoding the protein of interest. In some embodiments, the intron is the second PAH intron. Alternatively, the intron is a 2116 bp truncated form of the hPAH $2^{nd}$ intron. In other embodiments, the intronic sequence is a composite beta-globin/A1AT intron.

Inclusion of an intron element may enhance expression compared with expression in the absence of the intron element (see e.g. Kurachi et al., 1995, J Biol Chem. 1995 Mar. 10; 270(10):5276-81). AAV vectors typically accept inserts of DNA having a defined size range which is generally about 4 kb to about 5.2 kb, or slightly more. However, there is no minimum size for packaging and small vector genomes package very efficiently. Introns and intron fragments (e.g. portion of intron 2 of PAH) fulfill this requirement while also enhancing expression. Thus, the present disclosure is not limited to the inclusion of PAH intron 2 sequences in the AAV vector, and include other introns or other DNA sequences in place of portions of PAH intron 2. Additionally, other 5' and 3' untranslated regions of nucleic acid may be used in place of those recited for human PAH.

A "portion of PAH intron 2" as used herein, means a region of PAH intron 2 having a nucleotide length of from about 0.1 kb to about 2.1 kb, which region enhances expression of PAH, typically by about 1.5-fold or more on a plasmid or viral vector template when compared with expression of PAH in the absence of a portion of PAH intron 2. A more specific portion is a 2116 bp portion of PAH intron 2.

Polynucleotides and polypeptides including modified forms can be made using various standard cloning, recombinant DNA technology, via cell expression or in vitro translation and chemical synthesis techniques known to those of skill in the art (Sambrook et al., *Molecular Cloning: A Laboratory Manual,* 2nd edition).

5.1.4 Methods of Gene Delivery

Also provided is a vector comprising the nucleic acid molecule of the present disclosure. In one embodiment, the vector may be a gene delivery vector. Such a gene delivery vector may be a viral gene delivery vector or a non-viral gene delivery vector. Viral vectors include lenti-, adeno-, herpes viral vectors. It is preferably a recombinant adeno-associated viral (rAAV) vector. Alternatively, non-viral systems may be used, including using naked DNA (with or without chromatin attachment regions) or conjugated DNA that is introduced into cells by various transfection methods such as lipids or electroporation.

Sequences of non-limiting examples of the AAV vectors are provided in SEQ ID NOs: 15-23. For example, the nucleotide sequence for an AAV vector including the ApoE-HCR-hAAT promoter, beta globin intron, wild-type coding sequence for human PAH, and bGH poly(A) sequence is set forth in SEQ ID NO: 15 ((Vector 1), ApoE-HCR-hAAT.GI.hPAH.bGH); the nucleotide sequence for an AAV vector including the ApoE-hAAT promoter, beta globin intron, codon-optimized human PAH sequence (hPAH-Genius1), and bGH poly(A) sequence is set forth in SEQ ID NO: 16 (ApoE-HCR-hAAT.GI.hPAHco1.bGH); the nucleotide sequence for an AAV vector including the ApoE-hAAT promoter, with composite globin/A1AT intron, wild-type coding sequence for human PAH, and bGH poly(A) sequence is set forth in SEQ ID NO: 17 ((V1-LG-Intron), ApoE-HCR-hAAT.cGA1ATI.hPAH.bGH); the nucleotide sequence for an AAV vector including the ApoE-hAAT promoter, with composite globin/A1AT intron, codon-optimized human PAH sequence, and bGH poly(A) sequence is set forth in SEQ ID NO: 18 ((LGI-hPAH-Geneius1), ApoE-HCR-hAAT.cG-A1ATI.hPAHco1.bGH); the nucleotide sequence for an AAV vector including the ApoE-hAAT promoter, wild-type coding sequence for human PAH with truncated $2^{nd}$ intron included, and bGH poly(A) sequence is set forth in SEQ ID NO: 19 ((hPAH+truncated $2^{nd}$ intron), ApoE-HCR-hAAT.hPAH-tI2.bGH); the nucleotide sequence for an AAV vector including the ApoE-hAAT promoter, beta globin intron, codon-optimized human PAH sequence (hPAH-Genius2), and bGH poly(A) sequence is set forth in SEQ ID NO: 20 ((pFB-ApoE-hAAT-hPAH-Genius2), ApoE-HCR-hAAT.GI.hPAHco2.bGH); the nucleotide sequence for an AAV vector including the ApoE-hAAT promoter, beta globin intron, codon-optimized human PAH sequence (hPAH-JCAT), and bGH poly(A) sequence is set forth in SEQ ID NO: 21 ((pFB-ApoE-hAAT-hPAH-JCAT), ApoE-HCR-hAAT.GI.hPAHco3.bGH); the nucleotide sequence for an AAV vector including the TBG promoter with two macroglobulin sites, beta globin intron, wild-type coding sequences for human PAH, and bGH poly(A) sequence is set forth in SEQ ID NO: 22 ((pFB-hPAHV1-TBG2uGlob), TBG.GI.hPAH.bGH); and the nucleotide sequence for an AAV vector including the TTR promoter, beta globin intron, wild-type coding sequences for human PAH, and bGH poly(A) sequence is set forth in SEQ ID NO: 23 ((pFB-hPAHV1-TTR), TTR.GI.hPAH.bGH).

In some embodiments, the AAV vector comprises a nucleotide sequence having at least about 90%, at least about 95%, at least about 96%, at least about 97%, at least about 98%, at least about 99%, or more, sequence identity to SEQ ID NOs: 15-23. In some embodiments, the AAV vector comprises a nucleotide sequence having at least about 90%, at least about 95%, at least about 96%, at least about 97%, at least about 98%, at least about 99%, or more, sequence identity to SEQ ID NO: 18.

5.1.5 Non-Viral Gene Delivery

Non-viral gene delivery may be carried out using naked DNA which is the simplest method of non-viral transfection. It may be possible, for example, to administer a nucleic acid provided herein using naked plasmid DNA. Alternatively, methods such as electroporation, sonoporation or the use of a "gene gun", which shoots DNA coated gold particles into the cell using, for example, high pressure gas or an inverted .22 calibre gun, may be used (Helios® Gene Gun System (BIO-RAD)).

To improve the delivery of a nucleic acid into a cell, it may be necessary to protect it from damage and its entry into the cell may be facilitated. To this end, lipoplexes and polyplexes may be used that have the ability to protect a nucleic acid from undesirable degradation during the transfection process.

Plasmid DNA may be coated with lipids in an organized structure such as a micelle or a liposome. When the organized structure is complexed with DNA it is called a lipoplex. Anionic and neutral lipids may be used for the construction of lipoplexes for synthetic vectors. In one embodiment, cationic lipids, due to their positive charge, may be used to condense negatively charged DNA molecules so as to facilitate the encapsulation of DNA into liposomes. If may be necessary to add helper lipids (usually electroneutral lipids, such as DOPE) to cationic lipids so as to form lipoplexes (Dabkowska et al., *J R Soc Interface.* 2012 Mar. 7; 9(68): 548-561).

In certain embodiments, complexes of polymers with DNA, called polyplexes, may be used to deliver a nucleic acid. Most polyplexes consist of cationic polymers and their production is regulated by ionic interactions. Polyplexes typically cannot release their DNA load into the cytoplasm. Thus, co-transfection with endosome-lytic agents (to lyse the endosome that is made during endocytosis, the process by which the polyplex enters the cell), such as inactivated adenovirus, may be necessary (Akinc et al., *The Journal of Gene Medicine.* 7 (5): 657-63).

In certain embodiments, hybrid methods may be used to deliver a nucleic acid that combines two or more techniques. Virosomes are one example; they combine liposomes with an inactivated HIV or influenza virus. In another embodiment, other methods involve mixing other viral vectors with cationic lipids or hybridizing viruses and may be used to deliver a nucleic acid (Khan, Firdos Alam, *Biotechnology Fundamentals*, CRC Press, Nov. 18, 2015, p. 395).

In certain embodiments, a dendrimer may be used to deliver a nucleic acid, in particular, a cationic dendrimer, i.e. one with a positive surface charge. When in the presence of genetic material as DNA or RNA, charge complementarity leads to a temporary association of the nucleic acid with the cationic dendrimer. On reaching its destination the dendrimer-nucleic acid complex is then imported into the cell via endocytosis (Amiji, Mansoor M. ed., *Polymeric Gene Delivery: Principles and Applications, CRC Press, Sep.* 29, 2004, p. 142.)

5.1.6 Viral Particles

In one embodiment, a suitable viral gene delivery vector may be used to deliver a nucleic acid. In certain embodiments, viral vectors suitable for use herein may be a parvovirus, an adenovirus, a retrovirus, a lentivirus or a herpes simplex virus. The parvovirus may be an adenovirus-associated virus (AAV).

Accordingly, the present disclosure provides gene delivery vectors (comprising a nucleic acid provided herein) based on animal parvoviruses, in particular dependoviruses such as infectious human or simian AAV, and the components thereof (e.g., an animal parvovirus genome) for use as vectors for introduction and/or expression of a Factor VIII polypeptide in a mammalian cell. The term "parvoviral" as used herein thus encompasses dependoviruses such as any type of AAV.

Viruses of the Parvoviridae family are small DNA animal viruses. The family Parvoviridae may be divided between two subfamilies: the Parvovirinae, which infect vertebrates, and the Densovirinae, which infect insects. Members of the subfamily Parvovirinae are herein referred to as the parvoviruses and include the genus Dependovirus. As may be deduced from the name of their genus, members of the Dependovirus are unique in that they usually require coinfection with a helper virus such as adenovirus or herpes virus for productive infection in cell culture. The genus Dependovirus includes AAV, which normally infects humans (e.g., serotypes 1, 2, 3A, 3B, 4, 5, and 6), primates (e.g., serotypes 1 and 4), and related viruses that infect other warm-blooded animals (e.g., bovine, canine, equine, mice, rats, and ovine adeno-associated viruses) in addition to birds and reptiles. Further information on parvoviruses and other members of the Parvoviridae is described in Kenneth I. Berns, "Parvoviridae: The Viruses and Their Replication," Chapter 69 in Fields Virology (3d Ed. 1996). For convenience the present disclosure is further exemplified and described herein by reference to AAV. It is, however, understood that the present disclosure is not limited to AAV but may equally be applied to other parvoviruses.

AAV "rep" and "cap" genes are genes encoding replication and encapsidation proteins, respectively. AAV rep and cap genes have been found in all AAV serotypes examined to date, and are described herein and in the references cited. In wild-type AAV, the rep and cap genes are generally found adjacent to each other in the viral genome (i.e., they are "coupled" together as adjoining or overlapping transcriptional units), and they are generally conserved among AAV serotypes. AAV rep and cap genes are also individually and collectively referred to as "AAV packaging genes." The AAV cap genes for use herein encode Cap proteins which are capable of packaging AAV vectors in the presence of rep and adeno helper function and are capable of binding target cellular receptors. In some embodiments, the AAV cap gene encodes a capsid protein having an amino acid sequence derived from a particular AAV serotype.

The AAV sequences employed for the production of AAV can be derived from the genome of any AAV serotype. Generally, the AAV serotypes have genomic sequences of significant homology at the amino acid and the nucleic acid levels, provide a similar set of genetic functions, produce virions which are essentially physically and functionally equivalent, and replicate and assemble by practically identical mechanisms. For the genomic sequence of AAV serotypes and a discussion of the genomic similarities. (See, e.g., GenBank Accession number U89790; GenBank Accession number J01901; GenBank Accession number AF043303; GenBank Accession number AF085716; Chiorini et al., *J. Vir.* (1997) vol. 71, pp. 6823-6833; Srivastava et al., *J. Vir.* (1983) vol. 45, pp. 555-564; Chiorini et al., *J. Vir.* (1999) vol. 73, pp. 1309-1319; Rutledge et al., *J. Vir.* (1998) vol. 72, pp. 309-319; and Wu et al., *J. Vir.* (2000) vol. 74, pp. 8635-8647).

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. The Rep genes encode the Rep proteins, Rep78, Rep68, Rep52, and Rep40. Rep78 and Rep68 are transcribed from the p5 promoter, and Rep 52 and Rep40 are transcribed from the p19 promoter. The cap genes encode the VP proteins, VP1, VP2, and VP3. The cap genes are transcribed from the p40 promoter. The ITRs employed in the vectors of the present embodiment may correspond to the same serotype as the associated cap genes, or may differ. In one embodiment, the ITRs employed herein correspond to an AAV2 serotype and the cap genes correspond to an AAV5 serotype.

The AAV VP proteins are known to determine the cellular tropicity of the AAV virion. The VP protein-encoding sequences are significantly less conserved than Rep proteins and genes among different AAV serotypes. The ability of Rep and ITR sequences to cross-complement corresponding sequences of other serotypes allows for the production of pseudotyped AAV particles comprising the capsid proteins of a serotype (e.g., AAV1, 5 or 8) and the Rep and/or ITR sequences of another AAV serotype (e.g., AAV2). Such pseudotyped rAAV particles are a part of the present disclosure.

In one embodiment, the AAV ITR sequences for use in the context of the present disclosure are derived from AAV1, AAV2, AAV4 and/or AAV6. Likewise, the Rep (Rep78 and Rep52) coding sequences are in one embodiment derived from AAV1, AAV2, AAV4 and/or AAV6. The sequences coding for the VP1, VP2, and VP3 capsid proteins for use in the context of the present disclosure may however be taken from any of the known 42 serotypes, such as from AAV1, AAV2, AAV3, AAV4, AAV5, AAV6, AAV7, AAV8 or AAV9 or newly developed AAV-like particles obtained by e.g. capsid shuffling techniques and AAV capsid libraries.

Modified "AAV" sequences also can be used in the context of the present disclosure, e.g. for the production of AAV gene therapy vectors. Such modified sequences e.g. include sequences having at least about 70%, at least about 75%, at least about 80%, at least about 85%, at least about 90%, at least about 95%, or more nucleotide and/or amino acid sequence identity (e.g., a sequence having about 75-99% nucleotide sequence identity) to an AAV1, AAV2, AAV3, AAV4, AAV5, AAV6, AAV7, AAV8 or AAV9 ITR, Rep, or VP can be used in place of wild-type AAV ITR, Rep, or VP sequences.

In some embodiments, a nucleic acid sequence encoding an AAV capsid protein is operably linked to expression control sequences for expression in a specific cell type, such as Sf9 or HEK cells. Techniques known to one skilled in the art for expressing foreign genes in insect host cells or mammalian host cells can be used to practice the embodiment. Methodology for molecular engineering and expression of polypeptides in insect cells is described, for example, in Summers and Smith (1986) A Manual of Methods for Baculovirus Vectors and Insect Culture Procedures, Texas Agricultural Experimental Station Bull. No. 7555, College Station, Tex.; Luckow (1991) In Prokop et al., Cloning and Expression of Heterologous Genes in Insect Cells with Baculovirus Vectors' Recombinant DNA Technology and Applications, 97-152; King, L. A. and R. D. Possee (1992) The baculovirus expression system, Chapman and Hall, United Kingdom; O'Reilly, D. R., L. K. Miller, V. A. Luckow (1992) Baculovirus Expression Vectors: A Laboratory Manual, New York; W. H. Freeman and Richardson, C.

D. (1995) Baculovirus Expression Protocols, Methods in Molecular Biology, volume 39; U.S. Pat. No. 4,745,051; US2003148506; and WO 03/074714, all of which are incorporated by reference in their entireties. A particularly suitable promoter for transcription of a nucleotide sequence encoding an AAV capsid protein is e.g. the polyhedron promoter. However, other promoters that are active in insect cells are known in the art, e.g. the p10, p35 or IE-1 promoters and further promoters described in the above references are also contemplated.

Use of insect cells for expression of heterologous proteins is well documented, as are methods of introducing nucleic acids, such as vectors, e.g., insect-cell compatible vectors, into such cells and methods of maintaining such cells in culture. (See, e.g., METHODS IN MOLECULAR BIOLOGY, ed. Richard, Humana Press, N J (1995); O'Reilly et al., BACULOVIRUS EXPRESSION VECTORS, A LABORATORY MANUAL, Oxford Univ. Press (1994); Samulski et al., *J. Vir.* (1989) vol. 63, pp. 3822-3828; Kajigaya et al., *Proc. Nat'l. Acad. Sci. USA* (1991) vol. 88, pp. 4646-4650; Ruffing et al., *J. Vir.* (1992) vol. 66, pp. 6922-6930; Kirnbauer et al., *Vir.* (1996) vol. 219, pp. 37-44; Zhao et al., *Vir.* (2000) vol. 272, pp. 382-393; and U.S. Pat. No. 6,204,059). In some embodiments, the nucleic acid construct encoding AAV in insect cells is an insect cell-compatible vector. An "insect cell-compatible vector" or "vector" as used herein refers to a nucleic acid molecule capable of productive transformation or transfection of an insect or insect cell. Exemplary biological vectors include plasmids, linear nucleic acid molecules, and recombinant viruses. Any vector can be employed as long as it is insect cell-compatible. The vector may integrate into the insect cells genome but the presence of the vector in the insect cell need not be permanent and transient episomal vectors are also included. The vectors can be introduced by any means known, for example by chemical treatment of the cells, electroporation, or infection. In some embodiments, the vector is a baculovirus, a viral vector, or a plasmid. In one embodiment, the vector is a baculovirus, i.e. the construct is a baculoviral vector. Baculoviral vectors and methods for their use are described in the above cited references on molecular engineering of insect cells.

5.2 Methods for Producing Recombinant AAVs

The present disclosure provides materials and methods for producing recombinant AAVs in insect or mammalian cells. In some embodiments, the viral construct further comprises a promoter and a restriction site downstream of the promoter to allow insertion of a polynucleotide encoding one or more proteins of interest, wherein the promoter and the restriction site are located downstream of the 5' AAV ITR and upstream of the 3' AAV ITR. In some embodiments, the viral construct further comprises a posttranscriptional regulatory element downstream of the restriction site and upstream of the 3' AAV ITR. In some embodiments, the viral construct further comprises a polynucleotide inserted at the restriction site and operably linked with the promoter, where the polynucleotide comprises the coding region of a protein of interest. As a skilled artisan will appreciate, any one of the AAV vectors disclosed in the present application can be used in the method as the viral construct to produce the recombinant AAV.

In some embodiments, the helper functions are provided by one or more helper plasmids or helper viruses comprising adenoviral or baculoviral helper genes. Non-limiting examples of the adenoviral or baculoviral helper genes include, but are not limited to, E1A, E1B, E2A, E4 and VA, which can provide helper functions to AAV packaging.

Helper viruses of AAV are known in the art and include, for example, viruses from the family Adenoviridae and the family Herpesviridae. Examples of helper viruses of AAV include, but are not limited to, SAdV-13 helper virus and SAdV-13-like helper virus described in US Publication No. 20110201088 (the disclosure of which is incorporated herein by reference), and helper vectors pHELP (Applied Viromics). A skilled artisan will appreciate that any helper virus or helper plasmid of AAV that can provide adequate helper function to AAV can be used herein.

In some embodiments, the AAV cap genes are present in a plasmid. The plasmid can further comprise an AAV rep gene which may or may not correspond to the same serotype as the cap genes. The cap genes and/or rep gene from any AAV serotype (including, but not limited to, AAV1, AAV2, AAV4, AAV5, AAV6, AAV7, AAV8, AAV9, AAV10, AAV11, AAV12, AAV13 and any variants thereof) can be used herein to produce the recombinant AAV. In some embodiments, the AAV cap genes encode a capsid from serotype 1, serotype 2, serotype 4, serotype 5, serotype 6, serotype 7, serotype 8, serotype 9, serotype 10, serotype 11, serotype 12, serotype 13 or a variant thereof.

In some embodiments, the insect or mammalian cell can be transfected with the helper plasmid or helper virus, the viral construct and the plasmid encoding the AAV cap genes; and the recombinant AAV virus can be collected at various time points after co-transfection. For example, the recombinant AAV virus can be collected at about 12 hours, about 24 hours, about 36 hours, about 48 hours, about 72 hours, about 96 hours, about 120 hours, or a time between any of these two time points after the co-transfection.

Recombinant AAV can also be produced using any conventional methods known in the art suitable for producing infectious recombinant AAV. In some instances, a recombinant AAV can be produced by using an insect or mammalian cell that stably expresses some of the necessary components for AAV particle production. For example, a plasmid (or multiple plasmids) comprising AAV rep and cap genes, and a selectable marker, such as a neomycin resistance gene, can be integrated into the genome of the cell. The insect or mammalian cell can then be co-infected with a helper virus (e.g., adenovirus or baculovirus providing the helper functions) and the viral vector comprising the 5' and 3' AAV ITR (and the nucleotide sequence encoding the heterologous protein, if desired). The advantages of this method are that the cells are selectable and are suitable for large-scale production of the recombinant AAV. As another non-limiting example, adenovirus or baculovirus rather than plasmids can be used to introduce rep and cap genes into packaging cells. As yet another non-limiting example, both the viral vector containing the 5' and 3' AAV LTRs and the rep-cap genes can be stably integrated into the DNA of producer cells, and the helper functions can be provided by a wild-type adenovirus to produce the recombinant AAV.

In one embodiment, a method for the preparation of a AAV gene delivery vector is provided, the method comprising the steps of:

(a) providing an insect cell comprising one or more nucleic acid constructs comprising:
   (i) a nucleic acid molecule provided herein that is flanked by at least one AAV inverted terminal repeat nucleotide sequence;
   (ii) a first expression cassette comprising a nucleotide sequence encoding one or more AAV Rep proteins which is operably linked to a promoter that is capable of driving expression of the Rep protein(s) in the insect cell;

(iii) a second expression cassette comprising a nucleotide sequence encoding one or more AAV capsid proteins which is operably linked to a promoter that is capable of driving expression of the capsid protein(s) in the insect cell;

(iv) and optionally AAP and MAAP contained in the VP2/3 mRNA (b) culturing the insect cell defined in (a) under conditions conducive to the expression of the Rep and the capsid proteins; and, optionally, (c) recovering the AAV gene delivery vector.

Typically then, a method provided herein for producing a AAV gene delivery vector comprises: providing to a cell permissive for AAV replication (a) a nucleotide sequence encoding a template for producing vector genome of the present disclosure (as described in detail herein); (b) nucleotide sequences sufficient for replication of the template to produce a vector genome (the first expression cassette defined above); (c) nucleotide sequences sufficient to package the vector genome into an AAV capsid (the second expression cassette defined above), under conditions sufficient for replication and packaging of the vector genome into the AAV capsid, whereby AAV particles comprising the vector genome encapsidated within the AAV capsid are produced in the cell.

A method provided herein may comprise the step of affinity-purification of the (virions comprising the) recombinant parvoviral (rAAV) vector using an anti-AAV antibody, in one embodiment an immobilized antibody. In another embodiment, the anti-AAV antibody is a monoclonal antibody. One antibody for use herein is a single chain camelid antibody or a fragment thereof as e.g. obtainable from camels or llamas (see e.g. Muyldermans, 2001, Biotechnol. 74: 277-302). The antibody for affinity-purification of rAAV is an antibody that specifically binds an epitope on a AAV capsid protein, whereby in one embodiment the epitope is an epitope that is present on capsid protein of more than one AAV serotype. For example, the antibody may be raised or selected on the basis of specific binding to AAV2 capsid but at the same time also it may also specifically bind to AAV1, AAV3, AAV5, AAV6, AAV8 or AAV9 capsids.

5.3 Cell Types Used in AAV Production

The viral particles comprising the AAV vectors of the embodiment may be produced using any invertebrate cell type which allows for production of AAV or biologic products and which can be maintained in culture. For example, the insect cell line used can be from *Spodoptera frugiperda*, such as SF9, SF21, SF900+, drosophila cell lines, mosquito cell lines, e.g., *Aedes albopictus* derived cell lines, domestic silkworm cell lines, e.g. *Bombyx mori* cell lines, *Trichoplusia ni* cell lines such as High Five cells or Lepidoptera cell lines such as *Ascalapha odorata* cell lines. In one embodiment, insect cells are cells from the insect species which are susceptible to baculovirus infection, including High Five, Sf9, Se301, SeIZD2109, SeUCR1, Sf9, Sf900+, Sf21, BTI-TN-5B1-4, MG-1, Tn368, HzAm1, BM-N, Ha2302, Hz2E5 and Ao38.

Baculoviruses are enveloped DNA viruses of arthropods, two members of which are well known expression vectors for producing recombinant proteins in cell cultures. Baculoviruses have circular double-stranded genomes (80-200 kbp) which can be engineered to allow the delivery of large genomic content to specific cells. The viruses used as a vector are generally *Autographa californica* multicapsid nucleopolyhedrovirus (AcMNPV) or *Bombyx mori* nucleopolyhedrovirus (BmNPV) (Kato et al., (2010), Applied Microbiology and Biotechnology, vol. 85, Issue 3, pp 459-470).

Baculoviruses are commonly used for the infection of insect cells for the expression of recombinant proteins. In particular, expression of heterologous genes in insects can be accomplished as described in for instance U.S. Pat. No. 4,745,051; EP 127,839; EP 155,476; Vlak et al., (1988), Journal of General Virology, vol. 68, pp 765-776; Miller et al., (1988), Annual Review of Microbiology, vol. 42, pp 177-179; Carbonell et al., (1998), Gene, vol. 73, Issue 2, pp 409-418; Maeda et al., (1985), Nature, vol. 315, pp 592-594; Lebacq-Veheyden et al., (1988), Molecular and Cellular Biology, vol. 8, no. 8, pp 3129-3135; Smith et al., (1985), PNAS, vol. 82, pp 8404-8408; and Miyajima et al., (1987), Gene, vol. 58, pp 273-281. Numerous baculovirus strains and variants and corresponding permissive insect host cells that can be used for protein production are described in Luckow et al., (1988), Nature Biotechnology, vol. 6, pp 47-55; Maeda et al., (1985), Nature, vol. 315, pp 592-594; and McKenna et al., (1998), Journal of Invertebrate Pathology, vol. 71, Issue 1, pp 82-90.

In another embodiment, the methods provided herein are carried out with any mammalian cell type which allows for replication of AAV or production of biologic products, and which can be maintained in culture. In one embodiment, mammalian cells used can be HEK293, HeLa, CHO, NSO, SP2/0, PER.C6, Vero, RD, BHK, HT 1080, A549, Cos-7, ARPE-19, and MRC-5 cells.

5.3.1 Host Organism and/or Cells

In a further embodiment, a host is provided comprising the vector described above. In one embodiment, the vector is capable of expressing the nucleic acid molecule provided herein in the host. The host may be any suitable host. In another embodiment, the PKU therapeutic includes PKU cell therapy (see, e.g., Harding, C., *Clin Genet*., August; 74(2) pages 97-104 (2008).

As used herein, the term "host" refers to organisms and/or cells which harbour a nucleic acid molecule or a vector of the present disclosure, as well as organisms and/or cells that are suitable for use in expressing a recombinant gene or protein. It is not intended that the present disclosure be limited to any particular type of cell or organism. Indeed, it is contemplated that any suitable organism and/or cell will find use herein as a host. A host cell may be in the form of a single cell, a population of similar or different cells, for example in the form of a culture (such as a liquid culture or a culture on a solid substrate), an organism or part thereof. In one embodiment, a host cell may permit the expression of a nucleic acid molecule provided herein. Thus, the host cell may be, for example, a bacterial, a yeast, an insect or a mammalian cell.

In another embodiment, provided is a means for delivering a nucleic acid provided herein into a broad range of cells, including dividing and non-dividing cells. The present disclosure may be employed to deliver a nucleic acid provided herein to a cell in vitro, e. g. to produce a polypeptide encoded by such a nucleic acid molecule in vitro or for ex vivo gene therapy.

The nucleic acid molecule, vector, cells and methods/use of the present disclosure are additionally useful in a method of delivering a nucleic acid provided hereinto a host, typically a host suffering from PKU.

The present disclosure finds use in both veterinary and medical applications. Suitable subjects for gene delivery methods as described herein include both avians and mammals, with mammals being preferred. The term "avian" as used herein includes, but is not limited to, chickens, ducks, geese, quail, turkeys and pheasants. The term "mammal" as used herein includes, but is not limited to, humans, bovines, ovines, caprines, equines, felines, canines, lagomorphs, etc. Human subjects include neonates, infants, juveniles, and adults.

5.4 Pharmaceutical Formulations

In one embodiment, provided is a pharmaceutical composition comprising a nucleic acid or a vector provided herein and a pharmaceutically acceptable carrier and/or other medicinal agent, pharmaceutical agent or adjuvant, etc.

In other embodiments, provided herein are pharmaceutical formulations of therapeutic protein expressing AAV vectors/virions useful for administration to subjects suffering from a genetic disorder. In certain embodiments, the pharmaceutical formulations provided herein are liquid formulations that comprise recombinant therapeutic protein expressing AAV virions produced from the vectors disclosed herein, wherein the concentration of recombinant AAV virions in the formulation may vary widely. In certain embodiments, the concentration of recombinant AAV virion in the formulation may range from 1E12 vg/ml to 2E16 vg/ml. In one embodiment, the concentration of recombinant AAV virion in the formulation is about 2E13 vg/ml.

In other embodiments, the AAV pharmaceutical formulation provided herein comprises one or more pharmaceutically acceptable excipients to provide the formulation with advantageous properties for storage and/or administration to subjects for the treatment of the genetic disorder. In certain embodiments, the pharmaceutical formulations provided herein are capable of being stored at −65° C. for a period of at least 2 weeks, in one embodiment at least 4 weeks, in another embodiment at least 6 weeks and yet another embodiment at least about 8 weeks, without detectable change in stability. In this regard, the term "stable" means that the recombinant AAV virus present in the formulation essentially retains its physical stability, chemical stability and/or biological activity during storage. In certain embodiments, the recombinant AAV virus present in the pharmaceutical formulation retains at least about 80% of its biological activity in a human patient during storage for a determined period of time at −65° C., in other embodiments at least about 85%, 90%, 95%, 98% or 99% of its biological activity in a human subject. In one embodiment the subjects are juvenile human subjects.

In certain aspects, the formulation comprising recombinant AAV virions further comprises one or more buffering agents. For example, in various embodiments, the formulation provided herein comprises sodium phosphate dibasic at a concentration of about 0.1 mg/ml to about 3 mg/ml, about 0.5 mg/ml to about 2.5 mg/ml, about 1 mg/ml to about 2 mg/ml, or about 1.4 mg/ml to about 1.6 mg/ml. In one embodiment, the AAV formulation provided herein comprises about 1.42 mg/ml of sodium phosphate, dibasic (dried). Another buffering agent that may find use in the recombinant AAV formulations provided herein is sodium phosphate, monobasic monohydrate which, in some embodiments, finds use at a concentration of from about 0.1 mg/ml to about 3 mg/ml, about 0.5 mg/ml to about 2.5 mg/ml, about 1 mg/ml to about 2 mg/ml, or about 1.3 mg/ml to about 1.5 mg/ml. In one embodiment, the AAV formulation of the present embodiment comprises about 1.38 mg/ml of sodium phosphate, monobasic monohydrate. In another embodiment, the recombinant AAV formulation provided herein comprises about 1.42 mg/ml of sodium phosphate, dibasic and about 1.38 mg/ml of sodium phosphate, monobasic monohydrate.

In another embodiment, the recombinant AAV formulation provided herein may comprise one or more isotonicity agents, such as sodium chloride, in one embodiment at a concentration of about 1 mg/ml to about 20 mg/ml, for example, about 1 mg/ml to about 10 mg/ml, about 5 mg/ml to about 15 mg/ml, or about 8 mg/ml to about 20 mg/ml. In another embodiment, the formulation provided herein comprises about 8.18 mg/ml sodium chloride. Other buffering agents and isotonicity agents known in the art are suitable and may be routinely employed for use in the formulations provided herein.

In another embodiment, the recombinant AAV formulations provided herein may comprise one or more bulking agents. Exemplary bulking agents include without limitation mannitol, sucrose, dextran, lactose, trehalose, and povidone (PVP K24). In certain embodiments, the formulations provided herein comprise mannitol, which may be present in an amount from about 5 mg/ml to about 40 mg/ml, or from about 10 mg/ml to about 30 mg/ml, or from about 15 mg/ml to about 25 mg/ml. In another embodiment, mannitol is present at a concentration of about 20 mg/ml.

In yet another embodiment, the recombinant AAV formulations provided herein may comprise one or more surfactants, which may be non-ionic surfactants. Exemplary surfactants include ionic surfactants, non-ionic surfactants, and combinations thereof. For example, the surfactant can be, without limitation, TWEEN 80 (also known as polysorbate 80, or its chemical name polyoxyethylene sorbitan monooleate), sodium dodecylsulfate, sodium stearate, ammonium lauryl sulfate, TRITON AG 98 (Rhone-Poulenc), poloxamer 407, poloxamer 188 and the like, and combinations thereof. In one embodiment, the formulation of the present embodiment comprises poloxamer 188, which may be present at a concentration of from about 0.1 mg/ml to about 4 mg/ml, or from about 0.5 mg/ml to about 3 mg/ml, from about 1 mg/ml to about 3 mg/ml, about 1.5 mg/ml to about 2.5 mg/ml, or from about 1.8 mg/ml to about 2.2 mg/ml. In another embodiment, poloxamer 188 is present at a concentration of about 2.0 mg/ml.

The recombinant therapeutic protein expressing AAV virus-containing formulations provided herein are stable and can be stored for extended periods of time without an unacceptable change in quality, potency, or purity. In one aspect, the formulation is stable at a temperature of about 5° C. (e.g., 2° C. to 8° C.) for at least 1 month, for example, at least 1 month, at least 3 months, at least 6 months, at least 12 months, at least 18 months, at least 24 months, or more. In another embodiment, the formulation is stable at a temperature of less than or equal to about −20° C. for at least 6 months, for example, at least 6 months, at least 12 months, at least 18 months, at least 24 months, at least 36 months, or more. In another embodiment, the formulation is stable at a temperature of less than or equal to about −40° C. for at least 6 months, for example, at least 6 months, at least 12 months, at least 18 months, at least 24 months, at least 36 months, or more. In another embodiment, the formulation is stable at a temperature of less than or equal to about −60° C. for at least 6 months, for example, at least 6 months, at least 12 months, at least 18 months, at least 24 months, at least 36 months, or more.

Pharmaceutical compositions are typically sterile and stable under the conditions of manufacture and storage. Pharmaceutical compositions may be formulated as a solution, microemulsion, liposome, or other ordered structure suitable to accommodate high drug concentration. The carrier may be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In some embodiments, isotonic agents, for example, sugars, polyalcohols such as mannitol, sorbitol, or sodium chloride are included in the composition. Prolonged absorption of the injectable compositions can be brought about by including in the composition an agent which delays absorption, for example, monostearate salts and gelatin. In certain embodiments, a nucleic acid or vector provided hereinmay be administered in a time or controlled release formulation, for example in a composition which includes a slow release polymer or other carriers that will protect the compound against rapid release, including implants and microencapsulated delivery systems. Biodegradable, biocompatible polymers may for example be used, such as ethylene vinyl acetate, polyanhydrides, polyglycolic acid, collagen, polyorthoesters, polylactic acid and polylactic, polyglycolic copolymners (PLG).

In certain embodiments, the pharmaceutical composition comprising the AAV vector provided herein may be of use in transferring genetic material to a cell. Such transfer may take place in vitro, ex vivo or in vivo. Accordingly, one embodiment provides a method for delivering a nucleotide sequence to a cell, which method comprises contacting a nucleic acid, a vector, or a pharmaceutical composition as described herein under conditions such the nucleic acid or vector provided herein enters the cell. The cell may be a cell in vitro, ex vivo or in vivo 5.5 Methods of Treatment In certain embodiments, provided herein are methods for treating a subject suffering from a genetic disorder comprising administering to the subject a therapeutically effective amount of an AAV vector expressing a therapeutic protein or a pharmaceutical composition comprising the same. In this instance, a "therapeutically effective amount" is an amount of AAV vector that after administration results in the expression of the therapeutic protein in a level sufficient to at least partially and preferably fully ameliorate the symptoms of the genetic disorder.

In one embodiment, provided herein is a method of treating PKU comprising administering a therapeutically effective amount of a nucleic acid, a protein, a vector or cells or a pharmaceutical composition provided herein to a patient suffering from PKU. In one embodiment, the patient is human. In one embodiment, the subject patient population is patients with moderate to severe hyperphenylalaninemia, including those with PKU, variant PKU or non-PKU hyperphenylalaninemia. In one embodiment, the goal for the AAV vector treatment is conversion of severe PKU patients to either moderate or mild PKU thus lessening the burden associated with a severely limited phenylalanine diet.

In one embodiment, provided herein are methods for increasing circulating PAH protein levels in a subject in need thereof comprising administering to the subject any of the AAV vectors provided herein, or viral particles provided herein or a viral particle produced by a method provided herein that express the PAH protein. In one embodiment, the vector dose delivers PAH to result in a reduction of plasma phenylalanine levels to less than 160 μM.

In another embodiment, provided herein is the use of an effective amount of recombinant AAV PAH virus for the preparation of a medicament for the treatment of a subject suffering from PKU. In one embodiment, the subject suffering from PKU is a human. In one embodiment, the medicament is administered by intravenous (IV) administration. In another embodiment, administration of the medicament results in expression of PAH protein in the bloodstream of the subject sufficient to alter the neurotransmitter metabolite or neurotransmitter levels in the subject. In certain embodiments, the medicament also comprises a prophylactic and/or therapeutic corticosteroid for the prevention and/or treatment of any hepatotoxicity associated with administration of the AAV PAH virus. The medicament comprising a prophylactic or therapeutic corticosteroid treatment may comprise at least 5, 10, 15, 20, 25, 30, 35, 40, 45, 50, 55, 60, or more mg/day of the corticosteroid. In certain embodiments, the medicament comprising a prophylactic or therapeutic corticosteroid may be administered over a continuous period of at least about 3, 4, 5, 6, 7, 8, 9, 10 weeks, or more. In another embodiment, the PKU therapy provided herein optionally includes tyrosine supplements.

A "therapeutically effective amount" of an AAV vector or virus or a pharmaceutical composition comprising the same for purposes of treatment as described herein may be determined empirically and in a routine manner. In certain embodiments, however, a "therapeutically effective amount" of recombinant AAV virus ranges from about 1E12 vg/kg body weight to about 1E14 vg/kg body weight, in one embodiment from about 6E12 vg/kg body weight to about 6E13 vg/kg body weight. In another embodiment, a therapeutically effective amount of recombinant AAV virus is about 2E13 vg/kg body weight. In another embodiment, a therapeutically effective amount of recombinant AAV virus is about 6E13 vg/kg body weight.

In one embodiment, recombinant AAV vectors/virus provided herein may be administered to a subject, in one embodiment a mammalian subject, or a human subject, through a variety of known administration techniques. In another embodiment, the recombinant AAV gene therapy virus is administered by intravenous injection either as a single bolus or over a prolonged time period, which may be at least about 1, 5, 10, 15, 30, 45, 60, 75, 90, 120, 150, 180, 210 or 240 minutes, or more. In other embodiments the recombinant AAV virus administered expresses PAH.

In certain embodiments involving an AAV vector expressing PAH to treat PKU in subjects, the effectiveness of the AAV vector can be monitored by measuring levels of phenylalanine in the blood of the treated subject. Precise quantitate assays for determining circulating levels of phenylalanine are well known in the art and include fluorometric assays (see, McCaman, M. W. and Robins, E., (1962) *J. Lab. Clin. Med., vol.* 59, pp. 885-890); thin layer chromatography based assays (see, Tsukerman, G. L. (1985) *Laboratornoe delo*, vol. 6, pp. 326-327); enzymatic assays (see, La Du, B. N., et al. (1963) *Pediatrics*, vol. 31, pp. 39-46; and Peterson, K., et al. (1988) *Biochem. Med. Metab. Biol*., vol. 39, pp. 98-104); methods employing high pressure liquid chromatography (HPLC) (see, Rudy, J. L., et al. (1987) *Clin. Chem*., vol. 33, pp. 1152-1154); and high-throughput automation (see, Hill, J. B., et al. (1985) *Clin. Chem*., vol. 5, pp. 541-546).

Administration of an AAV virus of the present disclosure may, in some cases, result in an observable degree of hepatotoxicity. Hepatotoxicity may be measured by a variety of well-known and routinely used techniques for example, measuring concentrations of certain liver-associated enzyme(s) (e.g., alanine transaminase, ALT) in the bloodstream of a subject both prior to AAV administration (i.e., baseline) and after AAV administration. An observable increase in ALT concentration after AAV administration (as compared to prior to administration) is indicative of drug-induced hepatotoxicity. In certain embodiments, in addition to administration of a therapeutically effective amount of AAV virus, the subject may be treated either prophylactically, therapeutically, or both with a corticosteroid to prevent and/or treat any hepatotoxicity associated with administration of the AAV virus.

"Prophylactic" corticosteroid treatment refers to the administration of a corticosteroid to prevent hepatotoxicity and/or to prevent an increase in measured ALT levels in the subject. "Therapeutic" corticosteroid treatment refers to the administration of a corticosteroid to reduce hepatotoxicity caused by administration of an AVV virus and/or to reduce an elevated ALT concentration in the bloodstream of the subject caused by administration of an AAV virus. In certain embodiments, prophylactic or therapeutic corticosteroid treatment may comprise administration of at least 5, 10, 15, 20, 25, 30, 35, 40, 45, 50, 55, 60, or more mg/day of the corticosteroid to the subject. In certain embodiments, prophylactic or therapeutic corticosteroid treatment of a subject may occur over a continuous period of at least about 3, 4, 5, 6, 7, 8, 9, 10 weeks, or more. Corticosteroids that find use in the methods described herein include any known or routinely-employed corticosteroid including, for example, dexamethasone, prednisone, fludrocortisone, hydrocortisone, and the like.

5.6 Detection of Anti-AAV Antibodies

To maximize the likelihood of successful liver transduction with systemic AAV-mediated therapeutic gene transfer, prior to administration of an AAV vector in a therapeutic regimen to a human patient as described above, the prospective patient may be assessed for the presence of anti-AAV capsid antibodies that are capable of blocking cell transduction or otherwise reduce the overall efficiency of the therapeutic regimen. Such antibodies may be present in the serum of the prospective patient and may be directed against an AAV capsid of any serotype. In one embodiment, the serotype against which pre-existing antibodies are directed is AAV5.

Methods to detect pre-existing AAV immunity are well known and routinely employed in the art and include cell-based in vitro transduction inhibition (TI) assays, in vivo (e.g., in mice) TI assays, and ELISA-based detection of total anti-capsid antibodies (TAb) (see, e.g., Masat et al., *Discov. Med.*, vol. 15, pp. 379-389 and Boutin et al., (2010) *Hum. Gene Ther.*, vol. 21, pp. 704-712). TI assays may employ host cells into which an AAV-inducible reporter vector has been previously introduced. The reporter vector may comprise an inducible reporter gene such as GFP, etc. whose expression is induced upon transduction of the host cell by an AAV virus. Anti-AAV capsid antibodies present in human serum that are capable of preventing/reducing host cell transduction would thereby reduce overall expression of the reporter gene in the system. Therefore, such assays may be employed to detect the presence of anti-AAV capsid antibodies in human serum that are capable of preventing/reducing cell transduction by the therapeutic AAV PAH virus.

TAb assays to detect anti-AAV capsid antibodies may employ solid-phase-bound AAV capsid as a "capture agent" over which human serum is passed, thereby allowing anti-capsid antibodies present in the serum to bind to the solid-phase-bound capsid "capture agent". Once washed to remove non-specific binding, a "detection agent" may be employed to detect the presence of anti-capsid antibodies bound to the capture agent. The detection agent may be an antibody, an AAV capsid, or the like, and may be detectably-labeled to aid in detection and quantitation of bound anti-capsid antibody. In one embodiment, the detection agent is labeled with ruthenium or a ruthenium-complex that may be detected using electrochemiluminescence techniques and equipment.

The same above-described methodology may be employed to assess and detect the generation of an anti-AAV capsid immune response in a patient previously treated with a therapeutic AAV virus of interest. As such, not only may these techniques be employed to assess the presence of anti-AAV capsid antibodies prior to treatment with a therapeutic AAV virus, they may also be employed to assess and measure the induction of an immune response against the administered therapeutic AAV virus after administration. As such, contemplated herein are methods that combine techniques for detecting anti-AAV capsid antibodies in human serum and administration of a therapeutic AAV virus for the treatment of PKU, wherein the techniques for detecting anti-AAV capsid antibodies in human serum may be performed either prior to or after administration of the therapeutic AAV virus.

Other aspects and advantages of the present disclosure will be understood upon consideration of the following illustrative examples.

6. EXAMPLES

6.1 Example 1: Phenylalanine Metabolic Pathway and Assay Methodology

The PAH mediated conversion of phenylalanine to tyrosine serves as the precursor reaction for the production of a number of neurotransmitters as shown in Scheme 1.

Scheme 1

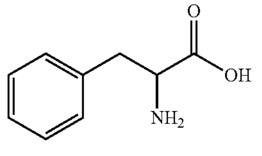

L-Phe

PAH

-continued
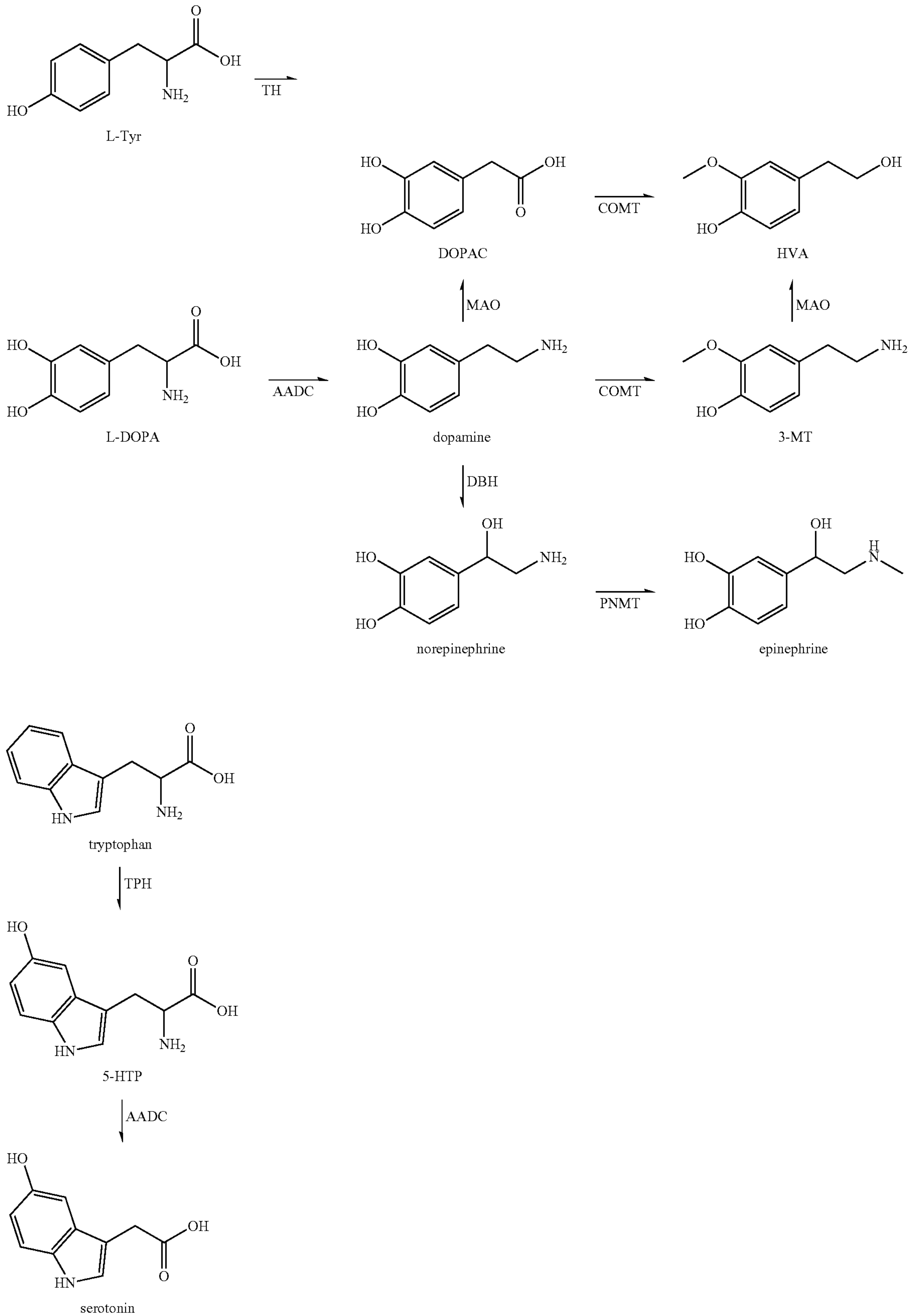
L-Tyr
DOPAC
HVA
L-DOPA
dopamine
3-MT
norepinephrine
epinephrine
tryptophan
5-HTP
serotonin The loss of PAH activity in PKU patients results in the build-up of phenylalanine as noted by the increase in plasma phenylalanine levels. However, the neurocognitive effects of PKU are mostly caused by the loss of a precursor metabolic step that leads to the production of a number of neurotransmitters and metabolites.

A sensitive liquid-chromatography coupled mass spectrometry (LC/MS) based assay was used to measure the levels of various amino acids, neurotransmitters, and neurotransmitter metabolites. In brief, when amino acids, neurotransmitter metabolites, and neurotransmitters are reacted with ethyl chloroformate and pyridine or benzoyl chloride and sodium carbonate, they produce reaction products that have defined increases in molecular mass that allows for their identification and quantification using LC/MS. This reaction process is illustrated in detail in Scheme 2 for the neurotransmitter dopamine where the 153.08 Da dopamine is converted to the 369.14 Da dopamine-ECF.

Scheme 2

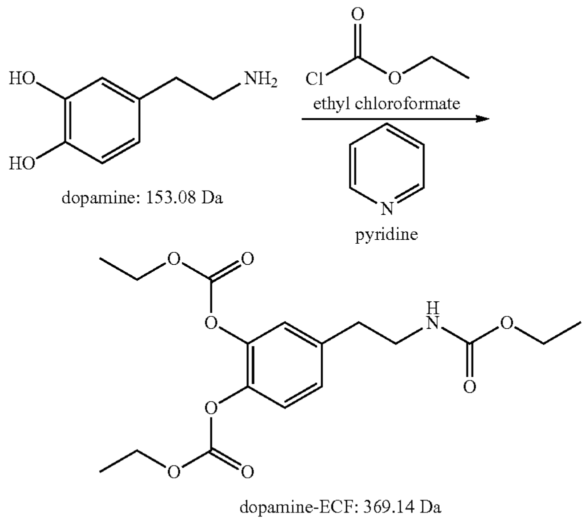

The ethyl chloroformate and pyridine reaction products and their exact masses are shown for the amino acids, neurotransmitters, neurotransmitter metabolites that are produced downstream of the phenylalanine PAH enzyme reaction are shown in Scheme 3.

Scheme 3

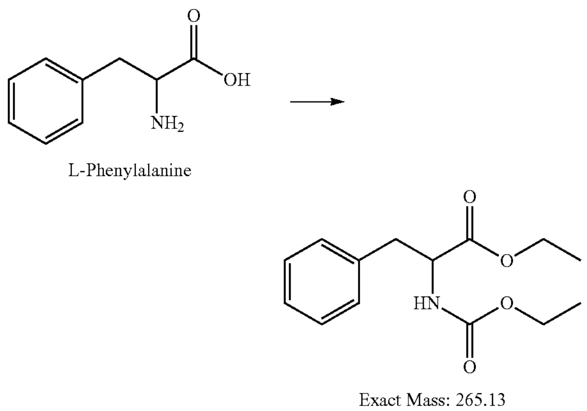

-continued

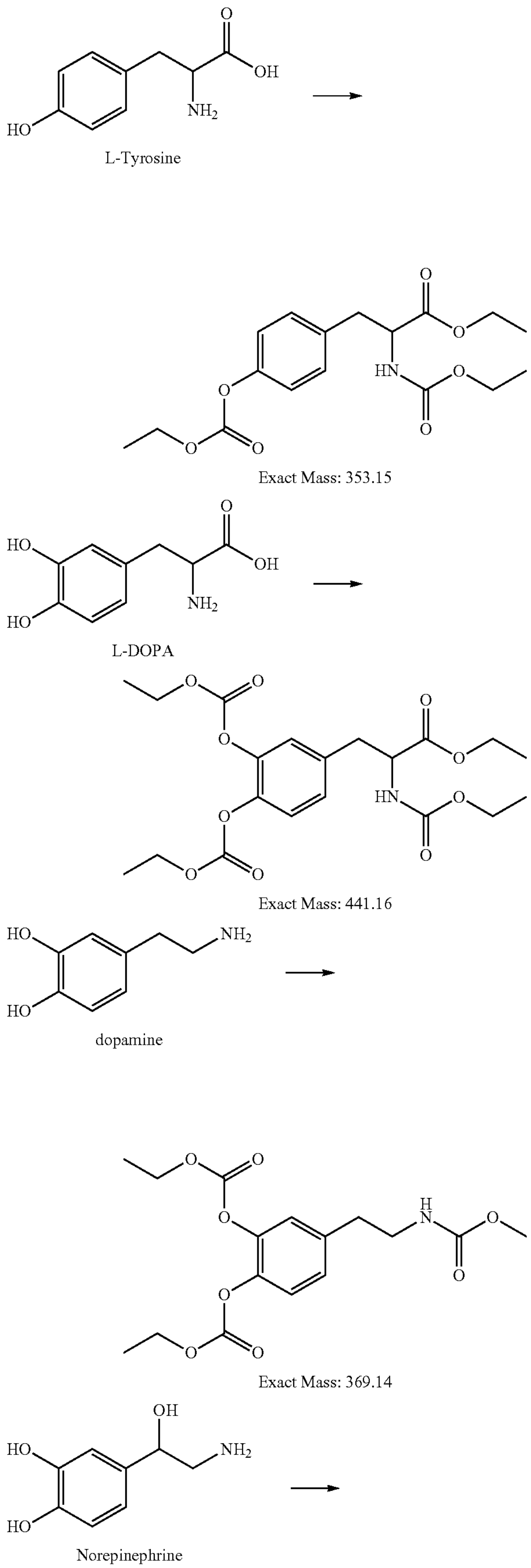

Figure 1:
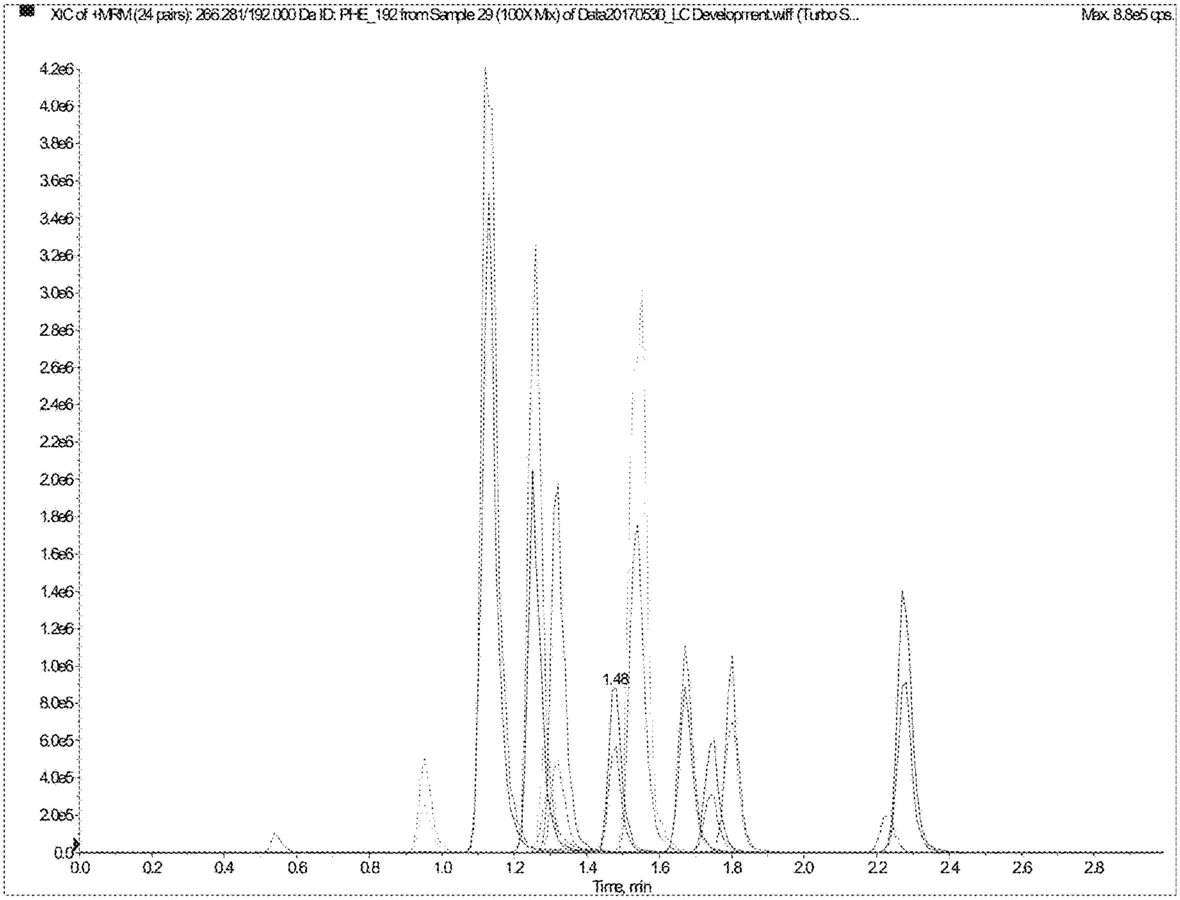
Figure 2A:
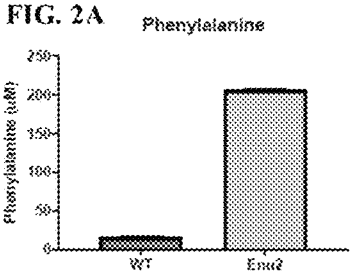
Figure 2B:
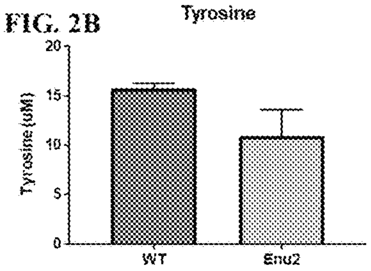
Figure 2C:
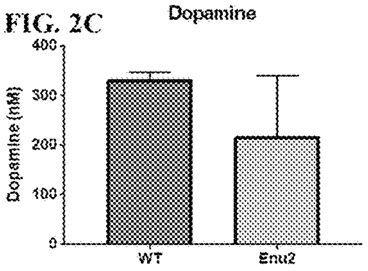
Figure 2D:
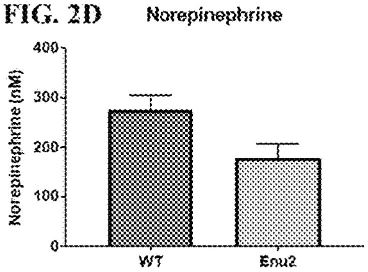
Figure 2E:
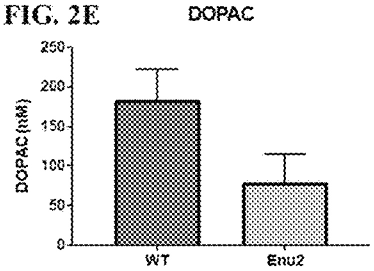
Figure 2F:
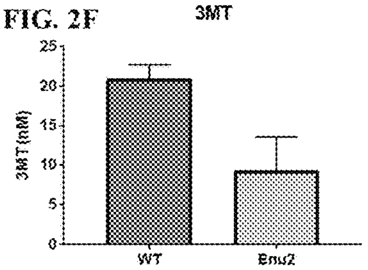
Figure 2G:
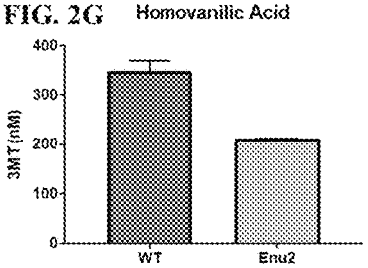
Figure 2H:
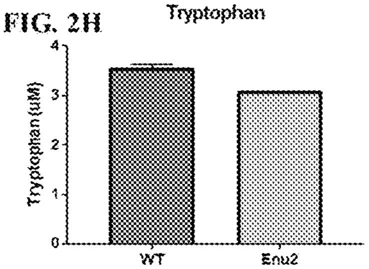
Figure 2I:
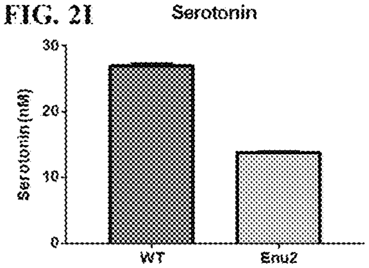
Figure 3A:
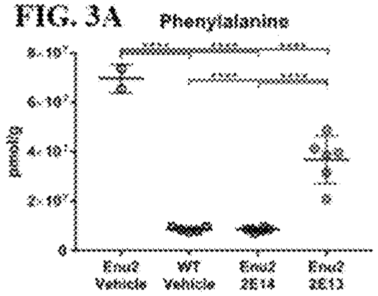
Figure 3B:
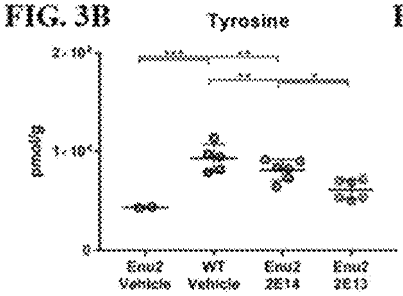
Figure 3C:
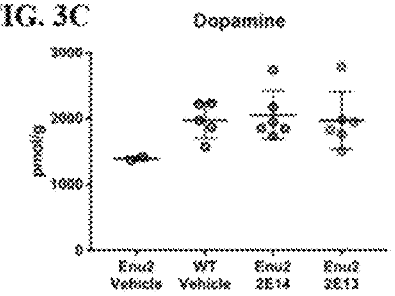
Figure 3D:
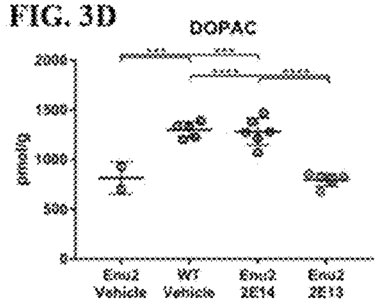
Figure 3E:
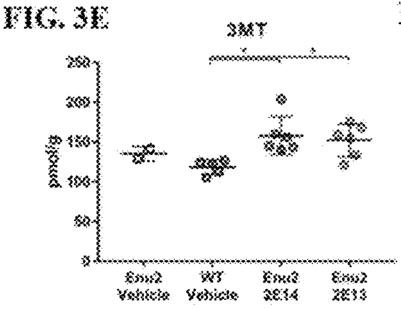
Figure 3F:
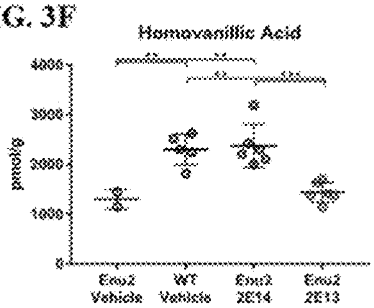
Figure 3G:
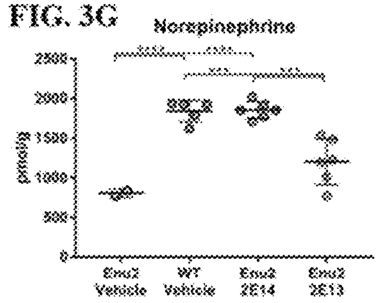
Figure 3H:
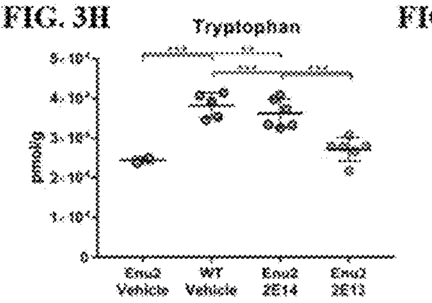
Figure 3I:
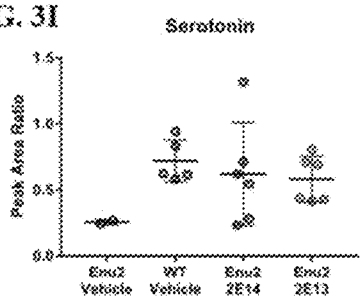

-continued
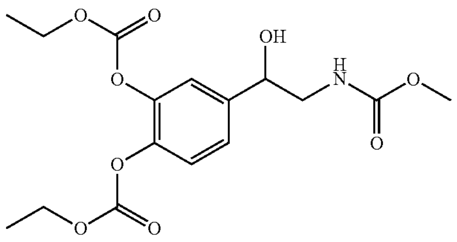
Exact Mass: 385.14
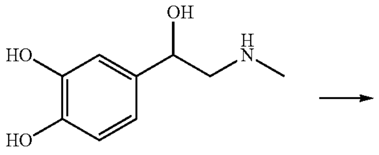
Epinephrine
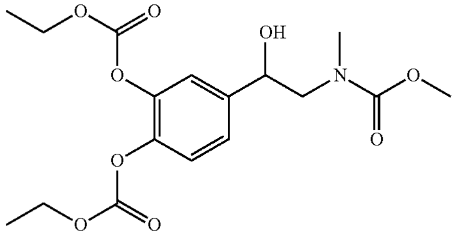
Exact Mass: 399.15
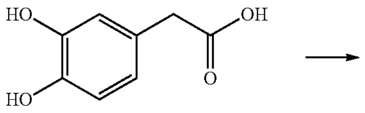
DOPAC
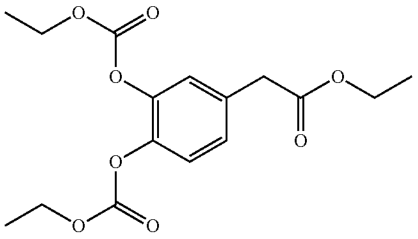
Exact Mass: 340.12
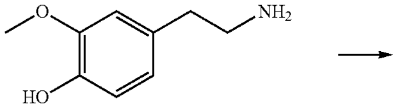
3-MT
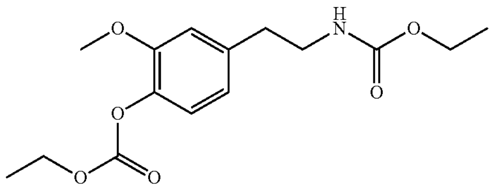
Exact Mass: 311.14
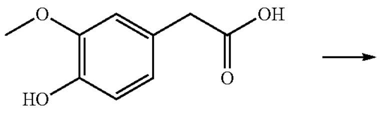
Homovanillic Acid
-continued
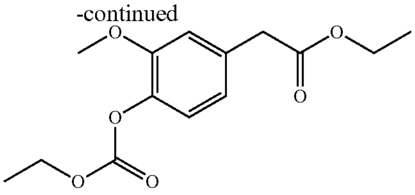
Exact Mass: 282.11
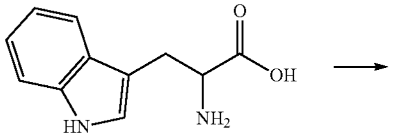
L-Tryptophan
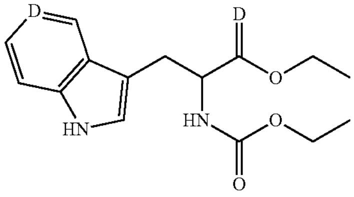
Exact Mass: 279.17
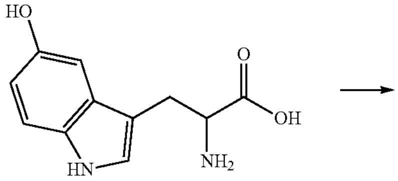
5-HTP
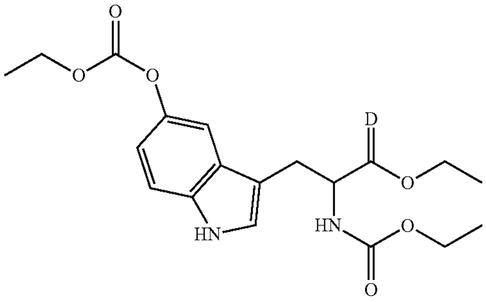
Exact Mass: 392.16
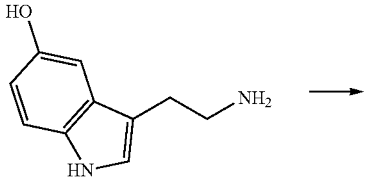
Serotonin
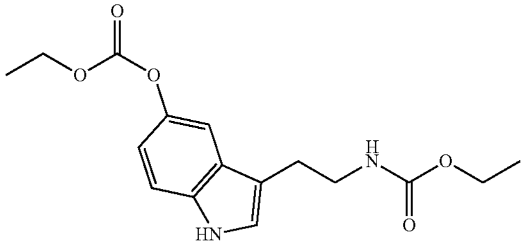
Exact Mass: 320.14
FIG. 1 shows an illustrative example of a liquid chromatography-mass spectrometry (LC/MS) chromatogram of phenylalanine derived amino acids, neurotransmitters, and neurotransmitter metabolites after reaction with ethyl chloroformate and pyridine or benzoyl chloride and sodium carbonate. As seen in FIG. 1, each of the reaction products can be clearly defined and quantitated.

6.2 Example 2: Neurotransmitter Levels are Consistently Lower in Enu2 Mouse Samples Compared to Wild-Type Mouse Samples The assay described above in Example 1 was used to measure the levels of amino acids, neurotransmitters, and neurotransmitter metabolites in biological samples obtained from Enu2 and wild-type mice to determine the effect of PAH loss on neurotransmitter production. As shown in FIG. 2, the Enu2 mice consistently demonstrated lower levels of neurotransmitter and neurotransmitter metabolites compared to wild-type mice in brain samples. The Enu2 mice had decreased levels of tyrosine, dopamine, 3-methoxytyramine (3-MT), DOPAC, homovanillic acid, norepinephrine, tryptophan, and serotonin in their brains compared to the levels found in the brains of wild-type mice. These data demonstrate that loss of PAH activity results in a reduction of a number of key neurotransmitters.

6.3 Example 3: Neurotransmitter Levels Serve as Surrogate Marker for Identifying an Effective Dose of a PKU Therapeutic Enu2 mice were treated with two doses (2E13 vg/kg and 2E14 vg/kg) of an adeno associated virus vector expressing human PAH (AAV-PAH). The AAV is constructed with the ITRs of the AAV2 serotype and the capsid genes of the AAV5 serotype. Enu2 and wild-type mice were also treated with vehicle as controls. Twelve weeks after virus administration, the levels of amino acids, neurotransmitters, and neurotransmitter metabolites were measured in brain samples collected from each group of animals. As shown in FIG. 3, vehicle-treated Enu2 mice had increased levels of phenylalanine, and decreased levels of tyrosine, dopamine, DOPAC, homovanillic acid, norepinephrine, tryptophan, and serotonin relative to the levels measured in vehicle treated wild-type mice. Administration of the higher dose of AAV-PAH (2E14 vg/kg) to Enu2 mice, but not the lower dose (2E13 vg/kg), restored the levels of phenylalanine, tyrosine, dopamine, DOPAC, homovanillic acid, norepinephrine, tryptophan, and serotonin to levels seen in the vehicle-treated wild-type control. These data demonstrate that the levels of certain amino acids, neurotransmitters, and neurotransmitter metabolites in the brain can be used to determine the effective dose of a PKU therapeutic needed to restore the neurotransmitter metabolic pathways to those seen in wild-type controls.

Figure 4:
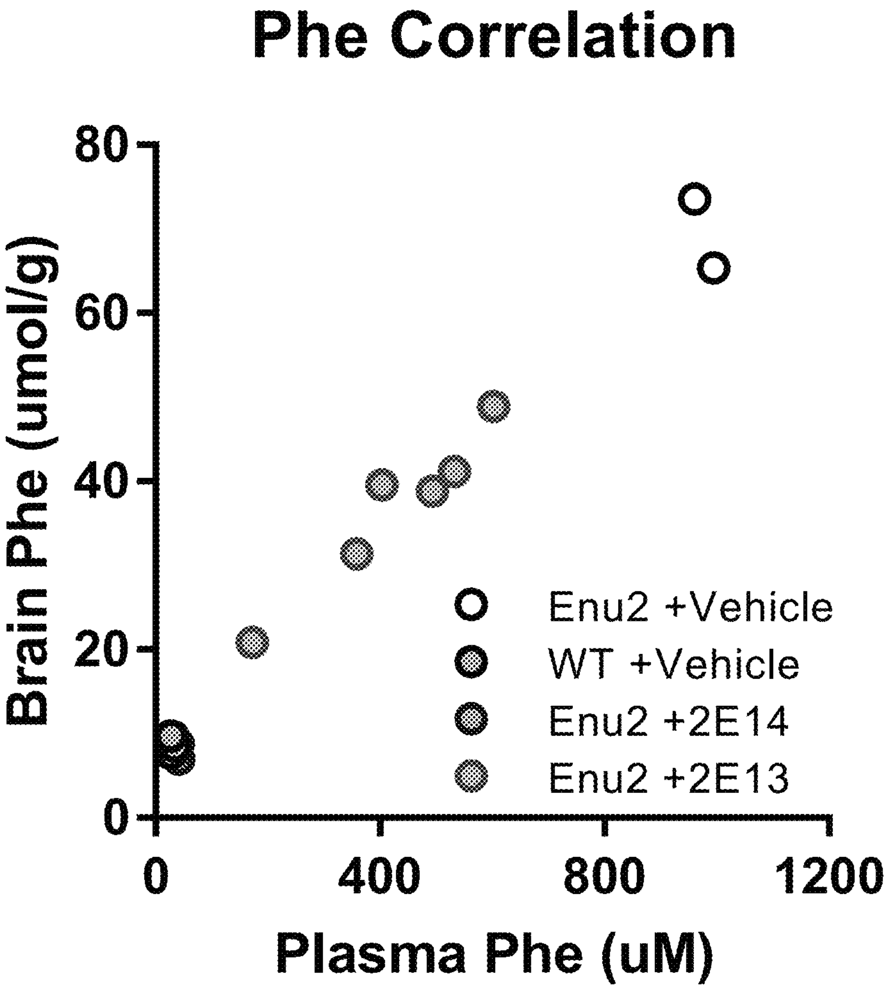
Figure 6A:
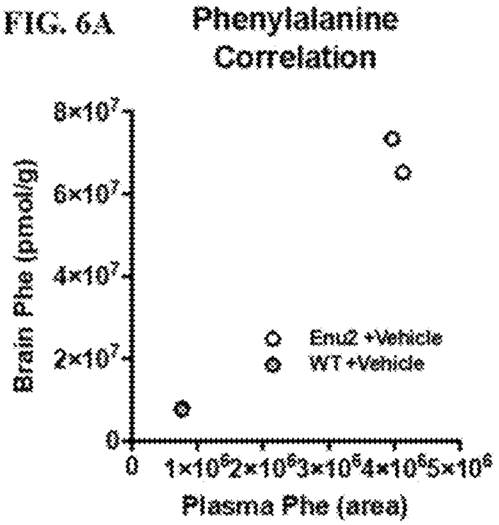
Figure 6B:
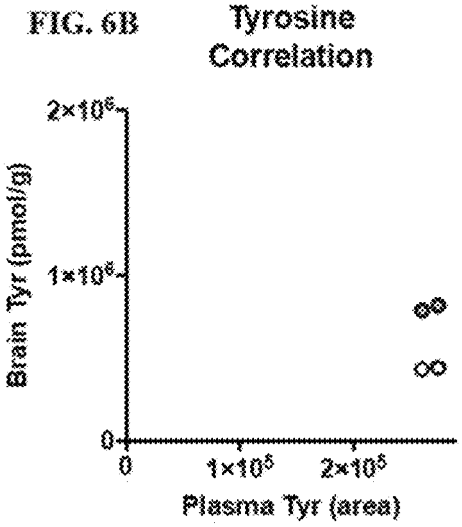
Figure 6C:
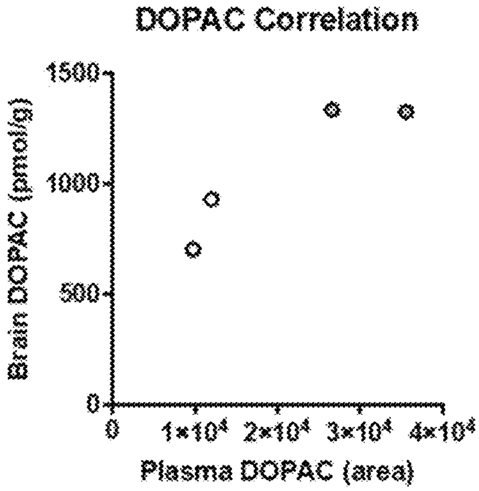
Figure 6D:
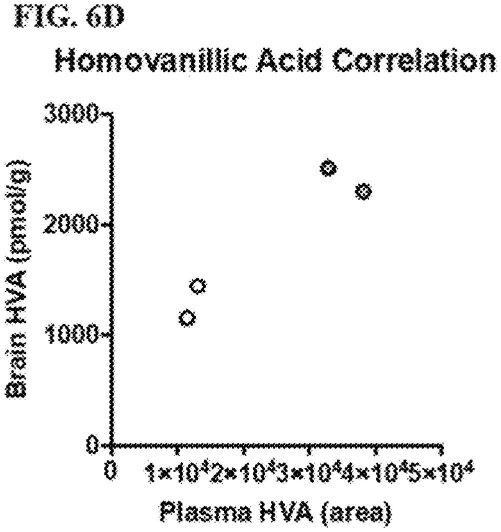

6.4 Example 4: Plasma Levels of Phenylalanine Correlate with the Levels Detected in Brain Urine, blood, serum, and plasma phenylalanine levels are a known biomarker for PKU diagnosis and disease management monitoring. Plasma and brain phenylalanine levels were measured and compared to vehicle-treated wild-type and Enu2 mice, and Enu2 mice treated with 2E13 vg/kg and 2E14 vg/kg AAV-PAH. As shown in FIG. 4, there is a strong linear correlation between plasma and brain phenylalanine in individual animals. Moreover, the correlation holds regardless of PAH status and AAV-PAH treatment dose. These data provide further support for the value of plasma phenylalanine as a surrogate biomarker for neurocognitive PKU symptoms because brain phenylalanine levels may dictate the levels of neurotransmitters generated.

Figure 8A:
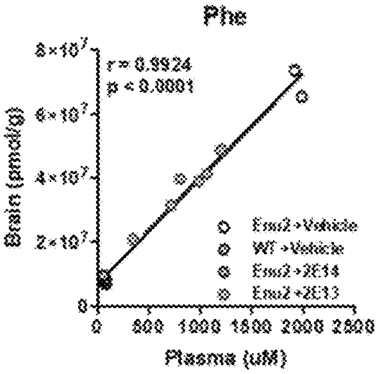
Figure 8B:
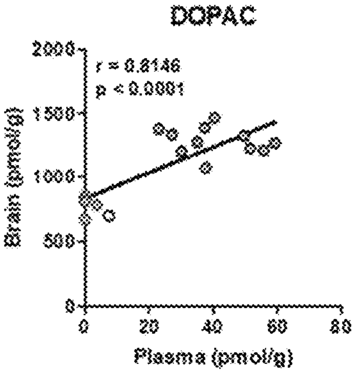
Figure 8C:
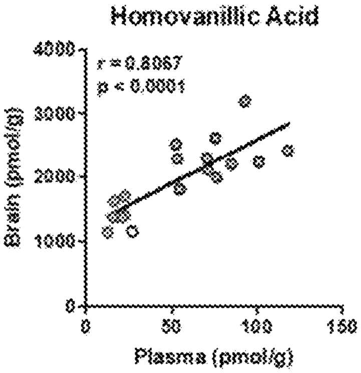
Figure 9A:
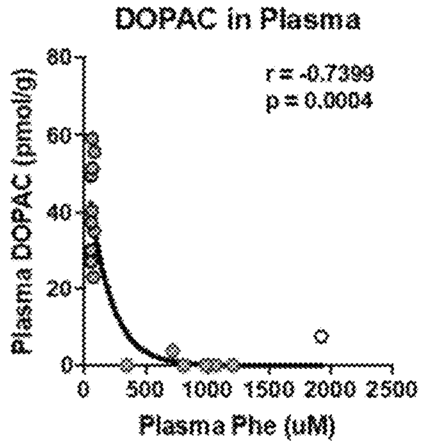
Figure 9B:
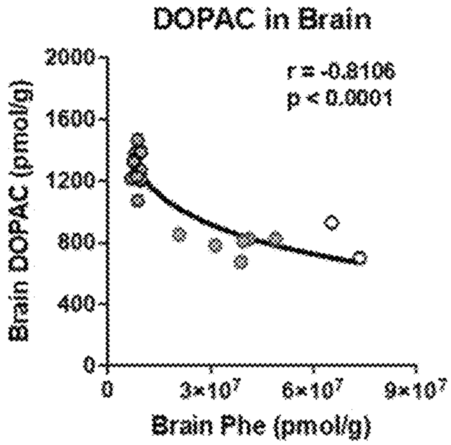
Figure 9C:
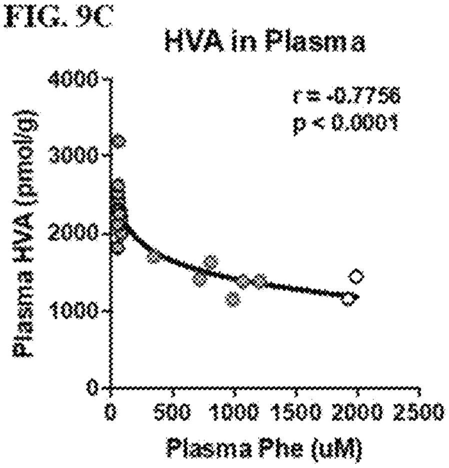
Figure 9D:
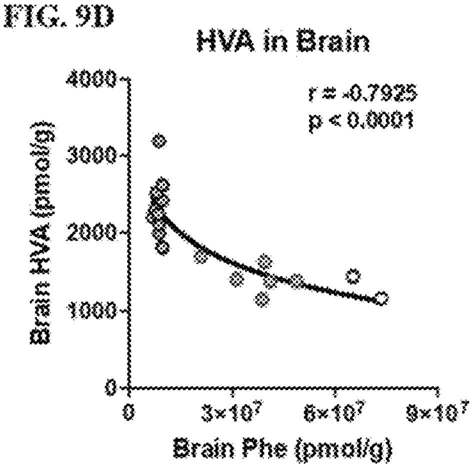

6.5 Example 5: Neurotransmitter and Neurotransmitter Metabolite Levels in Plasma of Enu2 and Wild-Type Mice The levels of the neurotransmitter metabolites DOPAC and homovanillic acid were measured in wild-type and Enu2 mice. As shown in FIG. 5, Enu2 mice have lower levels of neurotransmitter metabolites in their plasma compared to wild-type mice. Moreover, the plasma levels of these metabolites correlate with the levels detected in brain (FIGS. 6 and 8). These data demonstrate that plasma DOPAC and homovanillic acid can act as surrogates for understanding the levels of these metabolites in brain, and can serve as relatively easily obtained biomarkers of neurocognitive symptoms.

Figure 10A:
Figure 10B:
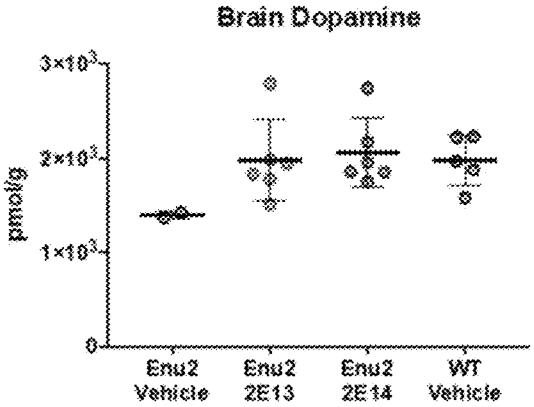
Figure 10C:
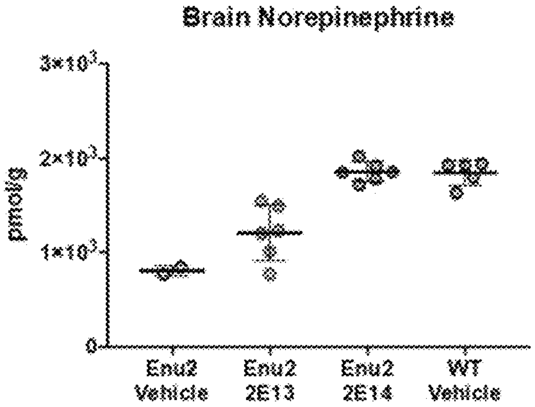
Figure 11A:
Figure 11B:
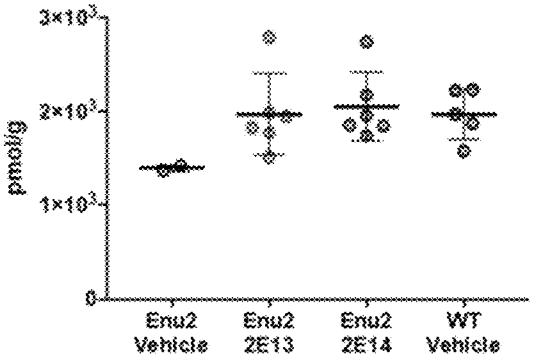
Figure 11C:
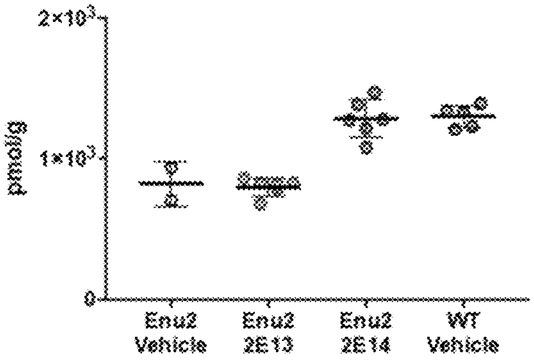

The plasma and brain levels of phenylalanine, tyrosine, dopamine, DOPAC, 3 MT, homovanillic acid, norepinephrine, tryptophan, and serotonin in vehicle-treated wild-type and Enu2 mice, and in Enu2 mice treated with 2E13 vg/kg and 2E14 vg/kg AAV-PAH was measured. As shown in FIG. 7, the 2E14 vg/kg dose of AAV-PAH increased the plasma levels of the measured amino acids (except phenylalanine which was reduced to wild-type levels), neurotransmitters, and neurotransmitter metabolites to those seen in wild-type mice. In contrast, the 2E13 vg/kg dose of AAV-PAH did not completely restore the levels of the measured amino acids, neurotransmitter metabolites, and neurotransmitters. Further, there is an inverse correlation between the levels of phenylalanine and the levels of the neurotransmitter metabolites DOPAC and homovanillic acid (FIG. 9). This is consistent with the notion that loss of PAH activity results in a marked reduction of the metabolites which is the basis for the neurocognitive symptoms of PKU. Accordingly, the plasma or brain levels of these neurotransmitters or their resultant metabolites can serve as companion diagnostics for determining the effective amount of a PKU therapeutic needed to treat or ameliorate the neurocognitive symptoms of PKU. This is shown, as non-limiting illustrative examples, in FIGS. 10 and 11. In this case, the brain levels of dopamine, norepinephrine and DOPAC were measured in vehicle-treated wild-type and Enu2 mice, and in Enu2 mice treated with 2E13 vg/kg and 2E14 vg/kg AAV-PAH. As shown in FIGS. 10 and 11, the lower dose of 2E13 vg/kg was sufficient to restore the levels of dopamine, but was insufficient to restore the levels of DOPAC and norepinephrine. In contrast, the higher dose of 2E14 vg/kg fully restored the levels of dopamine, DOPAC, and norepinephrine in the Enu2 animals to the levels seen in the wild-type control. This set of surrogate markers was sufficient to determine that the 2E14 vg/kg dose was effective for restoring these neurocognitive pathways, whereas the lower dose was not.

Figure 12A:
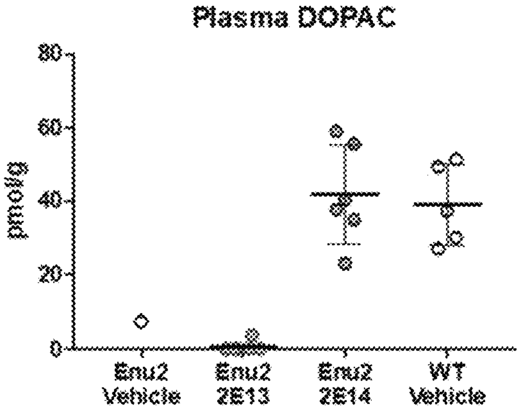
Figure 12B:
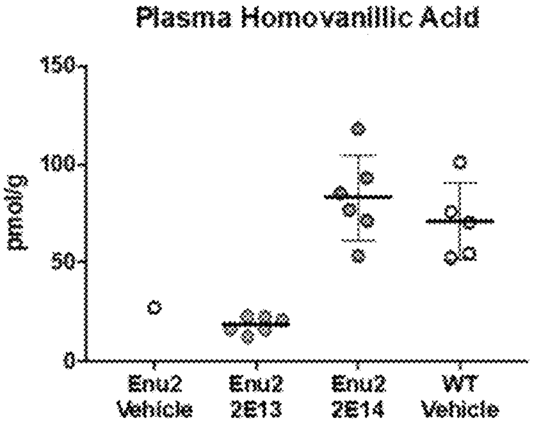
Figure 13A:
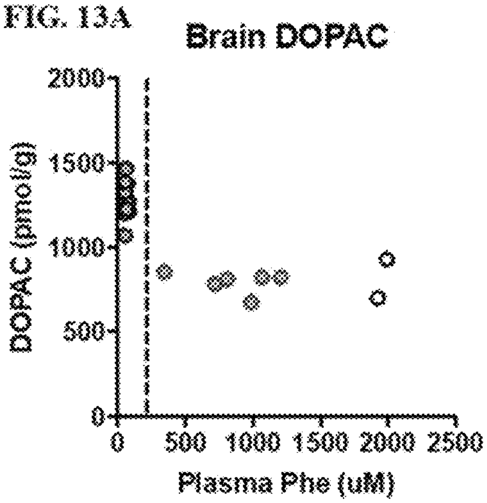
Figure 13B:
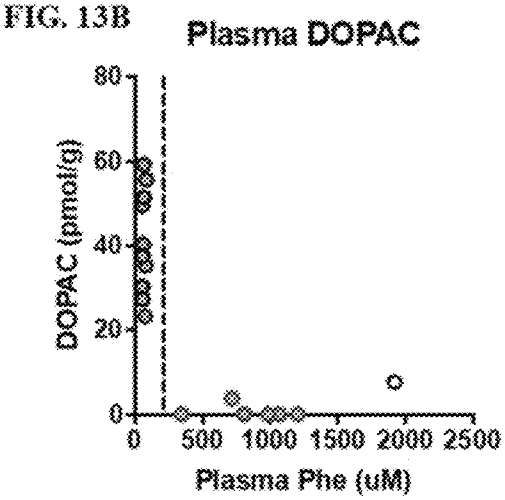
Figure 13C:
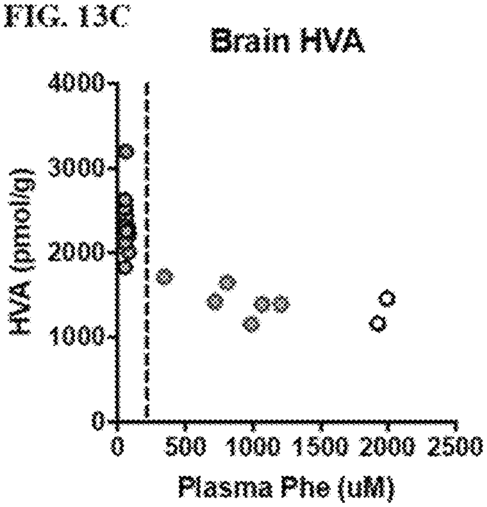
Figure 13D:
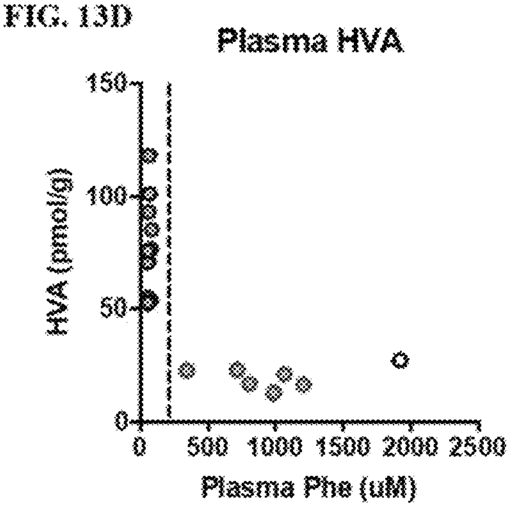
Figure 14A:
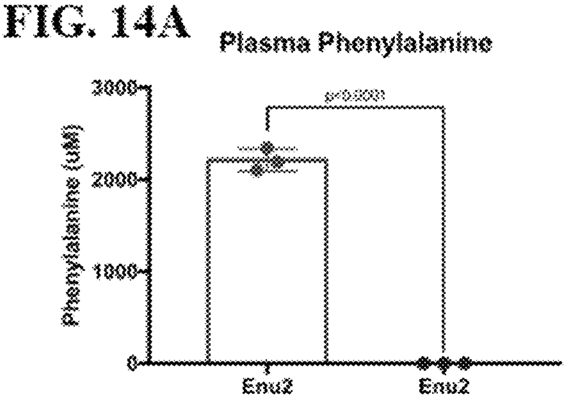
Figure 14B:
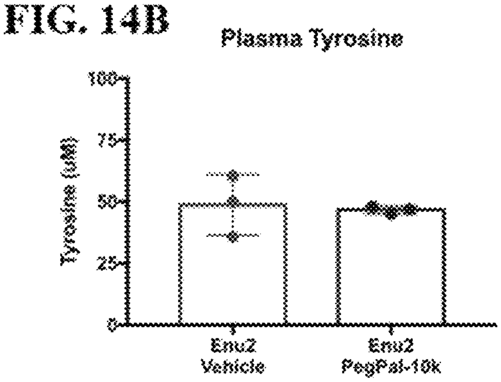
Figure 14C:
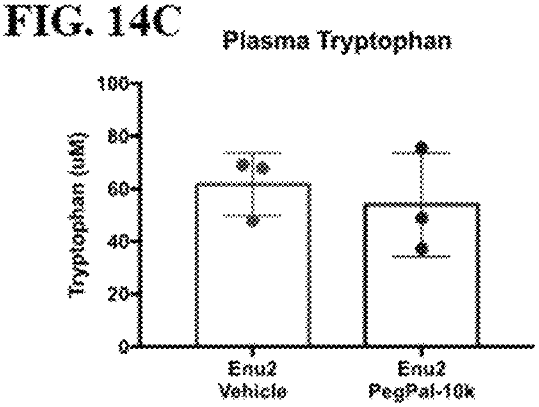
Figure 14D:
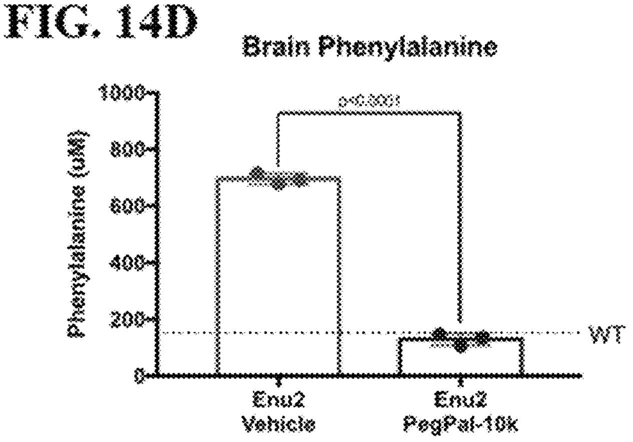
Figure 14E:
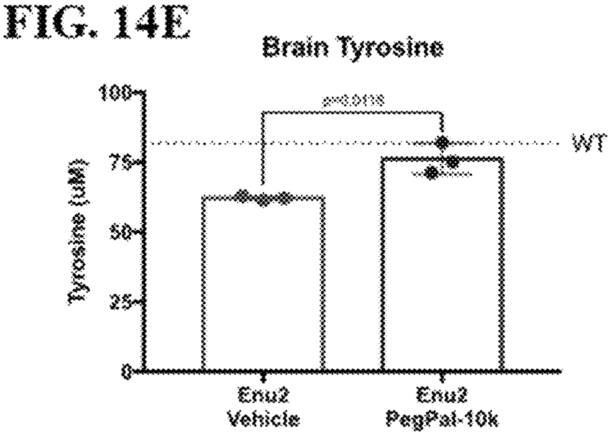
Figure 14F:
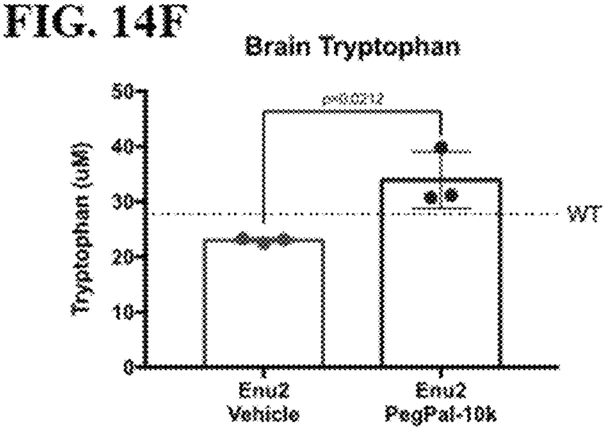

As an additional example, the use of plasma levels of neurotransmitter metabolites as surrogate marker of an effective dose is shown in FIGS. 12 and 13. Here, the plasma levels of DOPAC and homovanillic acid were measured in vehicle treated wild-type and Enu2 mice, and in Enu2 mice treated with 2E13 vg/kg and 2E14 vg/kg AAV-PAH. As shown in FIG. 12, the high dose of 2E14 vg/kg was able to restore the plasma levels of DOPAC and homovanillic acid to those seen in wild-type, whereas the low dose of 2E13 vg/kg was not. Furthermore, as shown in FIG. 13, plasma and brain levels of these markers had an inverse correlation to the plasma and brain levels of their amino acid precursor phenylalanine.

Figure 15A:
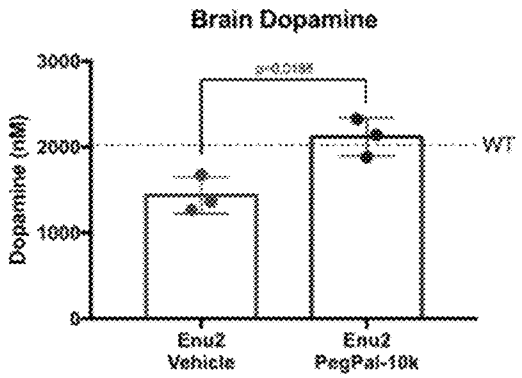
Figure 15B:
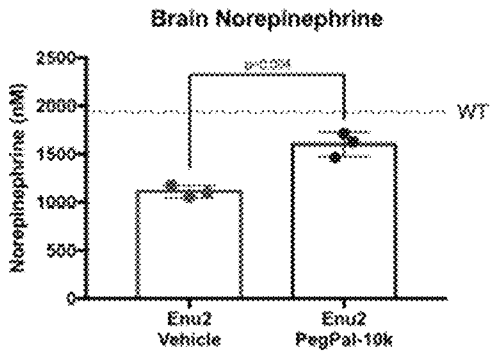
Figure 15C:
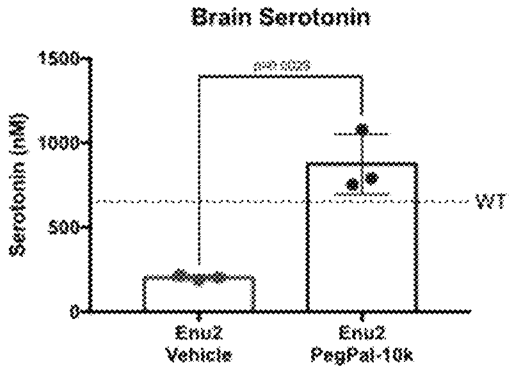
Figure 16A:
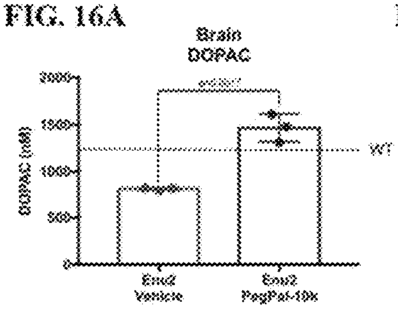
Figure 16B:
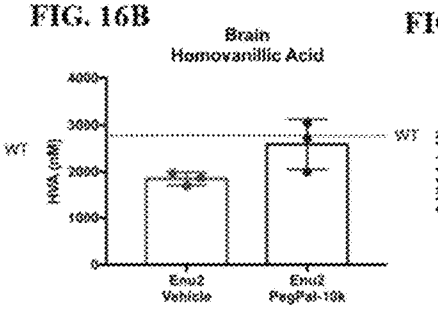
Figure 16C:
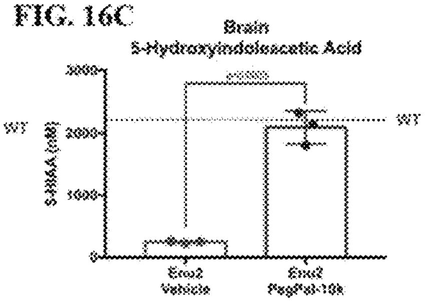
Figure 16D:
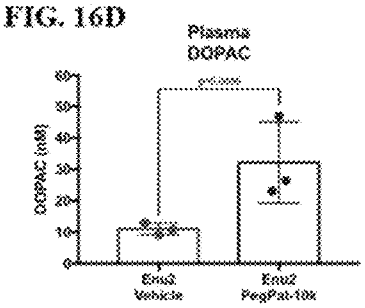
Figure 16E:
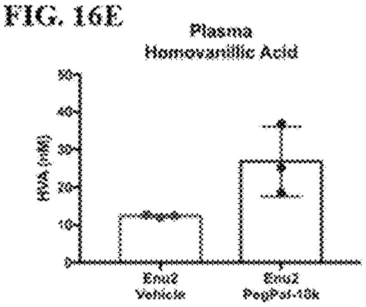
Figure 16F:
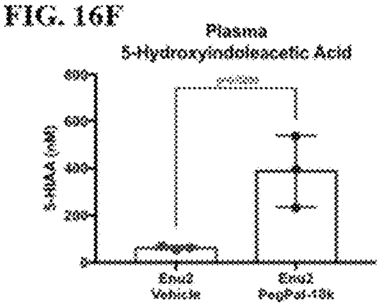

6.6 Example 6: An Effective Amount of PALYNZIQ® (Pegvaliase-Pqpz) Restores Neurotransmitter Levels Enu2 mice were treated with the PKU therapeutic, PALYNZIQ® (pegvaliase-pqpz), or with vehicle. After three days of PALYNZIQ® (pegvaliase-pqpz) dosing, the mice were euthanized and the blood and brain was collected and examined for the presence of selected neurotransmitters and neurotransmitter metabolites. As shown in FIGS. 14, 15, and 16, Enu2 mice treated with PALYNZIQ® (pegvaliase-pqpz) displayed increased levels of both plasma and brain neurotransmitters and neurotransmitter metabolites as compared to those treated with vehicle. Three days of PALYNZIQ® (pegvaliase-pqpz) treatment restored brain phenylalanine, tyrosine, and tryptophan levels to those seen in wild-type, and the plasma levels of phenylalanine, tyrosine, and tryptophan served as approximate surrogates of the corresponding brain levels (FIG. 14). Further, three days of PALYNZIQ® (pegvaliase-pqpz) were also able to normalize the brain levels of dopamine, norepinephrine, and serotonin (FIG. 15). The PALYNZIQ® (pegvaliase-pqpz) treatment also restored brain DOPAC, homovanillic acid, and 5-hydroxylindoleacetic acid to levels seen in normal mouse brain, and the plasma levels of all three metabolites served as surrogates for the levels seen in brain. These data further demonstrate the value of using plasma neurotransmitter and metabolite levels as surrogate markers for identifying an effective dose of a PKU therapeutic.

Various dose levels of PALYNZIQ® (pegvaliase-pqpz) (10-80 mg/kg) or vehicle (tris buffered saline/2 mM trans-cinnamate; 4 ml/kg)) were administered to male C57BL6-Pahenu2 mice (n=7) by subcutaneous (SQ) injection on Day 0. After warming the mouse briefly under a heating lamp to induce vasodilation, blood was sampled from each animal prior to and 24 hours post-administration by making a transverse nick in the skin of the tail, approximately 0.1 cm in length, using a sterile surgical blade. The ensuing blood was collected into a single lithium-heparinized capillary tube, which was immediately centrifuged to yield plasma. The plasma was decanted into clean, labeled tubes and stored at −80° C. Seventy-two hours post-PALYNZIQ® (pegvaliase-pqpz) administration, each animal was deeply anesthetized with isofluorane delivered via nose cone (4% for induction, 1.5% for maintenance). A terminal blood sample was collected via cardiac puncture and placed in a tube containing lithium heparin. The animals were then euthanized by exsanguination, performance of a thoracotomy prior to a whole body perfusion with PBS via the heart for ~10 minutes, followed by cervical dislocation. The brain of each mouse was then excised, halved sagittally, snap frozen, and stored in labeled tubes at −80° C. Blood samples were centrifuged to yield plasma, which was decanted into clean, labeled tubes and stored at −80° C.

Figure 17A:
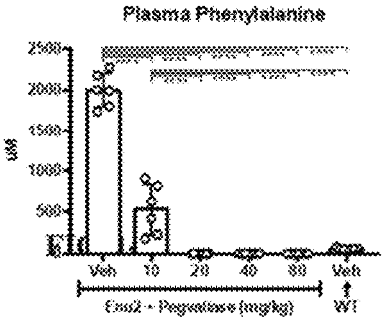
Figure 17B:
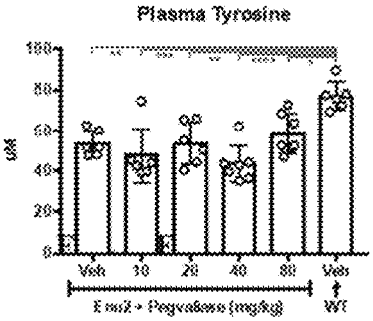
Figure 17C:
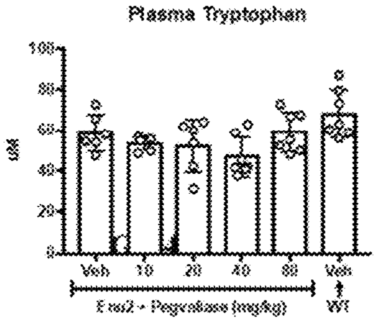

The assays described in Examples 12 and 13 were used to measure the levels of amino acids, neurotransmitters, and neurotransmitter metabolites. As shown in FIGS. 17-18, 72 hours after a single dose of PALYNZIQ® (pegvaliase-pqpz) of 40 mg/kg or 80 mg/kg, phenylalanine levels in both the brain and plasma and tryptophan levels in the brain were normalized to levels seen in wild type mice. FIG. 19 shows that a single dose of PALYNZIQ® (pegvaliase-pqpz) of 40 mg/kg or 80 mg/kg normalized levels of phenethylamine, dopamine, and serotonin and increased norepinephrine levels 72 hours after administration. Levels of phenethylamine and serotonin metabolites in plasma were also normalized to wild type levels as seen in FIG. 20. All levels of neurotransmitter metabolites in the brain increased relative to vehicle-treated Enu2 mice upon PALYNZIQ® (pegvaliase-pqpz) treatment (FIG. 21A-C).

6.7 Example 7: Marker Levels Correlate in ENU Mice

Figures 18A, 18B, 18C, 18D, 18E, 18F:
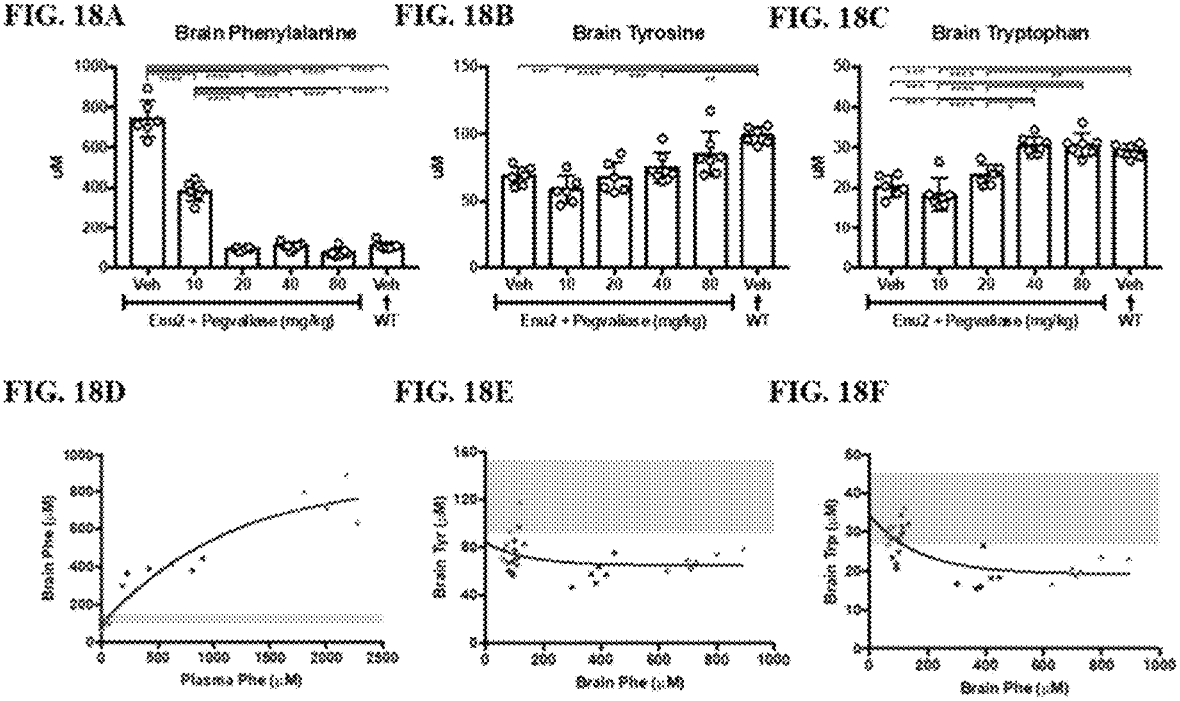

6.7.1 Amino Acid Levels in Brain Correlate with Plasma Phe Reduction in ENU Mice Amino acid levels were quantified in plasma and brain homogenates from $PAH^{Enu2}$ and $PAH^{WT}$ mice 72 hours after vehicle or PALYNZIQ® (pegvaliase-pqpz) treatment (FIGS. 17 and 18A). PALYNZIQ® (pegvaliase-pqpz) above 10 mg/kg reduced plasma Phe levels in $PAH^{Enu2}$ mice from 1999.0±85.0 μM (mean±SEM) to <1.0 μM ($PAH^{WT}$=60.4±4.4 μM) (FIG. 17, left). In contrast to plasma, brain Phe levels were normalized relative to $PAH^{WT}$ upon PALYNZIQ® (pegvaliase-pqpz) treatment and decreased from 743.7±37.4 to 107.7+6.6 μM ($PAH^{WT}$=108.8±6.7 μM) (FIG. 18A, left).

Although brain Phe levels did not reduce below $PAH^{WT}$ as observed in plasma Phe, a strong correlation was measured between the two compartments with an r value of 0.89 (95% confidence interval (CI) 0.81-0.94, p<0.0001) (FIG. 18B, left).

While plasma Tyr remained low in all $PAH^{Enu2}$ groups relative to $PAH^{WT}$ (FIG. 17, middle), brain Tyr in PALYNZIQ® (pegvaliase-pqpz) treated PAH' mice increased from 68.8±2.9 to 85.1±6.1 μM ($PAH^{WT}$=99.0±2.6 μM) (FIG. 18A, middle). Brain Tyr correlated with a reduction in brain Phe below 400 μM (FIG. 18B, middle).

Plasma Trp levels remained normal in all treatment groups (FIG. 17, right). Interestingly, brain Trp in $PAH^{Enu2}$ mice treated with PALYNZIQ® (pegvaliase-pqpz) normalized relative to $PAH^{WT}$, and increased from 20.4±1.1 μM to 30.5±0.8 μM ($PAH^{WT}$=29.2±0.7 μM) (FIG. 18A, right). Brain Trp levels were normalized when brain Phe dropped below 400 μM (FIG. 18B, right).

Figure 19A:
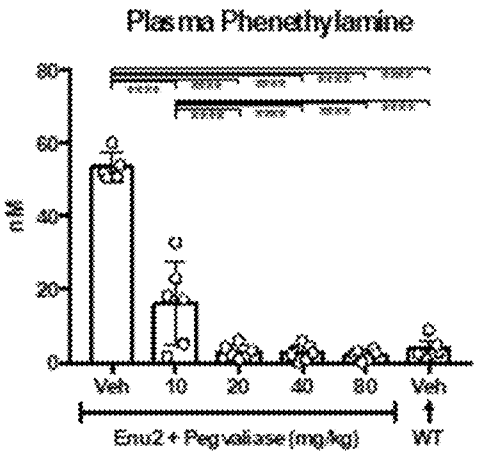

6.7.2 Neurotransmitter Levels Correlate with Amino Acid Correction in Mouse Brains All neurotransmitter levels were normalized relative to $PAH^{WT}$ upon PALYNZIQ® (pegvaliase-pqpz) treatment; plasma PEA decreased from 53.6±1.8 to 2.7±0.8 nM ($PAH^{WT}$=3.7±1.0 nM), brain dopamine increased from 1115±78.6 to 1506±96.5 nM ($PAH^{WT}$=1492±138.4 nM), brain norepinephrine increased from 1335±54.0 to 1855±78.0 nM ($PAH^{WT}$=2247±54.9 nM), and brain serotonin increased from 166±12.5 to 583.8±45.6 ($PAH^{WT}$=502±47.6 nM) (FIG. 19A).

Figure 19B:
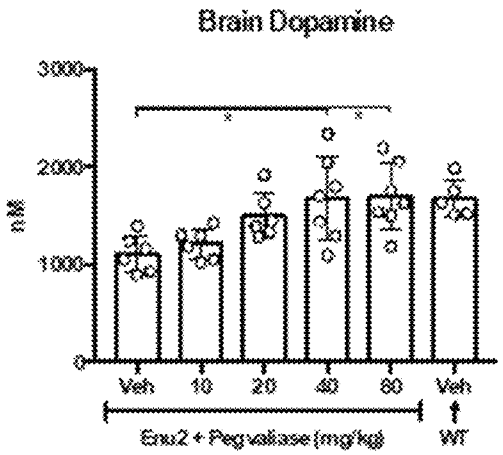
Figure 19C:
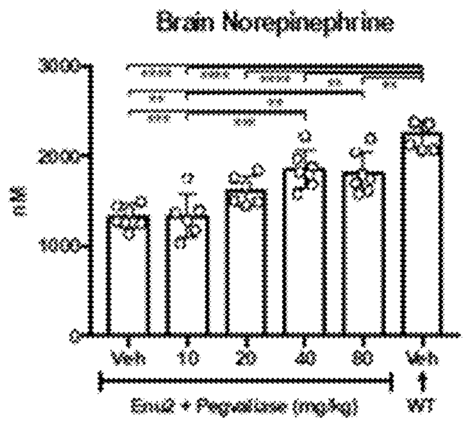
Figure 19D:
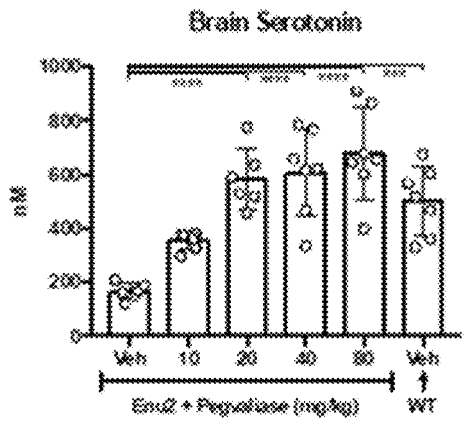
Figure 19E:
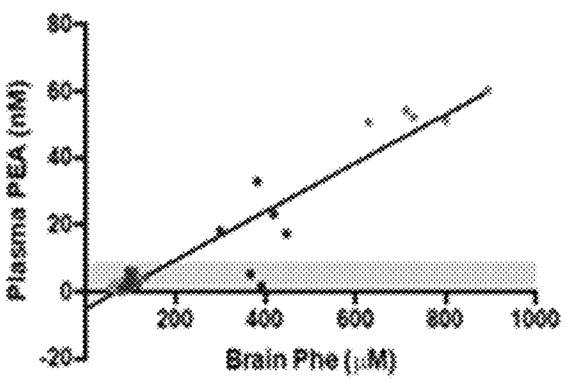
Figure 19F:
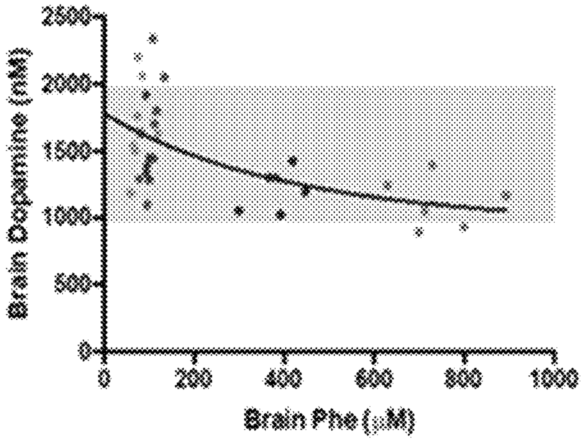
Figure 19G:
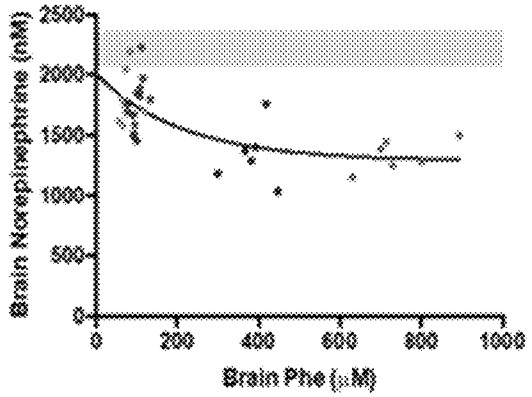
Figure 19H:
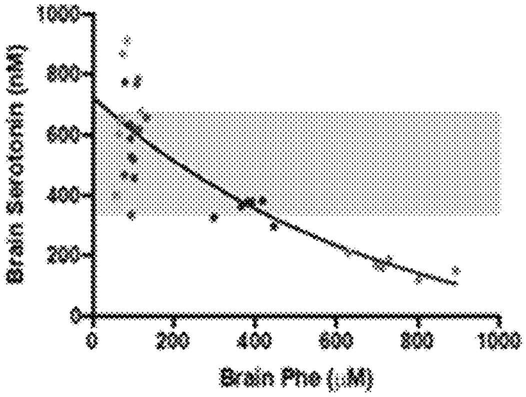

A strong positive correlation between plasma PEA and brain Phe was observed with an r value of 0.95 (95% CI 0.89-0.97, p<0.0001). Brain dopamine, norepinephrine, and serotonin correlated inversely with brain Phe, with r values of −0.61 (95% CI −0.79 to −0.34, p=0.0002), −0.63 (95% CI −0.80 to −0.35, p=0.0001), and −0.92 (95% CI −0.96 to −0.84, p<0.0001), respectively (FIG. 19B).

6.7.3 Neurotransmitter Metabolite Levels Correlate with Neurotransmitter Levels in Mice All neurotransmitter metabolite levels in brain increased relative to vehicle-treated $PAH^{Enu2}$ upon PALYNZIQ® (pegvaliase-pqpz) treatment; brain HVA increased from 869±41.01 to 1073±67.5 nM, brain MOPEG increased from 640.5±55.22 to 746±40.7 nM, and brain 5HIAA increased from 280.2±20.2 to 1318.0±37.4 nM (FIG. 21).

Figure 20A:
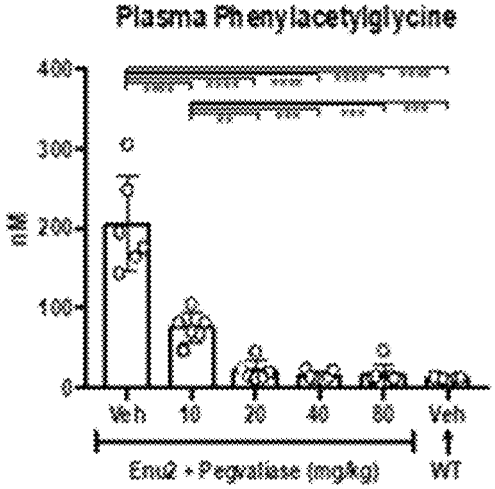
Figure 21A:
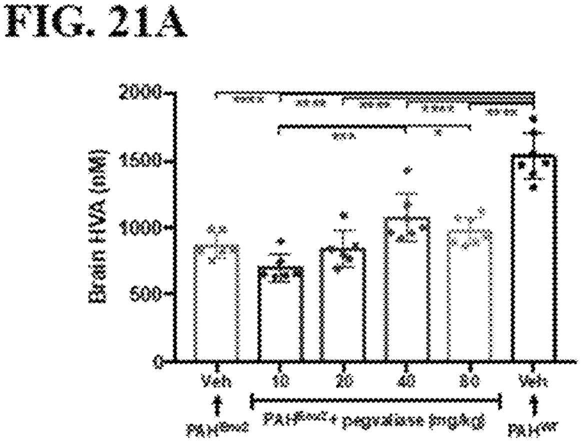
Figure 21B:
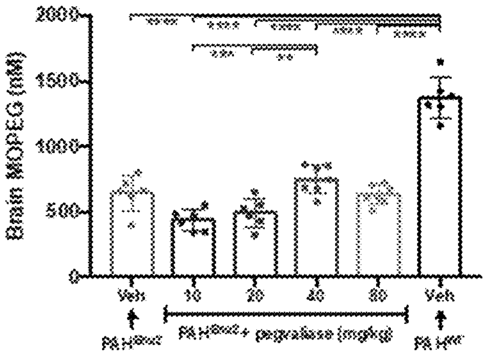
Figure 21C:
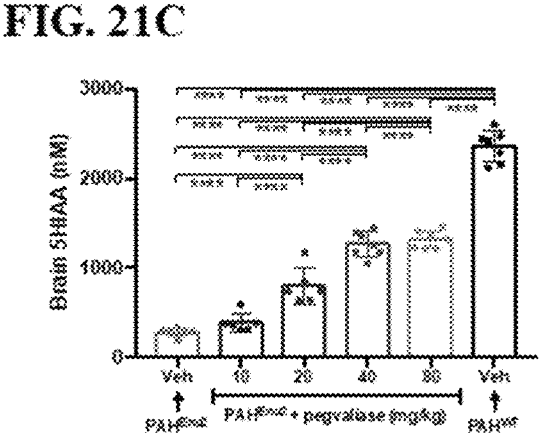

Plasma PAGly levels were normalized relative to $PAH^{WT}$ upon PALYNZIQ® (pegvaliase-pqpz) treatment and decreased from 205.7±24.8 nM to 14.69±2.2 nM ($PAH^{WT}$=11.9±0.7 nM) (FIG. 20A, left). Plasma HVA and MOPEG were similar to their corresponding brain levels; few $PAH^{Enu2}$ mice reached plasma $PAH^{WT}$ levels (FIG. 20A, middle). Plasma 5HIAA levels were similar to brain 5HIAA levels, until reaching a plateau at 400 nM in both high dose and $PAH^{WT}$ groups (FIG. 20A, right).

Figure 20B:
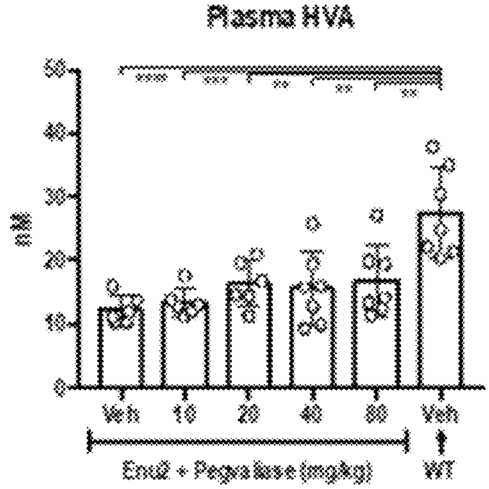
Figure 20C:
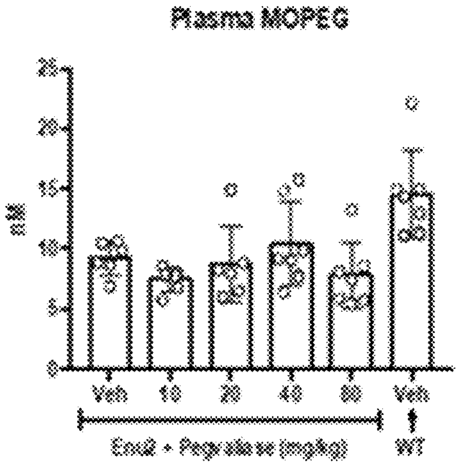
Figure 20D:
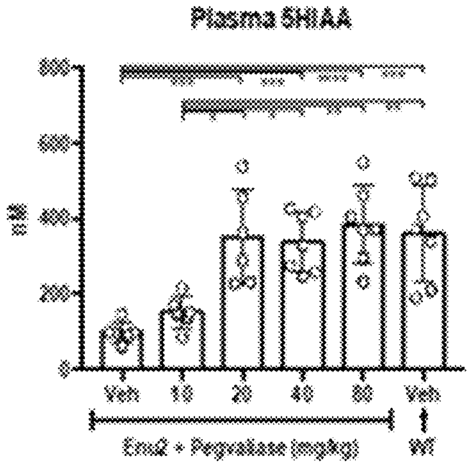
Figure 20E:
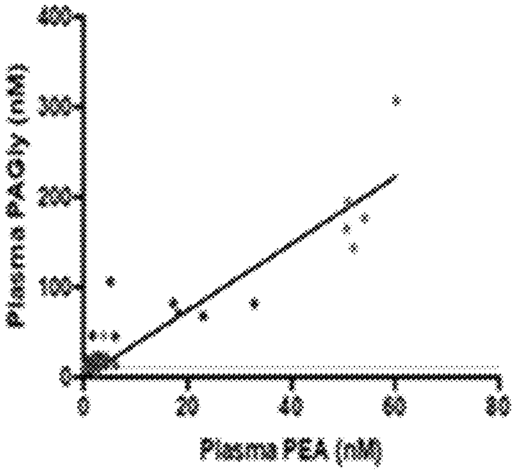
Figure 20F:
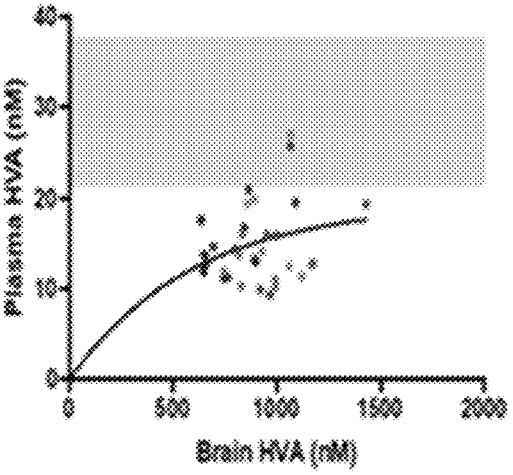
Figure 20G:
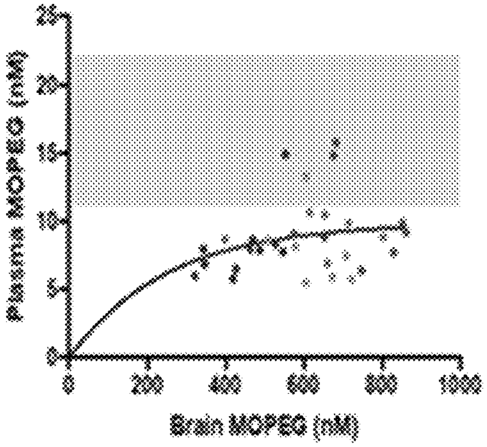
Figure 20H:
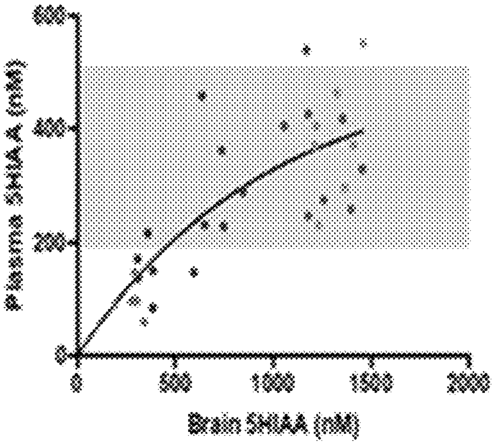

Plasma PAGly directly correlated with plasma PEA with an r value of 0.93 (95% CI 0.86-0.96, p<0.0001) suggesting a direct relationship to the metabolite (FIG. 20B, left). Plasma HVA, MOPEG, and 5HIAA correlated with the corresponding brain neurotransmitter metabolite levels with r values of 0.62 (95% CI 0.37-0.78, p<0.0001), 0.556 (95% CI 0.29-0.74, p=0.0003), and 0.66 (95% CI 0.40-0.79, p<0.0001), respectively (FIG. 20B, middle and right).

6.8 Example 8: Tyrosine Supplementation in Combination with Palynzio® (Pegvaliase-Popz) Treatment Increases Brain Norepinephrine Levels in $PAH^{ENU2}$ Mice In a separate study, male C57BL6-$PAH^{Enu2}$ mice were supplemented with tyrosine suspended in phosphate buffered saline (PBS), 60 mg/kg, three times per day via oral gavage, or vehicle control, beginning one day prior to SQ administration of PALYNZIQ® (pegvaliase-pqpz), 40 mg/kg, or vehicle, and continued daily for 4 days post-PALYNZIQ® (pegvaliase-pqpz) dose. Blood was sampled prior to Tyr dose initiation, and 24 and 96 hours post-PALYNZIQ® (pegvaliase-pqpz) administration. Brains were collected 96 hours post-PALYNZIQ® (pegvaliase-pqpz) dose and 1 hour after the final Tyr dose.

Sectioned brains were weighed and homogenized in PBS (4:1 (v/w) containing 1% NP-40, 0.5% sodium deoxycholate and 0.1% sodium dodecyl sulfate) using standard protocols on a FastPrep-24 5G instrument (MP Biomedicals 116005500). Supernatants were prepared by centrifuging brain homogenates at 21,000 g for 15 minutes at 4° C., then stored in aliquots at −80° C.

Figure 22A:
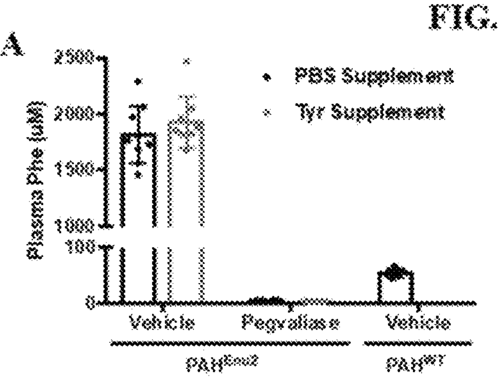
Figure 22B:
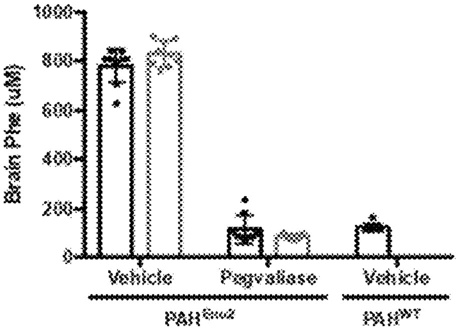
Figure 22C:
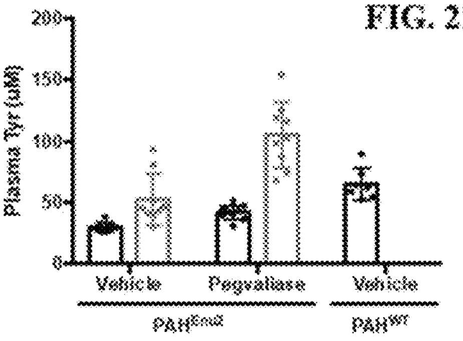
Figure 22D:
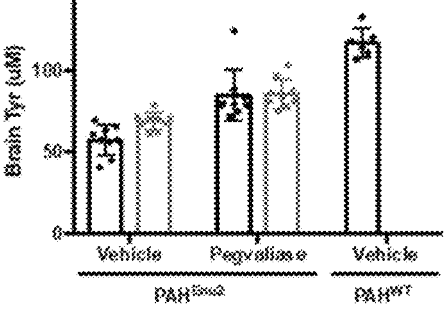
Figure 22E:
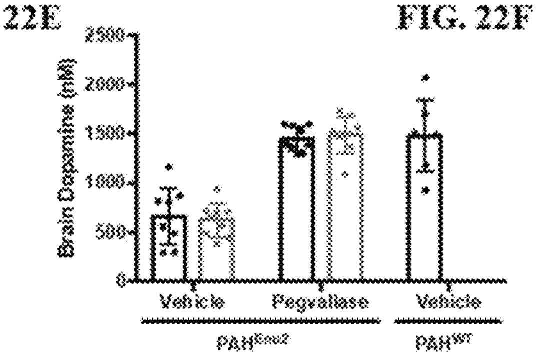
Figure 22F:
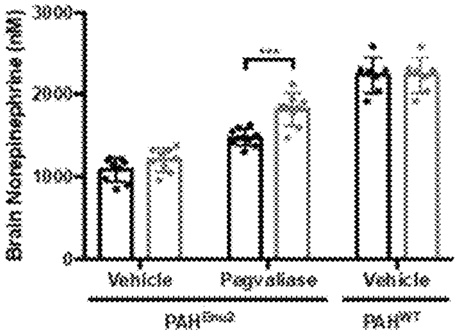

Tyrosine supplementation (180 mg/kg/day) increased plasma Tyr levels in vehicle and PALYNZIQ® (pegvaliase-pqpz)-treated $PAH^{Enu2}$ mice (FIG. 22C). Tyr supplementation slightly increased brain Tyr levels in vehicle-treated $PAH^{Enu2}$ mice but had no effect in PALYNZIQ® (pegvaliase-pqpz)-treated $PAH^{Enu2}$ mice (FIG. 22D). Brain dopamine reached $PAH^{WT}$ levels in PALYNZIQ® (pegvaliase-pqpz)-treated $PAH^{Enu2}$ mice regardless of Tyr supplementation (FIG. 22E). Most strikingly, Tyr supplementation in PALYNZIQ® (pegvaliase-pqpz)-treated $PAH^{Enu2}$ mice increased brain norepinephrine over PBS supplementation (p=0.0002) from 1481±34.8 to 1818±62.7 nM (FIG. 22F).

6.9 Example 9: Neurotransmitter Metabolites Levels Increased in Subjects with PKU with Reduced Plasma Phe The data in $PAH^{Enu2}$ mice with PALYNZIQ® (pegvaliase-pqpz) treatment suggests lowering plasma Phe restores neurotransmitters to $PAH^{WT}$ levels in brain, with plasma neurotransmitter metabolites showing similar trends. To determine whether these findings could translate to human subjects with PKU, neurotransmitter metabolite levels were evaluated in plasma samples from a subset of subjects in phase 3 clinical trials of PALYNZIQ® (pegvaliase-pqpz) with pre-treatment blood Phe levels >900 μM. Plasma samples from 23 subjects that had participated in the phase 3 PALYNZIQ® (pegvaliase-pqpz) clinical trials (PRISM-1 NCT01819727 or PRISM-2, NCT01889862) were evaluated. All subjects provided informed written consent. Adult control plasma samples were obtained from Discovery Life Sciences (Los Osos, Calif.) and were not statistically different for age and sex. BMI was not available for controls. The control samples were de-identified remnant samples leftover from a diagnostic procedure not related to PKU. Methods for plasma Phe and ADHD-RS IV assessments in the PALYNZIQ® (pegvaliase-pqpz) clinical trials have been previously described (Thomas et al).

Subjects were divided into two cohorts, those that had plasma Phe levels of >900 μM or those that had plasma Phe levels of <360 μM after 12 months of treatment. A plasma Phe of <360 μM is the upper limit of the target Phe range recommended in the ACMG PKU treatment guideline (Vockley et al., 2014), while a plasma Phe of >900 μM is a Phe level substantially above both the ACMG and EU PKU treatment guidelines (Vockley et al., 2014; van Spronsen et al 2018). Baseline characteristics were matched for the 2 cohorts based on age, sex, ADHD-RS IV and plasma Phe and described in Table 1 below:

TABLE 1

Baseline subject characteristics:

| | Group 1 (Phe < 360 μM) | Group 2 (Phe > 900 μM) | Control | P value (two tailed t-test) |
|---|---|---|---|---|
| Age, years (SD) | 29.7 (10.1) | 32.7 (10.2) | 39.0 (12.2) | 0.5 |
| Phe, μM (SD) | 1524.2 (285.6) | 1380.9 (403.6) | 49.5 (8.0) | 0.3 |
| BMI, $kg/m^2$ (SD) | 30.6 (6.9) | 30.8 (9.1) | NA | 0.9 |
| Sex | 46% female | 46% female | 30% female | |

The plasma Phe levels of patients treated with PALYNZIQ® (pegvaliase-pqpz) were compared to samples from a control group without PKU. The assays described in Examples 10 and 11 were used to evaluate the levels of neurotransmitter metabolite levels in all plasma samples at 0, 6, and 12 months of treatment.

Figure 23A:
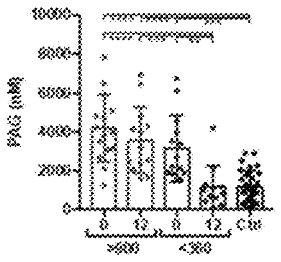
Figure 23B:
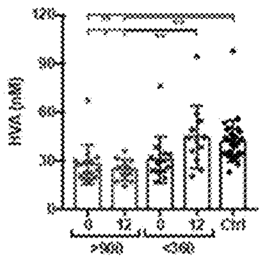
Figure 23C:
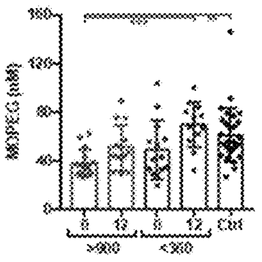
Figure 23D:
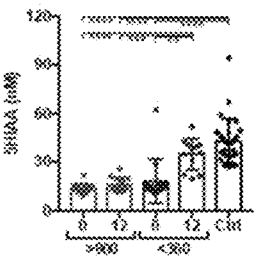

After 12 months of PALYNZIQ® (pegvaliase-pqpz) treatment, plasma phenylacetylglutamine (PAG) in the >900 μM Phe group remained unchanged from 4177±446.3 to 3565±481.9 nM; PAG levels in the <360 μM Phe group normalized relative to controls and decreased from 3133±452.2 to 1133±317.3 nM (control=1167±150.0 nM) (FIG. 23A). Plasma HVA remained unchanged (27.6±3.2 to 24.35±1.72 nM) and below controls (42.1±2.45 nM) in the >900 μM group; plasma HVA normalized relative to controls in the <360 μM group, increasing from 30.6±3.9 to 44.8±5.6 nM (FIG. 23B). Plasma MOPEG increased from 38.2±2.9 to 50.9±5.3 nM in the >900 μM group; plasma MOPEG normalized relative to controls in the <360 μM group, increasing from 49±6.4 to 70±5.4 nM (control=61.0±4.1 nM) (FIG. 23C). Finally, plasma 5HIAA remained unchanged (13.4±0.8 to 15.9±1.22 nM) and below controls (43.1±2.5 nM) in the >900 μM group; while plasma 5HIAA approached control levels in the <360 μM group, increasing from 18.1±3.6 to 34.9±2.8 nM (p=0.0017) (FIG. 23D).

Figure 23E:
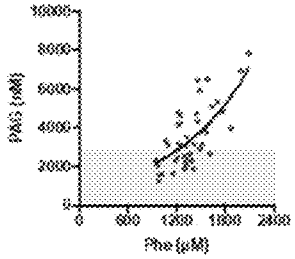
Figure 23F:
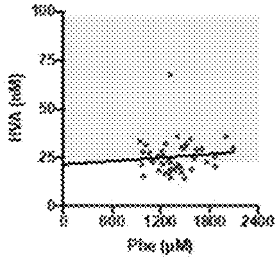
Figure 23G:
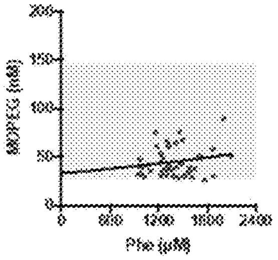
Figure 23H:
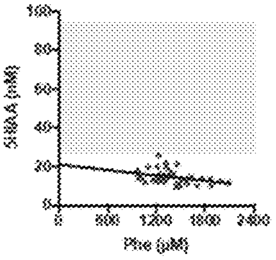
Figure 23I:
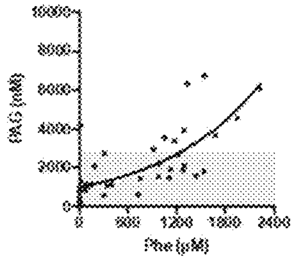
Figure 23J:
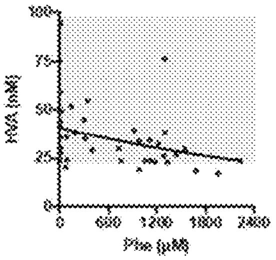
Figure 23K:
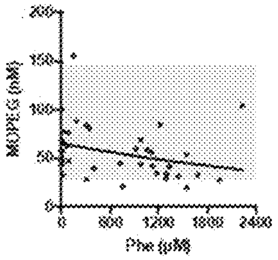
Figure 23L:
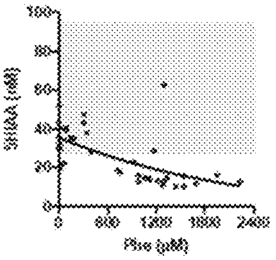
Figure 23M:
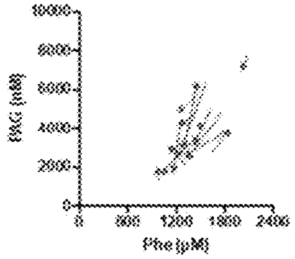
Figure 23N:
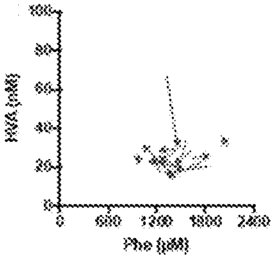
Figure 23O:
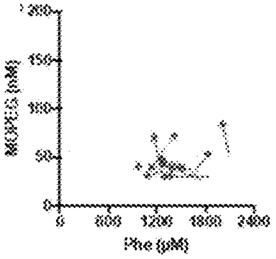
Figure 23P:
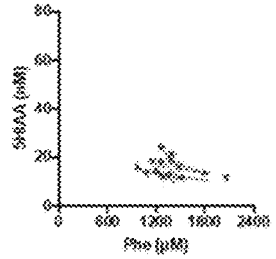

6.10 Example 10: Neurotransmitter Levels Correlate with Plasma Phe Levels in Subjects with PKU Plasma PAG correlated with plasma Phe in the >900 μM (r=0.68; 95% CI 0.48-0.72; p<0.0001) and <360 μM groups (r=0.72; 95% CI 0.52-0.84; p<0.0001; FIG. 23E), suggesting that a reduction of plasma Phe at all concentrations led to a reduction of brain Phe and subsequently PAG. Similar to $PAH^{Enu2}$ mice, subjects with plasma Phe levels <30 uM maintained PAG levels in the same range as controls.

Plasma HVA and MOPEG only correlated with plasma Phe in the <360 μM group (HVA: r=−0.42; 95% CI −0.64-−0.12; p=0.0075; MOPEG: r=−0.35; 95% CI −0.60-−0.049; p=0.0246) suggesting lower plasma Phe levels are needed for an appreciable impact on dopamine and norepinephrine metabolite levels. Plasma 5-HIAA correlated with plasma Phe reduction in both the >900 μM (r=−0.38; 95% CI −0.61 to −0.088; p=0.0126) and <360 μM (r=−0.72; 95% CI −0.84 to −0.53; p<0.0001) groups (FIG. 23E-L). Plasma 5-HIAA more strongly correlated with plasma Phe in the <360 μM group, where 5-HIAA levels reached the range of control samples.

Figure 23Q:
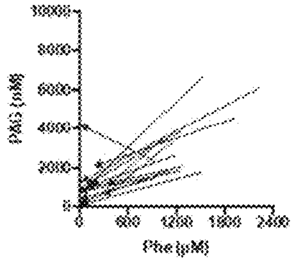
Figure 23R:
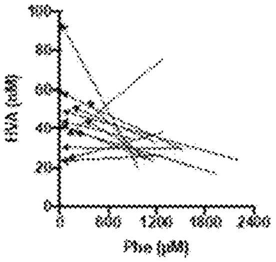
Figure 23S:
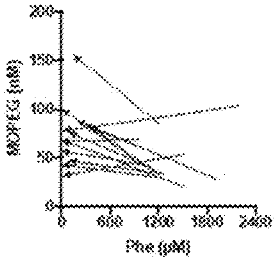
Figure 23T:
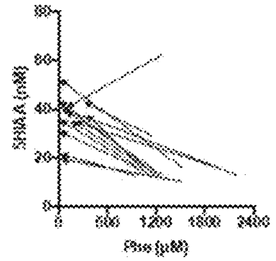

Subject-level trajectories of each neurotransmitter metabolite and Phe were analyzed for the baseline to 12 month samples assayed. In the >900 μM group, the subject-level trajectories for PAG and 5-HIAA with Phe were modest in magnitude and were observed in a minority of subjects, and no consistent trends in trajectory were observed for HVA or MOPEG in this group (FIGS. 23M-P). The strongest and most consistent changes in neurotransmitter metabolite levels relative to Phe changes were observed in the <360 μM group. More strikingly, in the <360 μM group, individual subject's trajectory trends were greater in magnitude and all but one subject experienced a reduction in PAG with a reduction in plasma Phe (FIG. 23Q). For HVA, a positive trend in trajectories was observed; all but three subjects experienced an increase in HVA with a reduction of Phe (FIG. 23R). Similarly, for MOPEG, all but three subjects experienced an increase in MOPEG with a reduction in plasma Phe (FIG. 23S). For 5HIAA, all but one subject experienced an increase in 5HIAA with a reduction in plasma Phe after 12 months (FIG. 23T).

In some embodiments a combination of two or more amino acids, neurotransmitters, and neurotransmitter metabolites from a subject can be measured for the diagnosis and/or management of PKU. As a non-limiting example, Phe and PAG can be measured for the diagnosis and/or management of PKU.

6.11 Example 11: Inattention Score Improvements Correlate with Plasma MOPEG Levels in Subjects with PKU The inattention subscale domain of the Attention Deficit Hyperactivity Disorder Rating Scale IV (ADHD RS-IV IA) was used to evaluate neuropsychological symptoms of inattention in clinical studies of subjects with PKU treated with PALYNZIQ® (pegvaliase-pqpz). An improvement in mean inattention subscale scores was associated with reductions in mean plasma Phe in subjects continuing long-term PALYNZIQ® (pegvaliase-pqpz) treatment. The association was particularly evident in subjects reporting inattention symptoms at baseline, indicated by an ADHD RS-IV IA score ≥9 (Thomas et al 2018).

Figure 24A:
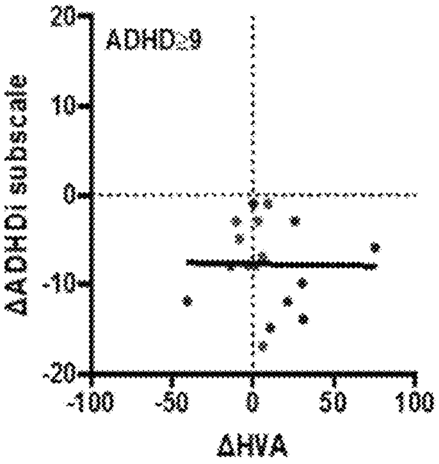
Figure 24B:
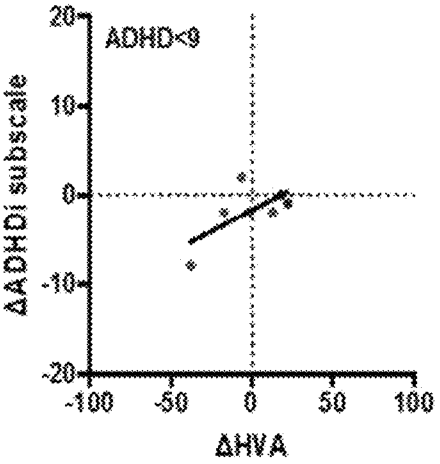
Figure 24C:
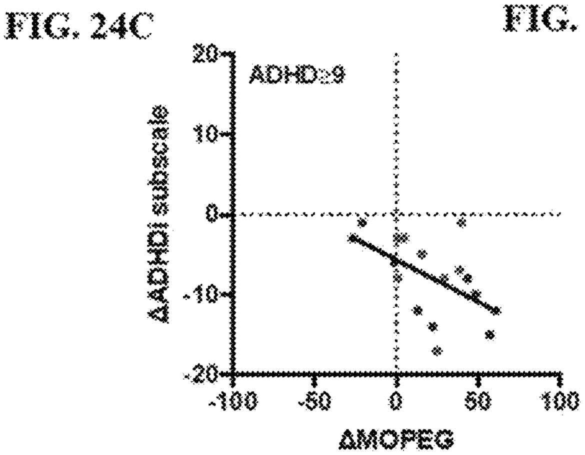
Figure 24D:
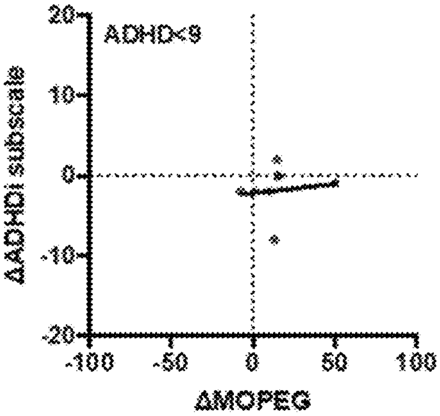
Figure 25:
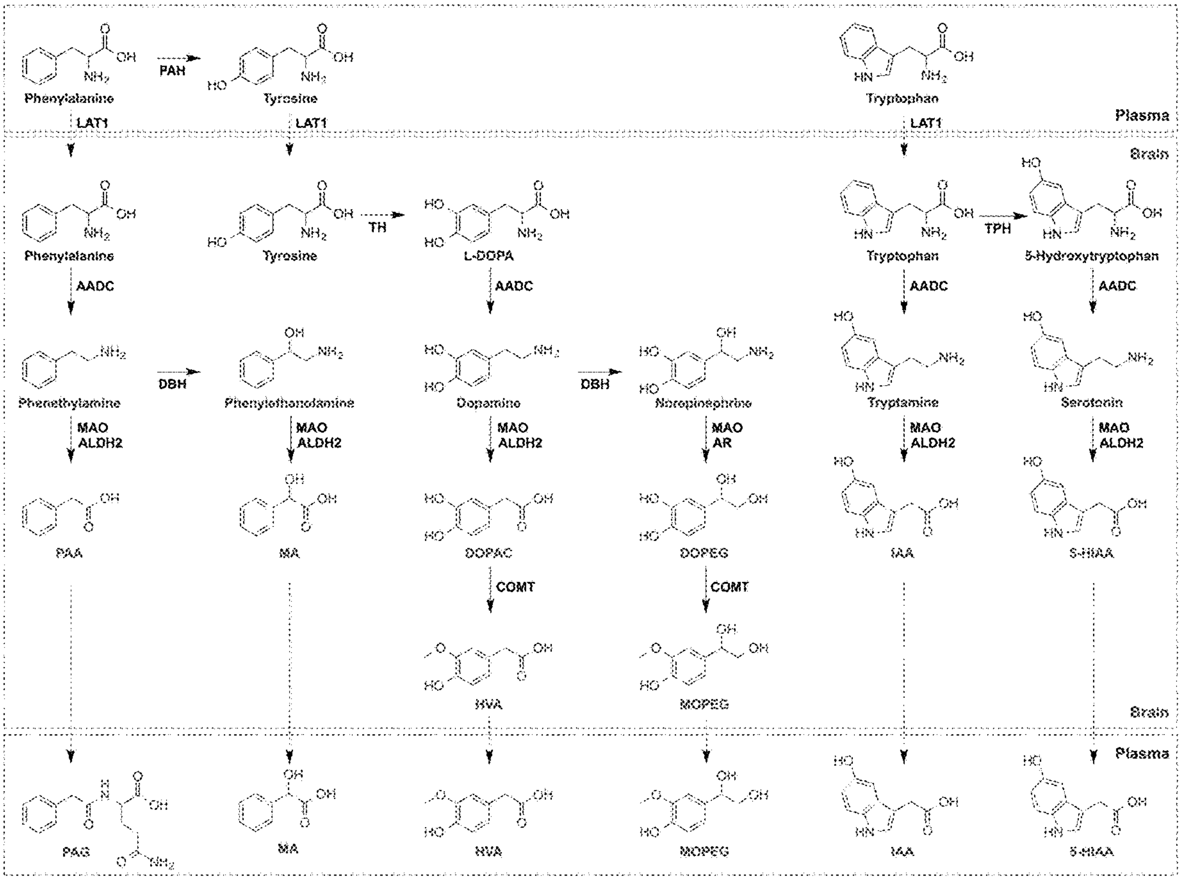

Reductions in norepinephrine and dopamine levels have been associated with ADHD symptoms, and there is an indication that reduction in norepinephrine is strongly associated with symptoms of inattention. Therefore, the assays described in Examples 10 and 11 were used to explore the associations between changes in ADHD RS-IV IA scores and the dopamine and norepinephrine neurotransmitter metabolites, HVA and MOPEG respectively (FIG. 24). No correlation was found between a change in HVA and ADHD RS-IV IA, in subjects with baseline ADHD RS-IV IA scores ≥9 or <9 (FIG. 24A-B). A correlation was found between a change in MOPEG and change in ADHD RS-IV IA in subjects with a baseline ADHD RS-IV IA score (r=−0.5434, p=0.0242). As MOPEG levels increased (for both the >900 μM and <360 μM groups) change in ADHD RS-IV IA scores was negative, indicating improvement in scores. No correlation between HVA or MOPEG and change in ADHD RS-IV IA score was found in subjects with baseline ADHD RS-IV IA score <9 (FIG. 24C-D).

In some embodiments, a combination of two or more amino acids, neurotransmitters, and neurotransmitter metabolites from a subject can be measured for the diagnosis and/or management of ADHD. As a non-limiting example, dopamine/HVA, norepinephrine/MOPEG, and/or serotonin/5HIAA can be measured for the diagnosis and/or management of ADHD.

6.12 Example 12: Derivatization of Plasma or Brain Homogenates

In a 96-well plate, 20 μL of brain homogenate or plasma was precipitated with 80 μL of ice-cold acetonitrile containing internal standards. After centrifugation, 20 μL of supernatant was derivatized in a new plate with 10 μL of 100 mM sodium carbonate and 10 μL BzCl (6% (v/v) in acetonitrile). Reactions were quenched with 60 μL formic acid (0.16% (v/v) in water).

6.13 Example 13: Neurotransmitter Analysis by LC/MS

Samples derivatized as described in Example 12 were analyzed by LC/MS on an Acquity UPLC (Waters H-Class) coupled to a Sciex 6500 Q-Trap mass spectrometer using positive, scheduled MRM mode. 10 μL were injected on an Acquity HSS C18 column (2.1 mm×150 mm, 1.8 μM, 100 A pore size Waters 186003534) and eluted using a gradient of 10 mM ammonium formate with 0.15% formic acid (MPA) and acetonitrile (MPB) at a flow rate of 0.5 mL/min over 8 minutes.

Settings for each analyte are found in Table 2. Peak integration was performed using MultiQuant software. Quadrupole mass analyzer 1 (Q1) and Q3 mass filters, time of elution, declustering potential (DP), entrance potential (EP), collision energy (CE), and collision cell exit potential (CXP) were optimized for each analyte. 5HIAA, 5-hydroxyindole acetic acid; DOPEG, 3,4-dihydroxy-phenylethyleneglycol; HVA, homovanillic acid; MOPEG, 3-methoxy-4-hydroxyphenylglycol; PAGlu, phenylacetylglutamate; PAGly, phenylacetylglycine; PEA-IS, phenylethylamine isotope; PHE, phenylalanine; SRO, serotonin; TYR-IS, tyrosine hydroxylase; TRP-IS, tryptophan hydroxylase.

TABLE 2

| LC/MS settings for each analyte. | | | | | | | |
|---|---|---|---|---|---|---|---|
| Q1 (Da) | Q3 (Da) | Time (min) ID | DP (V) | EP (V) | CE (V) | CXP (V) |
| 269.982 | 104.9 | 4.81 PHE | 55 | 10 | 21 | 18 |
| 390.004 | 240.1 | 6.41 TYR | 45 | 10 | 21 | 12 |
| 309.036 | 105 | 4.72 TRP | 45 | 10 | 29 | 12 |
| 225.752 | 105 | 5.79 PEA | 40 | 10 | 21 | 12 |
| 466.014 | 105.2 | 7.59 DPA | 50 | 10 | 23 | 12 |
| 482.022 | 105 | 7.32 NEP | 50 | 10 | 25 | 12 |
| 385.031 | 264.1 | 7.02 SRO | 40 | 10 | 25 | 14 |
| 265 | 129 | 2.02 PAGlu | 130 | 10 | 47 | 14 |
| 194.01 | 119.1 | 2.45 PAGly | 40 | 10 | 13 | 12 |
| 304.07 | 105.1 | 5.95 HVA | 40 | 10 | 19 | 12 |
| 306 | 105.1 | 5.06 MOPEG | 16 | 10 | 21 | 16 |
| 313.015 | 250 | 5.63 5HIA | 30 | 10 | 21 | 28 |
| 280.017 | 104.9 | 4.81 PHE-IS | 55 | 10 | 21 | 18 |
| 400.034 | 249.1 | 6.41 TYR-IS | 45 | 10 | 21 | 12 |
| 314.028 | 105.1 | 4.69 TRP-IS | 45 | 10 | 29 | 12 |
| 229.752 | 105.1 | 5.79 PEA-IS | 40 | 10 | 21 | 12 |
| 470.014 | 105.2 | 7.59 DPA-IS | 50 | 10 | 23 | 12 |
| 488.051 | 105.1 | 7.3 NEP-IS | 50 | 10 | 25 | 12 |
| 389.031 | 268.1 | 7.01 SRO-IS | 40 | 10 | 25 | 14 |
| 312.07 | 105.1 | 5.95 HVA-IS | 40 | 10 | 19 | 12 |
| 319.037 | 256 | 5.63 5HIA-IS | 30 | 10 | 21 | 28 |

The assays described in Examples 12 and 13 were used to measure the levels of amino acids, neurotransmitters, and neurotransmitter metabolites in biological samples described in Examples 6 to 11.

6.14 Example 14: Evaluation of a PAH Expression Cassette Introduced into rAAV Vector

6.14.1 Generation of Vectors Expressing Wild-Type Human or Mouse PAH

Figure 26:
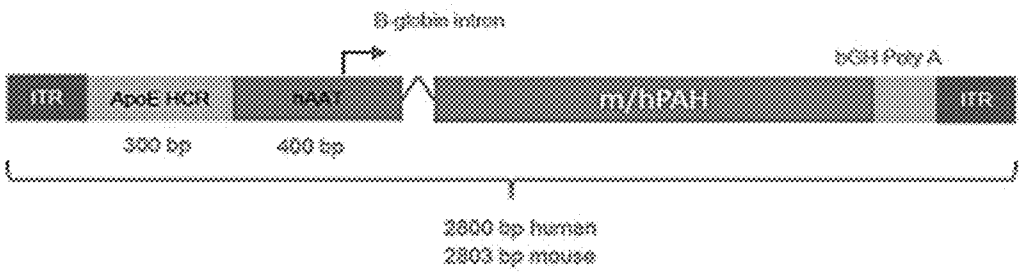

Initial studies were carried out with a recombinant AAV gene therapy vector comprising a wild type PAH cDNA (Vector 1; ApoE-HCR-hAAT.GI.hPAH.bGH; SEQ ID NO:15). Either the mouse (muPAH) or human PAH (hPAH) sequence was inserted into the vector. The vector genome was flanked by AAV serotype 2 (AAV2) derived inverted terminal repeats (ITRs) and the expression of PAH was driven by a hybrid human apolipoprotein E (ApoE)/HCR enhancer/human alpha anti-trypsin (AAT) promoter. The vector genome also included a beta-globin intron sequence (GI) and a bovine growth hormone polyadenylation signal (bGH). (FIG. 26). The vector genome sequence with the human PAH cDNA 2800 bp in length as shown in SEQ ID NO: 15. The vector was prepared using conventional cloning techniques as described e.g., by Gibson et al. (2009). "Enzymatic assembly of DNA molecules up to several hundred kilobases". Nature Methods. 6 (5): 343-345, and Gibson D G. (2011). "Enzymatic assembly of overlapping DNA fragments". Methods in Enzymology. 498: 349-361, which are incorporated herein by reference.

6.14.2 Assays to Test the Expression and Activity of AAV-PAH Vectors

Assays to test the recombinant AAV PAH vectors provided herein include, for example, (1) transient transfection of double-stranded DNA plasmids comprising the AAV vector nucleic acids in HepG2 cells, a cell line derived from human liver to check liver-specific mRNA expression and splicing, and PAH protein production and secretion in vitro; (2) production of AAV virions comprising the AAV PAH vectors in 293 cells and baculovirus-infected insect cells; (3) evaluation of the AAV vector nucleic acids by alkaline gel analysis and replication assays; and (4) evaluation of PAH expression, PAH activity, and Phe levels in ENU2 mice.

6.14.3 Transient Transfection Assays

A preliminary in vitro assay was performed to compare the PAH expression and activity from the AAV PAH vectors of the present embodiment. In one embodiment, plasmids of the AAV PAH vectors are transiently transfected into the human liver cell line, HepG2. After transfection, for example, 24 or 48 or 72 hours later, intracellular PAH expression is measured. Using this assay, the ApoE-HCR-hAAT.GI.hPAH.bGH vector was demonstrated to be capable of expressing PAH protein in transiently transfected HepG2 cells (see e.g.; FIG. 47), with quantitation provided in FIG. 51 (vector identified as WT-hPAH)).

6.14.4 Production of AAV PAH Virions in 293 Cells and Baculovirus-Infected Insect Cells To demonstrate that the recombinant AAV PAH vectors of the present embodiment indeed package the nucleic acids encoding PAH, the double-stranded forms of the AAV PAH vectors generated as described above (e.g. SEQ ID NO:15-23) are introduced into cells capable of producing AAV virions. In a first AAV virus production system, plasmids comprising the AAV PAH vector nucleic acids in double-stranded form are co-transfected into 293 cells together with a plasmid that expresses the AAV Cap and Rep proteins and a plasmid that expresses adenovirus helper functions needed to for AAV virion production. In a second AAV virus production system, baculovirus constructs are generated expressing the AAV PAH vector nucleic acids and the AAV Cap and Rep proteins, and then are co-infected into insect Sf9 cells. The resultant AAV virions produced in the transiently transfected 293 cells or baculovirus-infected Sf9 cells are purified and analyzed by standard methods known in the art.

6.14.5 Evaluation by Alkaline Gel and Replication Assay

An alkaline gel electrophoresis assay is used to determine the size of the packaged nucleic acid. A replication center assay is used to determine which AAV PAH vectors are packaged in an intact form by both packaging methods. A primer extension assay is used to quantify the amount of AAV PAH vector nucleic acids that have complete ends, i.e., terminate at the 5' end of the hairpin loop in the AAV2 5' ITR (sense strand) or 3' ITR (anti-sense strand). Alternatively, a PCR assay is used to determine whether the AAV PAH vectors nucleic acids have complete ends, i.e., terminate at the 5' end of the hairpin loop in the AAV2 5' ITR (sense strand) or 3' ITR (anti-sense strand).

Figure 27A:
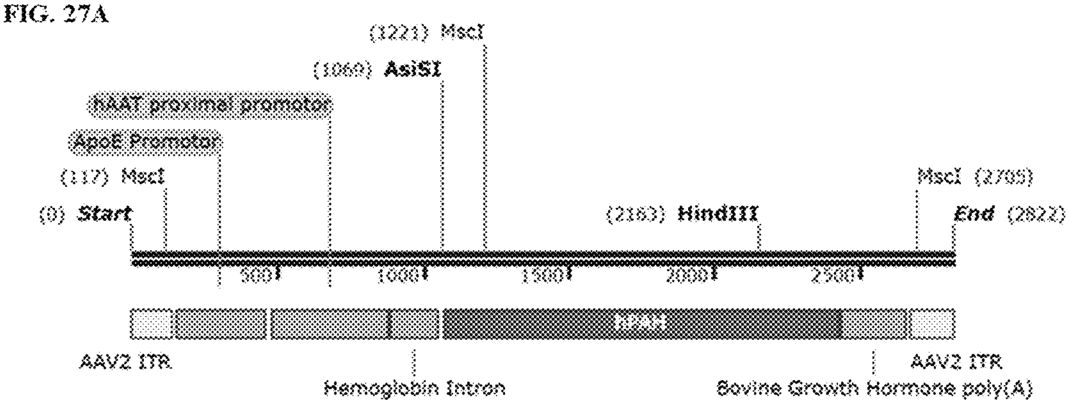
Figure 27B:
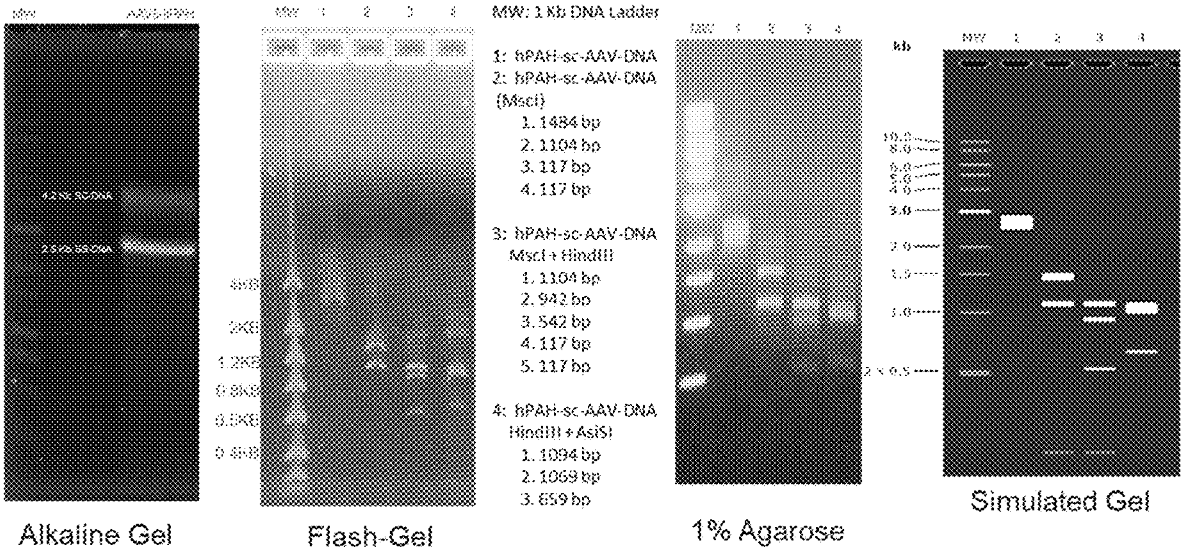
Figure 28A:
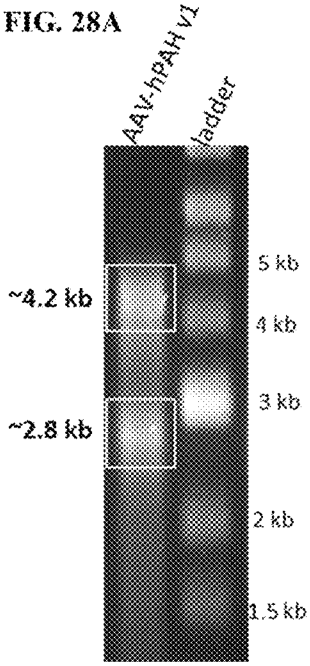
Figure 28B:
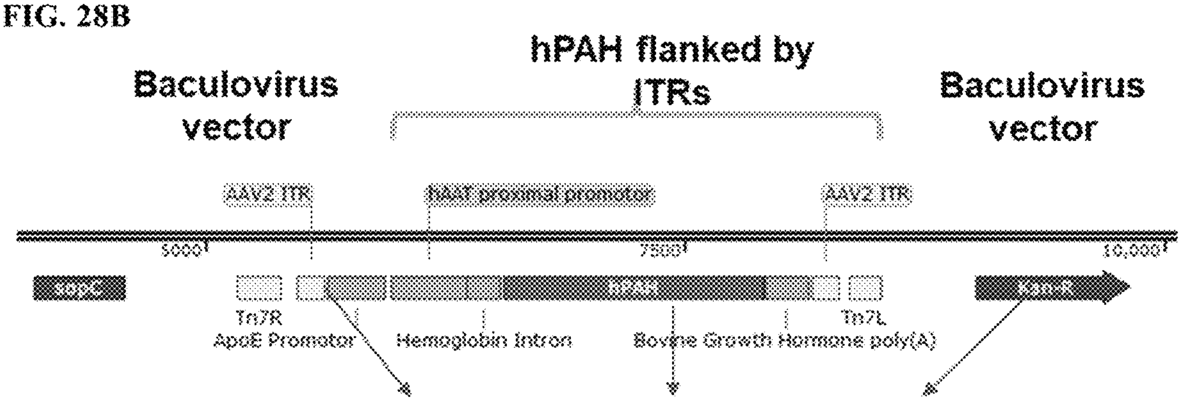

As shown in FIGS. 27 and 28, multiple bands were observed when this characterization was performed on the initial AAV-PAH vector (ApoE-HCR-hAAT.GI.hPAH.bGH) via alkaline gel electrophoresis. The ApoE-HCR-hAAT.GI.hPAH.bGH vector is identified as either hPAH-sc-AAV-DNA (FIG. 27) or AAV-hPAHv1 (FIG. 28). Primer extension and PCR assays were conducted to confirm that the two populations were self-complementary and single stranded. Baculovirus regions adjacent to hPAH were found to be ~100-300× lower than hPAH VG titer. Thus, the additional sequences in ~4.2 kb band are not derived from nearby baculovirus DNA.

6.14.6 Effect of AAV-PAH in PKU Affected Mice

The C57BL6-ENU2 or BTBR$^{emu2}$ mouse is homozygous mutant at the phenylalanine hydroxylase gene (PAH) locus resulting in an animal with severe hyperphenylalanemia. The high plasma phenylalanine (Phe) levels make this animal the appropriate model for evaluating the ability of AAV-PAH to reduce plasma Phe, as well as other parameters such as plasma Tyr, growth rate, brain amino acids and neurotransmitters, and safety biomarkers such as plasma ALT and liver histopathologies.

Various dose levels of vector (2e12-6e14 vg/kg) or vehicle (phosphate buffered saline; 4 ml/kg) were administered to male or female C57BL6-Pahenu2 mice or C57B16 control mice (n=7-10/group) by intravenous injection via the tail vein on Day 0. The weight of each mouse was measured and recorded prior to and every two weeks post-dose administration. At the same timepoints, blood was sampled from each animal. At the terminal timepoint (5 or 12 weeks post-dose), blood and tissue samples were collected.

6.14.7 Plasma Phe and Tyr Levels

Figure 29A:
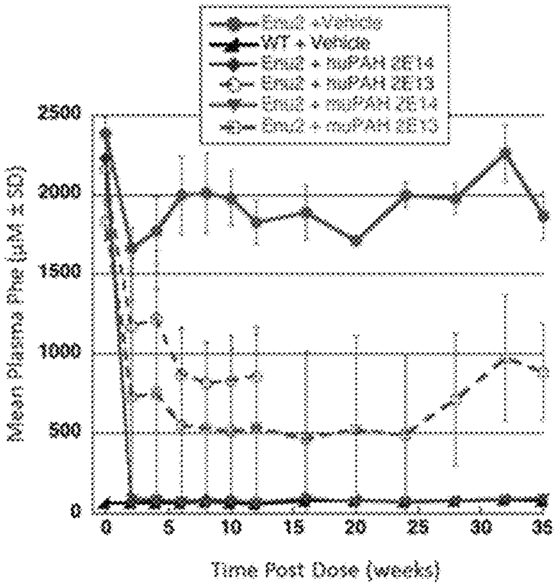

Enu2 mice were treated with two doses (2E13 vg/kg and 2E14 vg/kg) of an adeno associated virus vector (AAV) expressing either mouse (muPAH) or human PAH (hPAH). The AAV-PAH is constructed with the ITRs of the AAV2 serotype and the capsid genes of the AAV5 serotype as described above for the ApoE-HCR-hAAT.GI.mu/hPAH.bGH vector. Enu2 and wild-type mice were also treated with vehicle as controls. At various timepoints after virus administration, the plasma levels of Phenylalanine (Phe) and Tyrosine (Tyr) were measured in blood samples collected from each group of animals using an LC-MS/MS method with QTRAP 4500 Mass spectrometer. As shown in FIG. 29A, vehicle-treated Enu2 mice had increased levels of phenylalanine relative to the levels measured in vehicle treated wild-type mice.

Figure 29B:
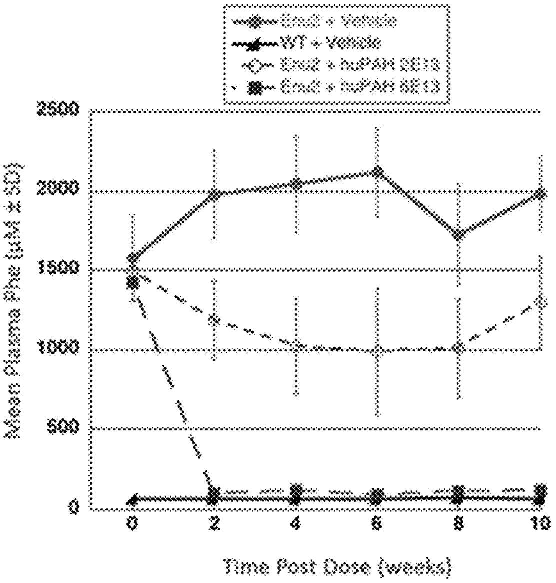

Administration of the higher dose of AAV-PAH (2E14 vg/kg) to Enu2 mice, but not the lower dose (2E13 vg/kg), restored the levels of phenylalanine to levels seen in the vehicle-treated wild-type control. These data demonstrate that the plasma Phe levels can be used to determine the effective dose of a PKU therapeutic needed to restore the neurotransmitter metabolic pathways to those seen in wild-type controls. Additional dose level studies indicated that AAV5-PAH≥6e13 vg/kg also led to near normalization of plasma Phe levels (FIG. 29B). As such, 2e13 vg/kg and 6e13 vg/kg set up as benchmarks for improving potency by vector design.

6.14.8 Growth Rate

Figure 30:
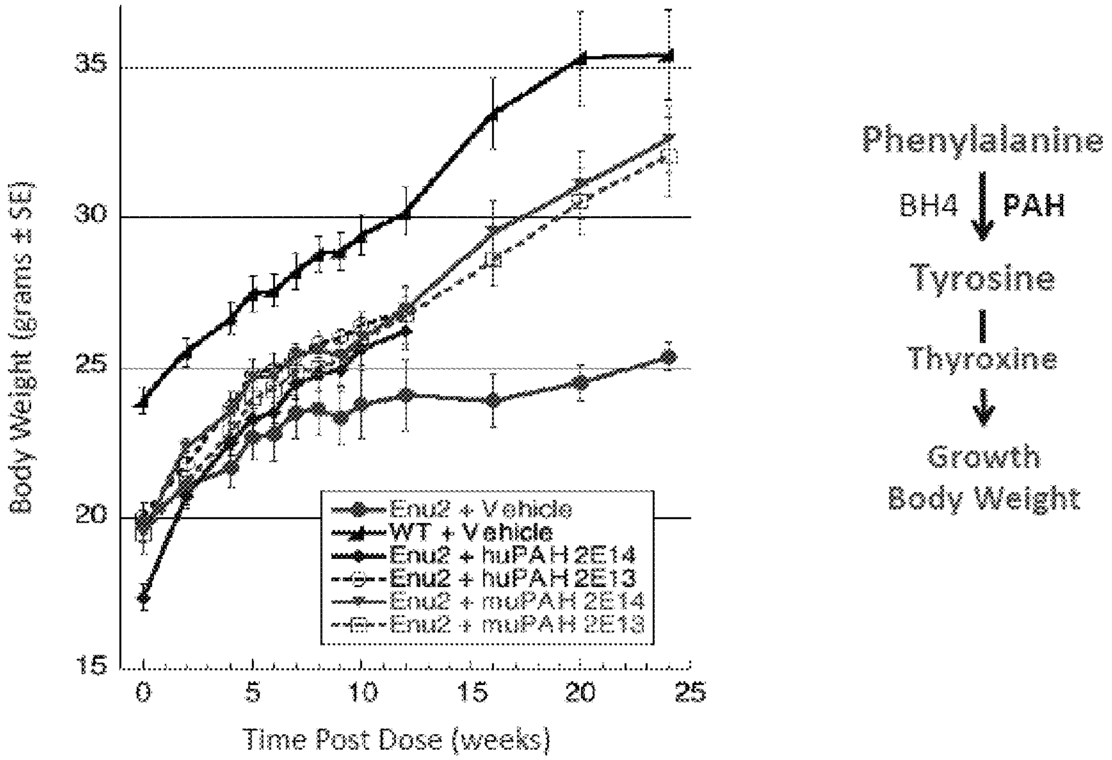
FIG. 30 shows that ENU2 mice treated with AAV5-PAH increases the rate of gain in body weight.

Growth rates were also measured in untreated Enu2 and wild-type mice treated with vehicle as controls and compared with the AAV-PAH treated Enu2 mice based on body weight measurements before plasma sample retrieval. (FIG. 30) Treatment with AAV-PAH at both doses tested significantly increased the rate of gain in body weight.

6.14.9 Coat Color

Figure 31:
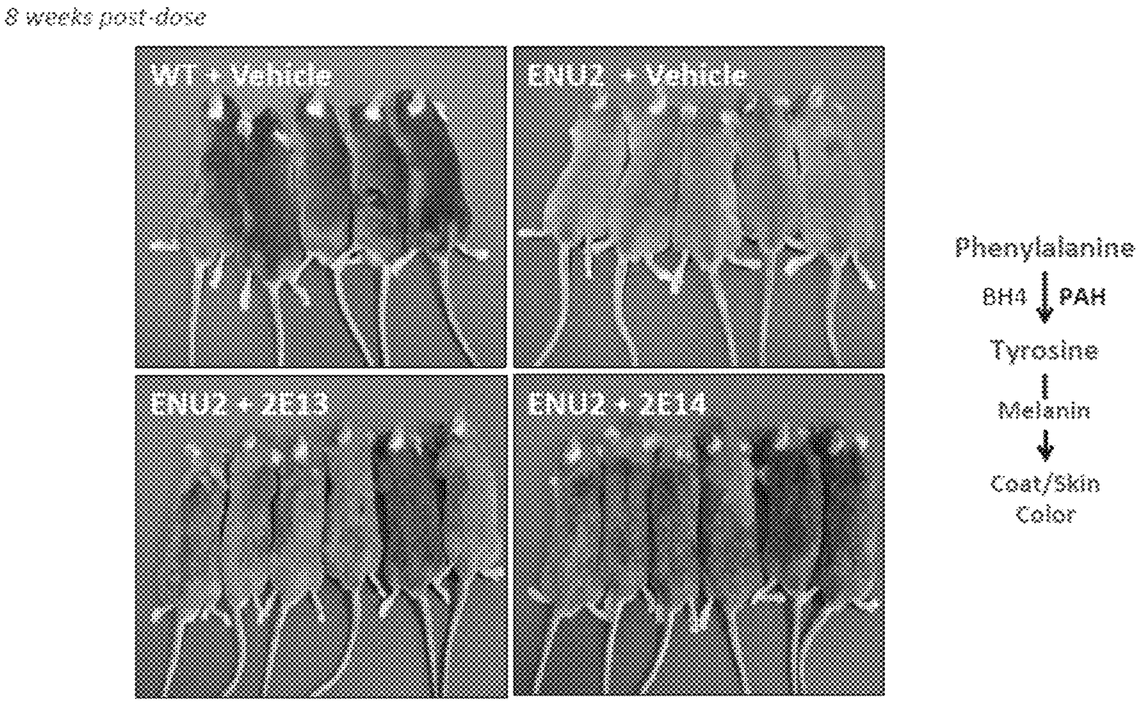
FIG. 31 shows that the coat color of ENU2 mice returns to wild type color when treated with AAV5-PAH.
Figure 32A:
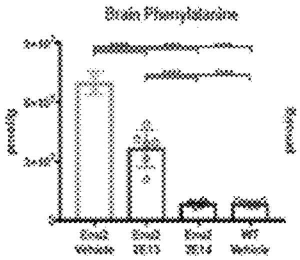
Figure 32B:
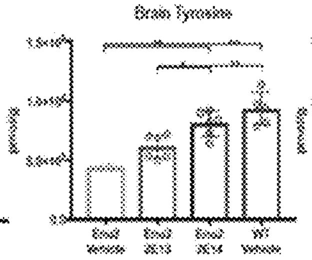
Figure 32C:
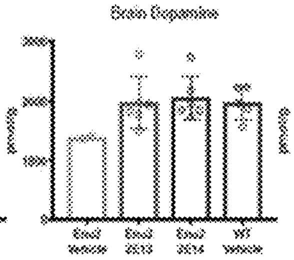
Figure 32D:
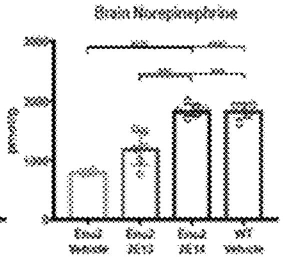
Figure 32E:
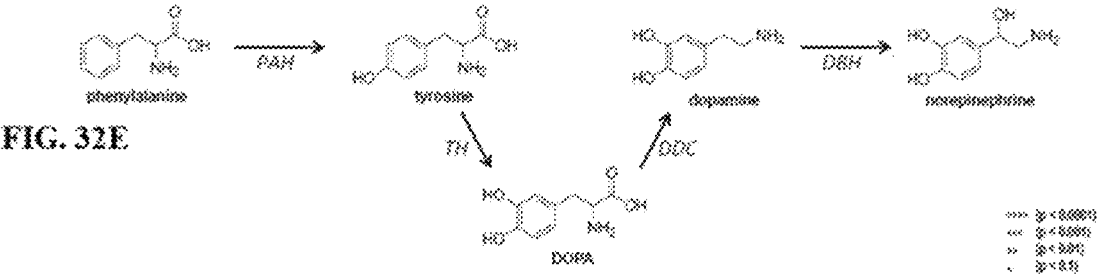

Hyperphenylalaninemia in Enu2 mice is associated with relative hypopigmentation of coat color. This effect is likely due to the competitive inhibition of tyrosinase enzyme in melanocytes by phenylalanine. (Miyamoto M, Fitzpatrick T. Competitive inhibition of mammalian tyrosinase by phenylalanine and its relationship to hair pigmentation in phenylketonuria. Nature. 1957; 179:199-200). Following administration of AAV-PAH and normalization of serum Phe levels, coat color gradually darkened in the treated mice at both doses tested (2E13 vg/kg and 2E14 vg/kg) (FIG. 31). Although the emergence of this effect was noticeable early on following injection and it appeared complete by 8 weeks.

6.14.10 Brain Amino Acids and Neurotransmitters

The PAH mediated conversion of phenylalanine to tyrosine serves as the precursor reaction for the production of a number of neurotransmitters as shown in FIG. 32. The loss of PAH activity in PKU patients results in the build-up of phenylalanine as noted by the increase in plasma phenylalanine levels. However, the neurocognitive effects of PKU are mostly caused by the loss of a precursor metabolic step that leads to the production of a number of neurotransmitters and metabolites.

A sensitive liquid-chromatography coupled mass spectrometry (LC/MS) based assay was used to measure the levels of various amino acids, neurotransmitters, and neurotransmitter metabolites. In brief, when amino acids, neurotransmitter metabolites, and neurotransmitters are reacted with ethyl chloroformate and pyridine or benzoyl chloride and sodium carbonate, they produce reaction products that have defined increases in molecular mass that allows for their identification and quantification using LC/MS. This assay was used to measure the levels of amino acids, neurotransmitters, and neurotransmitter metabolites in biological samples obtained from untreated Enu2 mice, wild-type control mice, and Enu2 mice treated with two doses (2E13 vg/kg and 2E14 vg/kg) of an adeno associated virus vector expressing human PAH (AAV-PAH) to determine the effect of PAH loss on neurotransmitter production. The AAV is constructed with the ApoE-HCR-hAAT.GI.mu/hPAH.bGH vector and the capsid genes of the AAV5 serotype.

As shown in FIG. 32, the untreated Enu2 mice consistently demonstrated lower levels of neurotransmitter and neurotransmitter metabolites compared to wild-type mice in brain samples. The Enu2 mice had decreased levels of tyrosine, dopamine, and norepinephrine in their brains compared to the levels found in the brains of wild-type mice. These data confirm that loss of PAH activity results in a reduction of a number of key neurotransmitters. Administration of the higher dose of AAV-PAH (2E14 vg/kg) to Enu2 mice, but not the lower dose (2E13 vg/kg), restored the levels of phenylalanine, tyrosine, dopamine, and norepinephrine to levels seen in the vehicle-treated wild-type control. These data demonstrate that the levels of certain amino acids, neurotransmitters, and neurotransmitter metabolites in the brain can be used to determine the effective dose of a PKU therapeutic needed to restore the neurotransmitter metabolic pathways to those seen in wild-type controls.

6.14.11 Duration of Efficacy

To determine the duration of efficacy after AAV5-muPAH (ApoE-HCR-hAAT.GI.muPAH.bGH vector) was administered to ENU2 mice, plasma Phe levels were monitored every 2 weeks post AAV vector dosing. After 60 weeks (study ongoing) a reduction in efficacy was seen with the suboptimal dose 2e13 vg/kg dose, but the duration of efficacy has been maintained at the 2e14 vg/kg dose (FIG. 33).

6.14.12 Preliminary Safety Data

Preliminary safety studies performed on wild-type animals treated with AAV5-hPAH at 2E13 or 2E14 vg/kg, revealed no increases in the liver enzyme alanine aminotransferase (ALT) (data not shown), minimal changes in Phe levels compared to WT (FIG. 34) and no histological evidence of hepatocyte injury or death (e.g. no TUNEL staining) (FIG. 36), despite increased levels of the PAH protein in treated mice as measured by Western blot (FIG. 35).

6.15 Example 15: Generation of AAV-PAH Constructs that Incorporate Intronic Sequences To generate additional recombinant AAV vectors designed to be near the AAV packaging capacity that both avoid heterogeneous processing by the baculo production system and increase expression of functional PAH, constructs were generated with alternate intronic sequences. In some embodiments, the constructs comprised truncated versions of the hPAH 2nd intron. In alternative embodiments, the constructs comprised a composite globin/A1 AT intron (as provided in SEQ ID NO: 14) or truncated versions thereof. These constructs were generated using standard DNA cloning techniques, as mentioned in Example 1, and representative sequences thereof are shown in SEQ ID NOS:19 and 17, respectively.

In initial efforts to increase the expression of the hPAH sequence in the ApoE-HCR-hAAT.GI.hPAH.bGH vector, a 2116 base pair (bp) truncated hPAH $2^{nd}$ intron was inserted between exons 2 and 3 in the hPAH coding sequence (ApoE-HCR-hAAT.hPAH-tI2.bGH) (FIG. 37). It is known that insertion of an intron possibly can result in increased level of mRNA expression in otherwise intron-less genes, such as, for example, the interferon genes. However, in this case we didn't use intron 1 because it is known to contain a promoter that is active in liver. Also, the truncated hPAH $2^{nd}$ intron has no exonic splice enhancers detected at the truncation junction by ESE finder. This vector was also designed to be near the AAV packaging capacity.

6.15.1 Measurement of Plasma Phe Levels in ENU2 Mice Treated with ApoE-HCR-hAAT.hPAH-tI2.bGH Vector Mice were injected with various concentrations of the ApoE-HCR-hAAT.hPAH-tI2.bGH vector and blood samples were collected weekly to evaluate plasma phenylalanine concentration. (FIG. 38) A higher level of phenylalanine was detected in the PAH KO/Enu2 mice before injection compared to the littermate controls, and 2 days after the vector injection the plasma phenylalanine level decreased in the mice given the 2E14 vg/kg dose, and to a lesser extent in the 6E13 and 2E13 vg/kg groups, while the controls remained stable. This result demonstrated that a single injection of ApoE-HCR-hAAT.hPAH-tI2.bGH vector at the 2E14 vg/kg dose could rescue the deficient PAH and reduce the pathological accumulation of phenylalanine in the blood. However, the ApoE-HCR-hAAT.hPAH-tI2.bGH vector was not as efficacious as the ApoE-HCR-hAAT.GI.hPAH.bGH vector with respect to reducing plasma Phe levels, which achieved reduction of Phe to wild-type levels at the 2 day timepoint with the 6E13 vg/kg dose (see FIG. 29B).

6.15.2 Amino Acid and Neurotransmitter Levels in the Brain of ApoE-HCR-hAAT.hPAH-tI2.bGH Vector Treated ENU2 Mice Using the neurotransmitter assay described above in Example 14, the levels of amino acids, neurotransmitters, and neurotransmitter metabolites were also measured in the mice treated with the ApoE-HCR-hAAT.hPAH-tI2.bGH vector. As shown in FIG. 39, the Enu2 mice treated with the two highest doses (2E14 vg/kg and 6E13 vg/kg) of the ApoE-HCR-hAAT.hPAH-tI2.bGH vector, but not the lower doses (≤2E13 vg/kg), restored the levels of the amino acids phenylalanine, tyrosine, and tryptophan (FIG. 39A), and levels of the neurotransmitter norepinephrine (FIG. 39B) as seen in the vehicle-treated wild-type control. 6.15.3 Large Intron-Vector 1 (ApoE-HCR-hAAT.cG-AIATI.hPAH.bGH)

In follow on efforts, a 1815 bp composite globin/A1AT intron (SEQ ID NO:14) was inserted in front of the hPAH coding sequence (ApoE-HCR-hAAT.cG-A1ATI.hPAH.bGH). (FIG. 40) This intron was also designed to bring the total size of the vector to near the AAV packaging capacity. The nucleotide sequence includes the ApoE-hAAT promoter, with the composite globin/A1AT intron, wild-type coding sequence for human PAH, and a bGH poly(A) sequence as set forth in SEQ ID NO: 17.

In vitro and in vivo assessments of this vector are included in Example 17 with comparisons to the codon-optimized vectors.

6.16 Example 16—Generation of Codon-Optimized AAV-PAH Constructs

In another attempt to further increase the expression of the hPAH in the ApoE-HCR-hAAT.GI.hPAH.bGH vector, additional recombinant AAV vectors were generated with codon-optimized PAH coding sequences (see SEQ ID NOs: 7-13). As described above, these constructs were generated using standard DNA cloning techniques and a representative vector sequence comprising the codon optimized SEQ ID NO: 7 sequence is shown in SEQ ID NO:16.

6.16.1 Generation of Codon Optimized PAH

The inventors have designed alternative hPAH constructs (codop-PAH) to test the hypothesis that replacing infrequently used codons in the cDNA with those more commonly found in mammalian genes ("codon optimization") will generate increased expression of hPAH following gene transfer. A similar exercise for coagulation factors VII, VIII and IX improved expression by up to 10 fold when compared to the wild type cognates (see e.g. U.S. Pat. No. 9,393,323). The strategy for the design of the codop-hPAH involved back translating the hPAH amino acid sequence with a set of codons most frequently found in highly expressed mammalian genes. This modified sequence was then carefully scanned and codons were further modified to improve mRNA stability and remove undesirable sequences, such as excess CpG dinucleotides, and cryptic splice sites.

The inventors employed 6 different methods of codon-optimization as described above which include:

GENEius 1/2 (Operon 1)—Operon/Eurofins Genomincs codon optimization software in conjunction with manually reducing CpG di-nucleotide content and removing any extra ORF in the sense and anti-sense direction.

Nathwani (NW2-Cop)—been codon optimized using codon usage table that Amit Nathwani used for Factor VIII codon optimization.

Nathwani-RCG (NW-RCG)—codon optimized using codon usage table that Amit Nathwani used for Factor VIII codon optimization in conjunction with manually reducing CpG di-nucleotide content and removing any extra ORF in the sense and anti-sense direction.

ATUM (DNA2.0-op/D20-P)—codon optimized using the DNA2.0 codon optimization algorithm ATUM-RCG (DNA2.0-Cop1)—codon optimized using the DNA2.0 codon optimization algorithm in conjunction with manually reducing CpG di-nucleotide content and removing any extra ORF in the sense and anti-sense direction JCAT (JCAT)—codon optimized using the Java Codon Adaptation Tool (www.jcat.de) in conjunction with manually reducing CpG di-nucleotide content and removing any extra ORF in the sense and anti-sense direction.

A sequence alignment of the codop-hPAH sequences is provided in FIG. 41 with charts comparing percent sequence identities, GC content and cladogram relationships in FIG. 42.

6.16.2 Codon-Optimized hPAH Vector Design

The final designed codop-hPAH sequences contain anywhere from 46-316 single bp changes from the wild type hPAH sequence, and are typically 47-57% G+C, relative to 47% G+C content of the wild type sequence. The inventors have cloned the codop PAH variants into their standard rAAV vector (Nathwani A. et al. Blood. 2007 Feb. 15; 109(4): 1414-1421) under the ApoE/hAAT promoter in various configurations (see FIG. 43). In a preferred embodiment, the codop-PAH has been cloned into a vector that includes an ApoE-hAAT promoter, with a composite globin/

A1AT intron, the codon optimized sequence for human PAH, and a bGH poly(A) sequence. The preferred composite globin/A1AT intron has the sequence of SEQ ID NO: 14.

6.16.3 HepG2 Transduction with Codon-Optimized hPAH AAV Vectors

Evaluation of these codon-optimized hPAH AAV vectors in HepG2 liver cell-line (FIG. 44) showed that GENEius1, GENEius2 and JCAT showed significant expression enhancement over WT-hPAH. Collectively, therefore, these data suggest that the inventors codop-PAH molecule is more potent than the WT-hPAH. Notably, the GENEius1 (ApoE-HCR-hAAT.GI.hPAHco1.bGH) and GENEius2 (ApoE-HCR-hAAT.GI.hPAHco2.bGH) vector plasmids consistently generate between 50-100% higher yields of vector than rAAV-WT-hPAH.

HepG2 cells were seeded at Day 0 with 5E5 cells/well in a 12 well plate. Cells were transduced on Day 1 at MOI ranging from 1.25E5 to 1E6 with 20 uM etoposide. Media was replaced on Day 2. Cells were harvested on Day 4 by removing media, detaching with TrypLE, subsequent neutralization with serum containing media, washing cells with DPBS and freezing cell pellet. Expression analysis was done by lysing cells with TPER+4 mM BMe, removal of the insoluble cell debris, measurement of protein concentration by A280, SDS-PAGE using 20 μg protein loads and WB using an anti-PAH mouse monoclonal primary Ab and a rabbit anti-mouse HRP-conjugated secondary Ab.

6.16.4 AML12 Transduction with AAV-Codop hPAH Vectors

AML12 cells are murine hepatocyte derived cells. Cells were seeded at Day 0 with 5E5 cells/well in a 12 well plate. Cells were transduced on Day 1 at 1E6 MOI with 20 uM etoposide. Media was replaced on Day 2. Cells were harvested on Day 4 by removing media, detaching with TrypLE, subsequent neutralization with serum containing media, washing cells with DPBS and freezing cell pellet. Expression analysis was done by lysing cells with TPER+4 mM BMe, removal of the insoluble cell debris, measurement of protein concentration by A280, SDS-PAGE using 80 μg protein loads and WB using an anti-PAH mouse monoclonal primary Ab and a rabbit anti-mouse HRP-conjugated secondary Ab. Results depicted in FIG. 45 compare the use of serum-containing media and serum free media from Day 1-4, the later having been previously shown to induce hepatocyte-like transcription regulation. Comparing the pattern of expression of codon optimized hPAH, cells maintained in SFM matched our results in HepG2 cells as well as murine in vivo experiments.

6.16.5 Measurement of Plasma Phe Levels in ENU2 Mice Treated with Codon Optimized AAV-PAH Vectors Enu2 mice were injected with 2E13 vg/kg of each codon optimized AAV-PAH vector, vehicle or an AAV vector with the wild-type PAH sequence. The blood samples were collected weekly to evaluate plasma phenylalanine concentration (FIG. 46A-B). A higher level of phenylalanine was detected in the ENU2 mice before injection compared to the littermate controls. Six weeks after the vector injection, the plasma phenylalanine level of the ENU2 mice decreased while the controls remained stable. This result demonstrated that a single injection of codon optimized AAV-PAH into PAH KO/ENU2 mice could rescue the deficient PAH and reduce the pathological accumulation of phenylalanine in the blood.

The effects of treatment with AAV-codop PAH constructs were further evaluated as body weight versus Phe reduction between the different constructs (FIG. 47). The GENEius1 (ApoE-HCR-hAAT.GI.hPAHco1.bGH), GENEius2 (ApoE-HCR-hAAT.GI.hPAHco2.bGH) and JCAT (ApoE-HCR-hAAT.GI.hPAHco3.bGH) constructs proved to be the most effect at reducing Phe levels, which also correlated with a greater increase in % body weight.

6.17 Example 17—Comparison of AAV-PAH Constructs with Codon-Optimization Versus Intron Insertion A series of experiments were performed to further compare the functionality and efficacy of the lead codon optimized vector (ApoE-HCR-hAAT.GI.hPAHco1.bGH) and the lead intron inserted vector (ApoE-HCR-hAAT.cG A1ATI.hPAH.bGH).

6.17.1 HepG2 Transient Transfection

HepG2 cells were seeded at Day 0 with 5E5 cells/well in a 12 well plate. Cells were transfected on Day 1 with using lug DNA/well with FuGene HD:DNA ratio of 4.5:1. Media was replaced on Day 2. Cells were harvested on Day 4 by removing media, detaching with TrypLE, subsequent neutralization with serum containing media, washing cells with DPBS and freezing cell pellet. Expression analysis was done by lysing cells with TPER+4 mM BMe, removal of the insoluble cell debris, measurement of protein concentration by A280, SDS-PAGE using 20ug protein loads and WB using an anti-PAH mouse monoclonal primary Ab and a rabbit anti-mouse HRP—conjugated secondary Ab. The data in FIG. 48A-B provide a comparison of V1 (ApoE-HCR-hAAT.GI.hPAHco1.bGH), V1+LG intron (ApoE-HCR-hAAT.cG-A1ATI.hPAH.bGH), Geneius1 (ApoE-HCR-hAAT.GI.hPAHco1.bGH) and Vector 2 (ApoE-HCR-hAAT.cGA1ATI.hPAHco1.bGH). Results show a benefit for including LGintron to V1, and the Geneius1+LGintron vector at least as strong as Geneius 1 alone.

6.17.2 Dose Response with Improved Potency Vectors

Increasing doses of ApoE-HCR-hAAT.GI.hPAHco1.bGH or ApoE-HCR-hAAT.cGA1ATI.hPAH.bGH were delivered to ENU2 mice to determine efficiency in reducing Phe levels. AAV5-PAH vectors were modified to include a codon optimized PAH gene, a large intron, and the effect of these modifications were tested in ENU2/PKU mouse model.

A dose response curve of AAV5-PAH modified with Geneius-1, or Large Intron is shown in FIG. 49A. AAV5-PAH variants were administered in ENU2 mice at doses in vg/kg indicated in the graph and plasma Phe was determined. FIG. 49B depicts a dose response at 2 weeks post AAV administration (ENU2 mice were not plotted), and FIG. 49C depicts the dose response at 4 weeks post AAV administration with y-axis narrowed to highlight dose response changes (ENU2 mice were not plotted).

6.17.3 PAH Biodistribution Comparison Between GENEius-1 and Large Intron AAV-PAH Constructs FIG. 50 characterizes the changes in PAH biodistribution in liver tissue with AAV-PAH treatment. AAV5-PAH vectors were modified to include a codon optimized PAH gene, a large intron, and the expression of PAH protein in liver hepatocytes was determined by IHC using standard techniques. PAH protein was stained using standard IHC techniques and the % of positive cells was determined and plotted against the AAV5-PAH doses in vg/kg (FIG. 50A). An increasing percentage of PAH expressing hepatocytes was observed with an increasing dose of either the large intron or GENEius-1 constructs. However, there was no significant difference in the % of PAH positive hepatocytes between constructs GENEius-1 and Large Intron at each dose. IHC images of liver from ENU2 mice dosed with these AAV5-PAH vectors at 2e13 vg/kg (FIG. 50B) and at 1e14 vg/kg (FIG. 50C) revealed that in both cases the majority of the PAH was localized to the area around the central vein, and minimal distribution was seen in the periportal area. Thus, it appear that PAH protein expression is observed in hepatocytes surrounding central veins at all dose levels.

6.18 Example 18—Generation of AAV-PAH Constructs Combining Codon-Optimization and Intron Insertion

6.18.1 Dose Response of Vector 2 in ENU2 Mice

To evaluate the kinetics of the dose response, plasma Phe is used as a surrogate marker for PAH activity in liver. After administration of AAV5-PAH variants in ENU2/PKU mouse model, a reduction in plasma Phe was observed within two weeks after AAV dosing. The response remained stable up to 5 weeks, and remains stable over an extended period based on other studies (FIG. 51A). The dose response of the AAV5-PAH variants administered in ENU2 mice was also graphed out at the 2 week timepoint to more clearly identify efficacy differences of the different doses (FIG. 51B). Gene1 (Geneius-1 variant) and LgIntron (Large intron variant) were used as reference controls at 4e13 vg/kg. Vector 2 was administered at different doses in male and female ENU2 mice and the efficacy was compared to other AAV5-PAH variants.

Correlation of Vector 2 dose with efficacy in male and female ENU2 mice is further exemplified in FIG. 52, with only minor differences observed in the efficacy of the Vector 2 between male and female ENU2 mice.

Comparison of the dose response between AAV5-PAH variants (GENEius-1 and large intron), and the Vector 2 is shown in FIG. 53. The response of the vectors in lowering plasma Phe in ENU2 mice at 2 weeks, when administered at 2e13 vg/kg is plotted. The graph indicates that Vector 2 has increased efficacy in lowering plasma Phe at 2e13 vg/kg when compared to other AAV5-PAH variants.

6.19 Example 19—Safety Analysis of AAV-PAH Constructs

6.19.1 Plasma ALT Levels

Alanine aminotransferase (ALT) activity in plasma can be used as an indicator of hepatocyte health, and higher levels of ALT are indicative of hepatocyte toxicity. Plasma samples were taken from mice before administration of AAV5-PAH (FIG. 54A) and 2 weeks after administration (FIG. 54B), and plasma ALT was measured using a commercial kit (Sigma). Graphs indicate that administration of AAV5-PAH at different doses did not lead to appreciable change in ALT levels.

6.19.2 TUNEL Staining Used to Measure Toxicity

Terminal deoxynucleotidyl transferase dUTP nick end labeling (TUNEL) is an enzymatic assay used to detect DNA fragmentation as a result of cell death from apoptotic signaling cascades. TUNEL positive cells were assessed in liver sections from mice treated with AAV5-PAH variants and minimal change in TUNEL positive cells was observed after AAV5-PAH administration at different doses (FIG. 55).

6.19.3 IBA and H&E Staining Used to Determine Inflammation Levels

As a further measure of liver health, IBA and H&E staining were used detect macrophage infiltration in animals dosed with AAV-hPAH. Allograft inflammatory factor 1 (AIF-1) also known as ionized calcium-binding adapter molecule 1 (MAO is found on activated macrophages. Activated macrophages are found in tissues during inflammation (FIG. 56A). IBA1 positive cells/foci were assessed in liver sections from mice treated with AAV5-PAH variants, to determine the extent of inflammation and macrophage infiltration after AAV5-PAH administration (FIG. 56B). Minimal change in IBA1 positive foci cells was observed after AAV5-PAH administration at different doses.

H&E (hematoxylin and eosin) staining of liver tissue was done in mice treated with AAV5-PAH variants and compared to the staining pattern of wild type mice. The staining pattern indicated minimal differences in tissue histology between wild type mice and mice treated with AAV5-PAH variants (FIG. 57A-C).

In view of the above, AAV5-PAH vectors and doses used are likely non-pathogenic in the ENU2 mice based on the lack of significant liver histopathology.

6.20 Example 20: Generation of Constructs with Improved Promoter/Enhancer Sequences To generate additional recombinant AAV vectors with strong promoters that increase expression of functional PAH, constructs were generated with modified enhancer and/or promoter sequences. Specifically, constructs were constructed using standard DNA cloning techniques with alternate liver-specific promoters were used such as the thyroxine binding globulin (TBG) promoter or transthyretin (TTR) promoter (see e.g. SEQ ID NOS: 22 and 23). Other suitable promoters include human albumin (Miyatake et al., *J. Virol,* 71:5124 32 (1997)), humAlb; the Liver Specific promoter (LSP), and hepatitis B virus core promoter, (Sandig et al, Gene Ther., 3: 1002 9 (1996). See, e.g., The Liver Specific Gene Promoter Database, Cold Spring Harbor, //rulai.schl.edifLSPD. Although less desired, other promoters, such as viral promoters, synthetic promoters, constitutive promoters, regulatable promoters (see, e.g., WO 2011/126808 and WO 2013/04943), or a promoter responsive to physiologic cues may be used in the vectors described herein.

6.21 Example 21: Gene Therapy Restores Pah Activity in Enu2 Mice

6.21.1 AAV5-PAH Vector Design

Adeno-associated virus serotype 5 (AAV5)-mediated delivery of the human PAH (hPAH) or murine PAH (muPAH) gene (under a liver-specific promoter) was utilized for these studies.

6.21.2 In Vivo Studies

All studies were conducted by BioMarin's Translational Biology Department in the vivarium located at the Buck Institute, Novato Calif. Animal breeding and experimental protocols were approved by the Institutional Animal Care and Use Committee (IACUC). Male ENU2 mice (C57BL/6-Pahenu2) and wild type (WT) control mice (C57BL/6J) were received from Jackson Laboratory.

ENU2 Mice were dosed at 8 weeks of age via tail vein injection with AAV5-muPAH or vehicle control. Wild type mice were treated with vehicle. Blood samples were taken every two weeks post-dosing by tail vein nick. At the conclusion of the study, blood was drawn via cardiac puncture and tissues (brain and liver) were perfused with phosphate buffered saline prior to collection.

The plasma Phe and Tyr levels in the mice were measured by LC-MS/MS, and the plasma alanine aminotransferase (ALT) was measured by immunoassay (Sigma Aldrich) according to manufacturer's instructions. As seen in FIG. 58A, plasma Phe levels in ENU2 mice treated with AAV5-muPAH were restored to WT levels by 2 weeks post dose.

This effect was sustained throughout the lifetime of the study (80 weeks). There was no statistical difference seen in the ALT levels between WT mice, ENU2 treated with vehicle, and ENU2 treated with AAV5-muPAH throughout the duration of the 80 week study (FIG. 58B). ENU2 mice dosed with vehicle remained a light brown color while ENU2 mice treated with AAV5-muPAH changed coat color to dark brown, similar to the coat color exhibited by WT controls (FIG. 58C). These data show sustained reduction in plasma Phe to near WT levels was achieved by a single-dose gene-therapy.

To examine the effect of the human PAH on brain amino acid and neurotransmitter metabolites, ENU2 mice were treated with AAV5-hPAH. After 12 weeks, frozen brain hemispheres were homogenized and resulting lysates processed for LC-MS/MS measurement of Phe, Tyr, Tryptophan, 5-hydroxyindoleacetic Acid (5-HIAA), homovanillicacid (HVA) and 3-methoxy-4-hydroxyphenylglycol (MOPEG). As shown by FIG. 59, treatment with AAV5-hPAH normalized brain amino acid (Phe, Tyr, and Tryptophan) levels (FIG. 59A), in addition to brain neurotransmitter metabolites, 5-hydroxyindoleacetic Acid (5-HIAA), homovanillicacid (HVA) and 3-methoxy-4-hydroxyphenylglycol (MOPEG), derived from serotonin, dopamine and norepinephrine respectively (FIG. 59B).

To examine the effect of the human PAH on liver PAH protein expression, WT mice treated with on AAV5-hPAH were examined for evidence of hypo-phenylalanine over the course of 12 weeks. FIG. 60A shows that WT mice treated with AAV5-hPAH had normal Phe levels throughout the duration of the study. At the conclusion of the 12 week study, frozen liver sections were homogenized and resulting lysates were reduced, akylatedand digested with Trypsin (Promega). PAH levels were measured by LC-MS/MS using peptides common to both mouse and human PAH. Wild type mice treated with AAV5-hPAH experienced a 2-fold increased of PAH protein levels as shown in FIG. 60B.

These data show that sustained reduction in plasma Phe to near WT levels can be achieved by a single-dose gene-therapy. Additionally, brain amino acid and neurotransmitter metabolites were also normalized to WT levels with treatment, and Phe level did not drop below reference range in WT animals treated with AAV5-hPAH. In sum, these experiments provide evidence that gene therapy based restoration of PAH activity is a viable therapeutic approach for treatment of PKU.

6.22 Example 22: Phenylalanine Hydroxylase (PAH) Liver Distribution and Characterization Following AAVs-hPAH Gene Therapy in Pah$^{Enu2}$ Mice

6.22.1 Biodistribution of Human PAH Transgene

ENU2 mice were administered a single dose of AAV5-hPAH via a tail vein injection. Animals were euthanized 12 weeks post vector administration, perfused with saline, and then the livers were collected. All median lobe liver samples were fixed in 4% paraformaldehyde for 48 hours and processed routinely for paraffin embedding within one month of receipt.

The mouse liver was sectioned and in situ hybridization performed as per manufacturer instruction (ACD) using a Roche Ventana Autostainer. Ten 40× images were taken per animal and hepatocytes scored as either negative or positive for DAB signal. FIG. 61 shows the biodistribution of the AAV5-hPAH vector genomes and transgene derived PAH protein in liver tissue in a mouse model of PKU. A dose-dependent increase in the number of hepatocytes staining positive for both hPAH DNA and protein was detected in ENU2 mouse livers (FIG. 61A-C). There was a greater abundance of both vector DNA and protein in the peri-central regions of the liver lobule when compared to the peri-portal region.

6.22.2 Evaluation of Inflammation and Apoptosis Following AAV5-hPAH Administration As above, ENU2 mice were administered a single dose of AAV5-hPAH and the livers were collected after 12 weeks post vector administration. To evaluate the effect of AAV5-PAH gene therapy and transgene-derived PAH protein on liver safety, the liver was processed for FFPE and immunohistochemistry to detect pro-inflammatory markers. FIG. 62A-C shows there was a slight increase in the number of IBA1 (total) and CD68 (M1/M2 activated) macrophages detected upond administration AAV5-hPAH and no significant staining on iNOS (M1 activated), a pro-inflammatory macrophage marker, was detected. In addition, such immunohistologic features as hepatocellular necrosis, kupffer cell hyperplasia, and portal triad inflammation or fibrosis were not observed which suggested that liver health is preserved following AAV5-hPAH administration. FIG. 62D shows a quantification of the stained sections.

Terminal deoxynucleotidyl transferase dUTP nick end labeling (TUNEL) staining of the FFPE livers showed no significant increase in apoptotic cell death in any of the gene therapy treated groups when compared to vehicle-treated WT mice or vehicle-treated ENU2 mice. FIG. 63 shows imaged TUNEL stained liver sections and image analysis was performed using ImageJ. Approximately 14,000-17,000 nuclei were counted per animal. These data show no histopathological evidence of increased cell death following AAV5-hPAH vector administration was observed, and there existed no marked signs of inflammation either (FIG. 62-63). These data support that AAV5-mediated gene delivery of hPAH may be a viable option as a potential therapeutic approach for patients with PKU.

6.23 Example 23: Effect of Vector 2

Vector 2 described in Example 17 (FIG. 48) and Example 18 (FIGS. 51-53) was selected for further study.

6.23.1 Biodistribution of Vector 2 DNA in Cynomolgus Monkeys

Vector 2 was delivered at two dose levels (high and low) by IV injection. Male and female cynomolgus monkeys were euthanized 4-weeks post administration. A real-time quantitative polymerase chain reaction (qPCR) assay was used to quantify the amount of Vector 2 vector DNA in genomic DNA (gDNA) extracted from cynomolgus monkey blood and tissues. FIG. 64 shows that the biodistribution of Vector 2 DNA following administration of IV Vector 2 was consistent with published literature on AAV5 capsids, with liver as the main target organ. The amounts of DNA detected in other tissues are presented as the percentage of DNA found in the liver. The spleen has the highest amount of vector DNA after the liver (filled squares), with testes and ovaries representing the lowest amount relative to liver (filled circles).

6.23.2 Effect of Vector 2 on Phenylalanine and Tyrosine in Cynomolgus Monkeys Vector 2 was delivered at two dose levels (high and low) by IV injection as above. Plasma was collected from male and female cynomolgus monkeys at regular intervals for 4-weeks post-administration. Acetonitrile precipitation and HPLC/MS/MS (C18 HPLC column followed by a triple quadrupole mass spectrometer) were used to determine the concentration of phenylalanine and tyrosine in cynomolgus lithium heparin plasma.

Plasma phenylalanine and tyrosine remained consistent throughout the duration of the study (4-weeks) (FIG. 65). Endogenous PAH is known to be allosterically regulated, and these data indicate that PAH delivered via gene therapy is also subject to allosteric regulation. This regulation minimizes the risk for hypo-phenylalaninemia.

6.23.3 Administration of ENU2 Mice with Vector 2 Resulted in Correction of Amino Acid Levels in Brain Homogenates Female and male ENU2 mice were administered various doses of Vector 2. After 12 weeks, mice were sacrificed and brain homogenates were analyzed to determine levels of specific amino acids. As shown in FIG. 66, both male and female mice showed a clear dose-dependent decrease of Phe to WT levels upon administration of Vector 2. Complete correction of brain Phe was seen when Vector 2 was administered a dose of 6E13 vg/kg in male mice and 2E14 vg/kg in female mice (FIG. 66A). Vector 2 at a dose of 2E13 vg/kg in ENU2 males and 6E13 vg/kg in ENU2 females increased brain Tyr to WT levels (FIG. 66B). Vector 2 at a dose of 2E13 vg/kg in ENU2 males and 2E14 vg/kg in ENU2 females increased brain Trp to near WT levels (FIG. 66C).

Figure 67A:
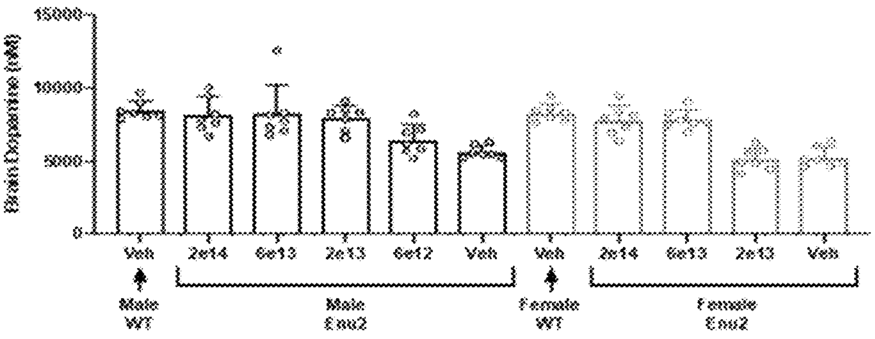
Figure 67B:
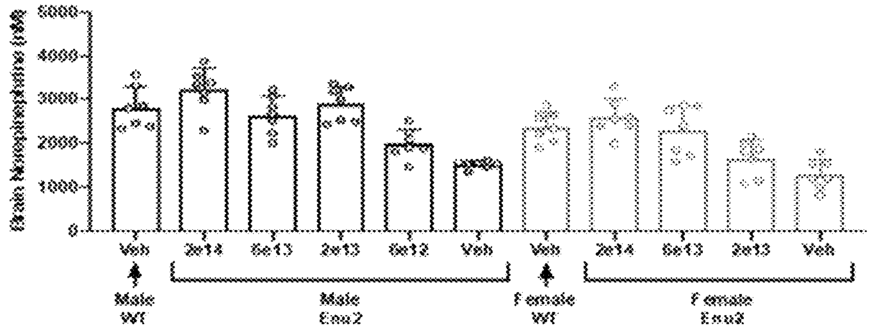
Figure 67C:
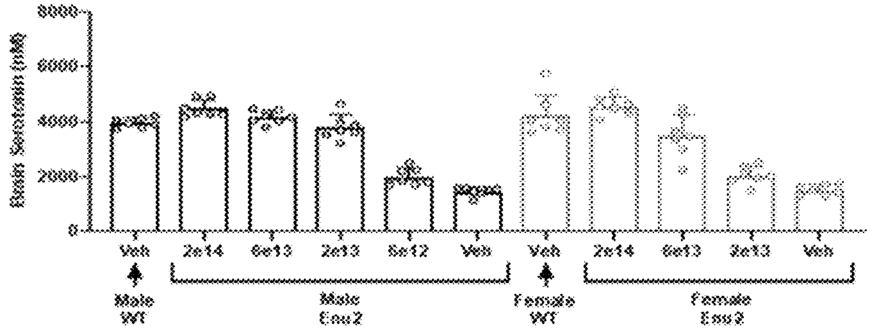
Figure 67D:
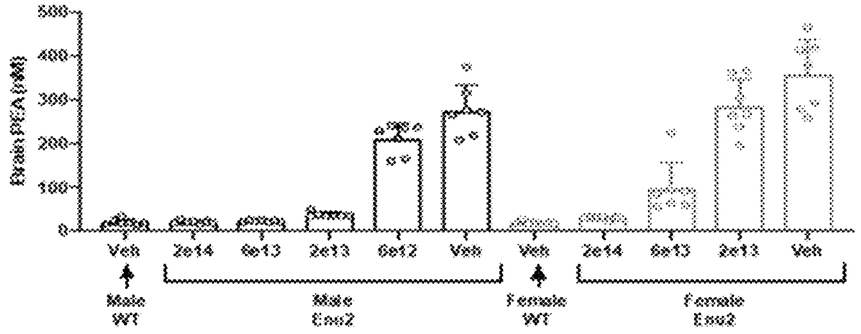

6.23.4 Administration of ENU2 Mice with Vector 2 Resulted in Correction of Neurotransmitter Levels in Brain Homogenates As above, female and male ENU2 mice were administered various doses of Vector 2, and after 12 weeks, mice were sacrificed and brain homogenates were analyzed to determine levels of neurotransmitters. Brain dopamine and norepinephrine, derived from Tyr, and serotonin, derived from Trp, increased to WT levels at doses of 2E13 vg/kg in ENU2 males and 6E13 vg/kg in ENU2 females (FIG. 67A-C). Additionally, levels of PEA, derived from Phe, decreased to levels seen in WT mice when ENU2 mice were administered 6E13 vg/kg (males) or 2E14 vg/kg (females) of Vector 2 (FIG. 67D).

6.23.5 Neurotransmitter Metabolite Correction Observed with High-Dose Vector 2

Neurotransmitter metabolites were measured in brain homogenates of ENU2 mice following treatment with Vector 2 as described above. Metabolites HVA, MOPEG, and 5-HIAA were all corrected to WT levels when Vector 2 was administered at 2E13 vg/kg in ENU2 male mice and 6E13 or 2E14 in ENU2 female mice (FIG. 68A-C).

The embodiments described herein are intended to be merely exemplary, and those skilled in the art will recognize, or will be able to ascertain using no more than routine experimentation, numerous equivalents of specific compounds, materials, and procedures. All such equivalents are considered to be within the scope of the disclosure.

All of the patents, patent applications and publications referred to herein are incorporated by reference herein in their entireties. Citation or identification of any reference in this application is not an admission that such reference is available as prior art to this application. The full scope of the disclosure is better understood with reference to the appended claims.

SEQUENCES

SEQ ID NO: 1 - wild-type human PAH nucleic acid sequence
ATGTCCACTGCGGTCCTGGAAAACCCAGGCTTGGGCAGGAAACTCTCTGACTTTGGACAGGAAA
CAAGCTATATTGAAGACAACTGCAATCAAAATGGTGCCATATCACTGATCTTCTCACTCAAAGA
AGAAGTTGGTGCATTGGCCAAAGTATTGCGCTTATTTGAGGAGAATGATGTAAACCTGACCCAC
ATTGAATCTAGACCTTCTCGTTTAAAGAAAGATGAGTATGAATTTTTCACCCATTTGGATAAAC
GTAGCCTGCCTGCTCTGACAAACATCATCAAGATCTTGAGGCATGACATTGGTGCCACTGTCCA
TGAGCTTTCACGAGATAAGAAGAAAGACACAGTGCCCTGGTTCCCAAGAACCATTCAAGAGCTG
GACAGATTTGCCAATCAGATTCTCAGCTATGGAGCGGAACTGGATGCTGACCACCCTGGTTTTA
AAGATCCTGTGTACCGTGCAAGACGGAAGCAGTTTGCTGACATTGCCTACAACTACCGCCATGG
GCAGCCCATCCCTCGAGTGGAATACATGGAGGAAGAAAAGAAAACATGGGGCACAGTGTTCAAG
ACTCTGAAGTCCTTGTATAAAACCCATGCTTGCTATGAGTACAATCACATTTTTCCACTTCTTG
AAAAGTACTGTGGCTTCCATGAAGATAACATTCCCCAGCTGGAAGACGTTTCTCAGTTCCTGCA
GACTTGCACTGGTTTCCGCCTCCGACCTGTAGCTGGCCTGCTTTCCTCTCGGGATTTCTTGGGT
GGCCTGGCCTTCCGAGTCTTCCACTGCACACAGTACATCAGACATGGATCCAAGCCCATGTATA
CCCCCGAACCTGACATCTGCCATGAGCTGTTGGGACATGTGCCCTTGTTTTCAGATCGCAGCTT
TGCCCAGTTTTCCCAGGAAATTGGCCTTGCCTCTCTGGGTGCACCTGATGAATACATTGAAAAG
CTCGCCACAATTTACTGGTTTACTGTGGAGTTTGGGCTCTGCAAACAAGGAGACTCCATAAAGG
CATATGGTGCTGGGCTCCTGTCATCCTTTGGTGAATTACAGTACTGCTTATCAGAGAAGCCAAA
GCTTCTCCCCCTGGAGCTGGAGAAGACAGCCATCCAAAATTACACTGTCACGGAGTTCCAGCCC
CTGTATTACGTGGCAGAGAGTTTTAATGATGCCAAGGAGAAAGTAAGGAACTTTGCTGCCACAA
TACCTCGGCCCTTCTCAGTTCGCTACGACCCATACACCCAAAGGATTGAGGTCTTGGACAATAC
CCAGCAGCTTAAGATTTTGGCTGATTCCATTAACAGTGAAATTGGAATCCTTTGCAGTGCCCTC
CAGAAAATAAAGTAA SEQ ID NO: 2 - wild-type human PAH amino acid sequence
MSTAVLENPG LGRKLSDFGQ ETSYIEDNCN QNGAISLIFS LKEEVGALAK
VLRLFEENDV NLTHIESRPS RLKKDEYEFF THLDKRSLPA LTNIIKILRH
DIGATVHELS RDKKKDTVPW FPRTIQELDR FANQILSYGA ELDADHPGFK
DPVYRARRKQ FADIAYNYRH GQPIPRVEYM EEEKKTWGTV FKTLKSLYKT
HACYEYNHIF PLLEKYCGFH EDNIPQLEDV SQFLQTCTGF RLRPVAGLLS
SRDFLGGLAF RVFHCTQYIR HGSKPMYTPE PDICHELLGH VPLFSDRSFA
QFSQEIGLAS LGAPDEYIEK LATIYWFTVE FGLCKQGDSI KAYGAGLLSS
FGELQYCLSE KPKLLPLELE KTAIQNYTVT EFQPLYYVAE SFNDAKEKVR
NFAATIPRPF SVRYDPYTQR IEVLDNTQQL KILADSINSE IGILCSALQK IK SEQ ID NO: 3 - hAAT promoter sequence
GATCTTGCTACCAGTGGAACAGCCACTAAGGATTCTGCAGTGAGAGCAGAGGGCCAGCTAAGTG
GTACTCTCCCAGAGACTGTCTGACTCACGCCACCCCCTCCACCTTGGACACAGGACGCTGTGGT
TTCTGAGCCAGGTACAATGACTCCTTTCGGTAAGTGCAGTGGAAGCTGTACACTGCCCAGGCAA
AGCGTCCGGGCAGCGTAGGCGGGCGACTCAGATCCCAGCCAGTGGACTTAGCCCCTGTTTGCTC
CTCCGATAACTGGGGTGACCTTGGTTAATATTCACCAGCAGCCTCCCCCGTTGCCCCTCTGGAT -continued

SEQUENCES

CCACTGCTTAAATACGGACGAGGACAGGGCCCTGTCTCCTCAGCTTCAGGCACCACCACTGACC
TGGGACAGTGAATCgtaagta SEQ ID NO: 4 - HCR enhancer or ApoE enhancer sequence
AGGCTCAGAGGCACACAGGAGTTTCTGGGCTCACCCTGCCCCCTTCCAACCCCTCAGTTCCCAT
CCTCCAGCAGCTGTTTGTGTGCTGCCTCTGAAGTCCACACTGAACAAACTTCAGCCTACTCATG
TCCCTAAAATGGGCAAACATTGCAAGCAGCAAACAGCAAACACACAGCCCTCCCTGCCTGCTGA
CCTTGGAGCTGGGGCAGAGGTCAGAGACCTCTCTGGGCCCATGCCACCTCCAACATCCACTCGA
CCCCTTGGAATTTCGGTGGAGAGGAGCAGAGGTTGTCCTGGCGTGGTTTAGGTAGTGTGAGAGG
G SEQ ID NO: 6 - synthetic promoter sequence (hAAT promoter, HCR enhancer/ApoE enhancer)
AGGCTCAGAGGCACACAGGAGTTTCTGGGCTCACCCTGCCCCCTTCCAACCCCTCAGTTCCCAT
CCTCCAGCAGCTGTTTGTGTGCTGCCTCTGAAGTCCACACTGAACAAACTTCAGCCTACTCATG
TCCCTAAAATGGGCAAACATTGCAAGCAGCAAACAGCAAACACACAGCCCTCCCTGCCTGCTGA
CCTTGGAGCTGGGGCAGAGGTCAGAGACCTCTCTGGGCCCATGCCACCTCCAACATCCACTCGA
CCCCTTGGAATTTCGGTGGAGAGGAGCAGAGGTTGTCCTGGCGTGGTTTAGGTAGTGTGAGAGG
GgtcgacGATCTTGCTACCAGTGGAACAGCCACTAAGGATTCTGCAGTGAGAGCAGAGGGCCAG
CTAAGTGGTACTCTCCCAGAGACTGTCTGACTCACGCCACCCCCTCCACCTTGGACACAGGACG
CTGTGGTTTCTGAGCCAGGTACAATGACTCCTTTCGGTAAGTGCAGTGGAAGCTGTACACTGCC
CAGGCAAAGCGTCCGGGCAGCGTAGGCGGGCGACTCAGATCCCAGCCAGTGGACTTAGCCCCTG
TTTGCTCCTCCGATAACTGGGGTGACCTTGGTTAATATTCACCAGCAGCCTCCCCCGTTGCCCC
TCTGGATCCACTGCTTAAATACGGACGAGGACAGGGCCCTGTCTCCTCAGCTTCAGGCACCACC
ACTGACCTGGGACAGTGAATCgtaagtatgcctttcactgcgaggggttctggagaggcttctg
agctccccatggcccaggcaggcagcaggtctggggcaggagggggggttgtggagtgggtatcc
gcctgctgaggtgcagggcagatggagaggctgcagctgagctcctattttcataataacagca
gccatgagggttgtgtcctgtttcccagtcctgcccggtccccccctcggtacctcctggtggat
acactggttcctgtaagcagaagtggatgagggtgtctaggtctgcagtcctggcaccccagga
tggggggacaccagccaagatacagcaacagcaacaaagcgcagccatttctttctgtttgcaca
gctcctctgtctgtcgggggctcctgtctgttgtctcctataagcctcaccacctctcctactg
cttgggcatgcatctttctccccttctatagatgaggaggttaaggtccagagaggggtgggga
ggaacgccggctcacattctccatcccctccagatatgaccaggaacagacctgtgccaggcct
cagccttacatcaaaatgggcctccccatgcaccgtggacctctgggccctcctgtcccagtgg
aggacaggaagctatgaggggcactgtcacccagggctcaagctggcattcctgaataatcgct
ctgcaccaggccacggctaagctcagtgcgtgattaagcctcataaccctccaaggcagttact
agtgtgattcccattttacagatgaggaagatggggacagagaggtgaataactggccccaaat
cacacaccatccataattcgggctcaggcacctggctccagtccccaaactcttgaacctggcc
ctagtgtcactgtttctcttgggtctcaggcgctggatggggaacaggaaacctgggctggact
tgaggcctctctgatgctcggtgacttcagacagttgctcaacctctctgttctcttgggcaaa
acatgataacctttgacttctgtcccctcccctcaccccacccgaccttgatctctgaagtgtt
ggaaggatttaatttttcctgcactgagttttggagacaggtcaaaaagatgaccaaggccaag
gtggccagtttcctatagaacgcctctaaaagacctgcagcaatagcagcaagaactggtattc
tcgagaacttgctgcgcagcaggcacttcttggcattttatgtgtatttaatttcacaatagct
ctatgacaaagtccacctttctcatctccaggaaactgaggttcagagaggttaagtaacttgt
ccaaggtcacacagctaatagcaagttgacgtggagcaatctggcctcagagcctttaattta
gccacagactgatgctcccctcttcatttagccaggctgcctctgaagttttctgattcaagac
ttctggcttcagctttgtacacagagatgattcaatgtcaggttttggagtgaaatctgtttaa
tcccagacaaaacatttaggattacatctcagttttgtaagcaagtagctctgtgatttttagt
gagttatttaatgctctttggggctcaatttttctatctataaaatagggctaataatttgcac
cttatagggtaagctttgaggacagattagatgatacggtgcctgtaaaacaccaggtgttagt
aagtgtggcaatgatggtgacgctgaggctgatgtttgcttagcatagggttaggcagctggca
ggcagtaaacagttggataatttaatggaaaatttgccaaactcagatgcTAGCAGCTACaatc
cagctaccattctgcttttattttatggttgggataaggctggattattctgagtccaagctag
gcccttttgctaatcatgttcatacctcttatcttcctcccacagctcctgggcaacgtgctgg
tctgtgtgctggcccatcactttggcaaagaattgcgatCGCCACC SEQ ID NO: 7 - codon optimised human PAH nucleic acid sequence (GENEius 1/Operon1)
ATGAGCACTGCTGTGCTGGAGAACCCTGGCCTGGGCAGAAAGCTGTCTGACTTTGGCCAGGAGA
CCAGCTACATTGAGGACAACTGCAACCAGAATGGAGCCATCAGCCTGATCTTCAGCCTGAAGGA
GGAGGTGGGAGCCCTGGCCAAGGTGCTGAGACTGTTTGAGGAGAATGATGTGAACCTGACCCAC
ATTGAGAGCAGACCCAGCAGACTGAAGAAGGATGAGTATGAGTTCTTCACCCACCTGGACAAGA
GAAGCCTGCCTGCCCTGACCAACATCATCAAGATCCTGAGACACGATATTGGAGCCACTGTGCA
CGAGCTGAGCAGAGACAAGAAGAAGGACACTGTGCCCTGGTTCCCCAGAACTATCCAGGAGCTG
GACAGATTTGCCAACCAGATCCTGAGCTATGGAGCTGAGCTGGATGCTGACCACCCTGGCTTCA
AGGACCCTGTGTACAGAGCCAGAAGAAAGCAGTTTGCTGACATTGCCTACAACTACAGACACGG
CCAGCCCATCCCCAGAGTGGAGTACATGGAGGAGGAGAAGAAGACCTGGGGCACTGTGTTCAAG
ACCCTGAAGAGCCTGTACAAGACCCACGCCTGCTATGAGTACAACCACATCTTCCCCCTGCTGG
AGAAGTACTGTGGCTTCCACGAGGACAACATCCCCCAGCTGGAGGATGTGAGCCAGTTCCTGCA
GACCTGCACTGGCTTCAGACTGAGACCTGTGGCTGGCCTGCTGAGCAGCAGAGACTTCCTGGGG
GGCCTGGCCTTCAGAGTGTTCCACTGCACCCAGTACATCAGACACGGCAGCAAGCCCATGTACA
CCCCTGAGCCTGATATCTGCCACGAGCTGCTGGGCCACGTGCCCCTGTTCTCTGACAGAAGCTT
TGCCCAGTTCAGCCAGGAGATTGGCCTGGCCAGCCTGGGAGCCCCTGATGAGTATATTGAGAAG
CTGGCCACTATCTACTGGTTCACTGTGGAGTTTGGCCTGTGCAAGCAGGGGGACAGCATCAAGG
CCTATGGAGCTGGCCTGCTGAGCAGCTTTGGGGAGCTGCAGTACTGCCTGTCTGAGAAGCCCAA
GCTGCTGCCCCTGGAGCTGGAGAAGACTGCCATCCAGAACTACACTGTGACTGAGTTCCAGCCC -continued

| SEQUENCES |
| --- |

CTGTACTATGTGGCTGAGAGCTTCAATGATGCCAAGGAGAAGGTGAGAAACTTTGCTGCCACCA
TCCCCAGACCCTTCTCTGTGAGATATGACCCCTACACCCAGAGAATTGAGGTGCTGGACAACAC
CCAGCAGCTGAAGATCCTGGCTGACAGCATCAACTCTGAGATTGGCATCCTGTGCTCTGCCCTG
CAGAAGATCAAGTAA

SEQ ID NO: 8 - codon optimised human PAH nucleic acid sequence (GENEius 2/Operon2)
ATGAGCACTGCTGTGCTGGAGAACCCTGGCCTGGGCAGAAAGCTGTCTGACTTTGGCCAGGAGA
CCAGCTACATTGAGGACAACTGCAACCAGAATGGGGCCATCAGCCTGATCTTCAGCCTGAAGGA
GGAGGTGGGGGCCCTGGCCAAGGTGCTGAGACTGTTTGAGGAGAATGATGTGAACCTGACCCAC
ATTGAGAGCAGACCCAGCAGACTGAAGAAGGATGAGTATGAGTTCTTCACCCACCTGGACAAGA
GAAGCCTGCCTGCCCTGACCAACATCATCAAGATCCTGAGACACGATATTGGGGCCACTGTGCA
CGAGCTGAGCAGAGACAAGAAGAAGGACACTGTGCCCTGGTTCCCCAGAACTATCCAGGAGCTG
GACAGATTTGCCAACCAGATCCTGAGCTATGGGGCTGAGCTGGATGCTGACCACCCTGGCTTCA
AGGACCCTGTGTACAGAGCCAGAAGAAAGCAGTTTGCTGACATTGCCTACAACTACAGACACGG
CCAGCCCATCCCCAGAGTGGAGTACATGGAGGAGGAGAAGAAGACCTGGGGCACTGTGTTCAAG
ACCCTGAAGAGCCTGTACAAGACCCACGCCTGCTATGAGTACAACCACATCTTCCCCCTGCTGG
AGAAGTACTGTGGCTTCCACGAGGACAACATCCCCCAGCTGGAGGATGTGAGCCAGTTCCTGCA
GACCTGCACTGGCTTCAGACTGAGACCTGTGGCTGGCCTGCTGAGCAGCAGAGACTTCCTGGGG
GGCCTGGCCTTCAGAGTGTTCCACTGCACCCAGTACATCAGACACGGCAGCAAGCCCATGTACA
CCCCTGAGCCTGATATCTGCCACGAGCTGCTGGGCCACGTGCCCCTGTTCTCTGACAGAAGCTT
TGCCCAGTTCAGCCAGGAGATTGGCCTGGCCAGCCTGGGGGCCCCTGATGAGTATATTGAGAAG
CTGGCCACTATCTACTGGTTCACTGTGGAGTTTGGCCTGTGCAAGCAGGGGGACAGCATCAAGG
CCTATGGGGCTGGCCTGCTGAGCAGCTTTGGGGAGCTGCAGTACTGCCTGTCTGAGAAGCCCAA
GCTGCTGCCCCTGGAGCTGGAGAAGACTGCCATCCAGAACTACACTGTGACTGAGTTCCAGCCC
CTGTACTATGTGGCTGAGAGCTTCAATGATGCCAAGGAGAAGGTGAGAAACTTTGCTGCCACCA
TCCCCAGACCCTTCTCTGTGAGATACGACCCCTACACCCAGAGAATTGAGGTGCTGGACAACAC
CCAGCAGCTGAAGATCCTGGCTGACAGCATCAACTCTGAGATTGGCATCCTGTGCTCTGCCCTG
CAGAAGATCAAGTGA SEQ ID NO: 9 - codon optimised human PAH nucleic acid sequence (Nathwani / NW2-Cop)
ATGTCCACTGCTGTCCTGGAAAACCCAGGCTTGGGCAGGAAACTCTCTGACTTTGGACAGGAAA
CAAGCTATATTGAAGACAACTGCAATCAAAATGGTGCCATATCACTGATCTTCTCACTCAAAGA
AGAAGTTGGTGCATTGGCCAAAGTACTGAGGTTATTTGAGGAGAATGATGTAAACCTGACCCAC
ATTGAATCTAGACCTTCTAGGTTAAAGAAAGATGAGTATGAATTTTTCACCCATTTGGATAAAA
GGAGCCTGCCTGCTCTGACAAACATCATCAAGATCTTGAGGCACGACATTGGTGCCACTGTCCA
CGAGCTTTCAAGGGATAAGAAGAAAGACACAGTGCCCTGGTTCCCAAGAACTATTCAAGAGCTG
GACAGATTTGCCAATCAGATTCTCAGCTATGGAGCTGAACTGGATGCTGACCACCCTGGTTTTA
AAGATCCTGTGTACAGGGCAAGAAGGAAGCAGTTTGCTGACATTGCCTACAACTACAGGCATGG
GCAGCCCATCCCTAGGGTGGAATACATGGAGGAAGAAAAGAAAACATGGGGCACAGTGTTCAAG
ACTCTGAAGTCCTTGTATAAAACCCACGCTTGCTATGAGTACAATCACATTTTTCCACTTCTTG
AAAAGTACTGTGGCTTCCACGAAGATAACATTCCCCAGCTGGAAGATGTTTCTCAGTTCCTGCA
GACTTGCACTGGTTTCAGGCTCAGGCCTGTAGCTGGCCTGCTTTCCTCTAGGGATTTCTTGGGT
GGCCTGGCCTTCAGGGTCTTCCACTGCACACAGTACATCAGACACGGCTCCAAGCCCATGTATA
CCCCTGAACCTGACATCTGCCACGAGCTGTTGGGACACGTGCCCTTGTTTTCAGATAGGAGCTT
TGCCCAGTTTTCCCAGGAAATTGGCCTTGCCTCTCTGGGTGCACCTGATGAATATATTGAAAAG
CTGGCCACAATCTACTGGTTTACTGTGGAGTTTGGGCTCTGCAAACAAGGAGACTCCATAAAGG
CATATGGTGCTGGGCTCCTGTCATCCTTTGGTGAATTACAGTACTGCTTATCAGAGAAGCCAAA
GCTTCTCCCCCTGGAGCTGGAGAAGACAGCCATCCAAAATTACACTGTCACTGAGTTCCAGCCC
CTGTATTATGTGGCAGAGAGTTTTAATGATGCCAAGGAGAAAGTAAGGAACTTTGCTGCCACAA
TACCTAGGCCCTTCTCAGTTAGGTATGACCCATACACCCAAAGGATTGAGGTCTTGGACAATAC
CCAGCAGCTTAAGATTTTGGCTGATTCCATTAACAGTGAAATTGGAATCCTTTGCAGTGCCCTC
CAGAAAATCAAGTAA SEQ ID NO: 10 - codon optimised human PAH nucleic acid sequence (Nathwani-RCG / NW-RCG)
ATGTCCACTGCTGTCCTGGAAAACCCAGGCTTGGGCAGGAAACTCTCTGACTTTGGACAGGAAA
CAAGCTATATTGAAGACAACTGCAATCAAAATGGTGCCATATCACTGATCTTCTCACTCAAAGA
AGAAGTTGGTGCATTGGCCAAAGTACTGAGGTTATTTGAGGAGAATGATGTAAACCTGACCCAC
ATTGAATCTAGACCTTCTAGGTTAAAGAAAGATGAGTATGAATTTTTCACCCATTTGGATAAAA
GGAGCCTGCCTGCTCTGACAAACATCATCAAGATCTTGAGGCACGACATTGGTGCCACTGTCCA
CGAGCTTTCAAGGGATAAGAAGAAAGACACAGTGCCCTGGTTCCCAAGAACTATTCAAGAGCTG
GACAGATTTGCCAATCAGATTCTCAGCTATGGAGCTGAACTGGATGCTGACCACCCTGGTTTTA
AAGATCCTGTGTACAGGGCAAGAAGGAAGCAGTTTGCTGACATTGCCTACAACTACAGGCATGG
GCAGCCCATCCCTAGGGTGGAATACATGGAGGAAGAAAAGAAAACATGGGGCACAGTGTTCAAG
ACTCTGAAGTCCTTGTATAAAACCCACGCTTGCTATGAGTACAATCACATTTTTCCACTTCTTG
AAAAGTACTGTGGCTTCCACGAAGATAACATTCCCCAGCTGGAAGATGTTTCTCAGTTCCTGCA
GACTTGCACTGGTTTCAGGCTCAGGCCTGTAGCTGGCCTGCTTTCCTCTAGGGATTTCTTGGGT
GGCCTGGCCTTCAGGGTCTTCCACTGCACACAGTACATCAGACACGGCTCCAAGCCCATGTATA
CCCCTGAACCTGACATCTGCCACGAGCTGTTGGGACACGTGCCCTTGTTTTCAGATAGGAGCTT
TGCCCAGTTTTCCCAGGAAATTGGCCTTGCCTCTCTGGGTGCACCTGATGAATATATTGAAAAG
CTGGCCACAATTTACTGGTTTACTGTGGAGTTTGGGCTCTGCAAACAAGGAGACTCCATAAAGG
CATATGGTGCTGGGCTCCTGTCATCCTTTGGTGAATTACAGTACTGCTTATCAGAGAAGCCAAA
GCTTCTCCCCCTGGAGCTGGAGAAGACAGCCATCCAAAATTACACTGTCACTGAGTTCCAGCCC
CTGTATTATGTGGCAGAGAGTTTTAATGATGCCAAGGAGAAAGTAAGGAACTTTGCTGCCACAA
TACCTAGGCCCTTCTCAGTTAGGTATGACCCATACACCCAAAGGATTGAGGTCTTGGACAATAC -continued

| SEQUENCES |
| --- |
| CCAGCAGCTTAAGATTTTGGCTGATTCCATTAACAGTGAAATTGGAATCCTTTGCAGTGCCCTC<br>CAGAAAATAAAGTAA |
| SEQ ID NO: 11 - codon optimised human PAH nucleic acid sequence<br>(ATUM (DNA2.0-op/D20-P))<br>ATGTCCACTGCGGTGTTGGAAAACCCCGGACTGGGCAGAAAGTTGTCCGACTTCGGCCAGGAAA<br>CCTCTTACATTGAGGACAACTGCAACCAGAACGGGGCCATCTCACTGATCTTTTCGCTGAAAGA<br>AGAAGTCGGAGCTCTGGCCAAAGTGCTGCGCCTGTTCGAGGAAAACGACGTCAACCTGACCCAC<br>ATCGAGTCAAGACCGAGCAGGCTGAAGAAGGATGAGTACGAGTTTTTCACCCATCTCGACAAGA<br>GATCCCTGCCTGCCCTGACCAATATTATCAAGATTTTGCGGCACGACATTGGCGCAACCGTGCA<br>TGAACTCTCCCGGGACAAGAAGAAGGACACCGTGCCGTGGTTCCCCCGAACCATCCAGGAACTC<br>GACCGCTTCGCTAACCAGATCCTGTCCTACGGCGCCGAACTGGATGCCGATCACCCTGGATTCA<br>AGGACCCAGTGTACAGAGCCCGGCGCAAGCAGTTCGCCGATATCGCCTACAATTATCGGCACGG<br>ACAGCCAATCCCGAGGGTGGAGTACATGGAGGAGGAAAAGAAAACCTGGGGAACTGTGTTCAAG<br>ACCTTGAAGTCCCTGTACAAGACTCACGCCTGCTACGAGTACAACCACATCTTCCCCCTGCTCG<br>AAAAGTACTGCGGGTTCCATGAGGACAACATCCCCCAACTGGAAGATGTGTCGCAGTTCCTGCA<br>AACCTGTACCGGATTCCGGCTGAGGCCTGTCGCGGGACTTCTGTCCTCCCGGGATTTTCTTGGC<br>GGTCTGGCCTTCCGGGTGTTCCACTGTACTCAGTACATTAGACACGGGAGCAAGCCTATGTACA<br>CTCCTGAACCCGACATTTGCCACGAACTCCTGGGTCATGTGCCCCTCTTCTCGGATCGGAGCTT<br>CGCCCAGTTCAGCCAAGAGATCGGTCTGGCTAGCTTGGGAGCACCCGACGAGTACATCGAGAAG<br>CTGGCCACTATCTACTGGTTTACCGTGGAATTCGGACTGTGCAAGCAGGGGGACTCAATCAAGG<br>CCTATGGCGCGGGACTCCTGAGCTCCTTCGGGGAGCTGCAGTACTGCCTGTCCGAAAAGCCAAA<br>GCTGCTCCCTCTTGAACTGGAGAAAACGGCCATCCAGAACTACACCGTGACCGAATTCCAGCCG<br>CTCTACTACGTCGCGGAGTCCTTCAACGATGCCAAGGAGAAGGTCCGCAACTTCGCCGCAACTA<br>TCCCGCGGCCGTTTTCCGTGCGCTATGACCCGTACACACAACGCATCGAAGTGCTGGACAACAC<br>CCAGCAACTTAAGATTCTGGCCGACTCGATCAACTCCGAGATTGGCATTCTGTGCTCGGCGCTG<br>CAGAAGATCAAGTAA |
| SEQ ID NO: 12 - codon optimised human PAH nucleic acid sequence<br>(ATUM-RCG (DNA2.0-Cop1))<br>ATGTCCACTGCGGTCCTGGAAAACCCTGGTCTGGGCCGCAAGCTTTCTGACTTTGGACAGGAAA<br>CCTCATACATTGAGGACAACTGTAACCAAAATGGTGCAATCAGCCTGATCTTCAGCCTCAAGGA<br>AGAAGTGGGAGCCCTGGCCAAGGTCCTGAGACTGTTTGAGGAGAATGATGTGAACCTGACCCAC<br>ATTGAGTCCAGGCCCTCCAGACTGAAGAAGGATGAATACGAATTCTTCACCCACCTGGACAAGC<br>GCTCCCTCCCTGCCCTCACCAACATCATTAAGATCCTGCGGCACGACATTGGAGCCACTGTGCA<br>TGAGTTGAGCCGGGACAAGAAGAAGGATACTGTGCCCTGGTTCCCGAGGACCATCCAGGAACTG<br>GACCGGTTTGCCAACCAAATTCTGTCCTATGGAGCTGAATTGGATGCAGACCACCCTGGCTTCA<br>AGGACCCAGTGTACAGAGCAAGGAGAAAGCAGTTTGCAGACATAGCCTACAACTACAGACATGG<br>ACAGCCCATCCCGAGGGTGGAGTACATGGAAGAGGAGAAGAAAACCTGGGGCACTGTGTTTAAG<br>ACCCTCAAGAGCCTGTACAAGACCCACGCCTGCTATGAGTACAACCACATCTTCCCACTCCTGG<br>AGAAATACTGTGGCTTCCATGAGGACAACATCCCACAGCTGGAGGATGTGTCCCAGTTCCTGCA<br>GACTTGCACTGGCTTCCGGTTGAGGCCTGTGGCTGGCCTGCTCTCCTCAAGGGACTTCTTGGGG<br>GGACTGGCATTCAGGGTGTTCCACTGCACCCAATACATCAGACACGGCAGCAAGCCAATGTACA<br>CCCCTGAACCGGACATCTGCCACGAACTCCTGGGCCACGTCCCTCTGTTCTCGGACAGAAGCTT<br>TGCCCAGTTCTCCCAAGAGATTGGCCTTGCCTCCCTGGGGGCCCCTGATGAATACATTGAAAAG<br>CTGGCCACAATCTACTGGTTCACTGTGGAATTTGGACTTTGCAAGCAGGGAGATAGCATCAAGG<br>CCTACGGGGCTGGACTTCTGTCCTCCTTCGGTGAACTGCAGTACTGTCTGTCAGAGAAGCCCAA<br>GCTGCTGCCCCTGGAACTGGAGAAAACTGCCATCCAAAACTACACTGTGACTGAGTTCCAGCCC<br>CTCTACTATGTGGCTGAGTCCTTCAATGATGCCAAAGAAAAGGTCAGAAATTTTGCGGCCACCA<br>TTCCTAGGCCTTTCTCAGTCCGCTATGACCCTTACACCCAGAGAATTGAGGTGCTGGACAACAC<br>CCAGCAGCTCAAGATCCTGGCAGACTCCATCAACTCAGAAATTGGGATCTTGTGCTCGGCCCTC<br>CAAAAGATCAAGTAA |
| SEQ ID NO: 13 - codon optimised human PAH nucleic acid sequence<br>(JCAT (JCAT))<br>ATGAGCACTGCTGTGCTGGAGAACCCTGGCCTGGGCAGAAAGCTGTCTGACTTTGGCCAGGAGA<br>CCAGCTACATTGAGGACAACTGCAACCAGAATGGGGCCATCAGCCTGATCTTCAGCCTGAAGGA<br>GGAGGTGGGGGCCCTGGCCAAGGTGCTGAGACTGTTTGAGGAGAATGATGTGAACCTGACCCAC<br>ATTGAGAGCAGACCCAGCAGACTGAAGAAGGATGAGTATGAGTTCTTCACCCACCTGGACAAGA<br>GAAGCCTGCCAGCCCTGACCAATATTATCAAGATCCTGAGGCACGATATTGGGGCCACAGTGCA<br>CGAGCTGAGCAGAGACAAGAAGAAGGACACAGTGCCCTGGTTCCCCAGGACTATCCAGGAGCTG<br>GACAGGTTTGCCAACCAGATCCTGAGCTACGGAGCTGAGCTGGATGCAGACCACCCTGGCTTCA<br>AGGACCCTGTGTACAGAGCCAGGAGAAAGCAGTTTGCAGATATAGCCTACAACTACAGGCACGG<br>CCAGCCAATCCCTAGAGTGGAGTACATGGAGGAGGAGAAGAAGACCTGGGGCACTGTGTTCAAG<br>ACCCTGAAGAGCCTGTACAAGACCCACGCCTGCTACGAGTACAACCACATCTTCCCCCTGCTGG<br>AGAAGTACTGTGGCTTCCACGAGGACAACATCCCCCAGCTGGAGGATGTGAGCCAGTTCCTGCA<br>GACCTGCACAGGCTTCAGGCTGAGACCAGTGGCAGGCCTGCTGAGCAGCAGGGACTTCCTGGGG<br>GGCCTGGCCTTCAGAGTGTTCCACTGCACCCAGTATATCAGGCACGGCAGCAAGCCAATGTACA<br>CCCCTGAGCCAGATATCTGCCACGAGCTGCTGGGCCACGTTCCCCTGTTCTCAGACAGAAGCTT<br>TGCCCAGTTCAGCCAGGAGATTGGCCTGGCCAGCCTGGGGGCCCCTGACGAGTATATTGAGAAG<br>CTGGCCACTATCTACTGGTTCACAGTGGAGTTTGGCCTGTGCAAGCAGGGGGACAGCATCAAGG<br>CCTATGGGGCTGGCCTGCTGAGCAGCTTTGGGGAGCTGCAGTACTGCCTGTCAGAGAAGCCAAA<br>GCTGCTGCCCCTGGAGCTGGAGAAGACAGCTATCCAGAACTACACTGTGACTGAGTTCCAGCCC<br>CTGTACTATGTGGCAGAGAGCTTCAATGATGCCAAGGAGAAGGTGAGAAACTTTGCTGCCACCA<br>TCCCCAGGCCCTTCTCTGTGAGATATGACCCCTACACCCAGAGGATTGAGGTGCTGGACAACAC<br>CCAGCAGCTGAAGATCCTGGCAGACAGCATCAACAGTGAGATTGGTATCCTGTGCTCTGCCCTG<br>CAGAAGATCAAGTAA |

-continued

SEQUENCES

SEQ ID NO: 14 - composite globin/AIAT intron nucleic acid sequence

```
Tgcctttcactgcgaggggttctggagaggcttctgagctccccatggcccaggcaggcagcag
gtctggggcaggagggggttgtggagtgggtatccgcctgctgaggtgcagggcagatggaga
ggctgcagctgagctcctattttcataataacagcagccatgagggttgtgtcctgtttcccag
tcctgcccggtccccccctcggtacctcctggtggatacactggttcctgtaagcagaagtggat
gagggtgtctaggtctgcagtcctggcaccccaggatgggggacaccagccaagatacagcaac
agcaacaaagcgcagccatttctttctgtttgcacagctcctctgtctgtcgggggctcctgtc
tgttgtctcctataagcctcaccacctctcctactgcttgggcatgcatctttctccccttcta
tagatgaggaggttaaggtccagagaggggtggggaggaacgccggctcacattctccatcccc
tccagatatgaccaggaacagacctgtgccaggcctcagccttacatcaaaatgggcctcccca
tgcaccgtggacctctgggccctcctgtcccagtggaggacaggaagctatgaggggcactgtc
acccagggctcaagctggcattcctgaataatcgctctgcaccaggccacggctaagctcagtg
cgtgattaagcctcataaccctccaaggcagttactagtgtgattcccattttacagatgagga
agatggggacagagaggtgaataactggccccaaatcacacaccatccataattcgggctcagg
cacctggctccagtccccaaactcttgaacctggccctagtgtcactgtttctcttgggtctca
ggcgctggatggggaacaggaaacctgggctggacttgaggcctctctgatgctcggtgacttc
agacagttgctcaacctctctgttctcttgggcaaaacatgataacctttgacttctgtcccct
cccctcaccccacccgaccttgatctctgaagtgttggaaggatttaatttttcctgcactgag
ttttggagacaggtcaaaaagatgaccaaggccaaggtggccagtttcctatagaacgcctcta
aaagacctgcagcaatagcagcaagaactggtattctcgagaacttgctgcgcagcaggcactt
cttggcattttatgtgtatttaatttcacaatagctctatgacaaagtccacctttctcatctc
caggaaactgaggttcagagaggttaagtaacttgtccaaggtcacacagctaatagcaagttg
acgtggagcaatctggcctcagagcctttaattttagccacagactgatgctcccctcttcatt
tagccaggctgcctctgaagttttctgattcaagacttctggcttcagctttgtacacagagat
gattcaatgtcaggttttggagtgaaatctgtttaatcccagacaaaacatttaggattacatc
tcagttttgtaagcaagtagctctgtgatttttagtgagttatttaatgctctttggggctcaa
tttttctatctataaaatagggctaataatttgcaccttatagggtaagctttgaggacagatt
agatgatacggtgcctgtaaaacaccaggtgttagtaagtgtggcaatgatggtgacgctgagg
ctgatgtttgcttagcatagggttaggcagctggcaggcagtaaacagttggataatttaatgg
aaaatttgccaaactcagatgcTAGCAGCTACaatccagctaccattctgcttttattttatgg
ttgggataaggctggattattctgagtccaagctaggccctttttgctaatcatgttcatacctc
ttatcttcctcccacagctcctgggcaacgtgctggtctgtgtgctggcccatcactttggcaa
agaattgcgatCGCCACC
```

SEQ ID NO: 15- Vector 1 (ApoE-HCR-hAAT.GI.hPAH.bGH) nucleic acid sequence

```
cctgcaggcagctgcgcgctcgctcgctcactgaggccgcccgggcaaagcccgggcgtcgggc
gacctttggtcgcccggcctcagtgagcgagcgagcgcgcagagagggagtggccaactccatc
actaggggttcctgcGGCCGCACGCGTAGGCTCAGAGGCACACAGGAGTTTCTGGGCTCACCCT
GCCCCCTTCCAACCCCTCAGTTCCCATCCTCCAGCAGCTGTTTGTGTGCTGCCTCTGAAGTCCA
CACTGAACAAACTTCAGCCTACTCATGTCCCTAAAATGGGCAAACATTGCAAGCAGCAAACAGC
AAACACACAGCCCTCCCTGCCTGCTGACCTTGGAGCTGGGGCAGAGGTCAGAGACCTCTCTGGG
CCCATGCCACCTCCAACATCCACTCGACCCCTTGGAATTTCGGTGGAGAGGAGCAGAGGTTGTC
CTGGCGTGGTTTAGGTAGTGTGAGAGGGGTCGACGATCTTGCTACCAGTGGAACAGCCACTAAG
GATTCTGCAGTGAGAGCAGAGGGCCAGCTAAGTGGTACTCTCCCAGAGACTGTCTGACTCACGC
CACCCCCTCCACCTTGGACACAGGACGCTGTGGTTTCTGAGCCAGGTACAATGACTCCTTTCGG
TAAGTGCAGTGGAAGCTGTACACTGCCCAGGCAAAGCGTCCGGGCAGCGTAGGCGGGCGACTCA
GATCCCAGCCAGTGGACTTAGCCCCTGTTTGCTCCTCCGATAACTGGGGTGACCTTGGTTAATA
TTCACCAGCAGCCTCCCCCGTTGCCCCTCTGGATCCACTGCTTAAATACGGACGAGGACAGGGC
CCTGTCTCCTCAGCTTCAGGCACCACCACTGACCTGGGACAGTGAATCgtaagtactagcagct
acaatccagctaccattctgcttttattttatggttgggataaggctggattattctgagtcca
agctaggccctttttgctaatcatgttcatacctcttatcttcctcccacagCTCCTGGGCAACG
TGCTGGTCTGTGTGCTGGCCCATCACTTTGGCAAAGAATTgcgatCGCCACCATGTCCACTGCG
GTCCTGGAAAACCCAGGCTTGGGCAGGAAACTCTCTGACTTTGGACAGGAAACAAGCTATATTG
AAGACAACTGCAATCAAAATGGTGCCATATCACTGATCTTCTCACTCAAAGAAGAAGTTGGTGC
ATTGGCCAAAGTATTGCGCTTATTTGAGGAGAATGATGTAAACCTGACCCACATTGAATCTAGA
CCTTCTCGTTTAAAGAAAGATGAGTATGAATTTTTCACCCATTTGGATAAACGTAGCCTGCCTG
CTCTGACAAACATCATCAAGATCTTGAGGCATGACATTGGTGCCACTGTCCATGAGCTTTCACG
AGATAAGAAGAAAGACACAGTGCCCTGGTTCCCAAGAACCATTCAAGAGCTGGACAGATTTGCC
AATCAGATTCTCAGCTATGGAGCGGAACTGGATGCTGACCACCCTGGTTTTAAAGATCCTGTGT
ACCGTGCAAGACGGAAGCAGTTTGCTGACATTGCCTACAACTACCGCCATGGGCAGCCCATCCC
TCGAGTGGAATACATGGAGGAAGAAAAGAAAACATGGGGCACAGTGTTCAAGACTCTGAAGTCC
TTGTATAAAACCCATGCTTGCTATGAGTACAATCACATTTTTCCACTTCTTGAAAAGTACTGTG
GCTTCCATGAAGATAACATTCCCCAGCTGGAAGACGTTTCTCAGTTCCTGCAGACTTGCACTGG
TTTCCGCCTCCGACCTGTAGCTGGCCTGCTTTCCTCTCGGGATTTCTTGGGTGGCCTGGCCTTC
CGAGTCTTCCACTGCACACAGTACATCAGACATGGATCCAAGCCCATGTATACCCCCGAACCTG
ACATCTGCCATGAGCTGTTGGGACATGTGCCCTTGTTTTCAGATCGCAGCTTTGCCCAGTTTTC
CCAGGAAATTGGCCTTGCCTCTCTGGGTGCACCTGATGAATACATTGAAAAGCTCGCCACAATT
TACTGGTTTACTGTGGAGTTTGGGCTCTGCAAACAAGGAGACTCCATAAAGGCATATGGTGCTG
GGCTCCTGTCATCCTTTGGTGAATTACAGTACTGCTTATCAGAGAAGCCAAAGCTTCTCCCCCT
GGAGCTGGAGAAGACAGCCATCCAAAATTACACTGTCACGGAGTTCCAGCCCCTGTATTACGTG
GCAGAGAGTTTTAATGATGCCAAGGAGAAAGTAAGGAACTTTGCTGCCACAATACCTCGGCCCT
TCTCAGTTCGCTACGACCCATACACCCAAAGGATTGAGGTCTTGGACAATACCCAGCAGCTTAA
GATTTTGGCTGATTCCATTAACAGTGAAATTGGAATCCTTTGCAGTGCCCTCCAGAAAATAAAG
TAACCTCGAGCTGTGCCTTCTAGTTGCCAGCCATCTGTTGTTTGCCCCTCCCCCGTGCCTTCCT
```

-continued

SEQUENCES

TGACCCTGGAAGGTGCCACTCCCACTGTCCTTTCCTAATAAAATGAGGAAATTGCATCGCATTG
TCTGAGTAGGTGTCATTCTATTCTGGGGGGTGGGGTGGGGCAGGACAGCAAGGGGGAGGATTGG
GAAGACAATAGCAGGCATGCTGGGGATGCGGTGGGCTCTATGGACCGGTGCggccgcaggaacc
cctagtgatggagttggccactccctctctgcgcgctcgctcgctcactgaggccgggcgacca
aaggtcgcccgacgcccgggctttgcccgggcggcctcagtgagcgagcgagcgcgcagctgcc
tgcagg SEQ ID NO: 16- GENEius1 (ApoE-HCR-hAAT.GI.hPAHco1.bGH) nucleic acid sequence
cctgcaggcagctgcgcgctcgctcgctcactgaggccgcccgggcaaagcccgggcgtcgggc
gacctttggtcgcccggcctcagtgagcgagcgagcgcgcagagagggagtggccaactccatc
actaggggttcctgcGGCCGCACGCGTAGGCTCAGAGGCACACAGGAGTTTCTGGGCTCACCCT
GCCCCCTTCCAACCCCTCAGTTCCCATCCTCCAGCAGCTGTTTGTGTGCTGCCTCTGAAGTCCA
CACTGAACAAACTTCAGCCTACTCATGTCCCTAAAATGGGCAAACATTGCAAGCAGCAAACAGC
AAACACACAGCCCTCCCTGCCTGCTGACCTTGGAGCTGGGGCAGAGGTCAGAGACCTCTCTGGG
CCCATGCCACCTCCAACATCCACTCGACCCCTTGGAATTTCGGTGGAGAGGAGCAGAGGTTGTC
CTGGCGTGGTTTAGGTAGTGTGAGAGGGGTCGACGATCTTGCTACCAGTGGAACAGCCACTAAG
GATTCTGCAGTGAGAGCAGAGGGCCAGCTAAGTGGTACTCTCCCAGAGACTGTCTGACTCACGC
CACCCCCTCCACCTTGGACACAGGACGCTGTGGTTTCTGAGCCAGGTACAATGACTCCTTTCGG
TAAGTGCAGTGGAAGCTGTACACTGCCCAGGCAAAGCGTCCGGGCAGCGTAGGCGGGCGACTCA
GATCCCAGCCAGTGGACTTAGCCCCTGTTTGCTCCTCCGATAACTGGGGTGACCTTGGTTAATA
TTCACCAGCAGCCTCCCCCGTTGCCCCTCTGGATCCACTGCTTAAATACGGACGAGGACAGGGC
CCTGTCTCCTCAGCTTCAGGCACCACCACTGACCTGGGACAGTGAATCgtaagtactagcagct
acaatccagctaccattctgcttttattttatggttgggataaggctggattattctgagtcca
agctaggcccttttgctaatcatgttcatacctcttatcttcctcccacagCTCCTGGGCAACG
TGCTGGTCTGTGTGCTGGCCCATCACTTTGGCAAAGAATTgcgatCGCCACCATGAGCACTGCT
GTGCTGGAGAACCCTGGCCTGGGCAGAAAGCTGTCTGACTTTGGCCAGGAGACCAGCTACATTG
AGGACAACTGCAACCAGAATGGAGCCATCAGCCTGATCTTCAGCCTGAAGGAGGAGGTGGGAGC
CCTGGCCAAGGTGCTGAGACTGTTTGAGGAGAATGATGTGAACCTGACCCACATTGAGAGCAGA
CCCAGCAGACTGAAGAAGGATGAGTATGAGTTCTTCACCCACCTGGACAAGAGAAGCCTGCCTG
CCCTGACCAACATCATCAAGATCCTGAGACACGATATTGGAGCCACTGTGCACGAGCTGAGCAG
AGACAAGAAGAAGGACACTGTGCCCTGGTTCCCCAGAACTATCCAGGAGCTGGACAGATTTGCC
AACCAGATCCTGAGCTATGGAGCTGAGCTGGATGCTGACCACCCTGGCTTCAAGGACCCTGTGT
ACAGAGCCAGAAGAAAGCAGTTTGCTGACATTGCCTACAACTACAGACACGGCCAGCCCATCCC
CAGAGTGGAGTACATGGAGGAGGAGAAGAAGACCTGGGGCACTGTGTTCAAGACCCTGAAGAGC
CTGTACAAGACCCACGCCTGCTATGAGTACAACCACATCTTCCCCCTGCTGGAGAAGTACTGTG
GCTTCCACGAGGACAACATCCCCCAGCTGGAGGATGTGAGCCAGTTCCTGCAGACCTGCACTGG
CTTCAGACTGAGACCTGTGGCTGGCCTGCTGAGCAGCAGAGACTTCCTGGGGGGCCTGGCCTTC
AGAGTGTTCCACTGCACCCAGTACATCAGACACGGCAGCAAGCCCATGTACACCCCTGAGCCTG
ATATCTGCCACGAGCTGCTGGGCCACGTGCCCCTGTTCTCTGACAGAAGCTTTGCCCAGTTCAG
CCAGGAGATTGGCCTGGCCAGCCTGGGAGCCCCTGATGAGTATATTGAGAAGCTGGCCACTATC
TACTGGTTCACTGTGGAGTTTGGCCTGTGCAAGCAGGGGGACAGCATCAAGGCCTATGGAGCTG
GCCTGCTGAGCAGCTTTGGGGAGCTGCAGTACTGCCTGTCTGAGAAGCCCAAGCTGCTGCCCCT
GGAGCTGGAGAAGACTGCCATCCAGAACTACACTGTGACTGAGTTCCAGCCCCTGTACTATGTG
GCTGAGAGCTTCAATGATGCCAAGGAGAAGGTGAGAAACTTTGCTGCCACCATCCCCAGACCCT
TCTCTGTGAGATATGACCCCTACACCCAGAGAATTGAGGTGCTGGACAACACCCAGCAGCTGAA
GATCCTGGCTGACAGCATCAACTCTGAGATTGGCATCCTGTGCTCTGCCCTGCAGAAGATCAAG
TAACCTCGAGCTGTGCCTTCTAGTTGCCAGCCATCTGTTGTTTGCCCCTCCCCCGTGCCTTCCT
TGACCCTGGAAGGTGCCACTCCCACTGTCCTTTCCTAATAAAATGAGGAAATTGCATCGCATTG
TCTGAGTAGGTGTCATTCTATTCTGGGGGGTGGGGTGGGGCAGGACAGCAAGGGGGAGGATTGG
GAAGACAATAGCAGGCATGCTGGGGATGCGGTGGGCTCTATGGACCGGTGCggccgcaggaacc
cctagtgatggagttggccactccctctctgcgcgctcgctcgctcactgaggccgggcgacca
aaggtcgcccgacgcccgggctttgcccgggcggcctcagtgagcgagcgagcgcgcagctgcc
tgcagg SEQ ID NO: 17- Large Intron-Vector 1 (ApoE-HCR-hAAT.cG-AIATI.hPAH.bGH) nucleic acid sequence
cctgcaggcagctgcgcgctcgctcgctcactgaggccgcccgggcaaagcccgggcgtcgggc
gacctttggtcgcccggcctcagtgagcgagcgagcgcgcagagagggagtggccaactccatc
actaggggttcctgcGGCCGCACGCGTAGGCTCAGAGGCACACAGGAGTTTCTGGGCTCACCCT
GCCCCCTTCCAACCCCTCAGTTCCCATCCTCCAGCAGCTGTTTGTGTGCTGCCTCTGAAGTCCA
CACTGAACAAACTTCAGCCTACTCATGTCCCTAAAATGGGCAAACATTGCAAGCAGCAAACAGC
AAACACACAGCCCTCCCTGCCTGCTGACCTTGGAGCTGGGGCAGAGGTCAGAGACCTCTCTGGG
CCCATGCCACCTCCAACATCCACTCGACCCCTTGGAATTTCGGTGGAGAGGAGCAGAGGTTGTC
CTGGCGTGGTTTAGGTAGTGTGAGAGGGGtcgacGATCTTGCTACCAGTGGAACAGCCACTAAG
GATTCTGCAGTGAGAGCAGAGGGCCAGCTAAGTGGTACTCTCCCAGAGACTGTCTGACTCACGC
CACCCCCTCCACCTTGGACACAGGACGCTGTGGTTTCTGAGCCAGGTACAATGACTCCTTTCGG
TAAGTGCAGTGGAAGCTGTACACTGCCCAGGCAAAGCGTCCGGGCAGCGTAGGCGGGCGACTCA
GATCCCAGCCAGTGGACTTAGCCCCTGTTTGCTCCTCCGATAACTGGGGTGACCTTGGTTAATA
TTCACCAGCAGCCTCCCCCGTTGCCCCTCTGGATCCACTGCTTAAATACGGACGAGGACAGGGC
CCTGTCTCCTCAGCTTCAGGCACCACCACTGACCTGGGACAGTGAATCgtaagtatgcctttca
ctgcgaggggttctggagaggcttctgagctccccatggcccaggcaggcagcaggtctggggc
aggaggggggttgtggagtgggtatccgcctgctgaggtgcagggcagatggagaggctgcagc
tgagctcctattttcataataacagcagccatgagggttgtgtcctgtttcccagtcctgcccg
gtccccccctcggtacctcctggtGgatacactggttcctgtaagcagaagtggatgagggtgtc
taggtctgcagtcctggcaccccaggatgggggacaccagccaagatacagcaacagcaacaaa
gcgcagccatttctttctgtttgcacagctcctctgtctgtcgggggctcctgtctgttgtctc -continued

SEQUENCES ctataagcctcaccacctctcctactgcttgggcatgcatctttctccccttctatagatgagg
aggttaaggtccagagaggggtggggaggaacgccggctcacattctccatcccctccagatat
gaccaggaacagacctgtgccaggcctcagccttacatCaaaatgggcctccccatgcaccgtg
gacctctgggccctcctgtcccagtggaggacaggaagctatgaggggcactgtcacccagggc
tcaagctggcattcctgaataatcgctctgcaccaggccacggctaagctcagtgcgtgattaa
gcctcataaccctccaaggcagttactagtgtgattcccattttacagatgaggaagatgggga
cagagaggtgaataactggccccaaatcacacaccatccataattcgggctcaggcacctggct
ccagtccccaaactcttgaacctggccctagtgtcactgtttctcttgggtCtcaggcgctgga
tggggaacaggaaacctgggctggacttgaggcctctctgatgctcggtgacttcagacagttg
ctcaacctctctgttctcttgggcaaaacatgataacctttgacttctgtcccctcccctcacc
ccacccgaccttgatctctgaagtgttggaaggatttaatttttcctgcactgagttttggaga
caggtcaaaaagatgaccaaggccaaggtggccagtttcctatagaacgcctctaaaagacctg
cagcaatagcagcaagaactggtattctcgagaacttgctgcgcagcaggcacttcttggcatt
ttAtgtgtatttaatttcacaatagctctatgacaaagtccacctttctcatctccaggaaact
gaggttcagagaggttaagtaacttgtccaaggtcacacagctaatagcaagttgacgtggagc
aatctggcctcagagcctttaatttagccacagactgatgctcccctcttcatttagccaggc
tgcctctgaagttttctgattcaagacttctggcttcagctttgtacacagagatgattcaatg
tcaggttttggagtgaaatctgtttaatcccagacaaaacatttaggattacatctcagttttg
taagcaagtagctctgtgatttttagtgagttatttaatgctctttggggctcaatttttctat
ctataaaatagggctaataatttgcaccttatagggtaagctttgaggacagattagatgatac
ggtgcctgtaaaacaccaggtgttagtaagtgtggcaatgatggtgacgctgaggctgatgttt
gcttagcatagggttaggcagctggcaggcagtaaacagttggataatttaatggaaaatttgc
caaactcagatgcTAGCAGCTACaatccagctaccattctgcttttattttatggttgggataa
ggctggattattctgagtccaagctaggcccttttgctaatcatgttcatacctcttatcttcc
tcccacagctcctgggcaacgtgctggtctgtgtgctggcccatcactttggcaaagaattgcg
atcgccaccATGTCCACTGCGGTCCTGGAAAACCCAGGCTTGGGCAGGAAACTCTCTGACTTTG
GACAGGAAACAAGCTATATTGAAGACAACTGCAATCAAAATGGTGCCATATCACTGATCTTCTC
ACTCAAAGAAGAAGTTGGTGCATTGGCCAAAGTATTGCGCTTATTTGAGGAGAATGATGTAAAC
CTGACCCACATTGAATCTAGACCTTCTCGTTTAAAGAAAGATGAGTATGAATTTTTCACCCATT
TGGATAAACGTAGCCTGCCTGCTCTGACAAACATCATCAAGATCTTGAGGCATGACATTGGTGC
CACTGTCCATGAGCTTTCACGAGATAAGAAGAAAGACACAGTGCCCTGGTTCCCAAGAACCATT
CAAGAGCTGGACAGATTTGCCAATCAGATTCTCAGCTATGGAGCGGAACTGGATGCTGACCACC
CTGGTTTTAAAGATCCTGTGTACCGTGCAAGACGGAAGCAGTTTGCTGACATTGCCTACAACTA
CCGCCATGGGCAGCCCATCCCTCGAGTGGAATACATGGAGGAAGAAAAGAAAACATGGGGCACA
GTGTTCAAGACTCTGAAGTCCTTGTATAAAACCCATGCTTGCTATGAGTACAATCACATTTTTC
CACTTCTTGAAAAGTACTGTGGCTTCCATGAAGATAACATTCCCCAGCTGGAAGACGTTTCTCA
GTTCCTGCAGACTTGCACTGGTTTCCGCCTCCGACCTGTAGCTGGCCTGCTTTCCTCTCGGGAT
TTCTTGGGTGGCCTGGCCTTCCGAGTCTTCCACTGCACACAGTACATCAGACATGGATCCAAGC
CCATGTATACCCCCGAACCTGACATCTGCCATGAGCTGTTGGGACATGTGCCCTTGTTTTCAGA
TCGCAGCTTTGCCCAGTTTTCCCAGGAAATTGGCCTTGCCTCTCTGGGTGCACCTGATGAATAC
ATTGAAAAGCTCGCCACAATTTACTGGTTTACTGTGGAGTTTGGGCTCTGCAAACAAGGAGACT
CCATAAAGGCATATGGTGCTGGGCTCCTGTCATCCTTTGGTGAATTACAGTACTGCTTATCAGA
GAAGCCAAAGCTTCTCCCCCTGGAGCTGGAGAAGACAGCCATCCAAAATTACACTGTCACGGAG
TTCCAGCCCCTGTATTACGTGGCAGAGAGTTTTAATGATGCCAAGGAGAAAGTAAGGAACTTTG
CTGCCACAATACCTCGGCCCTTCTCAGTTCGCTACGACCCATACACCCAAAGGATTGAGGTCTT
GGACAATACCCAGCAGCTTAAGATTTTGGCTGATTCCATTAACAGTGAAATTGGAATCCTTTGC
AGTGCCCTCCAGAAAATAAAGTAAcctcgagctgtgccttctagttgccagccatctgttgttt
gcccctcccccgtgccttccttgaccctggaaggtgccactcccactgtcctttcctAATAAAa
tgaggaaattgcatcgcattgtctgagtaggtgtcattctattctggggggtggggtggggcag
gacagcaagggggaggattgggaagacaatagcaggcatgctggggatgcggtgggctctatgg
accggtgcggccgcAGGAACCCCTAGTGATGGAGTTGGCCACTCCCTCTCTGCGCGCTCGCTCG
CTCACTGAGGCCGGGCGACCAAAGGTCGCCCGACGCCCGGGCTTTGCCCGGGCGGCCTCAGTGA
GCGAGCGAGCGCGCAGCTGCCTGCAGG SEQ ID NO: 18- Large Intron-GENEius 1 (ApoE-HCR-hAAT.cG-AIATI.hPAHco1.bGH) nucleic acid sequence
cctgcaggcagctgcgcgctcgctcgctcactgaggccgcccgggcaaagcccgggcgtcgggc
gacctttggtcgcccggcctcagtgagcgagcgagcgcgcagagagggagtggccaactccatc
actaggggttcctgcGGCCGCACGCGTAGGCTCAGAGGCACACAGGAGTTTCTGGGCTCACCCT
GCCCCCTTCCAACCCCTCAGTTCCCATCCTCCAGCAGCTGTTTGTGTGCTGCCTCTGAAGTCCA
CACTGAACAAACTTCAGCCTACTCATGTCCCTAAAATGGGCAAACATTGCAAGCAGCAAACAGC
AAACACACAGCCCTCCCTGCCTGCTGACCTTGGAGCTGGGGCAGAGGTCAGAGACCTCTCTGGG
CCCATGCCACCTCCAACATCCACTCGACCCCTTGGAATTTCGGTGGAGAGGAGCAGAGGTTGTC
CTGGCGTGGTTTAGGTAGTGTGAGAGGGgtcgacGATCTTGCTACCAGTGGAACAGCCACTAAG
GATTCTGCAGTGAGAGCAGAGGGCCAGCTAAGTGGTACTCTCCCAGAGACTGTCTGACTCACGC
CACCCCCTCCACCTTGGACACAGGACGCTGTGGTTTCTGAGCCAGGTACAATGACTCCTTTCGG
TAAGTGCAGTGGAAGCTGTACACTGCCCAGGCAAAGCGTCCGGGCAGCGTAGGCGGGCGACTCA
GATCCCAGCCAGTGGACTTAGCCCCTGTTTGCTCCTCCGATAACTGGGGTGACCTTGGTTAATA
TTCACCAGCAGCCTCCCCCGTTGCCCCTCTGGATCCACTGCTTAAATACGGACGAGGACAGGGC
CCTGTCTCCTCAGCTTCAGGCACCACCACTGACCTGGGACAGTGAATCgtaagtatgcctttca
ctgcgaggggttctggagaggcttctgagctccccatggcccaggcaggcagcaggtctggggc
aggagggggggttgtggagtgggtatccgcctgctgaggtgcagggcagatggagaggctgcagc
tgagctcctattttcataataacagcagccatgagggttgtgtcctgtttcccagtcctgcccg
gtccccccctcggtacctcctggtggatacactggttCctgtaagcagaagtggatgagggtgtc
taggtctgcagtcctggcaccccaggatgggggacaccagccaagatacagcaacagcaacaaa
gcgcagccatttctttctgtttgcacagctcctctgtctgtcgggggctcctgtctgttgtctc
ctataagcctcaccacctctcctactgcttgggcatgcatctttctccccttctatagatgagg -continued

| SEQUENCES |
|---|
| aggttaaggtccagagaggggtggggaggaacgccggctcacattctccatcccctccagatat<br>gaccaggaacagacctgtgccaggcctcagccttacatcaaaatgggcctccccAtgcaccgtg<br>gacctctgggccctcctgtcccagtggaggacaggaagctatgaggggcactgtcacccagggc<br>tcaagctggcattcctgaataatcgctctgcaccaggccacggctaagctcagtgcgtgattaa<br>gcctcataaccctccaaggcagttactagtgtgattcccattttacagatgaggaagatgggga<br>cagagaggtgaataactggccccaaatcacacaccatccataattcgggctcaggcacctggct<br>ccagtccccaaactcttgaacctggccctagtgtcactgtttctcttgggtctcaggcgctgga<br>tggggaAcaggaaacctgggctggacttgaggcctctctgatgctcggtgacttcagacagttg<br>ctcaacctctctgttctcttgggcaaaacatgataacctttgacttctgtcccctcccctcacc<br>ccacccgaccttgatctctgaagtgttggaaggatttaatttttcctgcactgagttttggaga<br>caggtcaaaaagatgaccaaggccaaggtggccagtttcctatagaacgcctctaaaagacctg<br>cagcaatagcagcaagaactggtattctcgagaacttgctgcgcagcaggcacttcttggcatt<br>ttatgtgtatttaatttcacaatagctCtatgacaaagtccacctttctcatctccaggaaact<br>gaggttcagagaggttaagtaacttgtccaaggtcacacagctaatagcaagttgacgtggagc<br>aatctggcctcagagcctttaattttagccacagactgatgctcccctcttcatttagccaggc<br>tgcctctgaagttttctgattcaagacttctggcttcagctttgtacacagagatgattcaatg<br>tcaggttttggagtgaaatctgtttaatcccagacaaaacatttaggattacatctcagttttg<br>taagcaagtagctctgtgatttttagtgagttatttaatgctctttggggctcaatttttctat<br>ctataaaatagggctaataatttgcaccttatagggtaagctttgaggacagattagatgatac<br>ggtgcctgtaaaacaccaggtgttagtaagtgtggcaatgatggtgacgctgaggctgatgttt<br>gcttagcatagggttaggcagctggcaggcagtaaacagttggataatttaatggaaaatttgc<br>caaactcagatgcTAGCAGCTACaatccagctaccattctgcttttattttatggttgggataa<br>ggctggattattctgagtccaagctaggccctttttgctaatcatgttcatacctcttatcttcc<br>tcccacagctcctgggcaacgtgctggtctgtgtgctggcccatcactttggcaaagaattgcg<br>atCGCCACCATGAGCACTGCTGTGCTGGAGAACCCTGGCCTGGGCAGAAAGCTGTCTGACTTTG<br>GCCAGGAGACCAGCTACATTGAGGACAACTGCAACCAGAATGGAGCCATCAGCCTGATCTTCAG<br>CCTGAAGGAGGAGGTGGGAGCCCTGGCCAAGGTGCTGAGACTGTTTGAGGAGAATGATGTGAAC<br>CTGACCCACATTGAGAGCAGACCCAGCAGACTGAAGAAGGATGAGTATGAGTTCTTCACCCACC<br>TGGACAAGAGAAGCCTGCCTGCCCTGACCAACATCATCAAGATCCTGAGACACGATATTGGAGC<br>CACTGTGCACGAGCTGAGCAGAGACAAGAAGAAGGACACTGTGCCCTGGTTCCCCAGAACTATC<br>CAGGAGCTGGACAGATTTGCCAACCAGATCCTGAGCTATGGAGCTGAGCTGGATGCTGACCACC<br>CTGGCTTCAAGGACCCTGTGTACAGAGCCAGAAGAAAGCAGTTTGCTGACATTGCCTACAACTA<br>CAGACACGGCCAGCCCATCCCCAGAGTGGAGTACATGGAGGAGGAGAAGAAGACCTGGGGCACT<br>GTGTTCAAGACCCTGAAGAGCCTGTACAAGACCCACGCCTGCTATGAGTACAACCACATCTTCC<br>CCCTGCTGGAGAAGTACTGTGGCTTCCACGAGGACAACATCCCCCAGCTGGAGGATGTGAGCCA<br>GTTCCTGCAGACCTGCACTGGCTTCAGACTGAGACCTGTGGCTGGCCTGCTGAGCAGCAGAGAC<br>TTCCTGGGGGGCCTGGCCTTCAGAGTGTTCCACTGCACCCAGTACATCAGACACGGCAGCAAGC<br>CCATGTACACCCCTGAGCCTGATATCTGCCACGAGCTGCTGGGCCACGTGCCCCTGTTCTCTGA<br>CAGAAGCTTTGCCCAGTTCAGCCAGGAGATTGGCCTGGCCAGCCTGGGAGCCCCTGATGAGTAT<br>ATTGAGAAGCTGGCCACTATCTACTGGTTCACTGTGGAGTTTGGCCTGTGCAAGCAGGGGGACA<br>GCATCAAGGCCTATGGAGCTGGCCTGCTGAGCAGCTTTGGGGAGCTGCAGTACTGCCTGTCTGA<br>GAAGCCCAAGCTGCTGCCCCTGGAGCTGGAGAAGACTGCCATCCAGAACTACACTGTGACTGAG<br>TTCCAGCCCCTGTACTATGTGGCTGAGAGCTTCAATGATGCCAAGGAGAAGGTGAGAAACTTTG<br>CTGCCACCATCCCCAGACCCTTCTCTGTGAGATATGACCCCTACACCCAGAGAATTGAGGTGCT<br>GGACAACACCCAGCAGCTGAAGATCCTGGCTGACAGCATCAACTCTGAGATTGGCATCCTGTGC<br>TCTGCCCTGCAGAAGATCAAGTAACCTCGAGCTGTGCCTTCTAGTTGCCAGCCATCTGTTGTTT<br>GCCCCTCCCCCGTGCCTTCCTTGACCCTGGAAGGTGCCACTCCCACTGTCCTTTCCTAATAAAA<br>TGAGGAAATTGCATCGCATTGTCTGAGTAGGTGTCATTCTATTCTGGGGGGTGGGGTGGGGCAG<br>GACAGCAAGGGGGAGGATTGGGAAGACAATAGCAGGCATGCTGGGGATGCGGTGGGCTCTATGG<br>ACCGGTGCggccgcaggaacccctagtgatggagttggccactccctctctgcgcgctcgctcg<br>ctcactgaggccgggcgaccaaaggtcgcccgacgcccgggctttgcccgggcggcctcagtga<br>gcgagcgagcgcgcagctgcctgcagg<br><br>SEQ ID NO: 19- hPAH + truncated 2nd intron (ApoE-HCR-hAAT.hPAH-tI2.bGH) nucleic acid sequence<br>cctgcaggcagctgcgcgctcgctcgctcactgaggccgcccgggcaaagcccgggcgtcgggc<br>gacctttggtcgcccggcctcagtgagcgagcgagcgcgcagagagggagtggccaactccatc<br>actaggggttcctgcggccgcacgcgtaggctcagaggcacacaggagtttctgggctcaccct<br>gccccettccaacccctcagttcccatcctccagcagctgtttgtgtgctgcctctgaagtcca<br>cactgaacaaacttcagcctactcatgtccctAaaatgggcaaacattgcaagcagcaaacagc<br>aaacacacagccctccctgcctgctgaccttggagctggggcagaggtcagagacctctctggg<br>cccatgccacctccaacatccactcgaccccttggaatttcggtggagaggagcagaggttgtc<br>ctggcgtggtttaggtagtgtgagaggggtcgacgatcttgctaccagtggaacagccactaag<br>gattctgcagtgagagcagagggccagctaagtggtactctcccagagactgtctgactcacgc<br>cacccccctccaccttggacacaggacgctgtggtttctgagCcaggtacaatgactcctttcgg<br>taagtgcagtggaagctgtacactgcccaggcaaagcgtccgggcagcgtaggcgggcgactca<br>gatcccagccagtggacttagcccctgtttgctcctccgataactggggtgaccttggttaata<br>ttcaccagcagcctcccccgttgcccctctggatccactgcttaaatacggacgaggacagggc<br>cctgtctcctcagcttcaggcaccaccactgacctgggacAGTGAATCagccagagacctcact<br>cccggggagccagcATGTCCACTGCGGTCCTGGAAAACCCAGGCTTGGGCAGGAAACTCTCTGA<br>CTTTGGACAGGAAACAAGCTATATTGAAGACAACTGCAATCAAAATGGTGCCATATCACTGATC<br>TTCTCACTCAAAGAAGAAGTTGGTGCATTGGCCAAAGTATTGCGCTTATTTGAGgtcagtgcta<br>caatcatgtttgtcttggataatgtcgtagcaaacttccatgttcttttctagttagatgcaat<br>gaaaagaacacaggatctggaacaggcagatttgaatttgagctcaagtttttacattaaccaa<br>ctgtgtgaccttaGttaagtcattcaatctctctgagcttcagtttttccattcataatatagt<br>gctgataatatgtgccttgtcagtttcaacaggaactttgtgatgaaataatgtgttttgtaaa<br>atgcctaatcatatgtgtgattaggcatgattaactataagtcatatgtgacacgtgattacat |

-continued

| SEQUENCES |
|---|
| ttcacataacatgtaatcacatgtgtcacatgtgattacagttaaagagtaaacaagaaataaa<br>tattaattcttttattcactaaattaatattgattgtcttctatgtataagtgtaaaataatat<br>gcaagacaccgtccctttcttcaagtagcttAacccaaaactatgctttagaaaatagctaatg<br>ttcttcaagacattggtaaatgtcttatgattaaagtggttccataattaataaacttgggaaa<br>ttcgggcatattattttacctgatttctttattataggacttttagagtctataaaactaatta<br>tactaagttgtttacagagagaaatgtatgtattattttccaaacttacttgactgtggatcct<br>ttttattttaagaacatgtattcacatctgggaacagagtttaggaaacgttgatttgggtgtt<br>tgctgggcagccaaacttcacagaactccaaataggtttcctcagccagAttccttccgagtac<br>tatgctaatattttttggtgggattttgtcccacctgaaaatacattgctttatgctaagattcc<br>tgtgacctctctagctgattgggaggcaggggtagcacattggtcagggctgtgcacatactta<br>gtgctcagtgtgtttgggcatgcaatcaacaaatccttttggggcatgactggatacgattaga<br>tatcttgtgaaaacctatgatgttctcagcactgtgggtggggaggaagatgggggacacatag<br>aaattgtaaggaagagaaactgcctcctttaggatctaacaggggaagcaaatattctgagcaG<br>ctggggagggaaggcagagcatgagaagttatctcagtaaaaggtagctttatagacatgatct<br>tattcagtctaatgaaaataacatgaggtaggagctatttctgcccccatttttcagagataga<br>aactgatgcttagaggggttaggtaaatgtgcccaaggtcaaacagctagtaaatacggaagaa<br>atcatttaaacccaggcattctgagtctagaacctacatacactcttaactgctattcagtact<br>gccccagacagaacgggcttcatagtttgcagggcgcagtgcaaaatgaaaacgtggggtctct<br>tcctcaataAcaggaaataatgctgttaaaagtactaaaatatataactttatcctttcttctg<br>tggtctctctcatgtcctgttatggtgtttttgatttgccatttagttgtgctctcctcccctg<br>ggcaccttggccctctaactgctgggttccctgtccagccagggctgggctgacagccaagccc<br>ctaccaaggatggggaaatccatcttccatttccgtggacctgctgcaccaacccacagtgatg<br>agctatcccccaagagattgtaacctctggaatgagaatggaaaggaagcTTGCCTGAACTTGG<br>TTTTAaagaagaaaaagtaaacaacttttgcaaatttaaggactttttatactcttataaaaa<br>taattgtattcttgaactctccatttgttgcgttaggttttcctgttctggttctgcatcttt<br>ggcctgcgttagttccagtgactgtctcctcAccctccccattctctcttctagGAGAATGATG<br>TAAACCTGACCCACATTGAATCTAGACCTTCTCGTTTAAAGAAAGATGAGTATGAATTTTTCAC<br>CCATTTGGATAAACGTAGCCTGCCTGCTCTGACAAACATCATCAAGATCTTGAGGCATGACATT<br>GGTGCCACTGTCCATGAGCTTTCACGAGATAAGAAGAAAGACACAGTGCCCTGGTTCCCAAGAA<br>CCATTCAAGAGCTGGACAGATTTGCCAATCAGATTCTCAGCTATGGAGCGGAACTGGATGCTGA<br>CCACCCTGGTTTTAAAGATCCTGTGTACCGTGCAAGACGGAAGCAGTTTGCTGACATTGCCTAC<br>AACTACCGCCATGGGCAGCCCATCCCTCGAGTGGAATACATGGAGGAAGAAAAGAAAACATGGG<br>GCACAGTGTTCAAGACTCTGAAGTCCTTGTATAAAACCCATGCTTGCTATGAGTACAATCACAT<br>TTTTCCACTTCTTGAAAAGTACTGTGGCTTCCATGAAGATAACATTCCCCAGCTGGAAGACGTT<br>TCTCAGTTCCTGCAGACTTGCACTGGTTTCCGCCTCCGACCTGTaGCTGGCCTGCTTTCCTCTC<br>GGGATTTCTTGGGTGGCCTGGCCTTCCGAGTCTTCCACTGCACACAGTACATCAGACATGGATC<br>CAAGCCCATGTATACCCCCGAACCTGACATCTGCCATGAGCTGTTGGGACATGTGCCCTTGTTT<br>TCAGATCGCAGCTTTGCCCAGTTTTCCCAGGAAATTGGCCTTGCCTCTCTGGGTGCACCTGATG<br>AATACATTGAAAAGCTCGCCACAATTTACTGGTTTACTGTGGAGTTTGGGCTCTGCAAACAAGG<br>AGACTCCATAAAGGCATATGGTGCTGGGCTCCTGTCATCCTTTGGTGAATTACAGTACTGCTTA<br>TCAGAGAAGCCAAAGCTTCTCCCCCTGGAGCTGGAGAAGACAGCCATCCAAAATTACACTGTCA<br>CGGAGTTCCAGCCCCTgTATTACGTGGCAGAGAGTTTTAATGATGCCAAGGAGAAAGTAAGGAA<br>CTTTGCTGCCACAATACCTCGGCCCTTCTCAGTTCGCTACGACCCATACACCCAAAGGATTGAG<br>GTCTTGGACAATACCCAGCAGCTTAAGATTTTGGCTGATTCCATTAACAGTGAAATTGGAATCC<br>TTTGCAGTGCCCTCCAGAAAATAAAGTAAcctcgagctgtgccttctagttgccagccatctgt<br>tgtttgcccctcccccgtgccttccttgaccctggaaggtgccactcccactgtcctttcctAA<br>TAAAatgaggaaattgcatcgcattgtctgagtaggtgtcattctattctggggggtggggtgg<br>ggcaggacagcaaggggggaggattgggaagacaatagcaggcatgctggggatgcggtgggctc<br>tatggaccggtgcggccgcAGGAACCCCTAGTGATGGAGTTGGCCACTCCCTCTCTGCGCGCTC<br>GCTCGCTCACTGAGGCCGGGCGACCAAAGGTCGCCCGACGCCCGGGCTTTGCCCGGGCGGCCTC<br>AGTGAGCGAGCGAGCGCGCAGCTGCCTGCAGG<br><br>SEQ ID NO: 20- pFB-ApoE-hAAT-hPAH-Genius2- vector sequence<br>cctgcaggcagctgcgcgctcgctcgctcactgaggccgcccgggcaaagcccgggcgtcgggc<br>gacctttggtcgcccggcctcagtgagcgagcgagcgcgcagagagggagtggccaactccatc<br>actaggggttcctgcGGCCGCACGCGTAGGCTCAGAGGCACACAGGAGTTTCTGGGCTCACCCT<br>GCCCCCTTCCAACCCCTCAGTTCCCATCCTCCAGCAGCTGTTTGTGTGCTGCCTCTGAAGTCCA<br>CACTGAACAAACTTCAGCCTACTCATGTCCCTAAAATGGGCAAACATTGCAAGCAGCAAACAGC<br>AAACACACAGCCCTCCCTGCCTGCTGACCTTGGAGCTGGGGCAGAGGTCAGAGACCTCTCTGGG<br>CCCATGCCACCTCCAACATCCACTCGACCCCTTGGAATTTCGGTGGAGAGGAGCAGAGGTTGTC<br>CTGGCGTGGTTTAGGTAGTGTGAGAGGGGTCGACGATCTTGCTACCAGTGGAACAGCCACTAAG<br>GATTCTGCAGTGAGAGCAGAGGGCCAGCTAAGTGGTACTCTCCCAGAGACTGTCTGACTCACGC<br>CACCCCCTCCACCTTGGACACAGGACGCTGTGGTTTCTGAGCCAGGTACAATGACTCCTTTCGG<br>TAAGTGCAGTGGAAGCTGTACACTGCCCAGGCAAAGCGTCCGGGCAGCGTAGGCGGGCGACTCA<br>GATCCCAGCCAGTGGACTTAGCCCCTGTTTGCTCCTCCGATAACTGGGGTGACCTTGGTTAATA<br>TTCACCAGCAGCCTCCCCCGTTGCCCCTCTGGATCCACTGCTTAAATACGGACGAGGACAGGGC<br>CCTGTCTCCTCAGCTTCAGGCACCACCACTGACCTGGGACAGTGAATCgtaagtactagcagct<br>acaatccagctaccattctgcttttattttatggttgggataaggctggattattctgagtcca<br>agctaggcccttttgctaatcatgttcatacctcttatcttcctcccacagCTCCTGGGCAACG<br>TGCTGGTCTGTGTGCTGGCCCATCACTTTGGCAAAGAATTgcgatCGCCACCATGAGCACTGCT<br>GTGCTGGAGAACCCTGGCCTGGGCAGAAAGCTGTCTGACTTTGGCCAGGAGACCAGCTACATTG<br>AGGACAACTGCAACCAGAATGGGGCCATCAGCCTGATCTTCAGCCTGAAGGAGGAGGTGGGGGC<br>CCTGGCCAAGGTGCTGAGACTGTTTGAGGAGAATGATGTGAACCTGACCCACATTGAGAGCAGA<br>CCCAGCAGACTGAAGAAGGATGAGTATGAGTTCTTCACCCACCTGGACAAGAGAAGCCTGCCTG<br>CCCTGACCAACATCATCAAGATCCTGAGACACGATATTGGGGCCACTGTGCACGAGCTGAGCAG<br>AGACAAGAAGAAGGACACTGTGCCCTGGTTCCCCAGAACTATCCAGGAGCTGGACAGATTTGCC<br>AACCAGATCCTGAGCTATGGGGCTGAGCTGGATGCTGACCACCCTGGCTTCAAGGACCCTGTGT |

-continued

| SEQUENCES |
| --- |

ACAGAGCCAGAAGAAAGCAGTTTGCTGACATTGCCTACAACTACAGACACGGCCAGCCCATCCC
CAGAGTGGAGTACATGGAGGAGGAGAAGAAGACCTGGGGCACTGTGTTCAAGACCCTGAAGAGC
CTGTACAAGACCCACGCCTGCTATGAGTACAACCACATCTTCCCCCTGCTGGAGAAGTACTGTG
GCTTCCACGAGGACAACATCCCCCAGCTGGAGGATGTGAGCCAGTTCCTGCAGACCTGCACTGG
CTTCAGACTGAGACCTGTGGCTGGCCTGCTGAGCAGCAGAGACTTCCTGGGGGGCCTGGCCTTC
AGAGTGTTCCACTGCACCCAGTACATCAGACACGGCAGCAAGCCCATGTACACCCCTGAGCCTG
ATATCTGCCACGAGCTGCTGGGCCACGTGCCCCTGTTCTCTGACAGAAGCTTTGCCCAGTTCAG
CCAGGAGATTGGCCTGGCCAGCCTGGGGGCCCCTGATGAGTATATTGAGAAGCTGGCCACTATC
TACTGGTTCACTGTGGAGTTTGGCCTGTGCAAGCAGGGGGACAGCATCAAGGCCTATGGGGCTG
GCCTGCTGAGCAGCTTTGGGGAGCTGCAGTACTGCCTGTCTGAGAAGCCCAAGCTGCTGCCCCT
GGAGCTGGAGAAGACTGCCATCCAGAACTACACTGTGACTGAGTTCCAGCCCCTGTACTATGTG
GCTGAGAGCTTCAATGATGCCAAGGAGAAGGTGAGAAACTTTGCTGCCACCATCCCCAGACCCT
TCTCTGTGAGATACGACCCCTACACCCAGAGAATTGAGGTGCTGGACAACACCCAGCAGCTGAA
GATCCTGGCTGACAGCATCAACTCTGAGATTGGCATCCTGTGCTCTGCCCTGCAGAAGATCAAG
TGACCTCGAGCTGTGCCTTCTAGTTGCCAGCCATCTGTTGTTTGCCCCTCCCCCGTGCCTTCCT
TGACCCTGGAAGGTGCCACTCCCACTGTCCTTTCCTAATAAAATGAGGAAATTGCATCGCATTG
TCTGAGTAGGTGTCATTCTATTCTGGGGGGTGGGGTGGGGCAGGACAGCAAGGGGGAGGATTGG
GAAGACAATAGCAGGCATGCTGGGGATGCGGTGGGCTCTATGGACCGGTGCggccgcaggaacc
cctagtgatggagttggccactccctctctgcgcgctcgctcgctcactgaggccgggcgacca
aaggtcgcccgacgcccgggctttgcccgggcggcctcagtgagcgagcgagcgcgcagctgcc
tgcagg SEQ ID NO: 21- pFB-ApoE-hAAT-hPAH-JCAT - vector sequence
cctgcaggcagctgcgcgctcgctcgctcactgaggccgcccgggcaaagcccgggcgtcgggc
gacctttggtcgcccggcctcagtgagcgagcgagcgcgcagagagggagtggccaactccatc
actaggggttcctgcGGCCGCACGCGTAGGCTCAGAGGCACACAGGAGTTTCTGGGCTCACCCT
GCCCCCTTCCAACCCCTCAGTTCCCATCCTCCAGCAGCTGTTTGTGTGCTGCCTCTGAAGTCCA
CACTGAACAAACTTCAGCCTACTCATGTCCCTAAAATGGGCAAACATTGCAAGCAGCAAACAGC
AAACACACAGCCCTCCCTGCCTGCTGACCTTGGAGCTGGGGCAGAGGTCAGAGACCTCTCTGGG
CCCATGCCACCTCCAACATCCACTCGACCCCTTGGAATTTCGGTGGAGAGGAGCAGAGGTTGTC
CTGGCGTGGTTTAGGTAGTGTGAGAGGGGTCGACGATCTTGCTACCAGTGGAACAGCCACTAAG
GATTCTGCAGTGAGAGCAGAGGGCCAGCTAAGTGGTACTCTCCCAGAGACTGTCTGACTCACGC
CACCCCCTCCACCTTGGACACAGGACGCTGTGGTTTCTGAGCCAGGTACAATGACTCCTTTCGG
TAAGTGCAGTGGAAGCTGTACACTGCCCAGGCAAAGCGTCCGGGCAGCGTAGGCGGGCGACTCA
GATCCCAGCCAGTGGACTTAGCCCCTGTTTGCTCCTCCGATAACTGGGGTGACCTTGGTTAATA
TTCACCAGCAGCCTCCCCCGTTGCCCCTCTGGATCCACTGCTTAAATACGGACGAGGACAGGGC
CCTGTCTCCTCAGCTTCAGGCACCACCACTGACCTGGGACAGTGAATCgtaagtactagcagct
acaatccagctaccattctgcttttattttatggttgggataaggctggattattctgagtcca
agctaggcccttttgctaatcatgttcatacctcttatcttcctcccacagCTCCTGGGCAACG
TGCTGGTCTGTGTGCTGGCCCATCACTTTGGCAAAGAATTgcgatCGCCACCATGAGCACTGCT
GTGCTGGAGAACCCTGGCCTGGGCAGAAAGCTGTCTGACTTTGGCCAGGAGACCAGCTACATTG
AGGACAACTGCAACCAGAATGGGGCCATCAGCCTGATCTTCAGCCTGAAGGAGGAGGTGGGGGC
CCTGGCCAAGGTGCTGAGACTGTTTGAGGAGAATGATGTGAACCTGACCCACATTGAGAGCAGA
CCCAGCAGACTGAAGAAGGATGAGTATGAGTTCTTCACCCACCTGGACAAGAGAAGCCTGCCAG
CCCTGACCAATATTATCAAGATCCTGAGGCACGATATTGGGGCCACAGTGCACGAGCTGAGCAG
AGACAAGAAGAAGGACACAGTGCCCTGGTTCCCCAGGACTATCCAGGAGCTGGACAGGTTTGCC
AACCAGATCCTGAGCTACGGAGCTGAGCTGGATGCAGACCACCCTGGCTTCAAGGACCCTGTGT
ACAGAGCCAGGAGAAAGCAGTTTGCAGATATAGCCTACAACTACAGGCACGGCCAGCCAATCCC
TAGAGTGGAGTACATGGAGGAGGAGAAGAAGACCTGGGGCACTGTGTTCAAGACCCTGAAGAGC
CTGTACAAGACCCACGCCTGCTACGAGTACAACCACATCTTCCCCCTGCTGGAGAAGTACTGTG
GCTTCCACGAGGACAACATCCCCCAGCTGGAGGATGTGAGCCAGTTCCTGCAGACCTGCACAGG
CTTCAGGCTGAGACCAGTGGCAGGCCTGCTGAGCAGCAGGGACTTCCTGGGGGGCCTGGCCTTC
AGAGTGTTCCACTGCACCCAGTATATCAGGCACGGCAGCAAGCCAATGTACACCCCTGAGCCAG
ATATCTGCCACGAGCTGCTGGGCCACGTTCCCCTGTTCTCAGACAGAAGCTTTGCCCAGTTCAG
CCAGGAGATTGGCCTGGCCAGCCTGGGGGCCCCTGACGAGTATATTGAGAAGCTGGCCACTATC
TACTGGTTCACAGTGGAGTTTGGCCTGTGCAAGCAGGGGGACAGCATCAAGGCCTATGGGGCTG
GCCTGCTGAGCAGCTTTGGGGAGCTGCAGTACTGCCTGTCAGAGAAGCCAAAGCTGCTGCCCCT
GGAGCTGGAGAAGACAGCTATCCAGAACTACACTGTGACTGAGTTCCAGCCCCTGTACTATGTG
GCAGAGAGCTTCAATGATGCCAAGGAGAAGGTGAGAAACTTTGCTGCCACCATCCCCAGGCCCT
TCTCTGTGAGATATGACCCCTACACCCAGAGGATTGAGGTGCTGGACAACACCCAGCAGCTGAA
GATCCTGGCAGACAGCATCAACAGTGAGATTGGTATCCTGTGCTCTGCCCTGCAGAAGATCAAG
TAACCTCGAGCTGTGCCTTCTAGTTGCCAGCCATCTGTTGTTTGCCCCTCCCCCGTGCCTTCCT
TGACCCTGGAAGGTGCCACTCCCACTGTCCTTTCCTAATAAAATGAGGAAATTGCATCGCATTG
TCTGAGTAGGTGTCATTCTATTCTGGGGGGTGGGGTGGGGCAGGACAGCAAGGGGGAGGATTGG
GAAGACAATAGCAGGCATGCTGGGGATGCGGTGGGCTCTATGGACCGGTGCggccgcaggaacc
cctagtgatggagttggccactccctctctgcgcgctcgctcgctcactgaggccgggcgacca
aaggtcgcccgacgcccgggctttgcccgggcggcctcagtgagcgagcgagcgcgcagctgcc
tgcagg SEQ ID NO: 22- pFB-hPAHV1-TBG2uGlob - vector sequence
cctgcaggcagctgcgcgctcgctcgctcactgaggccgcccgggcaaagcccgggcgtcgggc
gacctttggtcgcccggcctcagtgagcgagcgagcgcgcagagagggagtggccaactccatc
actaggggttcctgcggccgcaCGCGTCAGGTTAATTTTTAAAAAGCAGTCAAAAGTCCAAGTG
GCCCTTGGCAGCATTTACTCTCTCTGTTTGCTCTGGTTAATAATCTCAGGAGCACAAACATTCC
AGATCCAGGTTAATTTTTAAAAAGCAGTCAAAAGTCCAAGTGGCCCTTGGCAGCATTTACTCTC
TCTGTTTGCTCTGGTTAATAATCTCAGGAGCACAAACATTCCAGATCCGGCGCGCCAGGGCTGG
AAGCTACCTTTGACATCATTTCCTCTGCGAATGCATGTATAATTTCTACAGAACCTATTAGAAA -continued

| SEQUENCES |
| --- |
| GGATCACCCAGCCTCTGCTTTTGTACAACTTTCCCTTAAAAAACTGCCAATTCCACTGCTGTTT<br>GGCCCAATAGTGAGAACTTTTTCCTGCTGCCTCTTGGTGCTTTTGCCTATGGCCCCTATTCTGC<br>CTGCTGAAGACACTCTTGCCAGCATGGACTTAAACCCCTCCAGCTCTGACAATCCTCTTTCTCT<br>TTTGTTTTACATGAAGGGTCTGGCAGCCAAAGCAATCACTCAAAGTTCAAACCTTATCATTTTT<br>TGCTTTGTTCCTCTTGGCCTTGGTTTTGTACATCAGCTTTGAAAATACCATCCCAGGGTTAATG<br>CTGGGGTTAATTTATAACTAAGAGTGCTCTAGTTTTGCAATACAGGACATGCTATAAAAATGGA<br>AAGATGTTGCTTTCTGAGAGATGCAGGTGGATTCTTGGGCATTTGCTGTAAGTACTAGCAGCTA<br>CAATCCAGCTACCATTCTGCTTTTATTTTATGGTTGGGATAAGGCTGGATTATTCTGAGTCCAA<br>GCTAGGCCCTTTTGCTAATCATGTTCATACCTCTTATCTTCCTCCCACAGCTCCTGGGCAACGT<br>GCTGGTCTGTGTGCTGGCCCATCACTTTGGCAAAGAATTGCGATCGCCACCATGTCCACTGCGG<br>TCCTGGAAAACCCAGGCTTGGGCAGGAAACTCTCTGACTTTGGACAGGAAACAAGCTATATTGA<br>AGACAACTGCAATCAAAATGGTGCCATATCACTGATCTTCTCACTCAAAGAAGAAGTTGGTGCA<br>TTGGCCAAAGTATTGCGCTTATTTGAGGAGAATGATGTAAACCTGACCCACATTGAATCTAGAC<br>CTTCTCGTTTAAAGAAAGATGAGTATGAATTTTTCACCCATTTGGATAAACGTAGCCTGCCTGC<br>TCTGACAAACATCATCAAGATCTTGAGGCATGACATTGGTGCCACTGTCCATGAGCTTTCACGA<br>GATAAGAAGAAAGACACAGTGCCCTGGTTCCCAAGAACCATTCAAGAGCTGGACAGATTTGCCA<br>ATCAGATTCTCAGCTATGGAGCGGAACTGGATGCTGACCACCCTGGTTTTAAAGATCCTGTGTA<br>CCGTGCAAGACGGAAGCAGTTTGCTGACATTGCCTACAACTACCGCCATGGGCAGCCCATCCCT<br>CGAGTGGAATACATGGAGGAAGAAAAGAAAACATGGGGCACAGTGTTCAAGACTCTGAAGTCCT<br>TGTATAAAACCCATGCTTGCTATGAGTACAATCACATTTTTCCACTTCTTGAAAAGTACTGTGG<br>CTTCCATGAAGATAACATTCCCCAGCTGGAAGACGTTTCTCAGTTCCTGCAGACTTGCACTGGT<br>TTCCGCCTCCGACCTGTAGCTGGCCTGCTTTCCTCTCGGGATTTCTTGGGTGGCCTGGCCTTCC<br>GAGTCTTCCACTGCACACAGTACATCAGACATGGATCCAAGCCCATGTATACCCCCGAACCTGA<br>CATCTGCCATGAGCTGTTGGGACATGTGCCCTTGTTTTCAGATCGCAGCTTTGCCCAGTTTTCC<br>CAGGAAATTGGCCTTGCCTCTCTGGGTGCACCTGATGAATACATTGAAAAGCTCGCCACAATTT<br>ACTGGTTTACTGTGGAGTTTGGGCTCTGCAAACAAGGAGACTCCATAAAGGCATATGGTGCTGG<br>GCTCCTGTCATCCTTTGGTGAATTACAGTACTGCTTATCAGAGAAGCCAAAGCTTCTCCCCCTG<br>GAGCTGGAGAAGACAGCCATCCAAAATTACACTGTCACGGAGTTCCAGCCCCTGTATTACGTGG<br>CAGAGAGTTTTAATGATGCCAAGGAGAAAGTAAGGAACTTTGCTGCCACAATACCTCGGCCCTT<br>CTCAGTTCGCTACGACCCATACACCCAAAGGATTGAGGTCTTGGACAATACCCAGCAGCTTAAG<br>ATTTTGGCTGATTCCATTAACAGTGAAATTGGAATCCTTTGCAGTGCCCTCCAGAAAATAAAGT<br>AACCTCGAGCTGTGCCTTCTAGTTGCCAGCCATCTGTTGTTTGCCCCTCCCCCGTGCCTTCCTT<br>GACCCTGGAAGGTGCCACTCCCACTGTCCTTTCCTAATAAAATGAGGAAATTGCATCGCATTGT<br>CTGAGTAGGTGTCATTCTATTCTGGGGGGTGGGGTGGGGCAGGACAGCAAGGGGGAGGATTGGG<br>AAGACAATAGCAGGCATGCTGGGGATGCGGTGGGCTCTATGGACCGGTGC |
| SEQ ID NO: 23- - pFB-hPAHV1-TTR - vector sequence<br>cctgcaggcagctgcgcgctcgctcgctcactgaggccgcccgggcaaagcccgggcgtcgggc<br>gacctttggtcgcccggcctcagtgagcgagcgagcgcgcagagagggagtggccaactccatc<br>actaggggttcctgcggccgcGTCTGTCTGCACATTTCGTAGAGCGAGTGTTCCGATACTCTAA<br>TCTCCCTAGGCAAGGTTCATATTgactTAGGTTACTTATTCTCCTTTTGTTGACTAAGTCAATA<br>ATCAGAATCAGCAGGTTTGGAGTCAGCTTGGCAGGGATCAGCAGCCTGGGTTGGAAGGAGGGGG<br>TATAAAAGCCCCTTCACCAGGAGAAGCCGTCACACAGATCCACAAGCTCCTGACAGGagGCTTC<br>CCTTCGACTCTTCCTCCTTTGCCTCGCTGGACTGGTATTTGTGTCTGAAGCTGGCCCCGCGgta<br>agtactagcagctacaatccagctaccattctgcttttattttatggttgggataaggctggat<br>tattctgagtccaagctaggcccttttgctaatcatgttcatacctcttatcttcctcccacag<br>ctcctgggcaacgtgctggtctgtgtgctggcccatcactttggcaaagaattgcgatcgccac<br>cATGTCCACTGCGGTCCTGGAAAACCCAGGCTTGGGCAGGAAACTCTCTGACTTTGGACAGGAA<br>ACAAGCTATATTGAAGACAACTGCAATCAAAATGGTGCCATATCACTGATCTTCTCACTCAAAG<br>AAGAAGTTGGTGCATTGGCCAAAGTATTGCGCTTATTTGAGGAGAATGATGTAAACCTGACCCA<br>CATTGAATCTAGACCTTCTCGTTTAAAGAAAGATGAGTATGAATTTTTCACCCATTTGGATAAA<br>CGTAGCCTGCCTGCTCTGACAAACATCATCAAGATCTTGAGGCATGACATTGGTGCCACTGTCC<br>ATGAGCTTTCACGAGATAAGAAGAAAGACACAGTGCCCTGGTTCCCAAGAACCATTCAAGAGCT<br>GGACAGATTTGCCAATCAGATTCTCAGCTATGGAGCGGAACTGGATGCTGACCACCCTGGTTTT<br>AAAGATCCTGTGTACCGTGCAAGACGGAAGCAGTTTGCTGACATTGCCTACAACTACCGCCATG<br>GGCAGCCCATCCCTCGAGTGGAATACATGGAGGAAGAAAAGAAAACATGGGGCACAGTGTTCAA<br>GACTCTGAAGTCCTTGTATAAAACCCATGCTTGCTATGAGTACAATCACATTTTTCCACTTCTT<br>GAAAAGTACTGTGGCTTCCATGAAGATAACATTCCCCAGCTGGAAGACGTTTCTCAGTTCCTGC<br>AGACTTGCACTGGTTTCCGCCTCCGACCTGTAGCTGGCCTGCTTTCCTCTCGGGATTTCTTGGG<br>TGGCCTGGCCTTCCGAGTCTTCCACTGCACACAGTACATCAGACATGGATCCAAGCCCATGTAT<br>ACCCCCGAACCTGACATCTGCCATGAGCTGTTGGGACATGTGCCCTTGTTTTCAGATCGCAGCT<br>TTGCCCAGTTTTCCCAGGAAATTGGCCTTGCCTCTCTGGGTGCACCTGATGAATACATTGAAAA<br>GCTCGCCACAATTTACTGGTTTACTGTGGAGTTTGGGCTCTGCAAACAAGGAGACTCCATAAAG<br>GCATATGGTGCTGGGCTCCTGTCATCCTTTGGTGAATTACAGTACTGCTTATCAGAGAAGCCAA<br>AGCTTCTCCCCCTGGAGCTGGAGAAGACAGCCATCCAAAATTACACTGTCACGGAGTTCCAGCC<br>CCTGTATTACGTGGCAGAGAGTTTTAATGATGCCAAGGAGAAAGTAAGGAACTTTGCTGCCACA<br>ATACCTCGGCCCTTCTCAGTTCGCTACGACCCATACACCCAAAGGATTGAGGTCTTGGACAATA<br>CCCAGCAGCTTAAGATTTTGGCTGATTCCATTAACAGTGAAATTGGAATCCTTTGCAGTGCCCT<br>CCAGAAAATAAAGTAAcctcgagctgtgccttctagttgccagccatctgttgtttgcccctcc<br>cccgtgccttccttgaccctggaaggtgccactcccactgtcctttcctAATAAAatgaggaaa<br>ttgcatcgcattgtctgagtaggtgtcattctattctggggggtggggtggggcaggacagcaa<br>gggggaggattgggaagacaatagcaggcatgctggggatgcggtgggctctatggaccggtgc<br>ggccgcAGGAACCCCTAGTGATGGAGTTGGCCACTCCCTCTCTGCGCGCTCGCTCGCTCACTGA<br>GGCCGGGCGACCAAAGGTCGCCCGACGCCCGGGCTTTGCCCGGGCGGCCTCAGTGAGCGAGCGA<br>GCGCGCAGCTGCCTGCAGG |

The invention claimed is:

1. A recombinant adeno-associated virus (rAAV) vector genome comprising:

(a) a promoter; and (b) a codon optimized sequence encoding a human phenylalanine hydroxylase (hPAH), wherein the codon optimized sequence comprises:

(i) the nucleotide sequence of SEQ ID NO: 7, or a variant thereof having at least 95% sequence identity to the nucleotide sequence of SEQ ID NO: 7; or (ii) the nucleotide sequence of SEQ ID NO: 8, or a variant thereof having at least 95% sequence identity to the nucleotide sequence of SEQ ID NO: 8; or (iii) the nucleotide sequence of SEQ ID NO: 9, or a variant thereof having at least 98% sequence identity to the nucleotide sequence of SEQ ID NO: 9; or (iv) the nucleotide sequence of SEQ ID NO: 10, or a variant thereof having at least 98% sequence identity to the nucleotide sequence of SEQ ID NO: 10; or (v) the nucleotide sequence of SEQ ID NO: 11, or a variant thereof having at least 90% sequence identity to the nucleotide sequence of SEQ ID NO: 11; or (vi) the nucleotide sequence of SEQ ID NO: 12, or a variant thereof having at least 85% sequence identity to the nucleotide sequence of SEQ ID NO: 12; or (vii) the nucleotide sequence of SEQ ID NO: 13; or a variant thereof having at least 95% sequence identity to the nucleotide sequence of SEQ ID NO: 13.

2. The rAAV vector according to claim 1, wherein the codon optimized sequence comprises a nucleotide sequence having at least 98% sequence identity to the nucleotide sequence of SEQ ID NO: 7, SEQ ID NO: 8; SEQ ID NO: 9; SEQ ID NO: 10; SEQ ID NO: 11; SEQ ID NO: 12; or SEQ ID NO: 13.

3. The rAAV vector according to claim 1, wherein the promoter is a liver-specific promoter.

4. The rAAV vector according to claim 1, wherein the promoter is a thyroxine binding globulin (TBG) promoter, a transthyretin (TTR) promoter, a human albumin (humA1b) promoter, a Liver Specific promoter (LSP), or a hepatitis B virus core promoter.

5. The rAAV vector according to claim 1, wherein the promoter is a synthetic promoter sequence comprising portions of an hAAT promoter, a hepatic control region (HCR) enhancer, and an ApoE enhancer.

6. The rAAV vector according to claim 1, wherein the promoter comprises the nucleotide sequence of SEQ ID NO:3; SEQ ID NO:4; or SEQ ID NO:6, or a variant thereof having at least 80% sequence identity to the nucleotide sequence of SEQ ID NO:3; SEQ ID NO:4; or SEQ ID NO:6.

7. The rAAV vector according to claim 1, wherein the promoter comprises the nucleotide sequence of SEQ ID NO:3; SEQ ID NO:4; or SEQ ID NO:6.

8. The rAAV vector according to claim 1, wherein the vector genome further comprises an intron.

9. The rAAV vector according to claim 8, wherein the intron is a composite globin/A1AT intron sequence.

10. The rAAV vector according to claim 8, wherein the intron comprises the nucleotide sequence of SEQ ID NO:14, or a variant thereof having at least 80% sequence identity to SEQ ID NO:14.

11. The rAAV vector according to claim 1, wherein the vector genome further comprises a polyadenylation signal sequence.

12. The rAAV vector according to claim 11, wherein the polyadenylation signal sequence is a bovine growth hormone (bGH) poly(A), SV40 late poly(A), rabbit beta-globin (rBG) poly(A), thymidine kinase (TK) poly(A) sequences, or any variants thereof.

13. The rAAV vector according to claim 11, wherein the polyadenylation signal sequence is a bGH poly(A).

14. The rAAV vector according to claim 1, wherein the vector genome further comprises an AAV 5' inverted terminal repeat (ITR) sequence and/or an AAV 3' ITR.

15. The rAAV vector according to claim 14, wherein the AAV 5' ITR and/or the AAV 3' ITR is from AAV2.

16. The rAAV vector according to claim 1, wherein the vector genome is about 2 kb to about 3 kb, about 3 kb to about 4 kb, or about 4 kb to about 5 kb in size.

17. A rAAV particle comprising an AAV capsid and the vector genome of claim 1.

18. The rAAV particle according to claim 17, wherein the AAV capsid is an AAV5 capsid.

19. A method of producing rAAV particles of claim 17, comprising the steps of:

(a) culturing in cell culture a cell transfected or transduced with a rAAV vector genome comprising (I) a promoter; and (II) a codon optimized sequence encoding a hPAH, wherein the codon optimized sequence comprises:

(i) the nucleotide sequence of SEQ ID NO: 7, or a variant thereof having at least 95% sequence identity to the nucleotide sequence of SEQ ID NO: 7; or (ii) the nucleotide sequence of SEQ ID NO: 8, or a variant thereof having at least 95% sequence identity to the nucleotide sequence of SEQ ID NO: 8; or (iii) the nucleotide sequence of SEQ ID NO: 9, or a variant thereof having at least 98% sequence identity to the nucleotide sequence of SEQ ID NO: 9; or (iv) the nucleotide sequence of SEQ ID NO: 10, or a variant thereof having at least 98% sequence identity to the nucleotide sequence of SEQ ID NO: 10; or (v) the nucleotide sequence of SEQ ID NO: 11, or a variant thereof having at least 90% sequence identity to the nucleotide sequence of SEQ ID NO: 11; or (vi) the nucleotide sequence of SEQ ID NO: 12, or a variant thereof having at least 85% sequence identity to the nucleotide sequence of SEQ ID NO: 12; or (vii) the nucleotide sequence of SEQ ID NO: 13; or a variant thereof having at least 95% sequence identity to the nucleotide sequence of SEQ ID NO: 13, wherein the cell expresses AAV capsid and rep proteins; and (b) recovering rAAV particles from the supernatant of the cell.

20. The method of claim 19, wherein said cell is an insect cell or a mammalian cell.

21. A pharmaceutical composition comprising the rAAV particle of claim 17, and a pharmaceutically acceptable carrier.

22. The rAAV vector according to claim 1, wherein the codon optimized sequence comprises a nucleotide sequence having at least 90% sequence identity to the nucleotide sequence of SEQ ID NO: 11 or SEQ ID NO: 12.

23. The rAAV vector according to claim 1, wherein the codon optimized sequence comprises a nucleotide sequence having at least 98% sequence identity to the nucleotide sequence of SEQ ID NO: 7.

24. The rAAV vector according to claim 1, wherein the codon optimized sequence comprises the nucleotide sequence of SEQ ID NO: 7.

25. A rAAV vector genome comprising:

(a) a promoter; and (b) a codon optimized sequence encoding a hPAH, wherein the codon optimized sequence comprises the nucleotide sequence of SEQ ID NO: 7, SEQ ID NO: 8; SEQ ID NO: 9; SEQ ID NO: 10; SEQ ID NO: 11; SEQ ID NO: 12; or SEQ ID NO: 13.

26. A rAAV vector genome comprising (a) the nucleotide sequence of SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; or SEQ ID NO: 23; or (b) a variant thereof having at least 80% sequence identity to the nucleotide sequence of SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; or SEQ ID NO: 23.

27. The rAAV vector according to claim 26, wherein the vector genome sequence comprises the nucleotide sequence of SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; or SEQ ID NO: 23.

28. A rAAV particle comprising an AAV capsid and the vector genome of claim 27.

29. The rAAV particle according to claim 28, wherein the AAV capsid is an AAV5 capsid.

30. A method of producing rAAV particles of claim 28, comprising the steps of:

(a) culturing in cell culture a cell transfected or transduced with a rAAV vector genome comprising the nucleotide sequence of SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; or SEQ ID NO: 23, wherein the cell expresses AAV capsid and rep proteins; and (b) recovering rAAV particles from the supernatant of the cell.

31. A pharmaceutical composition comprising the rAAV particle of claim 28, and a pharmaceutically acceptable carrier.

32. The rAAV vector according to claim 26, wherein the vector genome sequence comprises a nucleotide sequence having at least 80% sequence identity to the nucleotide sequence of SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; or SEQ ID NO: 23.

33. The rAAV vector according to claim 26, wherein the vector genome sequence comprises a nucleotide sequence having at least 98% sequence identity to the nucleotide sequence of SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; or SEQ ID NO: 23.

34. The rAAV vector according to claim 26, wherein the vector genome sequence comprises the nucleotide sequence of SEQ ID NO: 16.

35. The rAAV vector according to claim 26, wherein the vector genome sequence comprises the nucleotide sequence of SEQ ID NO: 18.

36. A rAAV vector genome comprising:

(a) an AAV 5' ITR sequence;

(b) a liver-specific promoter;

(c) a codon optimized sequence encoding a hPAH, wherein the codon optimized sequence comprises the nucleotide sequence of SEQ ID NO: 7; or a variant thereof having at least 95% sequence identity to the nucleotide sequence of SEQ ID NO: 7;

(d) a composite globin/A1AT intron; and (e) an AAV 3' ITR.

37. The rAAV vector according to claim 36, wherein the promoter comprises a nucleotide sequence having at least 80% sequence identity to the nucleotide sequence of SEQ ID NO:3; SEQ ID NO:4; or SEQ ID NO:6.

38. The rAAV vector according to claim 36, wherein the promoter comprises the nucleotide sequence of SEQ ID NO:3; SEQ ID NO:4; or SEQ ID NO:6.

39. The rAAV vector according to claim 36, wherein the composite globin/A1AT intron comprises the nucleotide sequence of SEQ ID NO:14, or a variant thereof having at least 90% sequence identity to SEQ ID NO:14.

40. The rAAV vector according to claim 36, wherein the composite globin/A1AT intron comprises the nucleotide sequence of SEQ ID NO:14.

41. The rAAV vector according to claim 36, wherein the vector genome further comprises a polyadenylation signal sequence.

42. The rAAV vector according to claim 41, wherein the polyadenylation signal sequence is a bGH poly(A), SV40 late poly(A), rBG poly(A), TK poly(A) sequences, or any variants thereof.

43. The rAAV vector according to claim 41, wherein the polyadenylation signal sequence is a bGH poly(A).

44. The rAAV vector according to claim 36, wherein the AAV 5' ITR and the AAV 3' ITR are from AAV2.

45. A rAAV particle comprising an AAV capsid and the vector genome of claim 36.

46. A method of producing rAAV particles of claim 45, comprising the steps of:

(a) culturing in cell culture a cell transfected or transduced with a rAAV vector genome comprising (i) an AAV 5' ITR sequence; (ii) a liver-specific promoter; (iii) a codon optimized sequence encoding a hPAH, wherein the codon optimized sequence comprises the nucleotide sequence of SEQ ID NO: 7; or a variant thereof having at least 95% sequence identity to the nucleotide sequence of SEQ ID NO: 7; (iv) a composite globin/A1AT intron; and (v) an AAV 3' ITR, wherein the cell expresses AAV capsid and rep proteins; and (b) recovering rAAV particles from the supernatant of the cell.

47. A pharmaceutical composition comprising the rAAV particle of claim 45, and a pharmaceutically acceptable carrier.

48. The rAAV vector according to claim 36, wherein the codon optimized sequence comprises a nucleotide sequence having at least 98% sequence identity to the nucleotide sequence of SEQ ID NO: 7.

49. The rAAV vector according to claim 36, wherein the codon optimized sequence comprises the nucleotide sequence of SEQ ID NO: 7.

50. The rAAV vector according to claim 36, wherein the codon optimized sequence comprises the nucleotide sequence of SEQ ID NO: 8.

51. The rAAV vector according to claim 36, wherein the codon optimized sequence comprises the nucleotide sequence of SEQ ID NO: 13.

52. A rAAV vector genome comprising:

(a) an AAV 5' ITR sequence;

(b) a promoter comprising the nucleotide sequence of SEQ ID NO:3; SEQ ID NO:4; or SEQ ID NO:6;

(c) a codon optimized sequence encoding a hPAH, wherein the codon optimized sequence comprises the nucleotide sequence of SEQ ID NO: 7; SEQ ID NO: 8; SEQ ID NO: 9; SEQ ID NO: 10; SEQ ID NO: 11; SEQ ID NO: 12; or SEQ ID NO: 13;

(d) an intron comprising the nucleotide sequence of SEQ ID NO:14; and (e) an AAV 3' ITR.

53. The rAAV vector according to claim 52, wherein the vector genome further comprises a polyadenylation signal sequence.

54. The rAAV vector according to claim 53, wherein the polyadenylation signal sequence is a bGH poly(A), SV40 late poly(A), rBG poly(A), TK poly(A) sequences, or any variants thereof.

55. The rAAV vector according to claim 53, wherein the polyadenylation signal sequence is a bGH poly(A).

56. The rAAV vector according to claim 52, wherein the AAV 5' ITR and AAV 3' ITR are from AAV2.

57. A rAAV particle comprising an AAV capsid and the vector genome of claim 52.

58. A method of producing an rAAV particles of claim 57, comprising the steps of:

(a) culturing in cell culture a cell transfected or transduced with a rAAV vector genome comprising (i) an AAV 5' ITR sequence; (ii) a promoter comprising the nucleotide sequence of SEQ ID NO:3; SEQ ID NO:4; or SEQ ID NO:6; (iii) a codon optimized sequence encoding a hPAH, wherein the codon optimized sequence comprises the nucleotide sequence of SEQ ID NO: 7; SEQ ID NO: 8; SEQ ID NO: 9; SEQ ID NO: 10; SEQ ID NO: 11; SEQ ID NO: 12; or SEQ ID NO: 13; (iv) an intron comprising the nucleotide sequence of SEQ ID NO:14; and (v) an AAV 3' ITR, wherein the cell AAV capsid and rep proteins; and (b) recovering rAAV particles from the supernatant of the cell.

59. A pharmaceutical composition comprising the rAAV particle of claim 57, and a pharmaceutically acceptable carrier.

60. The rAAV vector according to claim 52, wherein the codon optimized sequence comprises the nucleotide sequence of SEQ ID NO: 7.

61. An isolated nucleic acid molecule comprising a nucleotide sequence having at least 98% homology to the nucleotide sequence of SEQ ID NO: 7; SEQ ID NO: 8; SEQ ID NO: 9; SEQ ID NO: 10; SEQ ID NO: 11; SEQ ID NO: 12; or SEQ ID NO: 13, and which encodes functional PAH.

* * * * *

UNITED STATES PATENT AND TRADEMARK OFFICE
CERTIFICATE OF CORRECTION

PATENT NO. : 11,739,345 B2
APPLICATION NO. : 16/407015
DATED : August 29, 2023
INVENTOR(S) : Berguig et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 907 days.

Signed and Sealed this
Twelfth Day of November, 2024

Katherine Kelly Vidal
*Director of the United States Patent and Trademark Office*